US009517989B2

(12) United States Patent
Makriyannis et al.

(10) Patent No.: US 9,517,989 B2
(45) Date of Patent: Dec. 13, 2016

(54) 2-CYCLOALKYL RESORCINOL CANNABINERGIC LIGANDS

(71) Applicant: Northeastern University, Boston, MA (US)

(72) Inventors: Alexandros Makriyannis, Watertown, MA (US); Marsha R. D'Souza, Boston, MA (US); Shama Bajaj, Somerville, MA (US); Spyridon P. Nikas, Waltham, MA (US); Ganeshsingh A. Thakur, Cambridge, MA (US)

(73) Assignee: NORTHEASTERN UNIVERSITY, Boston, MA (US)

( * ) Notice: Subject to any disclaimer, the term of this patent is extended or adjusted under 35 U.S.C. 154(b) by 0 days.

(21) Appl. No.: 14/436,865

(22) PCT Filed: Oct. 17, 2013

(86) PCT No.: PCT/US2013/065516
§ 371 (c)(1),
(2) Date: Apr. 17, 2015

(87) PCT Pub. No.: WO2014/062965
PCT Pub. Date: Apr. 24, 2014

(65) Prior Publication Data
US 2015/0274623 A1  Oct. 1, 2015

Related U.S. Application Data

(60) Provisional application No. 61/714,914, filed on Oct. 17, 2012.

(51) Int. Cl.
| | |
|---|---|
| *C07C 39/23* | (2006.01) |
| *C07C 69/16* | (2006.01) |
| *C07C 69/18* | (2006.01) |
| *C07D 311/78* | (2006.01) |
| *C07D 309/06* | (2006.01) |
| *C07C 69/63* | (2006.01) |
| *C07C 39/42* | (2006.01) |
| *C07C 43/168* | (2006.01) |
| *C07D 339/06* | (2006.01) |
| *C07C 47/27* | (2006.01) |
| *C07C 47/46* | (2006.01) |
| *C07C 49/747* | (2006.01) |
| *C07D 295/092* | (2006.01) |
| *C07C 62/32* | (2006.01) |
| *C07C 235/40* | (2006.01) |
| *C07C 247/06* | (2006.01) |
| *C07C 255/36* | (2006.01) |
| *C07C 255/38* | (2006.01) |
| *C07C 43/178* | (2006.01) |
| *C07C 49/603* | (2006.01) |

(Continued)

(52) U.S. Cl.
CPC .............. *C07C 39/23* (2013.01); *C07C 39/42* (2013.01); *C07C 43/168* (2013.01); *C07C 43/1788* (2013.01); *C07C 47/27* (2013.01); *C07C 47/46* (2013.01); *C07C 49/603* (2013.01); *C07C 49/747* (2013.01); *C07C 62/32* (2013.01); *C07C 69/16* (2013.01); *C07C 69/18* (2013.01); *C07C 69/63* (2013.01); *C07C 235/40* (2013.01); *C07C 245/24* (2013.01); *C07C 247/06* (2013.01); *C07C 255/36* (2013.01); *C07C 255/38* (2013.01); *C07D 295/092* (2013.01); *C07D 295/096* (2013.01); *C07D 295/192* (2013.01); *C07D 309/06* (2013.01); *C07D 311/78* (2013.01); *C07D 339/06* (2013.01); *C07C 2101/02* (2013.01); *C07C 2101/04* (2013.01); *C07C 2101/08* (2013.01); *C07C 2101/14* (2013.01); *C07C 2101/16* (2013.01); *C07C 2102/42* (2013.01); *C07C 2103/04* (2013.01); *C07C 2103/74* (2013.01)

(58) Field of Classification Search
CPC ...... C07C 39/23; C07C 69/16; C07D 295/092
See application file for complete search history.

(56) References Cited

U.S. PATENT DOCUMENTS 7,446,229 B2   11/2008   Makriyannis et al.
7,718,830 B2   5/2010    Chen et al.
(Continued)

FOREIGN PATENT DOCUMENTS

WO   WO-0195899 A2      12/2001
WO   WO-2005023741 A2   3/2005
WO   WO-2011006099 A1   1/2011

OTHER PUBLICATIONS

Papahatjis et al (2007): STN International HCAPLUS database, (Columbus, Ohio), Accession No. 2007:841173.*

(Continued)

*Primary Examiner* — Golam M M Shameem

(57) ABSTRACT

The present invention relates to novel 2-cycloalkyl resorcinol compounds; to pharmaceutical compositions comprising the compounds; and to methods of preparing the compounds and uses thereof. The disclosed compounds can bind to and modulate the cannabinoid receptors and thus, they are specific ligands for these receptors. The invented compounds, when administered in a therapeutically effective amount to an individual or animal, results in a sufficiently high level of that compound in the individual or animal to cause a physiological response. The physiological response may be useful to treat a number of physiological conditions.

18 Claims, 2 Drawing Sheets

(51) Int. Cl.
*C07C 245/24* (2006.01)
*C07D 295/096* (2006.01)
*C07D 295/192* (2006.01)

(56) References Cited

U.S. PATENT DOCUMENTS

2005/0020544 A1  1/2005  Garzon et al.
2007/0135388 A1  6/2007  Makriyannis et al.

OTHER PUBLICATIONS

International Search Report and Written Opinion issued by the U.S. Patent and Trademark Office as International Searching Authority for International Application No. PCT/US2013/065516 mailed Feb. 26, 2014 (43 pgs.).
Shah, V.J., "Synthesis of Cannabidiol Stereoisomers and Analogs as Potential Anticonvulsant Agents," The Universit of Arizona, Doctoral Dissertation, 118 pages (1988).
Chen, et al., GPCR Structure-Based Virtual Screeming Approach for CB2 Antagonist Search, Journal of Chemical Information and Modeling, vol. 47, No. 4, pp. 1626-1637 (Jun. 20, 2007).
Dominianni, et al., "Synthesis of 5-(tert-alkyl)resorcinols," J. Org. Chem., vol. 42, No. 344, pp. 344-346 (1977).
Drake, et al., "Classical/Nonclassical Hybrid Cannabinoids: Southern Aliphatic Chain-Functionalized C-6β Methyl, Ethyl, and Propyl Analogues" J. Med. Chem., vol. 41, pp. 3596-3608 (1998).
Lu, D. et al., "Adamantyl Cannabinoids: A Novel Class of Cannabinergic Ligands," J. Med. Chem., vol. 48, pp. 4576-4585 (2005).
Nikas et al., "A Concise Methodology for the Synthesis of (−)-Δ9-tetrahydrocannabinol and (−)-Δ9-tetrahydrocannabivarin Metabolites and Their Regiospecifically Deuterated Analogs," Tetrahedron, vol. 63, pp. 8112-8123 (2007).
Papahatjis et al., "Novel 1',1'-chain substituted 08-tetrahydrocannabinols," Bioorg. Med. Chem. Lett., vol. 12, pp. 3583-3586 (2002).
Papahatjis, et al., "A New Ring-Forming Methodology for the Synthesis of Conformationally Constrained Bioactive Molecules," Chem. Lett., vol. 30, No. 3, pp. 192-193 (2001).
Papahatjis, et al., "Pharmacophoric Requirements for the Cannabinoid Side Chain. Probing the Cannabinoid Receptor Subsite at C1'," J. Med. Chem., vol. 46, pp. 3221-3229 (2003).

\* cited by examiner

2-CYCLOALKYL RESORCINOL CANNABINERGIC LIGANDS

CROSS-REFERENCE TO RELATED APPLICATIONS

This is a National Stage application claiming priority to International Application No. PCT/US2013/065516, filed on Oct. 17, 2013, which claims the benefit of and priority to U.S. Provisional Patent Application No. 61/714,914, filed on Oct. 17, 2012, the contents of each of which are hereby incorporated by reference in their entirety.

GOVERNMENT LICENSE RIGHTS

This invention was made with government support under Grant # DA 7215 awarded by the National Institutes of Health. The government has certain rights in the invention.

FIELD OF THE INVENTION

The present disclosure relates generally to chemical compounds with cannabinergic activity. More particularly, the present disclosure is concerned with new 2-cycloalkyl resorcinol derivatives exhibiting high binding affinities for cannabinoid receptors, pharmaceutical preparations employing these derivatives and methods of administering therapeutically effective amounts of the analogs to provide a physiological effect.

BACKGROUND

The classical cannabinoid $\Delta^9$-tetrahydrocannabinol ($\Delta^9$-THC) is the major active constituent extracted from *Cannabis sativa*. The effects of cannabinoids are due to an interaction with specific high affinity receptors. Presently two $G_{i/o}$ protein coupled cannabinoid receptors, namely CB1 and CB2, have been characterized in mammals and other organisms. The CB1 receptor is very densely distributed through the central nervous system, and at lower levels in various peripheral tissues, including the myocardium, postgangliomic autonomic nerve terminals, and vascular endothelial and smooth muscle cells as well as the liver, skeletal muscle and adipose tissue (Pacher, et al., *Pharmacol. Rev.* (2006) 58:389-462; Batkai, et al., *Circulation* (2004) 110:1996-2002; Bonz, et al., *J. Cardiovasc. Pharmacol.* (2005) 41:657-664; Mukhopadhyay, et al., *J. Am. Coll. Cardiol.* (2007) 50:528-536; Rajesh, et al., *Am. J. Physiol. Heart Circ. Physiol.* (2007) 293:H2210-H2218; Rajesh, et al., *Br. J. Pharmacol.* (2008) 153:347-357; Mallat, et al. *Am. J. Physiol. Gastrointest. Liver Physiol.* (2008) 294:9-12; Osei-Hyiaman, et al., *J. Clin. Invest.* (2005) 115:1298-1305; Engeli, et al., *Diabetes* (2005) 54:2838-2843; Jeong, et al., *Cell. Metab.* (2008) 7:227-235; Pagotto, et al., *Endocr. Rev.* (2006) 27:73-100; Cota, et al., *J. Clin. Invest.* (2003) 112:423-431).

The CB2 receptor is present in immune and hematopoietic cells and recently has also been identified in the brain, myocardium, liver, and human coronary endothelial and smooth muscle cells (Van Sickle, et al., *Science* (2005) 310:329-332; Gong, et al., *Brain Res.* (2006) 1071:10-23; Mukhopadhyay, et al., *J. Am. Coll. Cardiol.* (2007) 50:528-536; Mallat, et al., *Am. J. Physiol. Gastrointest. Liver Physiol.* (2008) 294:9-12; Rajesh, et al. *Am. J. Physiol. Heart Circ. Physiol.* (2007) 293:H2210-2218; Rajesh, et al., *Br. J. Pharmacol.* (2008) 153:347-357).

Some compounds (cannabinergic ligands) can bind to the CB1 and/or CB2 receptors in an individual or animal. In vitro methods for assaying the ability of a compound to bind to CB1 and/or CB2 receptors are known. Results from the in vitro assay correlate with and predict the in vivo ability of that compound to bind to CB1 and/or CB2 receptors and modulate their function(s). When introduced in an individual or animal some of these cannabinergic ligands can bind to and modulate (activate or deactivate) the CB1 and/or CB2 receptors. Examples of some cannabinergic ligands include N-arachidonoyl ethanolamine (anandamide, AEA) and 2-arachidonoylglycerol (2-AG) (both endogenous ligands for the cannabinoid CB1 and CB2 receptors), (−)-$\Delta^9$-tetrahydrocannabinol ($\Delta^9$-THC, the principal bioactive constituent of *cannabis* preparations and exogenous ligand for the cannabinoid CB1 and CB2 receptors) and other synthetic cannabinergic analogs.

Ligands for the CB1/CB2 cannabinoid receptors, such as (−)-$\Delta^9$-tetrahydrocannabinol can bind to and modulate (activate or deactivate) the CB1/CB2 cannabinoid receptors and thereby provide a physiological effect in an individual or animal that is useful to treat a condition in that individual or animal. Conditions that may be treated by modulation of the CB1/CB2 cannabinoid receptors include for example: pain; central pain; peripheral pain; neuropathic pain; neuropathy; inflammatory pain; neurodegenerative diseases including multiple sclerosis, Parkinson's disease, Huntington's chorea, Alzheimer's disease and amyotrophic lateral sclerosis; mental disorders such as schizophrenia and depression; mood disorders; addiction disorders; memory disorders; gastrointestinal motility disorders such as irritable bowel syndrome and diarrhea; dyskinesia; migraine; osteoporosis, osteoarthritis; high blood pressure disease or hypertension; peripheral vascular disease; coronary artery disease; abnormal heart rate; cardiac insufficiency; pulmonary hypertension; ocular hypertension or glaucoma; to prevent or reduce endotoxic shock and hypotensive shock; to modulate appetite; to modulate the immune system; to modulate fertility; to prevent or reduce diseases associated with motor dysfunction such as Tourette's syndrome; to prevent or reduce inflammation; to provide neuroprotection; to produce peripheral vasodilation; to treat epilepsy; to treat nausea such as associated with cancer chemotherapy; AIDS wasting syndrome; to treat several types of cancer as well as other ailments in which cannabinoid system is implicated.

SUMMARY

Figure 1:
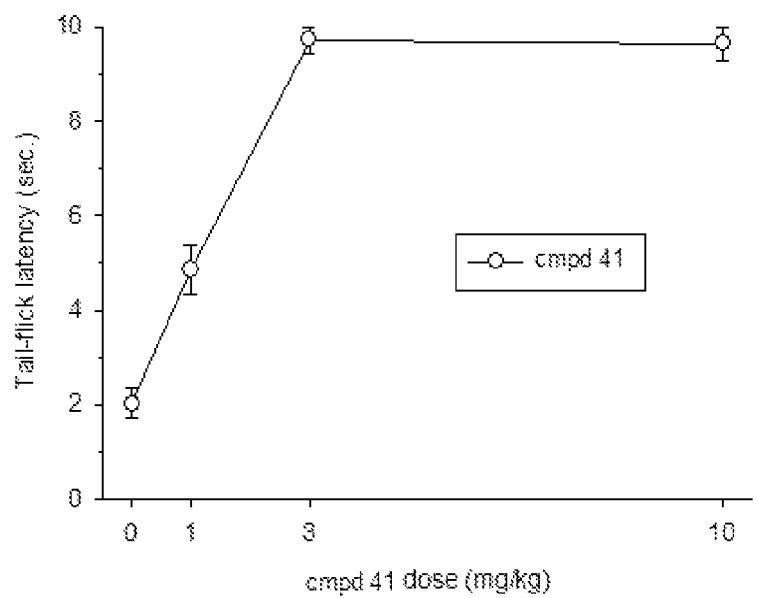
FIG. 1 is a chart showing the effects on antinociception of a compound of the present invention in an analgesia assay in mice.

Novel resorcinol derivatives represented by the general formulas I, II, III, IV, V and VI and methods for preparation and use are presented. The disclosed compounds can bind to and modulate the cannabinoid CB1/CB2 receptors and thus, they are specific ligands for these receptors. The disclosed compounds, when administered in a therapeutically effective amount to an individual or animal, results in a sufficiently high level of that compound in the individual or animal to cause a physiological response. The physiological response may be useful to treat a number of physiological conditions.

In one aspect, a compound of formula I or a pharmaceutically acceptable salt thereof, including all stereoisomers and enantiomers is disclosed:

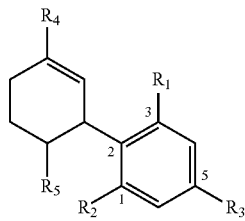

I wherein:
$R_1$ and $R_2$ are each independently selected from the group consisting of: —H, —F, —Cl, —Br, —I, —OH, —SH, —NH$_2$, —NO$_2$, —CN, —CF$_3$, —OC(O)CH$_3$, —C(O)CH$_3$, —C(O)CF$_3$, —O-alkyl, —OSi(alkyl)$_3$, —S-alkyl, —NH-alkyl, —N(alkyl)$_2$, —O—P(O)(OR)$_2$, —O—P(O)(OH)(OR) (wherein R is selected from the group consisting of H and alkyl), —P(O)(OR)$_2$, —P(O)(OH)(OR) (wherein R is selected from the group consisting of H and alkyl), —O-alkyl-COOR (wherein R is selected from the group consisting of H and alkyl), —O-alkyl-NR$_6$R$_7$, —O-alkyl-CONR$_6$R$_7$, —OC(O)—R (wherein R is selected from the group consisting of H and alkyl), —OC(O)—CH(OH)—CH$_2$OH, —OC(O)—C(CH$_2$OH)$_2$—CH$_3$, —OC(O)—CH$_2$OH, —OC(O)-alkyl-COOH, —OC(O)—CH═CHCOOH, —OC(O)-alkyl-NR$_6$R$_7$, —OC(O)-alkyl-C(O)NR$_6$R$_7$, —OC(O)—O-alkyl-NR$_6$R$_7$, and —OC(O)—CH(NH$_2$)—R$_8$ (wherein R$_8$ is selected from the group consisting of H, CH(OH)CH$_3$ and alkyl-X$_1$, and X$_1$ is selected from the group consisting of: —H, —NHC(═NH)NH$_2$, —C(O)NH$_2$, —COOH, —SH, —SCH$_3$, —OH, —NH$_2$, and an aromatic, heteroaromatic or heterocyclic ring);
$R_6$ and $R_7$ are each independently selected from the group consisting of: H and alkyl, or R$_6$ and R$_7$ together comprise part of a 3 to 7 membered saturated heterocyclic ring containing up to one additional heteroatom selected from the group consisting of N, O and S;
$R_3$ is selected from the group consisting of: -cycloalkyl-R$_9$, -heterocyclic-R$_9$, -adamantyl, -adamantyl-R$_9$, and -heteroadamantyl-R$_9$;
$R_9$ is selected from the group consisting of: —(CH$_2$)$_j$—R$_{10}$, —(CH$_2$)$_j$-A-(CH$_2$)$_k$—R$_{10}$, and —(CH$_2$)$_j$-A-(CH$_2$)$_k$—B—R$_{10}$;
A and B are each independently selected from the group consisting of: —CH$_2$—CH$_2$—, —C≡C—, —CH═CH—, —O—, —S—, —NH—, —C(O)—, —C(O)O—, —OC(O)—, —C(O)NH—, —NHC(O)—, —S(O)—, —SO$_2$—, —SO$_2$NH—, —NHSO$_2$—, —SO$_2$O— and —OSO$_2$—;
$R_{10}$ is selected from the group consisting of —H, —F, —Cl, —Br, —I, —OH, —SH, —NH$_2$, —CN, —N$_3$, —NCS, —NCO, —SO$_2$Cl, —SO$_2$F, —SO$_2$NH$_2$, —C(O)NH$_2$, —COOH, —NO$_2$, —CHO, —CF$_3$, —SO$_3$H, —O—P(O)(OH)$_2$, —Sn(alkyl)$_3$, —Si(alkyl)$_3$, —C≡CH, —CH═CH$_2$, and an aromatic, heteroaromatic or heterocyclic ring;
j is an integer from 0 to 8;
k is an integer from 0 to 8;
$R_4$ is selected from the group consisting of —H, —R$_{11}$, -alkyl-R$_{11}$, -alkyl-O-alkyl, -alkyl-O-alkyl-R$_{11}$, —C(O)O-alkyl, —OC(O)-alkyl, C$_{1-3}$alkyl-C(O)O-alkyl, and —C$_{1-3}$alkyl-OC(O)-alkyl;

$R_{11}$ is selected from the group consisting of: —F, —Cl, —Br, —I, —OH, —SH, —NH$_2$, —NH-alkyl, —N(alkyl)$_2$, —CN, —N$_3$, —NCS, —OC(O)CH$_3$, —C(O)OCH$_3$, —SO$_2$NH$_2$, —C(O)NH$_2$, —COOH, —NO$_2$, —CHO, —CF$_3$, —Sn(alkyl)$_3$, —Si(alkyl)$_3$, —C≡CH, —CH═CH$_2$, and an aromatic, heteroaromatic or heterocyclic ring;
$R_5$ is selected from the group consisting of —H, -alkyl, -alkyl-R$_{12}$, -alkenyl, -alkenyl-R$_{12}$, -alkynyl and -alkynyl-R$_{12}$; and
$R_{12}$ is selected from the group consisting of: —F, —Cl, —Br, —I, —OH, —SH, —NH$_2$, —NH-alkyl, —N(alkyl)$_2$, —CN, —N$_3$, —NCS, —OC(O)CH$_3$, —C(O)OCH$_3$, —SO$_2$NH$_2$, —C(O)NH$_2$, —COOH, —NO$_2$, —CHO, —CF$_3$, —Sn(alkyl)$_3$, —Si(alkyl)$_3$, —C≡CH, —CH═CH$_2$, —(CH$_2$)$_n$-Q (wherein Q is selected from the group consisting of —F, —Cl, —Br, —I, —OH, and n is an integer from 1 to 5), and an aromatic, heteroaromatic or heterocyclic ring.

In another aspect, a compound or a pharmaceutically acceptable salt thereof, including all stereoisomers and enantiomers, is disclosed, wherein the compound is selected from the groups consisting of:

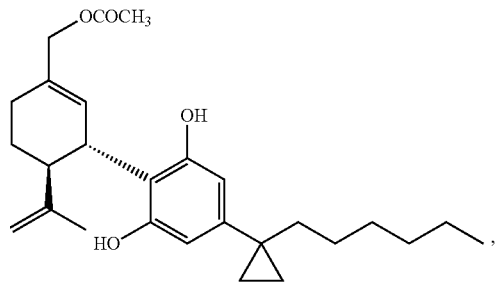

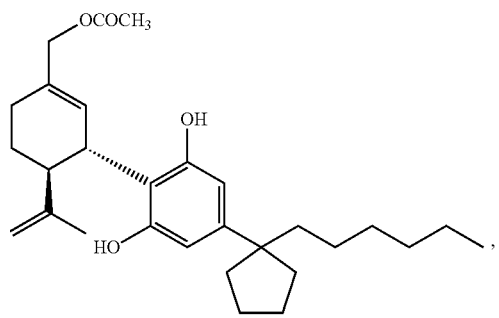

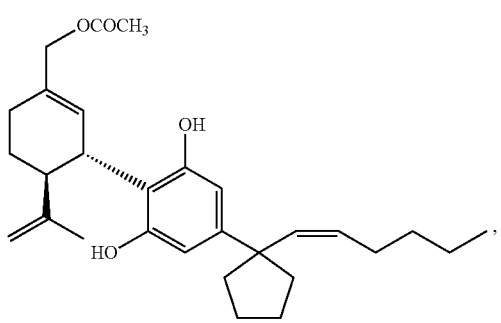

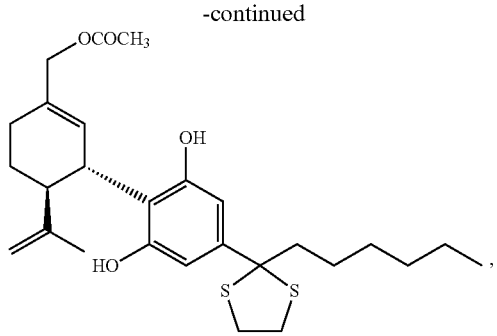
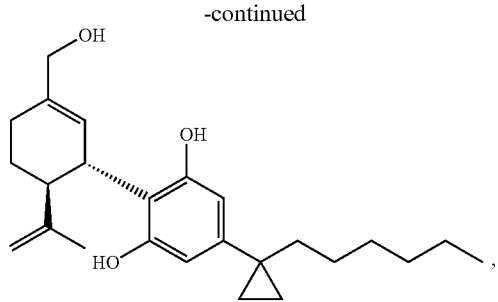
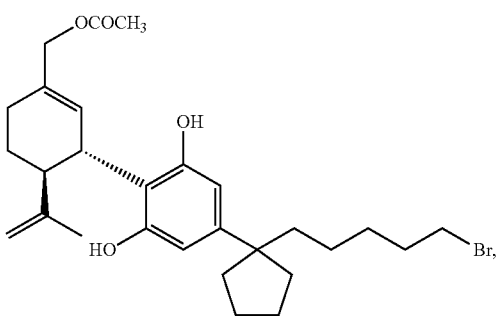
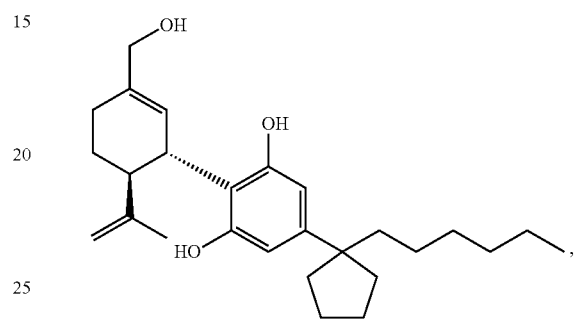
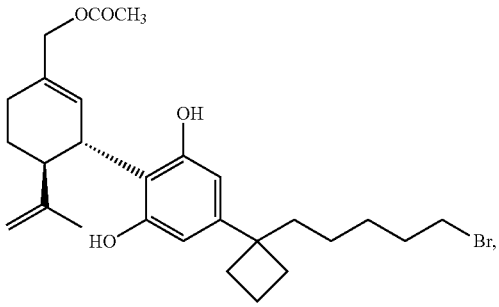
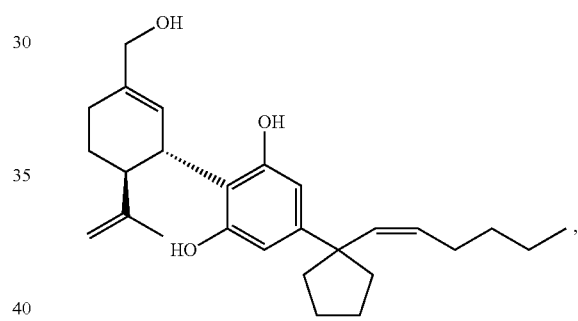
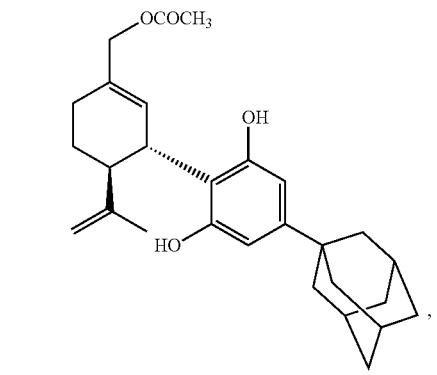
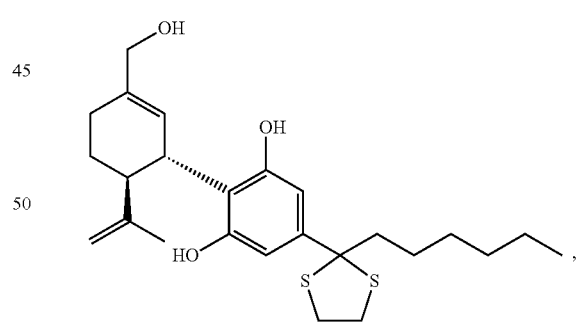
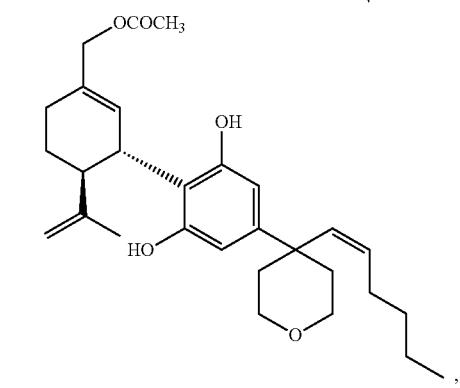
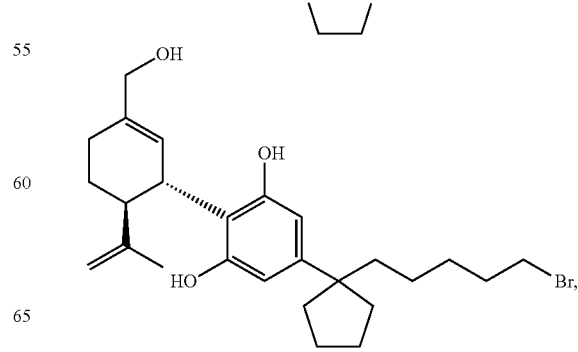

7
-continued

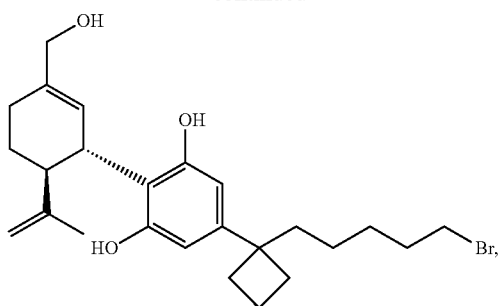

8
-continued

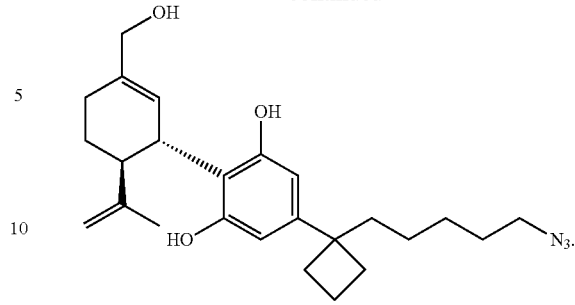

In another aspect, a compound of formula II or a pharmaceutically acceptable salt thereof, including all stereoisomers and enantiomers is disclosed:

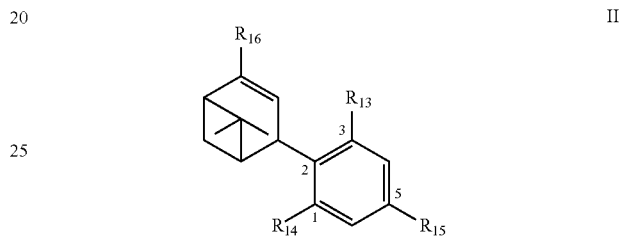

II wherein:
R$_{13}$ and R$_{14}$ are each independently selected from the group consisting of: —H, —F, —Cl, —Br, —I, —OH, —SH, —NH$_2$, —NO$_2$, —CN, —CF$_3$, —OC(O)CH$_3$, —C(O)CH$_3$, —C(O)CF$_3$, —O-alkyl, —OSi(alkyl)$_3$, —S-alkyl, —NH-alkyl, —N(alkyl)$_2$, —O—P(O)(OR)$_2$, —O—P(O)(OH)(OR) (wherein R is selected from the group consisting of H and alkyl), —P(O)(OR)$_2$, —P(O)(OH)(OR) (wherein R is selected from the group consisting of H and alkyl), —O-alkyl-COOR (wherein R is selected from the group consisting of H and alkyl), —O-alkyl-NR$_{17}$R$_{18}$, —O-alkyl-CONR$_{17}$R$_{18}$, —OC(O)—R (wherein R is selected from the group consisting of H and alkyl), —OC(O)—CH(OH)—CH$_2$OH, —OC(O)—C(CH$_2$OH)$_2$—CH$_3$, —OC(O)—CH$_2$OH, —OC(O)-alkyl-COOH, —OC(O)—CH=CHCOOH, —OC(O)-alkyl-NR$_{17}$R$_{18}$, —OC(O)-alkyl-C(O)NR$_{17}$R$_{18}$, —OC(O)—O-alkyl-NR$_{17}$R$_{18}$, and —OC(O)—CH(NH$_2$)—R$_8$ (wherein R$_8$ is selected from the group consisting of H, CH(OH)CH$_3$ and alkyl-X$_1$, and X$_1$ is selected from the group consisting of: H, —NH—C(=NH) NH$_2$, —C(O)NH$_2$, COOH, SH, SCH$_3$, OH, NH$_2$, and an aromatic, heteroaromatic or heterocyclic ring);
R$_{17}$ and R$_{18}$ are each independently selected from the group consisting of: H and alkyl, or R$_{17}$ and R$_{18}$ together comprise part of a 3 to 7 membered saturated heterocyclic ring containing up to one additional heteroatom selected from the group consisting of N, O and S;
R$_{15}$ is selected from the group consisting of: -cycloalkyl-R$_{19}$, -heterocyclic-R$_{19}$, adamantly, -adamantyl-R$_{19}$, and -heteroadamantyl-R$_{19}$;
R$_{19}$ is selected from the group consisting of: —(CH$_2$)$_t$—R$_{20}$, —(CH$_2$)$_t$-D-(CH$_2$)$_m$—R$_{20}$, and —(CH$_2$)$_t$-D-(CH$_2$)$_m$-G-R$_{20}$;
D and G are each independently selected from the group consisting of: —CH$_2$—CH$_2$—, —C≡C—, —CH=CH—, —S(O)—, —SO$_2$—, —SO$_2$NH—, —NHSO$_2$—, —SO$_2$O—, and —OSO$_2$—;

$R_{20}$ is selected from the group consisting of —H, —F, —Cl, —Br, —I, —OH, —SH, —NH$_2$, —CN, —N$_3$, —NCS, —NCO, —SO$_2$Cl, —SO$_2$F, —SO$_2$NH$_2$, —C(O)NH$_2$, —COOH, —NO$_2$, —CHO, —CF$_3$, —SO$_3$H, —O—P(O)(OH)$_2$, —Sn(alkyl)$_3$, —Si(alkyl)$_3$, —C≡CH, —CH=CH$_2$, and an aromatic, heteroaromatic or heterocyclic ring;

l is an integer from 0 to 8;

m is an integer from 0 to 8;

$R_{16}$ is selected from the group consisting of —H, -alkyl, —$R_{21}$, -alkyl-$R_{21}$, -alkyl-O-alkyl, -alkyl-O-alkyl-$R_{21}$, —C(O)O-alkyl, —OC(O)-alkyl, C$_{1-3}$alkyl-C(O)O-alkyl, and —C$_{1-3}$alkyl-OC(O)-alkyl; and $R_{21}$ is selected from the group consisting of: —F, —Cl, —Br, —I, —OH, —SH, —NH$_2$, —NH-alkyl, —N(alkyl)$_2$, —CN, —N$_3$, —NCS, —OC(O)CH$_3$, —C(O)OCH$_3$, —SO$_2$NH$_2$, —C(O)NH$_2$, —COOH, —NO$_2$, —CHO, —CF$_3$, —Sn(alkyl)$_3$, —Si(alkyl)$_3$, —C≡CH, —CH=CH$_2$, and an aromatic, heteroaromatic or heterocyclic ring.

In another aspect, a compound or a pharmaceutically acceptable salt thereof, including all stereoisomers and enantiomers, is disclosed, wherein the compound is selected from the groups consisting of:

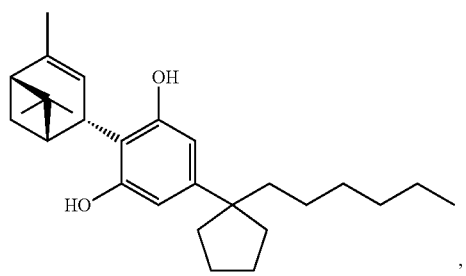

,

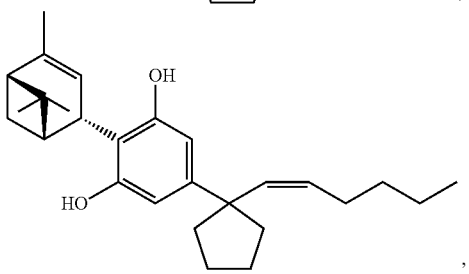

,

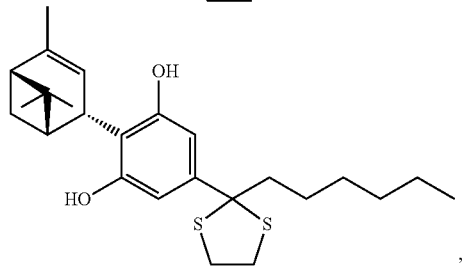

,

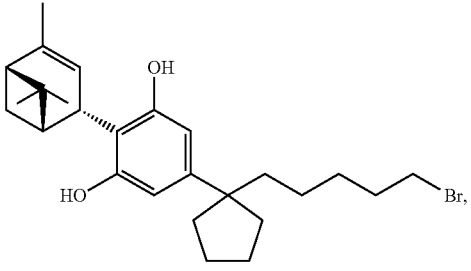

,

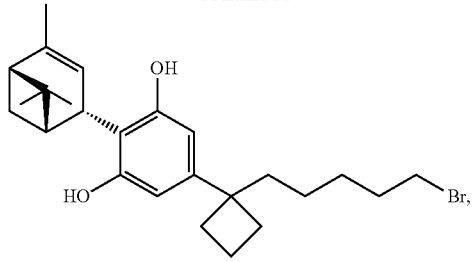

,

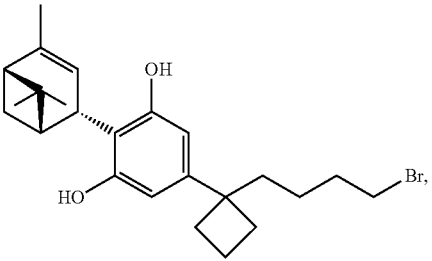

,

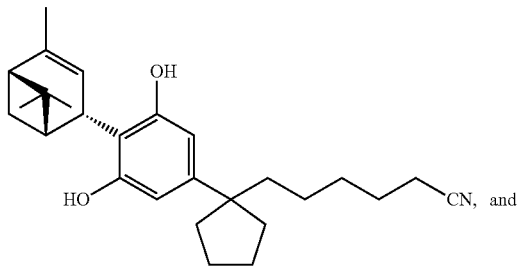

, and

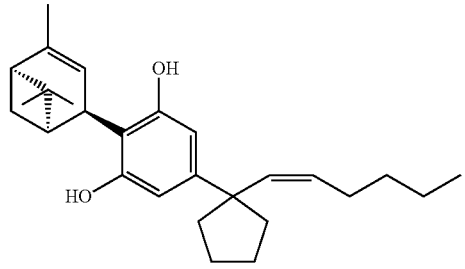

.

In another aspect, a compound of formula III below, and any pharmaceutically acceptable salts thereof including all stereoisomers and enantiomers is disclosed:

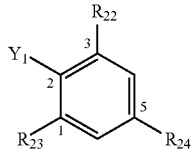

III wherein:

$R_{22}$ and $R_{23}$ are each independently selected from the group consisting of: —H, —F, —Cl, —Br, —I, —OH, —SH, —NH$_2$, —NO$_2$, —CN, —CF$_3$, —OC(O)CH$_3$, —C(O)CH$_3$, —C(O)CF$_3$, —O—P(O)(OR)$_2$ or —O—P(O)(OH)(OR) (wherein R is selected from H or alkyl), —P(O)(OR)$_2$ or —P(O)(OH)(OR) (wherein R is selected from H or alkyl), —OC(O)—R (wherein R is selected from H or alkyl), —OC(O)—CH(OH)—CH$_2$OH, —OC(O)—C(CH$_2$OH)$_2$—CH$_3$, —OC(O)—CH$_2$OH, —OC(O)-alkyl-COOH, —OC(O)—CH=CHCOOH, —OC(O)-alkyl-NR$_{25}$R$_{26}$, —OC(O)-alkyl-C(O)NR$_{25}$R$_{26}$, —OC(O)—O-alkyl-NR$_{25}$R$_{26}$, —OC(O)—CH(NH$_2$)—R$_8$ (wherein R$_8$ is selected from H, CH(OH)CH$_3$ or alkyl-X$_1$ and X$_1$ is selected from: H, —NH—C(=NH)NH$_2$, C(O)NH$_2$, COOH, SH, SCH$_3$, OH, NH$_2$, and an aromatic, heteroaromatic or heterocyclic ring);

R$_{25}$ and R$_{26}$ are each independently selected from the group consisting of: H, alkyl, or R$_{25}$ and R$_{26}$ together comprise part of a 3 to 7 membered saturated heterocyclic ring containing up to one additional heteroatom selected from N, O and S;

Y$_1$ is selected from:

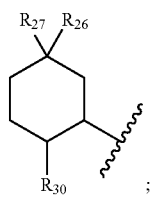

I1

R$_{27}$, R$_{28}$ taken together represent an oxygen or sulfur atom or an enol ether group (=O, =S, =CH—O-alkyl, respectively), or R$_{27}$, R$_{28}$ each independently is selected from: —R$_{31}$, —OC(O)-alkyl, C$_{1-3}$alkyl-C(O)O-alkyl, C$_{1-3}$alkyl-OC(O)-alkyl;

R$_{31}$ is selected from: —F, —Cl, —Br, —I, —OH, —SH, —NH$_2$, —NH-alkyl, —N(alkyl)$_2$, —CN, —N$_3$, —NCS, —OC(O)CH$_3$, —C(O)NH$_2$, —C(O)NR$_{36}$R$_{37}$, —SO$_2$NH$_2$, —COOH, —NO$_2$, —CHO, —CF$_3$, —Sn(alkyl)$_3$, —Si(alkyl)$_3$, —C≡CH, —CH=CH$_2$, and an aromatic, heteroaromatic or heterocyclic ring;

R$_{36}$ and R$_{37}$ are each independently selected from the group consisting of: H, alkyl, or R$_{36}$ and R$_{37}$ together comprise part of a 3 to 7 membered saturated heterocyclic ring containing up to one additional heteroatom selected from N, O and S;

R$_{30}$ is selected from —H, -alkyl, -alkyl-R$_{33}$, -alkenyl, -alkenyl-R$_{33}$, -alkynyl, -alkynyl-R$_{33}$;

R$_{33}$ is selected from —F, —Cl, —Br, —I, —OH, —SH, —NH$_2$, —NH-alkyl, —N(alkyl)$_2$, —CN, —N$_3$, —NCS, —OC(O)CH$_3$, —C(O)OCH$_3$, —SO$_2$NH$_2$, —C(O)NH$_2$, —COOH, —NO$_2$, —CHO, —CF$_3$, —Sn(alkyl)$_3$, —Si(alkyl)$_3$, —C≡CH, —CH=CH$_2$, —(CH$_2$)$_f$-L (wherein L is selected from —F, —Cl, —Br, —I, —OH and f is an integer from 1 to about 5), and an aromatic, heteroaromatic or heterocyclic ring;

R$_{24}$ is selected from -alkyl-R$_{34}$, -cycloalkyl-R$_{34}$, -heterocyclic-R$_{34}$, adamantyl, -adamantyl-R$_{34}$, -heteroadamantyl-R$_{34}$;

R$_{34}$ is selected from —(CH$_2$)$_p$—R$_{35}$, —(CH$_2$)$_p$—U—(CH$_2$)$_t$—R$_{35}$, —(CH$_2$)$_p$—U—(CH$_2$)$_t$—Z—R$_{35}$;

U and Z are each independently selected from: —CH$_2$—CH$_2$—, —C≡C—, —CH=CH—, —O—, —S—, —NH—, —C(O)—, —C(O)O—, —OC(O)—, —C(O)NH—, —NHC(O)—, —S(O)—, —SO$_2$—, —SO$_2$NH—, —NHSO$_2$—, —SO$_2$O— and —OSO$_2$—;

R$_{35}$ is selected from —H, —F, —Cl, —Br, —I, —OH, —SH, —NH$_2$, —CN, —N$_3$, —NCS, —NCO, —SO$_2$Cl, —SO$_2$F, —SO$_2$NH$_2$, —C(O)NH$_2$, —COOH, —NO$_2$, —CHO, —CF$_3$, —SO$_3$H, —O—P(O)(OH)$_2$, —Sn(alkyl)$_3$, —Si(alkyl)$_3$, —C≡CH, —CH=CH$_2$, and an aromatic, heteroaromatic or heterocyclic ring;

p is an integer from 0 to about 8; and t is an integer from 0 to about 8.

In another aspect, a compound or a pharmaceutically acceptable salt thereof, including all stereoisomers and enantiomers, is disclosed, wherein the compound is selected from the groups consisting of:

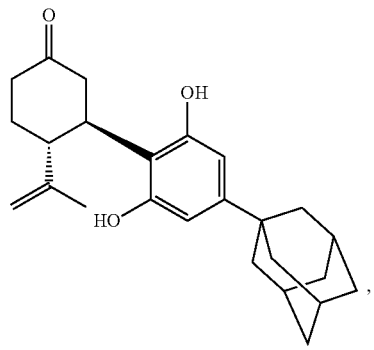,

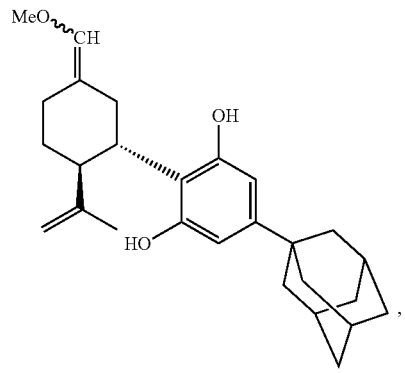,

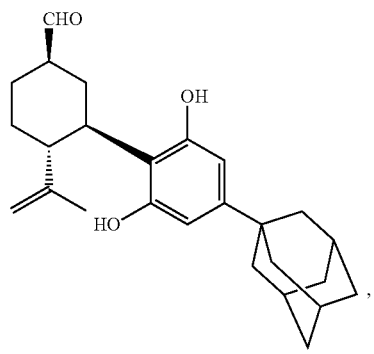,

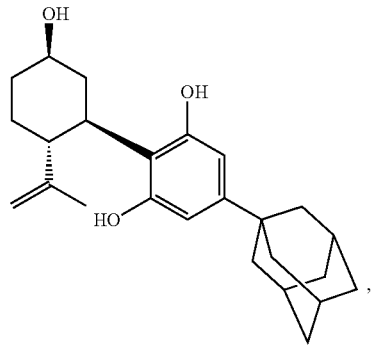,

-continued

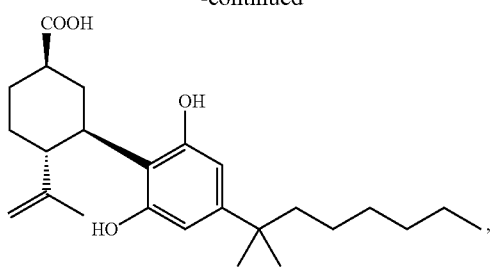

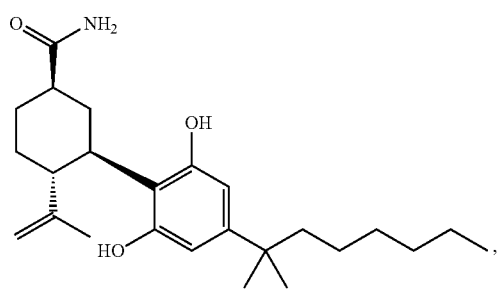

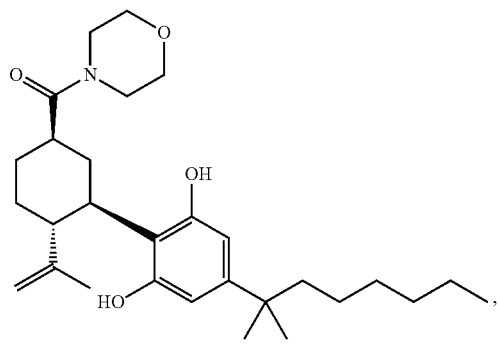

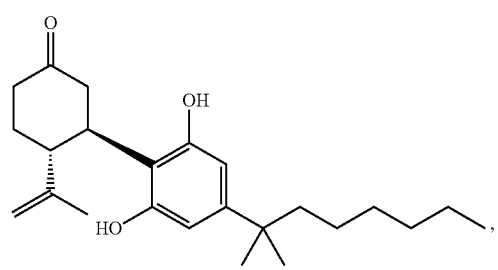

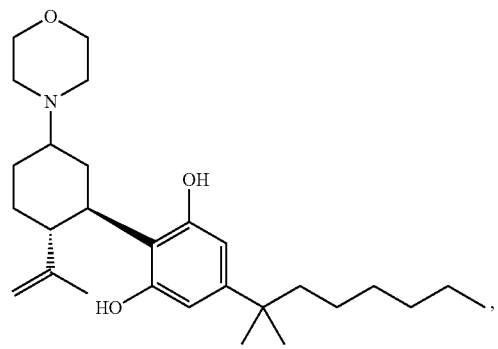

-continued

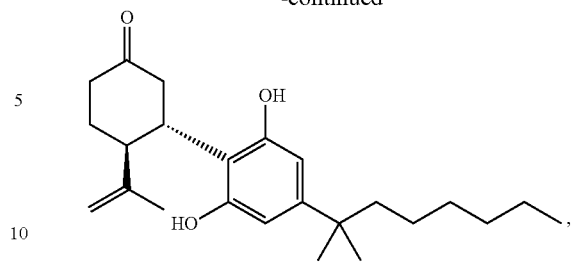

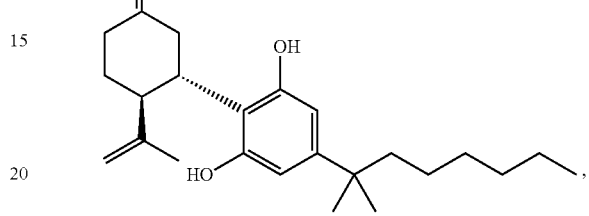

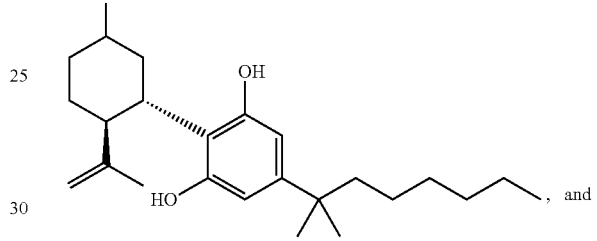

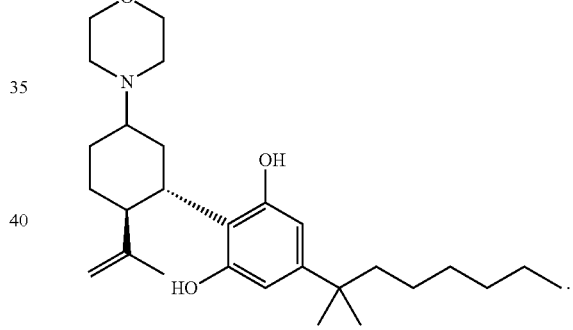

, and

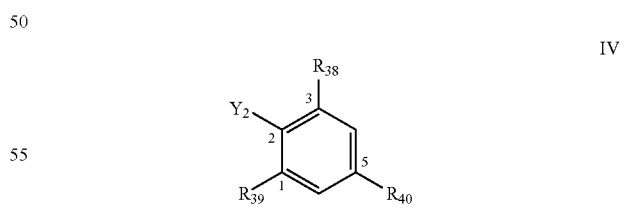

In another aspect, a compound of formula IV below, and any pharmaceutically acceptable salts thereof including all stereoisomers and enantiomers is disclosed:

$$\text{IV}$$

wherein:
$R_{38}$ and $R_{39}$ are each independently selected from the group consisting of: —H, —F, —Cl, —Br, —I, —OH, —SH, —NH$_2$, —NO$_2$, —CN, —CF$_3$, —OC(O)CH$_3$, —C(O)CH$_3$, —C(O)CF$_3$, —OSi(alkyl)$_3$, —O—P(O)(OR)$_2$ or —O—P(O)(OH)(OR) (wherein R is selected from H or alkyl), —P(O)(OR)$_2$ or —P(O)(OH)(OR) (wherein R is selected from H or alkyl), —OC(O)—R (wherein R is selected from H or alkyl), —OC(O)—CH(OH)—CH$_2$OH, —OC(O)—C (CH₂OH)₂—CH₃, —OC(O)—CH₂OH, —OC(O)-alkyl-COOH, —OC(O)—CH═CHCOOH, —OC(O)-alkyl-NR₄₁R₄₂, —OC(O)-alkyl-C(O)NR₄₁R₄₂, —OC(O)—O-alkyl-NR₄₁R₄₂, —OC(O)—CH(NH₂)—R₈ (wherein R₈ is selected from H, CH(OH)CH₃ or alkyl-X₁ and X₁ is selected from: H, —NH—C(═NH)NH₂, C(O)NH₂, COOH, SH, SCH₃, OH, NH₂, and an aromatic, heteroaromatic or heterocyclic ring);

R₄₁ and R₄₂ are each independently selected from the group consisting of: H, alkyl, or R₄₁ and R₄₂ together comprise part of a 3 to 7 membered saturated heterocyclic ring containing up to one additional heteroatom selected from N, O and S;

Y₂ is selected from:

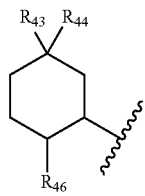

wherein:
R₄₃, R₄₄ taken together represent an oxygen or sulfur atom or an enol ether group (═O, ═S, ═CH—O-alkyl, respectively), or R₄₃, R₄₄ each independently is selected from: —H, -alkyl, —R₄₇, -alkyl-R₄₇, -alkyl-O-alkyl, -alkyl-O-alkyl-R₄₇, —C(O)O-alkyl, —OC(O)-alkyl, C₁₋₃alkyl-C(O)O— alkyl, C₁₋₃alkyl-OC(O)-alkyl;

R₄₇ is selected from: —F, —Cl, —Br, —I, —OH, —SH, —NH₂, —NH-alkyl, —N(alkyl)₂, —CN, —N₃, —NCS, —OC(O)CH₃, —C(O)OCH₃, —C(O)NH₂, —C(O)NR₃₆R₃₇, —SO₂NH₂, —COOH, —NO₂, —CHO, —CF₃, —Sn(alkyl)₃, —Si(alkyl)₃, —C≡CH, —CH═CH₂, and an aromatic, heteroaromatic or heterocyclic ring;

R₃₆ and R₃₇ are each independently selected from: H, alkyl, or R₃₆ and R₃₇ together comprise part of a 3 to 7 membered saturated heterocyclic ring containing up to one additional heteroatom selected from N, O and S;

R₄₆ is selected from —H, -alkyl, -alkyl-R₄₉, -alkenyl, -alkenyl-R₄₉, -alkynyl, -alkynyl-R₄₉;

R₄₉ is selected from: —F, —Cl, —Br, —I, —OH, —SH, —NH₂, —NH-alkyl, —N(alkyl)₂, —CN, —N₃, —NCS, —OC(O)CH₃, —C(O)OCH₃, —SO₂NH₂, —C(O)NH₂, —COOH, —NO₂, —CHO, —CF₃, —Sn(alkyl)₃, —Si(alkyl)₃, —C≡CH, —CH═CH₂, —(CH₂)ₙ-Q (wherein Q is selected from —F, —Cl, —Br, —I, —OH and n is an integer from 1 to about 5), and an aromatic, heteroaromatic or heterocyclic ring;

R₄₀ is selected from: -cycloalkyl-R₅₀, -heterocyclic-R₅₀, adamantyl, -adamantyl-R₅₀, -heteroadamantyl-R₅₀;

R₅₀ is selected from: —(CH₂)_q—R₅₁, —(CH₂)_q-M-(CH₂)_r—R₅₁, —(CH₂)_q-M-(CH₂)_r—V—R₅₀;

M and V are each independently selected from: —CH₂—CH₂—, —C≡C—, —CH═CH—, —O—, —S—, —NH—, —C(O)—, —C(O)O—, —OC(O)—, —C(O)NH—, —NHC(O)—, —S(O)—, —SO₂—, —SO₂NH—, —NHSO₂—, —SO₂O— and —OSO₂—;

R₅₁ is selected from —H, —F, —Cl, —Br, —I, —OH, —SH, —NH₂, —CN, —N₃, —NCS, —NCO, —SO₂Cl, —SO₂F, —SO₂NH₂, —C(O)NH₂, —COOH, —NO₂, —CHO, —CF₃, —SO₃H, —O—P(O)(OH)₂, —Sn(alkyl)₃, —Si(alkyl)₃, —C≡CH, —CH═CH₂, and an aromatic, heteroaromatic or heterocyclic ring;

q is an integer from 0 to about 8; and r is an integer from 0 to about 8.

In another aspect, a compound or a pharmaceutically acceptable salt thereof, including all stereoisomers and enantiomers, is disclosed, wherein the compound is selected from the groups consisting of:

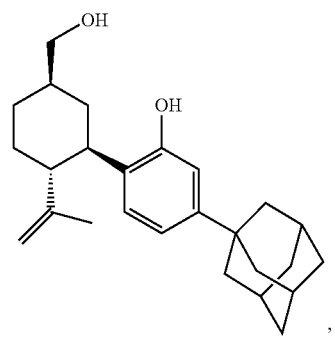

,

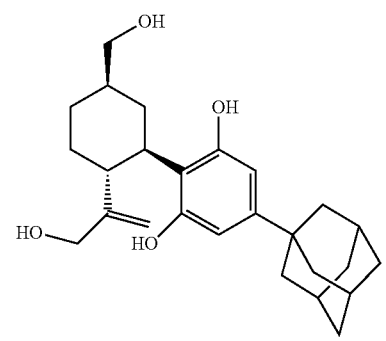

,

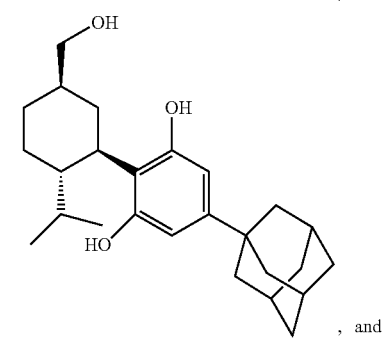

, and

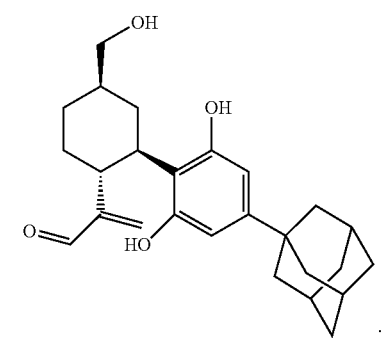

.

In another aspect, a compound of formula V or a pharmaceutically acceptable salt thereof, including all stereoisomers and enantiomers is disclosed:

V

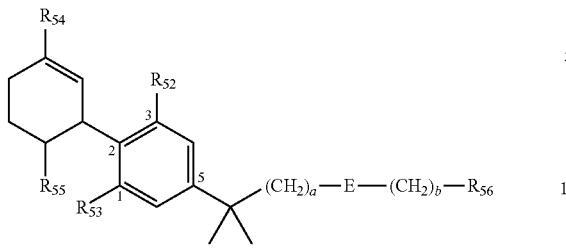

wherein:
R$_{52}$ and R$_{53}$ are each independently selected from the group consisting of: —H, —F, —Cl, —Br, —I, —OH, —SH, —NH$_2$, —NO$_2$, —CN, —CF$_3$, —OC(O)CH$_3$, —C(O)CH$_3$, —C(O)CF$_3$, —OSi(alkyl)$_3$, —O—P(O)(OR)$_2$, —O—P(O)(OH)(OR) (wherein R is selected from the group consisting of H and alkyl), —P(O)(OR)$_2$, —P(O)(OH)(OR) (wherein R is selected from the group consisting of H and alkyl), —OC(O)—R (wherein R is selected from the group consisting of H and alkyl), —OC(O)—CH(OH)—CH$_2$OH, —OC(O)—C(CH$_2$OH)$_2$—CH$_3$, —OC(O)—CH$_2$OH, —OC(O)-alkyl-COOH, —OC(O)—CH=CHCOOH, —OC(O)-alkyl-NR$_{57}$R$_{58}$, —OC(O)-alkyl-C(O)NR$_{57}$R$_{58}$, —OC(O)—O—alkyl-NR$_{57}$R$_{58}$, and —OC(O)—CH(NH$_2$)—R$_8$ (wherein R$_8$ is selected from the group consisting of H, CH(OH)CH$_3$ and alkyl-X$_1$, and X$_1$ is selected from the group consisting of: H, —NH—C(=NH)NH$_2$, C(O)NH$_2$, COOH, SH, SCH$_3$, OH, NH$_2$, and an aromatic, heteroaromatic or heterocyclic ring);
R$_{57}$ and R$_{58}$ are each independently selected from the group consisting of: H and alkyl, or R$_{57}$ and R$_{58}$ together comprise part of a 3 to 7 membered saturated heterocyclic ring containing up to one additional heteroatom selected from the group consisting of N, O and S;
R$_{54}$ is selected from the group consisting of: —OC(O)-alkyl, C$_{1-3}$alkyl-C(O)O-alkyl, and —C$_{1-3}$alkyl-OC(O)-alkyl;
R$_{55}$ is selected from the group consisting of —H, -alkyl and -alkyl-R$_{59}$;
R$_{59}$ is selected from the group consisting of: —F, —Cl, —Br, —I, —OH, —SH, —NH$_2$, —NH-alkyl, —N(alkyl)$_2$, —CN, —N$_3$, —NCS, —OC(O)CH$_3$, —C(O)OCH$_3$, —SO$_2$NH$_2$, —C(O)NH$_2$, —COOH, —NO$_2$, —CHO, —CF$_3$, —Sn(alkyl)$_3$, —Si(alkyl)$_3$, —C≡CH, —CH=CH$_2$, —(CH$_2$)$_n$-Q (wherein Q is selected from the group consisting of —F, —Cl, —Br, —I, and —OH and n is an integer from 1 to 5), and an aromatic, heteroaromatic or heterocyclic ring;
E is selected from the group consisting of: —CH$_2$—CH$_2$—, —C≡C—, —CH=CH—, —O—, —S—, —NH—, —C(O)—, —C(O)O—, —OC(O)—, —C(O)NH—, —NHC(O)—, —S(O)—, —SO$_2$—, —SO$_2$NH—, —NHSO$_2$—, —SO$_2$O— and —OSO$_2$—;
R$_{56}$ is selected from the group consisting of —H, —F, —Cl, —Br, —I, —OH, —SH, —NH$_2$, —CN, —N$_3$, —NCS, —NCO, —SO$_2$Cl, —SO$_2$F, —SO$_2$NH$_2$, —C(O)NH$_2$, —COOH, —NO$_2$, —CHO, —CF$_3$, —SO$_3$H, —O—P(O)(OH)$_2$, —Sn(alkyl)$_3$, —Si(alkyl)$_3$, —C≡CH, —CH=CH$_2$, and an aromatic, heteroaromatic or heterocyclic ring;
a is an integer from 0 to 8; and
b is an integer from 0 to 8.

In another aspect, a compound or a pharmaceutically acceptable salt thereof, including all stereoisomers and enantiomers, is disclosed, wherein the compound is selected from the groups consisting of:

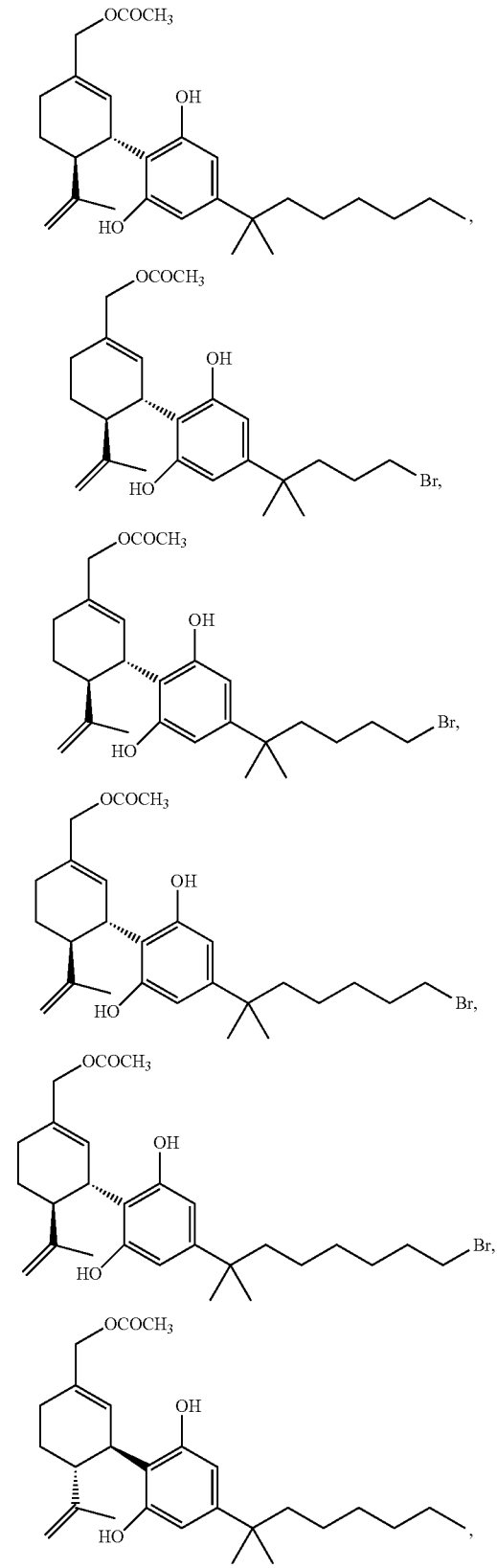

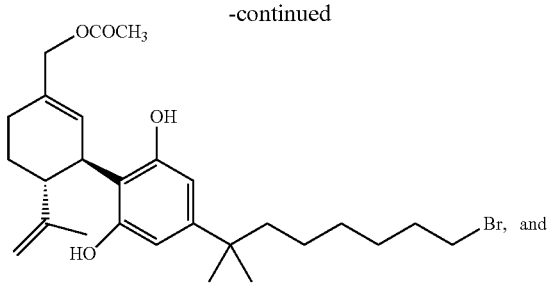

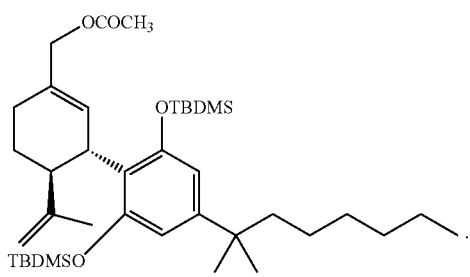

In another aspect, a compound of formula VI or a pharmaceutically acceptable salt thereof, including all stereoisomers and enantiomers is disclosed:

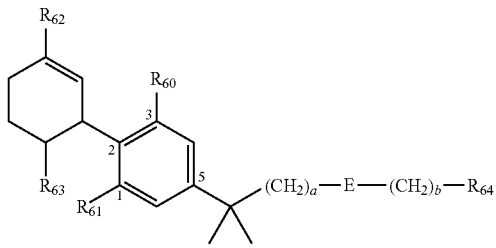

wherein:

$R_{60}$ and $R_{61}$ are each independently selected from the group consisting of: —OH and —O-alkyl;

$R_{62}$ is selected from the group consisting of —H, -alkyl, —$R_{65}$, and -alkyl-$R_{65}$;

$R_{65}$ is selected from the group consisting of: —F, —Cl, —Br, —I, —OH, —SH, —NH$_2$, —NH-alkyl, —N(alkyl)$_2$, —CN, —N$_3$, —NCS, —OC(O)CH$_3$, —C(O)OCH$_3$, —SO$_2$NH$_2$, —C(O)NH$_2$, —COOH, —NO$_2$, —CHO, —CF$_3$, —Sn(alkyl)$_3$, —Si(alkyl)$_3$, —C≡CH, —CH=CH$_2$, and an aromatic, heteroaromatic or heterocyclic ring;

$R_{63}$ is selected from the group consisting of —H, -alkyl, -alkenyl, and -alkynyl;

E is selected from the group consisting of: —CH$_2$—CH$_2$—, —C≡C—, and —CH=CH—;

$R_{64}$ is an aromatic, heteroaromatic or heterocyclic ring;

a is an integer from 0 to 8; and b is an integer from 0 to 8.

In another aspect, a compound or a pharmaceutically acceptable salt thereof, including all stereoisomers and enantiomers, is disclosed, wherein the compound is selected from the groups consisting of:

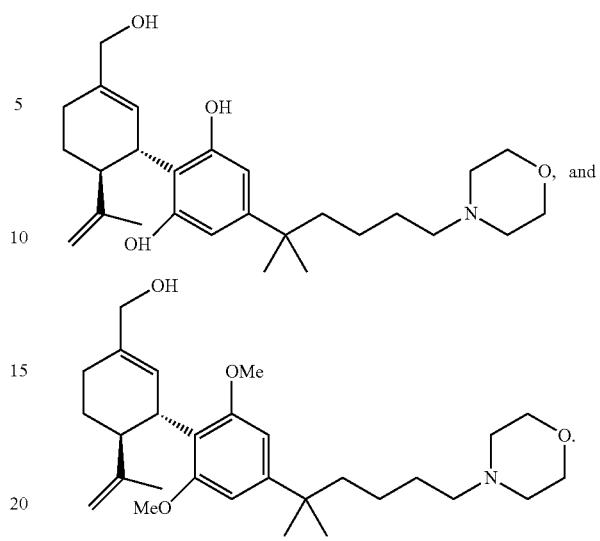

In another aspect, a pharmaceutical composition comprising a therapeutically effective amount of a compound of any preceding claim or a pharmaceutically acceptable salt thereof and a pharmaceutically acceptable carrier is disclosed.

In another aspect, method of treating a condition in a subject in need thereof is disclosed, the method comprising administering to the subject a therapeutically effective amount of a compound or pharmaceutically acceptable salt or a pharmaceutical composition disclosed herein; wherein the condition is selected from the group consisting of pain; central pain; peripheral pain; neuropathic pain; neuropathy; inflammatory pain; neurodegenerative diseases including multiple sclerosis, Parkinson's disease, Huntington's chorea, Alzheimer's disease and amyotrophic lateral sclerosis; mental disorders such as schizophrenia and depression; mood disorders; addiction disorders; memory disorders; gastrointestinal motility disorders such as irritable bowel syndrome and diarrhea; dyskinesia; migraine; osteoporosis, osteoarthritis; high blood pressure disease or hypertension; peripheral vascular disease; coronary artery disease; abnormal heart rate; cardiac insufficiency; pulmonary hypertension; ocular hypertension or glaucoma; endotoxic shock; hypotensive shock; appetite disorders; immune system disorders; fertility disorders; diseases associated with motor dysfunction such as Tourette's syndrome; inflammation; neurological disorders; epilepsy; nausea; AIDS wasting syndrome; cancer.

In another aspect, a method of stimulating a cannabinoid receptor in a subject is disclosed, the method comprising: administering to the subject an effective amount of a compound or pharmaceutically acceptable salt or a pharmaceutical composition disclosed herein.

In another aspect, a method of selectively stimulating a CB2 cannabinoid receptor in subject is disclosed, the method comprising: administering to the subject an effective amount of a compound or pharmaceutically acceptable salt or a pharmaceutical composition disclosed herein.

In another aspect, a method of selectively stimulating a cannabinoid receptor in the periphery of a subject is disclosed, the method comprising administering to the subject an effective amount of a compound or pharmaceutically acceptable salt or a pharmaceutical composition disclosed herein.

DETAILED DESCRIPTION

Unless otherwise defined, all technical and scientific terms used herein have the same meaning as commonly understood by one of ordinary skill in the art to which this invention belongs. Although methods and materials similar or equivalent to those described herein can be used in accordance with the present disclosure, suitable methods and materials are described below. All publications, patent applications, patents, and other references mentioned herein, including GenBank database sequences, are incorporated by reference in their entirety. In case of conflict, the present specification, including definitions, will control. In addition, the materials, methods, and examples are illustrative only and not intended to be limiting. Other features and advantages of the present disclosure will be apparent from the following detailed description, and from the claims.

A. Definitions

The compounds of this disclosure include any and all possible isomers, stereoisomers, enantiomers diastereomers, tautomers, pharmaceutically-acceptable salts, and solvates thereof. Thus, the terms "compound" and "compounds" as used in this disclosure refer to the compounds of this disclosure and any of all possible isomers, stereoisomers, enantiomers diastereomers, tautomers, pharmaceutically-acceptable salts, and solvates thereof.

The content of any publication cited herein is incorporated by reference.

Unless otherwise specifically defined, "acyl" refers to the general formula —C(O)alkyl.

Unless otherwise specifically defined, "alcohol" refers to the general formula alkyl-OH and includes primary, secondary and tertiary variations.

Unless otherwise specifically defined, "alkyl" refers to a linear or branched hydrocarbon radical which may be fully saturated, mono- or polyunsaturated and can include divalent radicals, having from 1 to about 15 carbon atoms if it is saturated, or from 2 to about 15 carbon atoms if it is unsaturated. Examples for saturated hydrocarbon radicals include, but are not limited to, groups such as methyl (Me), ethyl (Et), n-propyl, isopropyl, n-butyl, t-butyl, isobutyl, sec-butyl, homologs and isomers of, for example, n-pentyl, n-hexyl, n-heptyl, n-octyl, 1,1-dimethyl-heptyl, 1,2-dimethyl-heptyl, and the like. An unsaturated alkyl group includes one or more double bonds, triple bonds or combinations thereof. Examples of unsaturated alkyl groups include but are not limited to, vinyl, propenyl, isopropenyl, crotyl, 2-isopentenyl, allenyl, butenyl, butadienyl, pentenyl, pentadienyl, 3-(1,4-pentadienyl), hexenyl, hexadienyl, ethynyl, propynyl, butynyl, and higher homologs and isomers. The term "divalent alkyl radicals" unless otherwise specifically defined refers to the general formula: -alkyl-. The term "$C_{1-m}$-alkyl" refers to an alkyl having from 1 to about m carbon atoms.

Unless otherwise specifically defined, "alkenyl" refers to a linear or branched hydrocarbon radical which includes one or more double bonds and can include divalent radicals, having from 2 to about 15 carbon atoms. The term "divalent alkenyl radicals" unless otherwise specifically defined refers to the general formula: -alkenyl-. Examples of alkenyl groups include but are not limited to, vinyl, propenyl, isopropenyl, crotyl, 2-isopentenyl, allenyl, butenyl, butadienyl, pentenyl, pentadienyl, 3-(1,4-pentadienyl), hexenyl, hexadienyl, and higher homologs and isomers.

Unless otherwise specifically defined, "alkynyl" refers to a linear or branched hydrocarbon radical which includes one or more triple bonds and can include divalent radicals, having from 2 to about 15 carbon atoms. The term "divalent alkynyl radicals" unless otherwise specifically defined refers to the general formula: -alkynyl-. Examples of alkynyl groups include but are not limited to, ethynyl, propynyl, butynyl, and higher homologs and isomers.

Unless otherwise specifically defined, "alkoxy" refers to the general formula —O-alkyl.

Unless otherwise specifically defined, "alkylamino" refers to the general formula —(NH)-alkyl.

Unless otherwise specifically defined, "di-alkylamino" refers to the general formula —N-(alkyl)$_2$. Unless otherwise specifically limited di-alkylamino includes cyclic amine compounds such as piperidine and morpholine.

Unless otherwise specifically defined, "aroyl" refers to the general formula —C(O)-aryl.

Unless otherwise specifically defined, "aryl" or "aromatic ring" refers to a polyunsaturated, aromatic hydrocarbon, which can be a single ring or multiple rings (preferably from 1 to 3 rings) which are fused together or linked covalently and can include "divalent radicals". The term "divalent aryl radicals" unless otherwise specifically defined refers to the general formula: -aryl-. Examples of aryl groups include but are not limited to, phenyl, biphenyl, and naphthyl.

Unless otherwise specifically defined, "cycloalkyl" or "cycloalkyl ring" refers to a saturated or partially saturated ring structure having about 3 to about 8 ring members that has only carbon atoms as ring atoms and can include divalent radicals. The term "divalent cycloalkyl radicals" unless otherwise specifically defined refers to the general formula: -cycloalkyl-. Examples of cycloalkyl groups include but are not limited to, cyclopropyl, cyclobutyl, cyclopentyl, cyclohexyl, cyclohexene, cyclopentenyl, cyclohexenyl.

Unless otherwise specifically defined, "halogen" refers to an atom selected from fluorine, chlorine, bromine and iodine.

Unless otherwise specifically defined, "heterocyclic" or "heterocyclic ring" refers to a saturated ring structure having about 3 to about 8 ring members that has carbon atoms and one or more heteroatoms, including oxygen, nitrogen and/or sulfur, as ring atoms. The term "heterocyclic" or "heterocyclic ring" can include "divalent radicals". The term "divalent heterocyclic radicals" unless otherwise specifically defined refers to the general formula: -heterocyclic-. Examples of heterocyclic groups include but are not limited to, oxetane, thietane, azetidine, diazetidine, tetrahydrofuran, tetrahydropyran, thiolane, pyrrolidine, dioxolane, oxathiolane, imidazolidine, dioxane, piperidine, morpholine, piperazine, and their derivatives.

Unless otherwise specifically defined, "heteroaryl" or "heteroaromatic ring" refers to aryl groups (or rings) that contain one or more heteroatoms selected from oxygen, nitrogen and/or sulfur as ring atoms. Heteroaryl groups (or rings) also include fused polycyclic systems in which one or more monocyclic aryl or monocyclic heteroaryl group is fused to another heteroaryl group. "Heteroaryl" can include "divalent radicals", the term "divalent heteroaryl radicals" unless otherwise specifically defined refers to the general formula: -heteroaryl-. Examples of heteroaryl groups include but are not limited to, furanyl, thienyl, pyrrolyl, oxazolyl, thiazolyl, isoxazolyl, pyrazolyl, imidazolyl, oxadiazolyl, pyridinyl, pyrimidinyl, purinyl, benzoxazolyl, benzothiazolyl, benzimidazolyl, benzofuranyl, indolyl, quinolinyl, quinoxalinyl.

The phrase "pharmaceutically acceptable" is employed in this disclosure to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The terms "salt" and "salts", as employed in the disclosure, denotes acidic and/or basic salts formed with inorganic and/or organic acids and bases.

In certain embodiments, the disclosed compounds are isolated from a naturally occurring or synthetic material. In some embodiments, the isolated compound is contemporaneously or subsequently "purified" or "substantially purified". As used herein a "purified" or "substantially purified" compound means a compound that has been processed to a desired purity. A person of ordinary skill can establish the desired purity for a use and method to achieve that purity without undue effort. The purified compound may be used in any disclosed embodiment.

As used herein a "therapeutically effective amount" of a compound, is the quantity of a compound which, when administered to an individual or animal, results in a discernible physiological effect in the individual or animal. The compounds disclosed herein, and pharmaceutically acceptable salts thereof, have pharmacological properties when administered in therapeutically effective amounts for providing a physiological effect useful to treat a number of physiological conditions. Typically, a "therapeutically effective amount" of a compound is believed to range from about 5 mg/day to about 1,000 mg/day.

As used herein, an "individual" refers to a human. An "animal" refers to, for example, veterinary animals, such as dogs, cats, horses and the like, and farm animals, such as cows, pigs and the like.

As used in chemical formulas herein, when an integer is 0, the structural portion modified by that integer is absent and the adjacent subunits are directly connected.

The compositions of the disclosure may be alternately formulated to comprise, consist of, or consist essentially of, any appropriate components herein disclosed. The compositions of the disclosure may additionally, or alternatively, be formulated so as to be devoid, or substantially free, of any components, materials, ingredients, adjuvants or species used in the prior art compositions or that are otherwise not necessary to the achievement of the function and/or objectives of the present disclosure.

The compounds of the present disclosure may have unnatural ratios of atomic isotopes at one or more of their atoms. For example, the compounds may be labeled with isotopes, such as deuterium tritium carbon-11, carbon-14, iodine-123, iodine-125 or fluorine-18. The present disclosure encompasses all isotopic variations of the described compounds, whether radioactive or not.

The disclosed compounds, and pharmaceutically acceptable salts thereof may be used to prepare prodrugs. As used herein, the term "prodrug" refers to any derivative of the compounds of general formula I, II, III, IV, V and VI that are metabolized or otherwise converted into an active form upon introduction into the body of an individual or animal. Prodrugs are well known to those skilled in the art of pharmaceutical chemistry, and provide benefits such as increased adsorption and half-life. Those skilled in the art of drug delivery will readily appreciate that the pharmacokinetic properties of general formulas I, II, III, IV, V and VI may be controlled by an appropriate choice of moieties to produce prodrug derivatives.

One or more disclosed compounds, typically after purification, can be incorporated into a pharmaceutical composition or medicament. The disclosed compounds can be administered by a variety of known methods, including, for example, orally, rectally, or by parenteral routes (e.g., intramuscular, intravenous, subcutaneous, nasal or topical). The form in which the compounds are administered will be determined by the route of administration. Such forms include, but are not limited to, capsular and tablet formulations (for oral and rectal administration), liquid formulations (for oral, intravenous, intramuscular, subcutaneous, ocular, intranasal, inhalation-based and transdermal administration) and slow releasing microcarriers (for rectal, intramuscular or intravenous administration). The pharmaceutical composition or medicament can also contain a pharmaceutically acceptable vehicle, diluent, excipient or carrier and optional adjuvants, flavorings, colorants, wetting agents, emulsifying agents, pH buffering agents and preservatives. Some suitable pharmaceutically acceptable vehicles include, for example, saline, sterile water, Ringer's solution and isotonic sodium chloride solutions. The specific dosage level of active ingredient will depend upon a number of factors, including, for example, biological activity of the particular preparation, age, body weight, sex and general health of the individual being treated.

B. Embodiments

The present disclosure relates generally to chemical compounds with cannabinergic activity. These chemical compounds are specific ligands for the cannabinoid CB1 and CB2 receptors. The disclosure is more particularly concerned with new resorcinol derivatives that act on CB1 and CB2 cannabinoid receptors and use of these derivatives to cause a physiological response that is useful to treat a number of physiological conditions.

The present disclosure provides compounds that modulate cannabinoid receptors (for examples see Tables 1, 2, 3, 4, 5 and 6). In some embodiments the compounds can be new and structurally improved cannabinoid receptor ligands exhibiting enhanced binding affinities for the CB1 and/or CB2 receptors compared with known exogenous cannabinoids such as Cannabidiol (CBD) (CBD structure and its cannabinoid receptor binding affinities are shown on Table 1). In some embodiments the compounds comprise resorcinol derivatives bearing novel side chains at the C5 position as CB1 and/or CB2 receptor ligands. In some other embodiments the compounds comprise new and structurally modified monocyclic or bicyclic substituents at the C2 position of the resorcinol framework as CB1 and/or CB2 receptor ligands.

In one aspect, a compound of formula I or a pharmaceutically acceptable salt thereof, including all stereoisomers and enantiomers is disclosed:

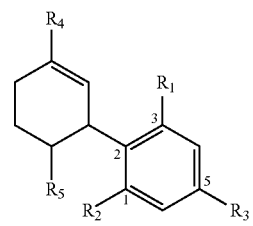

I wherein:

$R_1$ and $R_2$ are each independently selected from the group consisting of: —H, —F, —Cl, —Br, —I, —OH, —SH, —$NH_2$, —$NO_2$, —CN, —$CF_3$, —OC(O)$CH_3$, —C(O)$CH_3$, —C(O)$CF_3$, —O-alkyl, —OSi(alkyl)$_3$, —S-alkyl, —NH-alkyl, —N(alkyl)$_2$, —O—P(O)(OR)$_2$, —O—P(O)(OH)(OR) (wherein R is selected from the group consisting of H and alkyl), —P(O)(OR)$_2$, —P(O)(OH)(OR) (wherein R is selected from the group consisting of H and alkyl), —O-alkyl-COOR (wherein R is selected from the group consisting of H and alkyl), —O-alkyl-$NR_6R_7$, —O-alkyl-$CONR_6R_7$, —OC(O)—R (wherein R is selected from the group consisting of H and alkyl), —OC(O)—CH(OH)—$CH_2OH$, —OC(O)—C($CH_2OH$)$_2$—$CH_3$, —OC(O)—$CH_2OH$, —OC(O)-alkyl-COOH, —OC(O)—CH=CHCOOH, —OC(O)-alkyl-$NR_6R_7$, —OC(O)-alkyl-C(O)$NR_6R_7$, —OC(O)—O-alkyl-$NR_6R_7$, and —OC(O)—CH($NH_2$)—$R_8$ (wherein $R_8$ is selected from the group consisting of H, CH(OH)$CH_3$ and alkyl-$X_1$, and $X_1$ is selected from the group consisting of: —H, —NHC(=NH)$NH_2$, —C(O)$NH_2$, —COOH, —SH, —$SCH_3$, —OH, —$NH_2$, and an aromatic, heteroaromatic or heterocyclic ring);

$R_6$ and $R_7$ are each independently selected from the group consisting of: H and alkyl, or $R_6$ and $R_7$ together comprise part of a 3 to 7 membered saturated heterocyclic ring containing up to one additional heteroatom selected from the group consisting of N, O and S;

$R_3$ is selected from the group consisting of: -cycloalkyl-$R_9$, -heterocyclic-$R_9$, -adamantyl, -adamantyl-$R_9$, and -heteroadamantyl-$R_9$;

$R_9$ is selected from the group consisting of: —(CH$_2$)$_j$—$R_{10}$, —(CH$_2$)$_j$-A-(CH$_2$)$_k$—$R_{10}$, and —(CH$_2$)$_j$-A-(CH$_2$)$_k$—B—$R_{10}$;

A and B are each independently selected from the group consisting of: —$CH_2$—$CH_2$—, —C≡C—, —CH=CH—, —O—, —S—, —NH—, —C(O)—, —C(O)O—, —OC(O)—, —C(O)NH—, —NHC(O)—, —S(O)—, —$SO_2$—, —$SO_2$NH—, —$NHSO_2$—, —$SO_2$O— and —$OSO_2$—;

$R_{10}$ is selected from the group consisting of —H, —F, —Cl, —Br, —I, —OH, —SH, —$NH_2$, —CN, —$N_3$, —NCS, —NCO, —$SO_2$Cl, —$SO_2$F, —$SO_2NH_2$, —C(O)$NH_2$, —COOH, —$NO_2$, —CHO, —$CF_3$, —$SO_3H$, —O—P(O)(OH)$_2$, —Sn(alkyl)$_3$, —Si(alkyl)$_3$, —C≡CH, —CH=$CH_2$, and an aromatic, heterocyclic or heteroaromatic ring;

j is an integer from 0 to 8;
k is an integer from 0 to 8;

$R_4$ is selected from the group consisting of —H, —$R_{11}$, -alkyl-$R_{11}$, -alkyl-O-alkyl, -alkyl-O-alkyl-$R_{11}$, —C(O)O-alkyl, —OC(O)-alkyl, $C_{1-3}$alkyl-C(O)O-alkyl, and —$C_{1-3}$alkyl-OC(O)-alkyl;

$R_{11}$ is selected from the group consisting of: —F, —Cl, —Br, —I, —OH, —SH, —$NH_2$, —NH-alkyl, —N(alkyl)$_2$, —CN, —$N_3$, —NCS, —OC(O)$CH_3$, —C(O)O$CH_3$, —$SO_2NH_2$, —C(O)$NH_2$, —COOH, —$NO_2$, —CHO, —$CF_3$, —Sn(alkyl)$_3$, —Si(alkyl)$_3$, —C≡CH, —CH=$CH_2$, and an aromatic, heteroaromatic or heterocyclic ring;

$R_5$ is selected from the group consisting of —H, -alkyl, -alkyl-$R_{12}$, -alkenyl, -alkenyl-$R_{12}$, -alkynyl and -alkynyl-$R_{12}$; and $R_{12}$ is selected from the group consisting of: —F, —Cl, —Br, —I, —OH, —SH, —$NH_2$, —NH-alkyl, —N(alkyl)$_2$, —CN, —$N_3$, —NCS, —OC(O)$CH_3$, —C(O)O$CH_3$, —$SO_2NH_2$, —C(O)$NH_2$, —COOH, —$NO_2$, —CHO, —$CF_3$, —Sn(alkyl)$_3$, —Si(alkyl)$_3$, —C≡CH, —CH=$CH_2$, —(CH$_2$)$_n$-Q (wherein Q is selected from the group consisting of —F, —Cl, —Br, —I, —OH, and n is an integer from 1 to 5), and an aromatic, heteroaromatic or heterocyclic ring.

In some embodiments, each of $R_1$ and $R_2$ are independently selected from the group consisting of —H, —SH, —$NH_2$, —OH, —O-alkyl, —OSi(alkyl)$_3$, —OC(O)$CH_3$, and —O-alkyl-COOR (wherein R is selected from the group consisting of H and alkyl). In further embodiments, $R_1$ and $R_2$ are —OH.

In some embodiments, $R_3$ is selected from the group consisting of -cycloalkyl-$R_9$, -heterocyclic-$R_9$ and -adamantyl. In further embodiments, $R_3$ is selected from the group consisting of -cycloalkyl-$R_9$ and -heterocyclic-$R_9$, and $R_9$ is selected from the group consisting of —(CH$_2$)$_j$-A-(CH$_2$)$_k$—$R_{10}$ and —(CH$_2$)$_j$-A-(CH$_2$)$_k$—B—$R_{10}$.

In some embodiments, $R_9$ is —(CH$_2$)$_j$-A-(CH$_2$)$_k$—$R_{10}$. In further embodiments, $R_9$ is —(CH$_2$)$_j$-A-(CH$_2$)$_k$—B—$R_{10}$.

In some embodiments, A is selected from the group consisting of —$CH_2$—$CH_2$—, —CH=CH—, —C≡C—, —O—, —S—, —NH—, —C(O)—, —C(O)O—, —C(O)NH— and —NHC(O)—. In further embodiments, A is selected from the group consisting of —$CH_2$—$CH_2$— and —CH=CH—.

In some embodiments, each of A and B are independently selected from the group consisting of —$CH_2$—$CH_2$—, —CH=CH—, —C≡C—, —O—, —S—, —NH—, —C(O)—, —C(O)O—, —C(O)NH— and —NHC(O)—. In further embodiments, each of A and B are independently selected from the group consisting of —$CH_2$—$CH_2$— and —CH=CH—.

In some embodiments, $R_{10}$ is selected from the group consisting of —H, —F, —Cl, —Br, —I, —OH, —SH, —$NH_2$, —CN, and —$N_3$.

In some embodiments, j is selected from the group consisting of 0, 5 and 6.

In some embodiments, k is selected from the group consisting of 1 and 3.

In some embodiments, $R_4$ is selected from the group consisting of -alkyl-$R_{11}$ and —C(O)O-alkyl.

In some embodiments, $R_{11}$ is —OH.

In some embodiments, $R_5$ is -alkenyl.

In some embodiments, the compound is selected from the group consisting of:

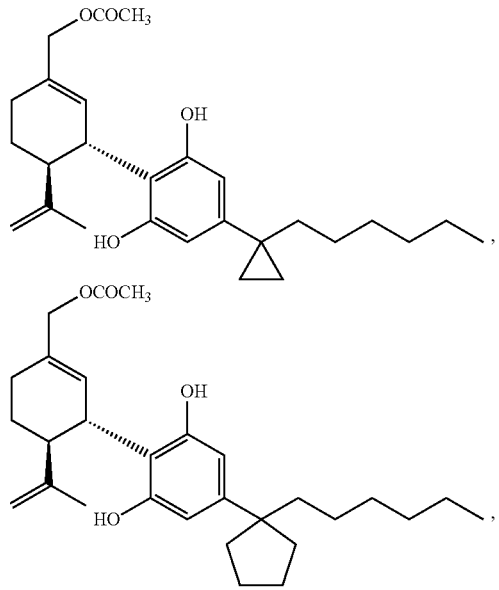

27
-continued
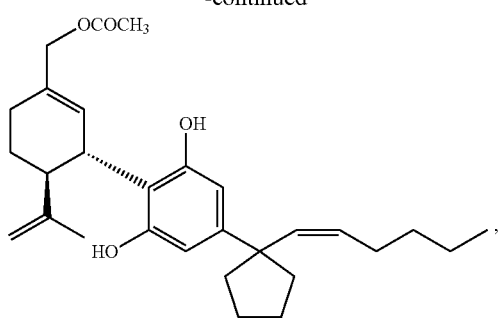
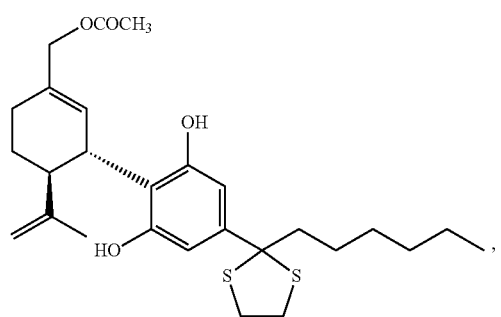
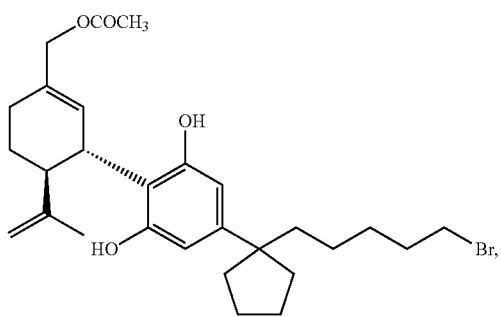
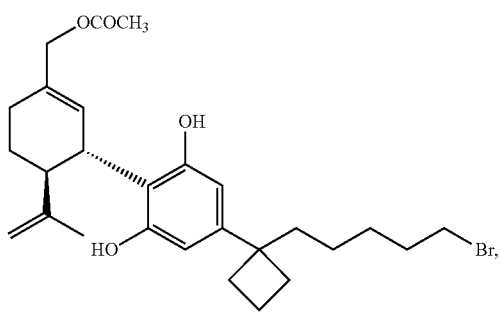
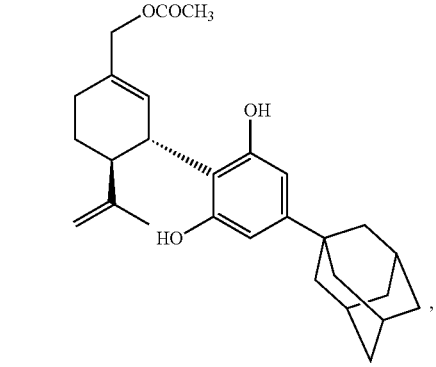
28
-continued
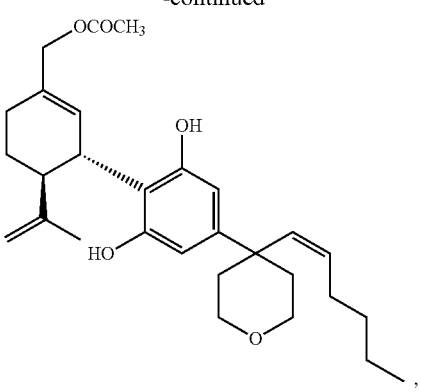
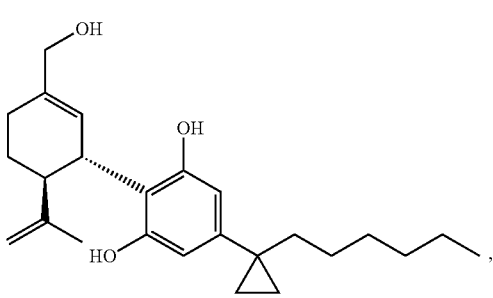
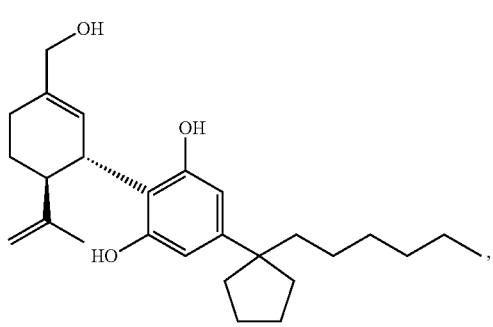
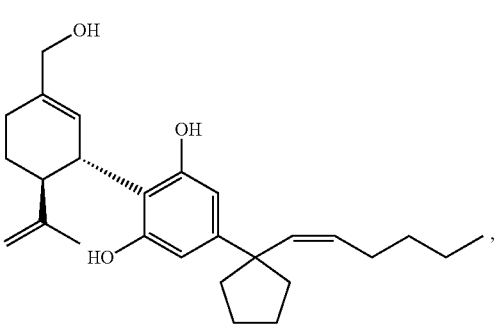
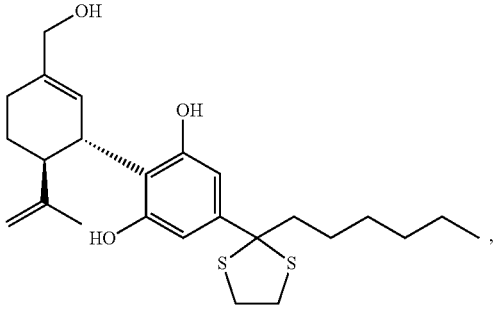

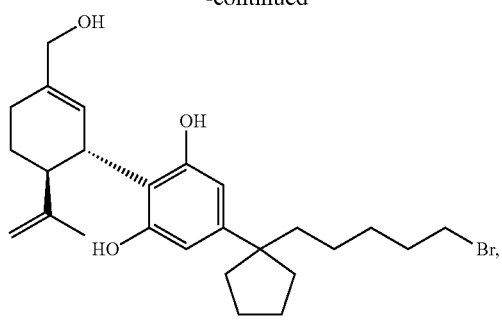
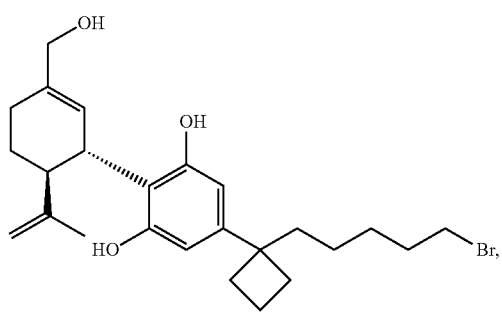
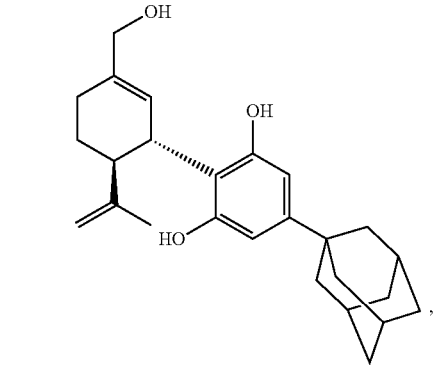
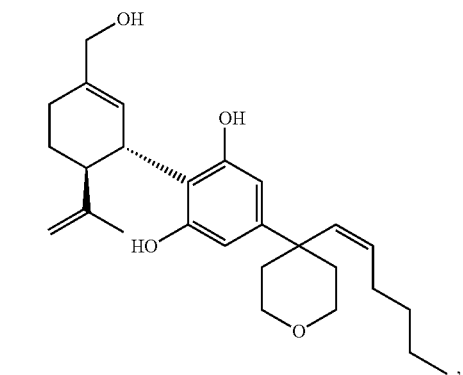
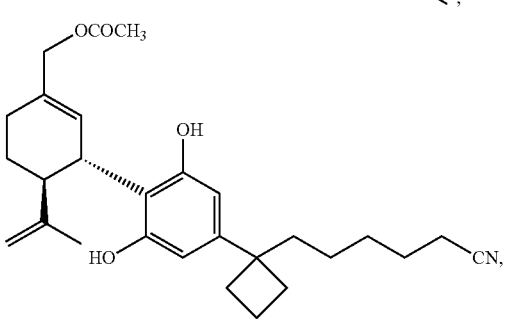
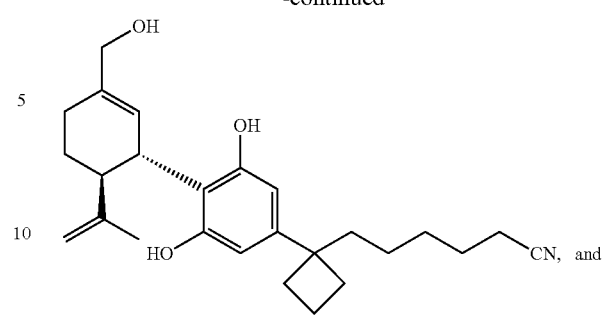
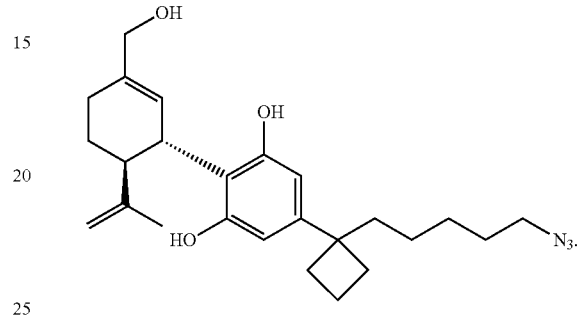
In another aspect, a compound or a pharmaceutically acceptable salt thereof, including all stereoisomers and enantiomers, is disclosed, wherein the compound is selected from the group consisting of:
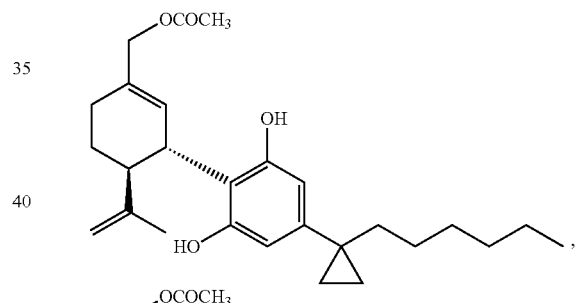
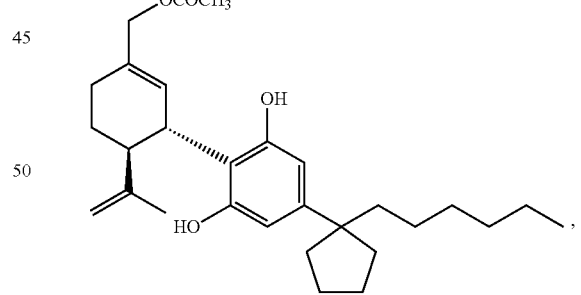
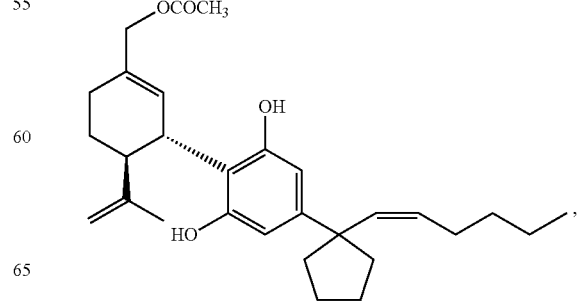

31
-continued
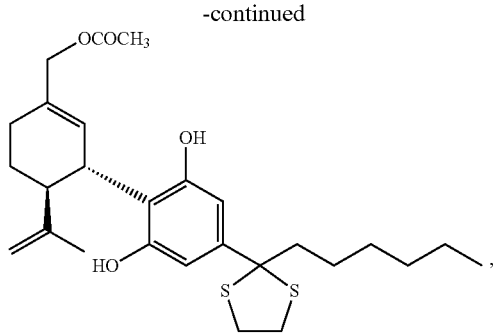
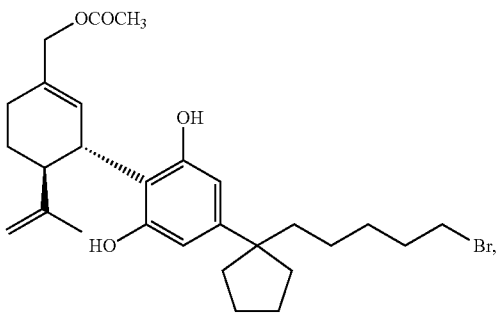
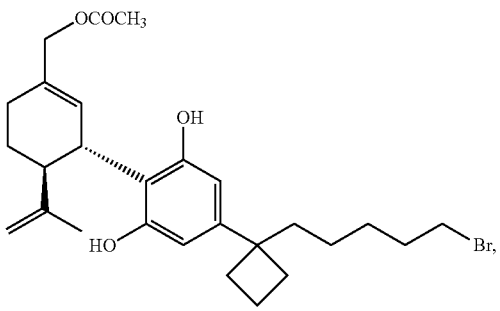
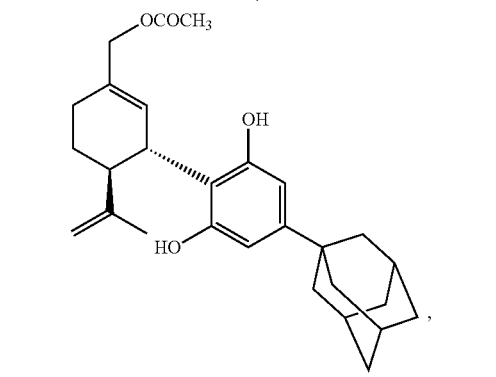
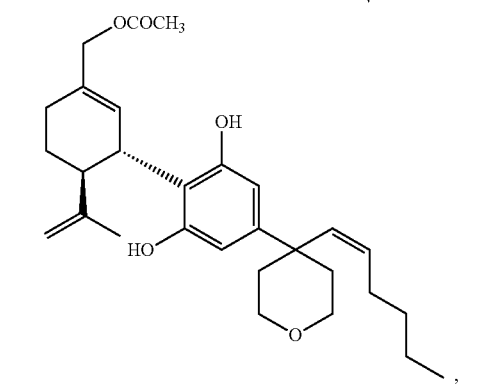
32
-continued
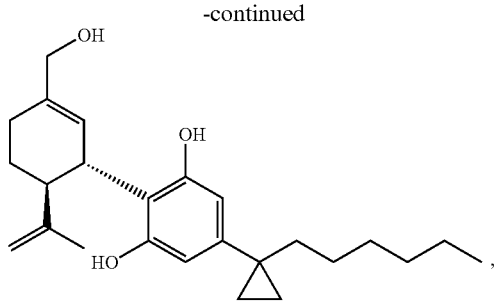
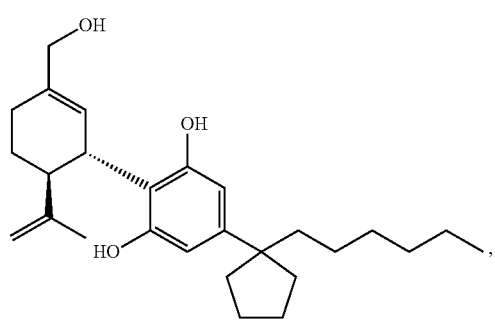
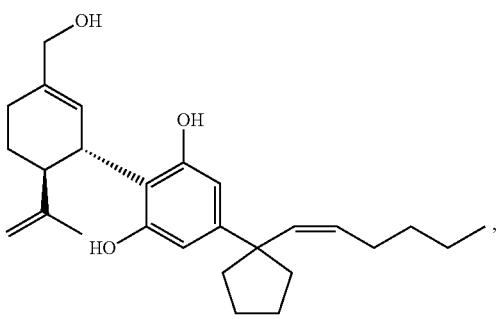
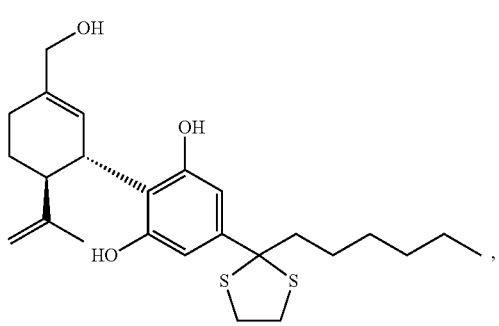
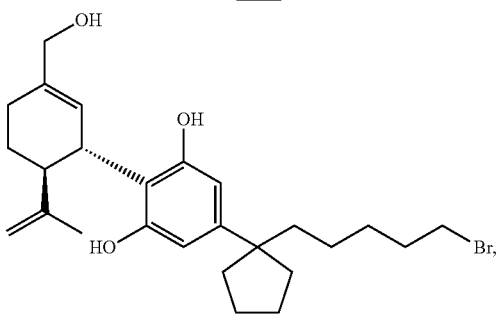

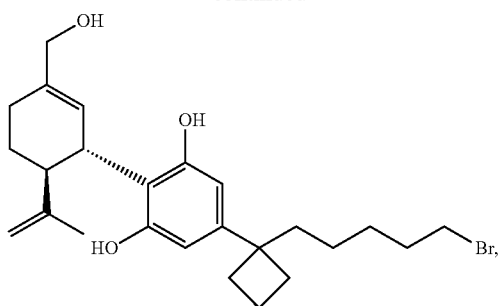

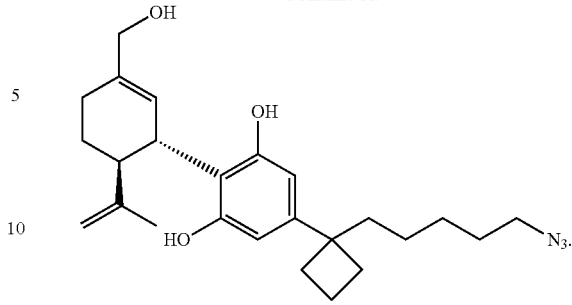

In another aspect, a compound of formula II or a pharmaceutically acceptable salt thereof, including all stereoisomers and enantiomers is disclosed:

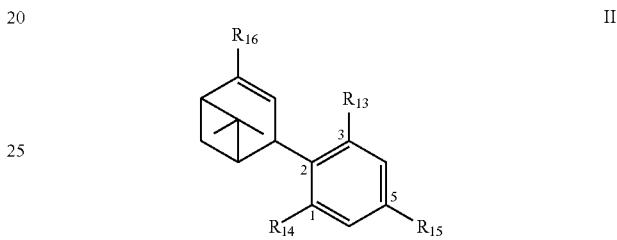

wherein:
R$_{13}$ and R$_{14}$ are each independently selected from the group consisting of: —H, —F, —Cl, —Br, —I, —OH, —SH, —NH$_2$, —NO$_2$, —CN, —CF$_3$, —OC(O)CH$_3$, —C(O)CH$_3$, —C(O)CF$_3$, —O-alkyl, —OSi(alkyl)$_3$, —S-alkyl, —NH-alkyl, —N(alkyl)$_2$, —O—P(O)(OR)$_2$, —O—P(O)(OH)(OR) (wherein R is selected from the group consisting of H and alkyl), —P(O)(OR)$_2$, —P(O)(OH)(OR) (wherein R is selected from the group consisting of H and alkyl), —O-alkyl-COOR (wherein R is selected from the group consisting of H and alkyl), —O-alkyl-NR$_{17}$R$_{18}$, —O-alkyl-CONR$_{17}$R$_{18}$, —OC(O)—R (wherein R is selected from the group consisting of H and alkyl), —OC(O)—CH(OH)—CH$_2$OH, —OC(O)—C(CH$_2$OH)$_2$—CH$_3$, —OC(O)—CH$_2$OH, —OC(O)—alkyl-COOH, —OC(O)—CH=CHCOOH, —OC(O)-alkyl-NR$_{17}$R$_{18}$, —OC(O)-alkyl-C(O)NR$_{17}$R$_{18}$, —OC(O)—O-alkyl-NR$_{17}$R$_{18}$, and —OC(O)—CH(NH$_2$)—R$_8$ (wherein R$_8$ is selected from the group consisting of H, CH(OH)CH$_3$ and alkyl-X$_1$, and X$_1$ is selected from the group consisting of: H, —NH—C(=NH) NH$_2$, —C(O)NH$_2$, COOH, SH, SCH$_3$, OH, NH$_2$, and an aromatic, heteroaromatic or heterocyclic ring);
R$_{17}$ and R$_{18}$ are each independently selected from the group consisting of: H and alkyl, or R$_{17}$ and R$_{18}$ together comprise part of a 3 to 7 membered saturated heterocyclic ring containing up to one additional heteroatom selected from the group consisting of N, O and S;
R$_{15}$ is selected from the group consisting of: -cycloalkyl-R$_{19}$, -heterocyclic-R$_{19}$, adamantly, -adamantyl-R$_{19}$, and -heteroadamantyl-R$_{19}$;
R$_{19}$ is selected from the group consisting of: —(CH$_2$)$_l$—R$_{20}$, —(CH$_2$)$_l$-D-(CH$_2$)$_m$—R$_{20}$, and —(CH$_2$)$_l$-D-(CH$_2$)$_m$-G-R$_{20}$;
D and G are each independently selected from the group consisting of: —CH$_2$—CH$_2$—, —C≡C—, —CH=CH—, —S(O)—, —SO$_2$—, —SO$_2$NH—, —NHSO$_2$—, —SO$_2$O—, and —OSO$_2$—;

$R_{20}$ is selected from the group consisting of —H, —F, —Cl, —Br, —I, —OH, —SH, —NH$_2$, —CN, —N$_3$, —NCS, —NCO, —SO$_2$Cl, —SO$_2$F, —SO$_2$NH$_2$, —C(O)NH$_2$, —COOH, —NO$_2$, —CHO, —CF$_3$, —SO$_3$H, —O—P(O)(OH)$_2$, —Sn(alkyl)$_3$, —Si(alkyl)$_3$, —C≡CH, —CH=CH$_2$, and an aromatic, heteroaromatic or heterocyclic ring;

l is an integer from 0 to 8;

m is an integer from 0 to 8;

$R_{16}$ is selected from the group consisting of —H, -alkyl, —R$_{21}$, -alkyl-R$_{21}$, -alkyl-O-alkyl, -alkyl-O-alkyl-R$_{21}$, —C(O)O-alkyl, —OC(O)-alkyl, C$_{1-3}$alkyl-C(O)O-alkyl, and —C$_{1-3}$alkyl-OC(O)-alkyl; and $R_{21}$ is selected from the group consisting of: —F, —Cl, —Br, —I, —OH, —SH, —NH$_2$, —NH-alkyl, —N(alkyl)$_2$, —CN, —N$_3$, —NCS, —OC(O)CH$_3$, —C(O)OCH$_3$, —SO$_2$NH$_2$, —C(O)NH$_2$, —COOH, —NO$_2$, —CHO, —CF$_3$, —Sn(alkyl)$_3$, —Si(alkyl)$_3$, —C≡CH, —CH=CH$_2$, and an aromatic, heteroaromatic or heterocyclic ring.

In some embodiments, $R_{15}$ is selected from the group consisting of: -cycloalkyl-R$_{19}$, adamantly, -adamantyl-R$_{19}$, and -heteroadamantyl-R$_{19}$.

In some embodiments, $R_{19}$ is selected from the group consisting of: —(CH$_2$)$_l$-D-(CH$_2$)$_m$—R$_{20}$, and —(CH$_2$)$_l$-D-(CH$_2$)$_m$-G-R$_{20}$.

In some embodiments, each of $R_{13}$ and $R_{14}$ are independently selected from the group consisting of —H, —SH, —NH$_2$, —OH, —O-alkyl, —OSi(alkyl)$_3$, —OC(O)R (wherein R is selected from the group consisting of H and alkyl), and —O-alkyl-COOR (wherein R is selected from the group consisting of H and alkyl).

In some embodiments, $R_{13}$ and $R_{14}$ are —OH.

In some embodiments, $R_{15}$ is selected from the group consisting of -cycloalkyl-R$_{19}$, -heterocyclic-R$_{19}$ and -adamantyl. In further embodiments, $R_{15}$ is selected from the group consisting of -cycloalkyl-R$_{19}$ and -heterocyclic-R$_{19}$, and $R_{19}$ is selected from the group consisting of —(CH$_2$)-D-(CH$_2$)$_m$—R$_{20}$ and —(CH$_2$)$_l$-D-(CH$_2$)$_m$-G-R$_{20}$.

In some embodiments, $R_{19}$ is —(CH$_2$)$_l$-D-(CH$_2$)$_m$—R$_{20}$. In further embodiments, $R_{19}$ is —(CH$_2$)$_l$-D-(CH$_2$)$_m$-G-R$_{20}$.

In some embodiments, D is selected from the group consisting of —CH$_2$—CH$_2$—, —CH=CH—, and —C≡C—. In further embodiments, D is selected from the group consisting of —CH$_2$—CH$_2$— and —CH=CH—.

In some embodiments, each of D and G are independently selected from the group consisting of —CH$_2$—CH$_2$—, —CH=CH—, and —C≡C—. In further embodiments, each of A and B are independently selected from the group consisting of —CH$_2$—CH$_2$— and —CH=CH—.

In some embodiments, $R_{20}$ is selected from the group consisting of —H, —F, —Cl, —Br, —I, —OH, —SH, —NH$_2$, —CN, and —N$_3$.

In some embodiments, l is selected from the group consisting of 0, 5 and 6.

In some embodiments, m is selected from the group consisting of 1 and 3.

In some embodiments, $R_{16}$ is selected from the group consisting of -alkyl-R$_{21}$ and —C(O)O-alkyl.

In some embodiments, $R_{21}$ is —OH.

In some embodiments, the compound is selected from the group consisting of:

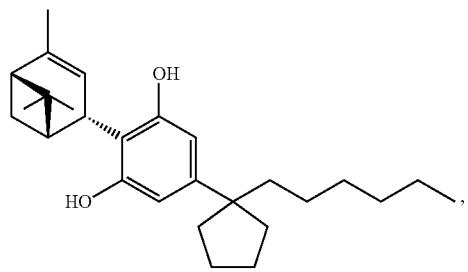

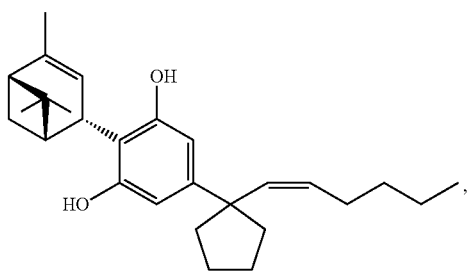

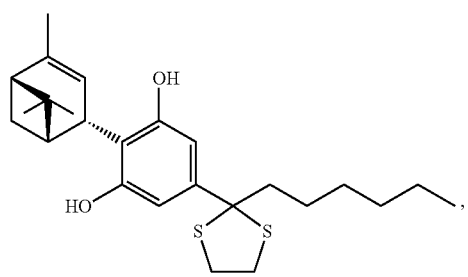

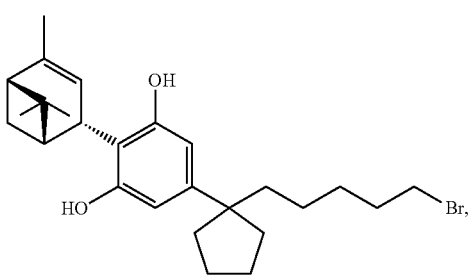

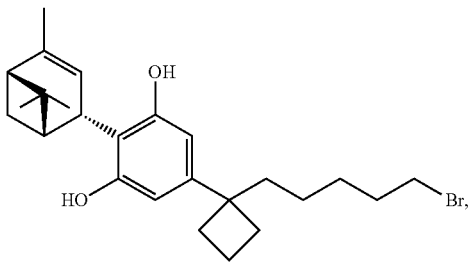

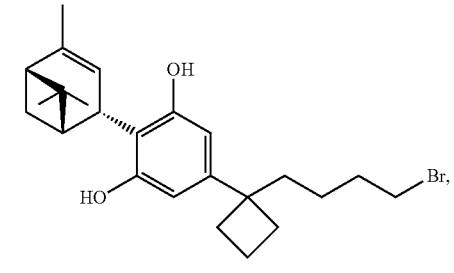

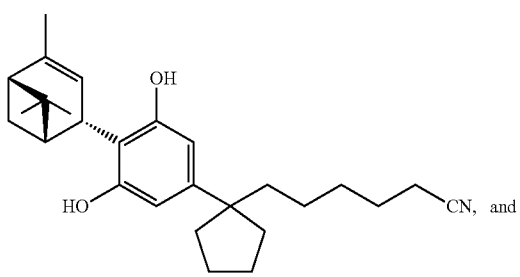

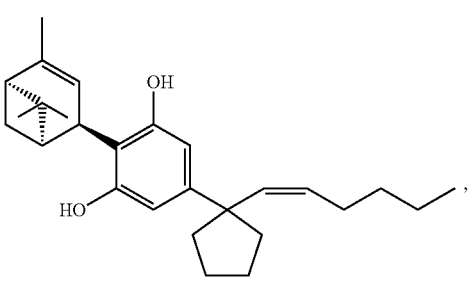

In another aspect, a compound or a pharmaceutically acceptable salt thereof, including all stereoisomers and enantiomers, is disclosed, wherein the compound is selected from the groups consisting of:

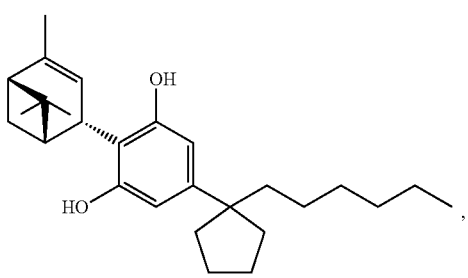

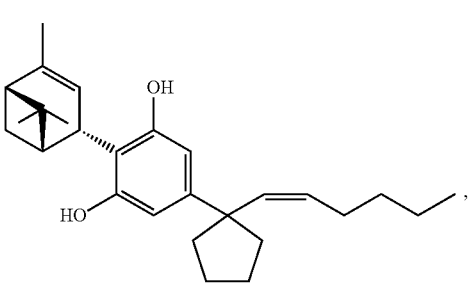

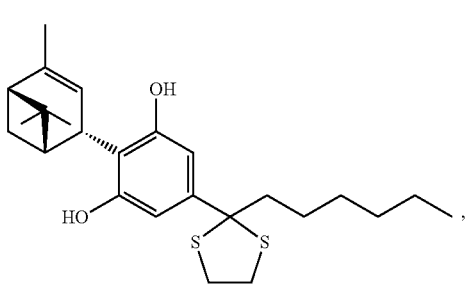

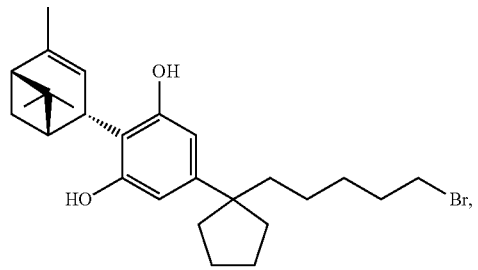

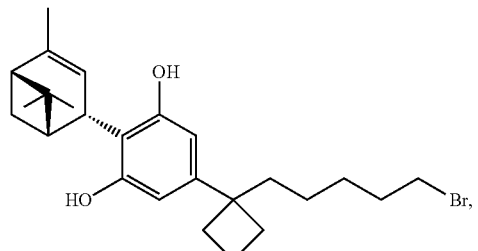

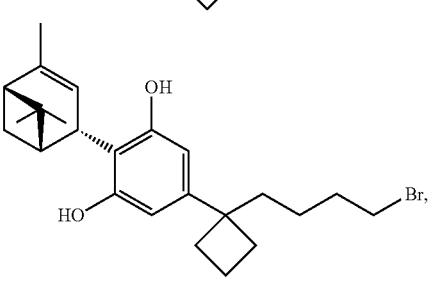

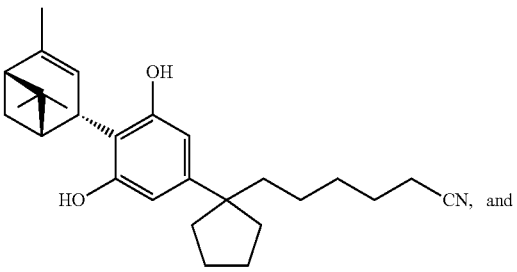

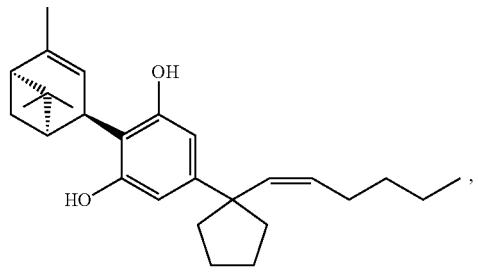

In another aspect, a compound of formula III below, and any pharmaceutically acceptable salts thereof including all stereoisomers and enantiomers is disclosed:

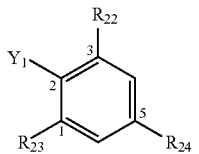

III wherein:
$R_{22}$ and $R_{23}$ are each independently selected from the group consisting of: —H, —F, —Cl, —Br, —I, —OH, —SH, —NH$_2$, —NO$_2$, —CN, —CF$_3$, —OC(O)CH$_3$, —C(O)CH$_3$, —C(O)CF$_3$, —O—P(O)(OR)$_2$ or —O—P(O)(OH)(OR) (wherein R is selected from H or alkyl), —P(O)(OR)$_2$ or —P(O)(OH)(OR) (wherein R is selected from H or alkyl), —OC(O)—R (wherein R is selected from H or alkyl), —OC(O)—CH(OH)—CH$_2$OH, —OC(O)—C(CH$_2$OH)$_2$—CH$_3$, —OC(O)—CH$_2$OH, —OC(O)-alkyl-COOH, —OC(O)—CH=CHCOOH, —OC(O)-alkyl-NR$_{25}$R$_{26}$, —OC(O)-alkyl-C(O)NR$_{25}$R$_{26}$, —OC(O)—O— alkyl-NR$_{25}$R$_{26}$, —OC(O)—CH(NH$_2$)—R$_8$ (wherein R$_8$ is selected from H, CH(OH)CH$_3$ or alkyl-X$_1$ and X$_1$ is selected from: H, —NH—C(=NH)NH$_2$, C(O)NH$_2$, COOH, SH, SCH$_3$, OH, NH$_2$, and an aromatic, heteroaromatic or heterocyclic ring);
$R_{25}$ and $R_{26}$ are each independently selected from the group consisting of: H, alkyl, or $R_{25}$ and $R_{26}$ together comprise part of a 3 to 7 membered saturated heterocyclic ring containing up to one additional heteroatom selected from N, O and S;
$Y_1$ is selected from:

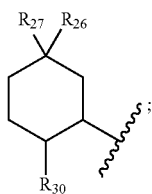

$R_{27}$, $R_{28}$ taken together represent an oxygen or sulfur atom or an enol ether group (=O, =S, =CH—O-alkyl, respectively), or $R_{27}$, $R_{28}$ each independently is selected from: —R$_{31}$, —OC(O)— alkyl, C$_{1-3}$alkyl-C(O)O-alkyl, C$_{1-3}$alkyl-OC(O)-alkyl;
$R_{31}$ is selected from: —F, —Cl, —Br, —I, —OH, —SH, —NH$_2$, —NH-alkyl, —N(alkyl)$_2$, —CN, —N$_3$, —NCS, —OC(O)CH$_3$, —C(O)NH$_2$, —C(O)NR$_{36}$R$_{37}$, —SO$_2$NH$_2$, —COOH, —NO$_2$, —CHO, —CF$_3$, —Sn(alkyl)$_3$, —Si(alkyl)$_3$, —C≡CH, —CH=CH$_2$, and an aromatic, heteroaromatic or heterocyclic ring;
$R_{36}$ and $R_{37}$ are each independently selected from the group consisting of: H, alkyl, or $R_{36}$ and $R_{37}$ together comprise part of a 3 to 7 membered saturated heterocyclic ring containing up to one additional heteroatom selected from N, O and S;
$R_{30}$ is selected from —H, -alkyl, -alkyl-R$_{33}$, -alkenyl, -alkenyl-R$_{33}$, -alkynyl, -alkynyl-R$_{33}$;
$R_{33}$ is selected from —F, —Cl, —Br, —I, —OH, —SH, —NH$_2$, —NH-alkyl, —N(alkyl)$_2$, —CN, —N$_3$, —NCS, —OC(O)CH$_3$, —C(O)OCH$_3$, —SO$_2$NH$_2$, —C(O)NH$_2$, —COOH, —NO$_2$, —CHO, —CF$_3$, —Sn(alkyl)$_3$, —Si(alkyl)$_3$, —C≡CH, —CH=CH$_2$, —(CH$_2$)$_f$-L (wherein L is selected from —F, —Cl, —Br, —I, —OH and f is an integer from 1 to about 5), and an aromatic, heteroaromatic or heterocyclic ring;
$R_{24}$ is selected from -alkyl-R$_{34}$, -cycloalkyl-R$_{34}$, -heterocyclic-R$_{34}$, adamantyl, -adamantyl-R$_{34}$, -heteroadamantyl-R$_{34}$;
$R_{34}$ is selected from —(CH$_2$)$_p$—R$_{35}$, —(CH$_2$)$_p$—U—(CH$_2$)$_t$—R$_{35}$, —(CH$_2$)$_p$—U—(CH$_2$)$_t$—Z—R$_{35}$;
U and Z are each independently selected from: —CH$_2$—CH$_2$—, —C≡C—, —CH=CH—, —O—, —S—, —NH—, —C(O)—, —C(O)O—, —OC(O)—, —C(O)NH—, —NHC(O)—, —S(O)—, —SO$_2$—, —SO$_2$NH—, —NHSO$_2$—, —SO$_2$O— and —OSO$_2$—;
$R_{35}$ is selected from —H, —F, —Cl, —Br, —I, —OH, —SH, —NH$_2$, —CN, —N$_3$, —NCS, —NCO, —SO$_2$Cl, —SO$_2$F, —SO$_2$NH$_2$, —C(O)NH$_2$, —COOH, —NO$_2$, —CHO, —CF$_3$, —SO$_3$H, —O—P(O)(OH)$_2$, —Sn(alkyl)$_3$, —Si(alkyl)$_3$, —C≡CH, —CH=CH$_2$, and an aromatic, heteroaromatic or heterocyclic ring;
p is an integer from 0 to about 8; and
t is an integer from 0 to about 8.

In some embodiments, $R_{27}$ and $R_{28}$ taken together represent an oxygen (=O) or enol ether (=CH—O-alkyl) group or $R_{27}$ and $R_{28}$ are each independently $R_{31}$.

In some embodiments, $R_{31}$ is selected from the group consisting of —OH, —SH, —NH$_2$, —NH— alkyl, —N(alkyl)$_2$, —OC(O)CH$_3$, —C(O)NH$_2$, —C(O)NR$_{36}$R$_{37}$, —COOH, —CHO, and an aromatic, heteroaromatic or heterocyclic ring. In further embodiments, $R_{31}$ is selected from the group consisting of —OH, —C(O)NH$_2$, —C(O)NR$_{36}$R$_{37}$, —COOH, —CHO and a heterocyclic ring.

In some embodiments, $R_{36}$ and $R_{37}$ together comprise part of a 6-membered saturated heterocyclic ring containing up to one additional heteroatom selected from the group consisting of N, O and S. In further embodiments, the one additional heteroatom is O.

In some embodiments, $R_{30}$ is selected from the group consisting of -alkyl, -alkenyl and -alkenyl-R$_{33}$.

In some embodiments, $R_{33}$ is selected from the group consisting of —OH and —CHO.

In some embodiments, each of $R_{22}$ and $R_{23}$ are independently selected from the group consisting of —H, —SH, —NH$_2$, —OH, and —OC(O)R (wherein R is selected from the group consisting of H and alkyl). In further embodiments, $R_{22}$ and $R_{23}$ are —OH.

In some embodiments, $R_{24}$ is selected from the group consisting of -alkyl-R$_{34}$, -cycloalkyl-R$_{34}$, -heterocyclic-R$_{34}$ and -adamantyl. In further embodiments, $R_{24}$ is selected from the group consisting of -alkyl-R$_{34}$, -cycloalkyl-R$_{34}$ and -heterocyclic-R$_{34}$, and $R_{34}$ is selected from the group consisting of —(CH$_2$)$_p$—U—(CH$_2$)$_t$—R$_{35}$ and —(CH$_2$)$_p$—U—(CH$_2$)$_t$—Z—R$_{35}$.

In some embodiments, $R_{34}$ is —(CH$_2$)$_p$—U—(CH$_2$)$_t$—R$_{35}$. In further embodiments, $R_{34}$ is —(CH$_2$)$_p$—U—(CH$_2$)$_t$—Z—R$_{35}$.

In some embodiments, U is selected from the group consisting of —CH$_2$—CH$_2$—, —CH=CH—, —C≡C—, —O—, —S—, —NH—, —C(O)—, —C(O)O—, —C(O)NH— and —NHC(O)—. In further embodiments, U is selected from the group consisting of —CH$_2$—CH$_2$— and —CH=CH—.

In some embodiments, each of U and Z are independently selected from the group consisting of —CH$_2$—CH$_2$—, —CH=CH—, —C≡C—, —O—, —S—, —NH—, —C(O)—, —C(O)O—, —C(O)NH— and —NHC(O)—. In further embodiments, each of U and Z are independently selected from the group consisting of —CH$_2$—CH$_2$— and —CH=CH—.

In some embodiments, $R_{35}$ is selected from the group consisting of —H, —F, —Cl, —Br, —I, —OH, —SH, —NH$_2$, —CN, and —N$_3$. In further embodiments, $R_{35}$ is —H.

In some embodiments, p is selected from the group consisting of 0, 1, 2, 3, 4, 5, 6 and 7.

In some embodiments, t is selected from the group consisting of 1, 2, 3 and 4.

In some embodiments, the compound is selected from the group consisting of:

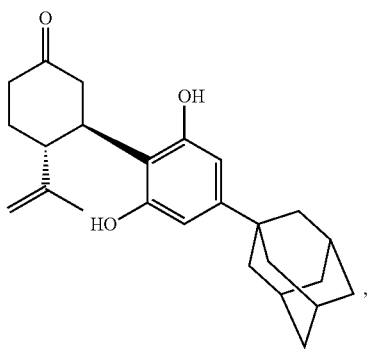
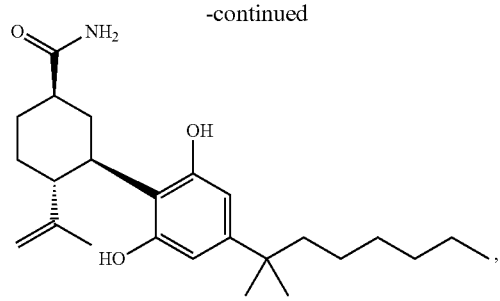
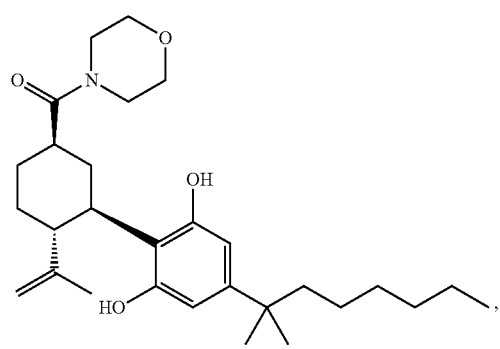
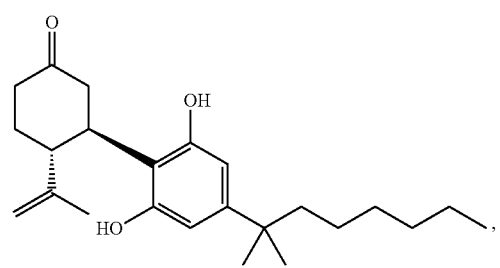
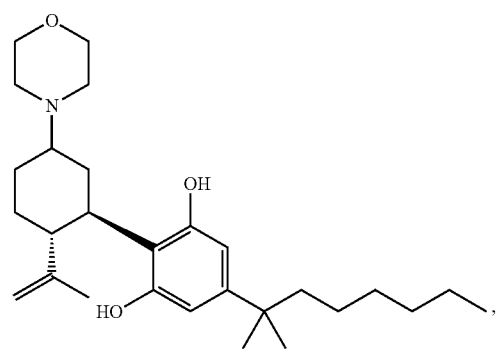
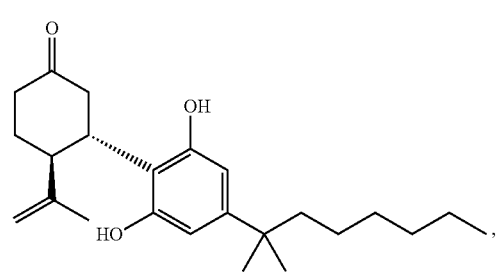

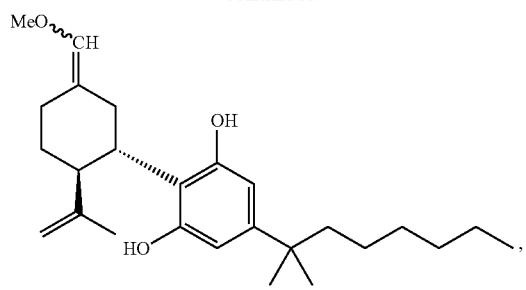
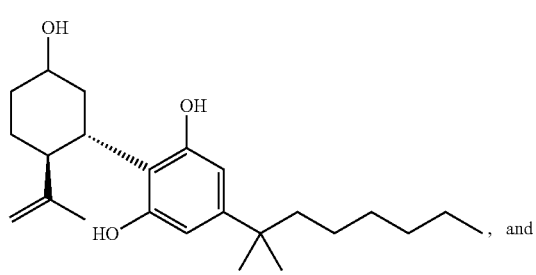
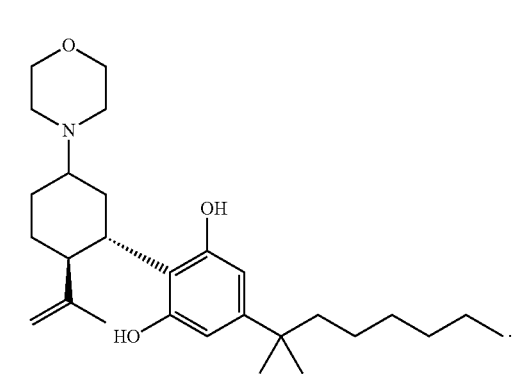
In another aspect, a compound or a pharmaceutically acceptable salt thereof, including all stereoisomers and enantiomers, is disclosed, wherein the compound is selected from the groups consisting of:
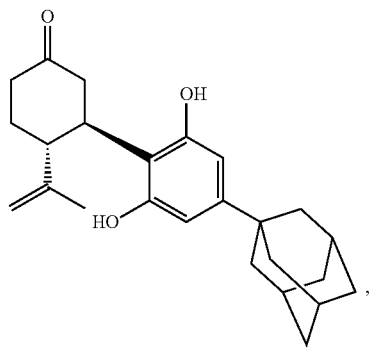
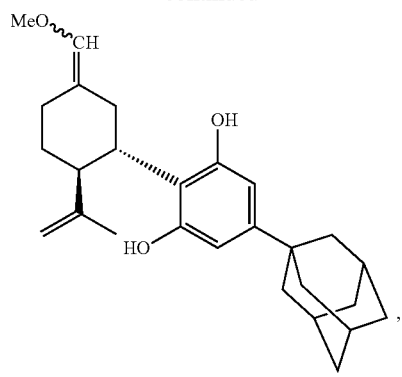
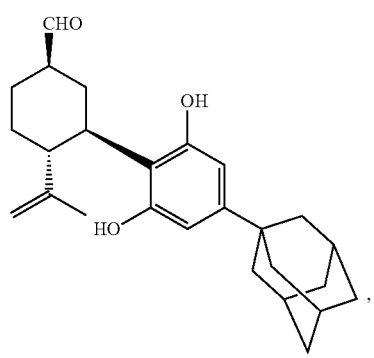
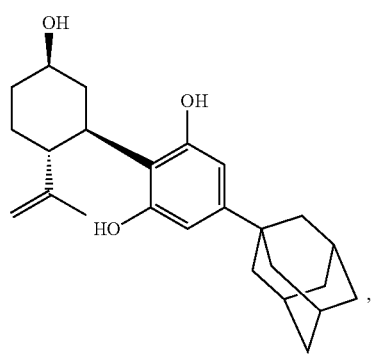
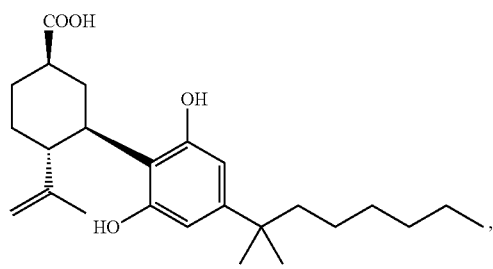
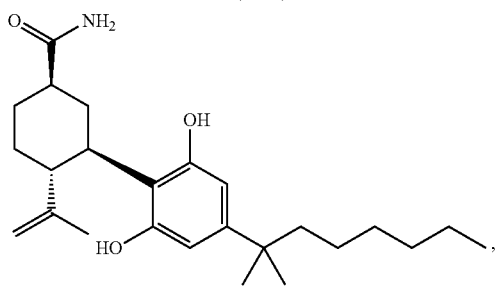

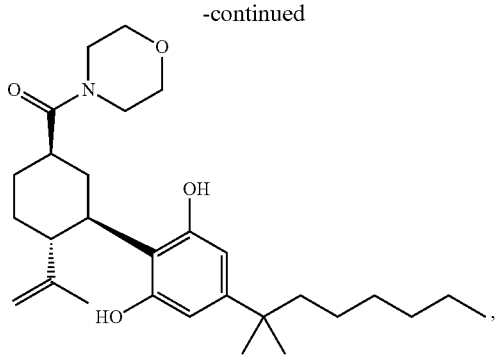

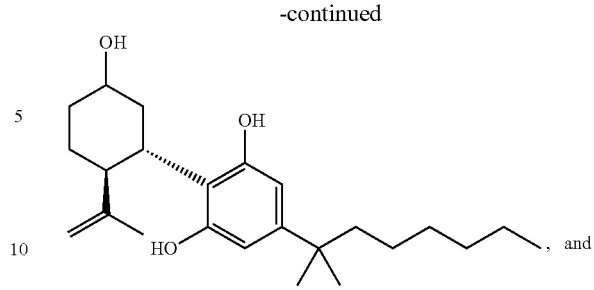

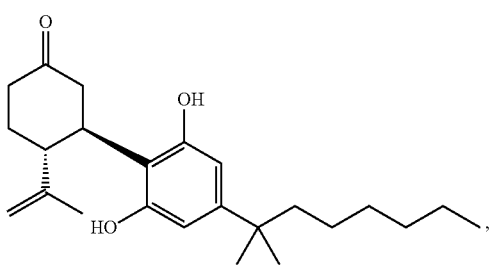

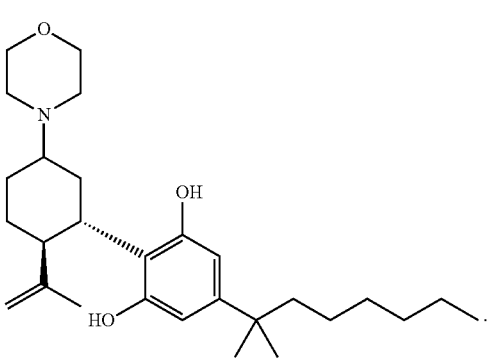

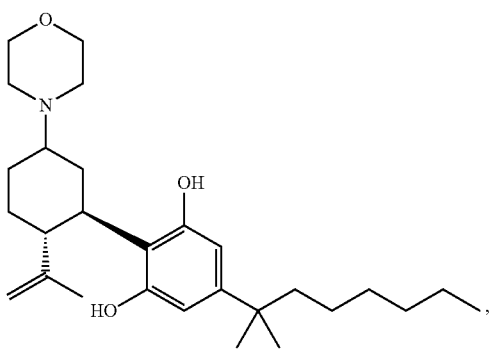

In another aspect, a compound of formula IV below, and any pharmaceutically acceptable salts thereof including all stereoisomers and enantiomers is disclosed:

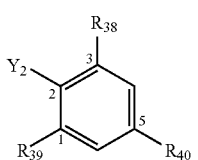

wherein:

$R_{38}$ and $R_{39}$ are each independently selected from the group consisting of: —H, —F, —Cl, —Br, —I, —OH, —SH, —NH$_2$, —NO$_2$, —CN, —CF$_3$, —OC(O)CH$_3$, —C(O)CH$_3$, —C(O)CF$_3$, —OSi(alkyl)$_3$, —O—P(O)(OR)$_2$ or —O—P(O)(OH)(OR) (wherein R is selected from H or alkyl), —P(O)(OR)$_2$ or —P(O)(OH)(OR) (wherein R is selected from H or alkyl), —OC(O)—R (wherein R is selected from H or alkyl), —OC(O)—CH(OH)—CH$_2$OH, —OC(O)—C(CH$_2$OH)$_2$—CH$_3$, —OC(O)—CH$_2$OH, —OC(O)-alkyl-COOH, —OC(O)—CH=CHCOOH, —OC(O)-alkyl-NR$_{41}$R$_{42}$, —OC(O)-alkyl-C(O)NR$_{41}$R$_{42}$, —OC(O)—O-alkyl-NR$_{41}$R$_{42}$, —OC(O)—CH(NH$_2$)—R$_8$ (wherein R$_8$ is selected from H, CH(OH)CH$_3$ or alkyl-X$_1$ and X$_1$ is selected from: H, —NH—C(=NH)NH$_2$, C(O)NH$_2$, COOH, SH, SCH$_3$, OH, NH$_2$, and an aromatic, heteroaromatic or heterocyclic ring);

$R_{41}$ and $R_{42}$ are each independently selected from the group consisting of: H, alkyl, or $R_{41}$ and $R_{42}$ together comprise part of a 3 to 7 membered saturated heterocyclic ring containing up to one additional heteroatom selected from N, O and S;

Y$_2$ is selected from:

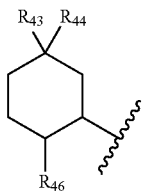

wherein:
R$_{43}$, R$_{44}$ taken together represent an oxygen or sulfur atom or an enol ether group (=O, =S, =CH—O-alkyl, respectively), or R$_{43}$, R$_{44}$ each independently is selected from: —H, -alkyl, —R$_{47}$, -alkyl-R$_{47}$, -alkyl-O-alkyl, -alkyl-O-alkyl-R$_{47}$, —C(O)O-alkyl, —OC(O)-alkyl, C$_{1-3}$alkyl-C(O)O— alkyl, C$_{1-3}$alkyl-OC(O)-alkyl;
R$_{47}$ is selected from: —F, —Cl, —Br, —I, —OH, —SH, —NH$_2$, —NH-alkyl, —N(alkyl)$_2$, —CN, —N$_3$, —NCS, —OC(O)CH$_3$, —C(O)OCH$_3$, —C(O)NH$_2$, —C(O)NR$_{36}$R$_{37}$, —SO$_2$NH$_2$, —COOH, —NO$_2$, —CHO, —CF$_3$, —Sn(alkyl)$_3$, —Si(alkyl)$_3$, —C≡CH, —CH=CH$_2$, and an aromatic, heteroaromatic or heterocyclic ring;
R$_{36}$ and R$_{37}$ are each independently selected from: H, alkyl, or R$_{36}$ and R$_{37}$ together comprise part of a 3 to 7 membered saturated heterocyclic ring containing up to one additional heteroatom selected from N, O and S;
R$_{46}$ is selected from —H, -alkyl, -alkyl-R$_{49}$, -alkenyl, -alkenyl-R$_{49}$, -alkynyl, -alkynyl-R$_{49}$;
R$_{49}$ is selected from: —F, —Cl, —Br, —I, —OH, —SH, —NH$_2$, —NH-alkyl, —N(alkyl)$_2$, —CN, —N$_3$, —NCS, —OC(O)CH$_3$, —C(O)OCH$_3$, —SO$_2$NH$_2$, —C(O)NH$_2$, —COOH, —NO$_2$, —CHO, —CF$_3$, —Sn(alkyl)$_3$, —Si(alkyl)$_3$, —C≡CH, —CH=CH$_2$, —(CH$_2$)$_n$-Q (wherein Q is selected from —F, —Cl, —Br, —I, —OH and n is an integer from 1 to about 5), and an aromatic, heteroaromatic or heterocyclic ring;
R$_{40}$ is selected from: -cycloalkyl-R$_{50}$, -heterocyclic-R$_{50}$, adamantyl, -adamantyl-R$_{50}$, -heteroadamantyl-R$_{50}$;
R$_{50}$ is selected from: —(CH$_2$)$_q$—R$_{51}$, —(CH$_2$)$_q$-M-(CH$_2$)$_r$—R$_{51}$, —(CH$_2$)$_q$-M-(CH$_2$)$_r$—V—R$_{51}$;
M and V are each independently selected from: —CH$_2$—CH$_2$—, —C≡C—, —CH=CH—, —O—, —S—, —NH—, —C(O)—, —C(O)O—, —OC(O)—, —C(O)NH—, —NHC(O)—, —S(O)—, —SO$_2$—, —SO$_2$NH—, —NHSO$_2$—, —SO$_2$O— and —OSO$_2$—;
R$_{51}$ is selected from —H, —F, —Cl, —Br, —I, —OH, —SH, —NH$_2$, —CN, —N$_3$, —NCS, —NCO, —SO$_2$Cl, —SO$_2$F, —SO$_2$NH$_2$, —C(O)NH$_2$, —COOH, —NO$_2$, —CHO, —CF$_3$, —SO$_3$H, —O—P(O)(OH)$_2$, —Sn(alkyl)$_3$, —Si(alkyl)$_3$, —C≡CH, —CH=CH$_2$, and an aromatic, heteroaromatic or heterocyclic ring;
q is an integer from 0 to about 8; and
r is an integer from 0 to about 8.
In some embodiments, R$_{43}$ and R$_{44}$ taken together represent an oxygen (=O) or enol ether (=CH—O-alkyl) group or R$_{43}$ and R$_{44}$ are each independently selected from the group consisting of —H and R$_{47}$.
In some embodiments, R$_{47}$ is selected from the group consisting of —OH, —SH, —NH$_2$, —NH— alkyl, —N(alkyl)$_2$, —OC(O)CH$_3$, —C(O)NH$_2$, —C(O)NR$_{36}$R$_{37}$, —COOH, —CHO, and an aromatic, heteroaromatic or heterocyclic ring. In further embodiments, R$_{47}$ is selected from the group consisting of —OH, —C(O)NH$_2$, —C(O)NR$_{36}$R$_{37}$, —COOH, —CHO and a heterocyclic ring.

In some embodiments, R$_{36}$ and R$_{37}$ together comprise part of a 6-membered saturated heterocyclic ring containing up to one additional heteroatom selected from the group consisting of N, O and S. In further embodiments, the one additional heteroatom is O.

In some embodiments, R$_{46}$ is selected from the group consisting of -alkyl, -alkenyl and -alkenyl-R$_{49}$.

In some embodiments, R$_{49}$ is selected from the group consisting of —OH and —CHO.

In some embodiments, each of R$_{38}$ and R$_{39}$ are independently selected from the group consisting of —H, —SH, —NH$_2$, —OH, —OSi(alkyl)$_3$, and —OC(O)R (wherein R is selected from the group consisting of H and alkyl). In further embodiments, R$_{38}$ and R$_{39}$ are —OH.

In some embodiments, R$_{40}$ is selected from the group consisting of -cycloalkyl-R$_{50}$, -heterocyclic-R$_{50}$ and -adamantyl. In further embodiments, R$_{40}$ is selected from the group consisting of -cycloalkyl-R$_{50}$ and -heterocyclic-R$_{50}$, and R$_{50}$ is selected from the group consisting of —(CH$_2$)$_q$-M-(CH$_2$)$_r$—R$_{51}$ and —(CH$_2$)$_q$-M-(CH$_2$)$_r$—V—R$_{51}$.

In some embodiments, R$_{50}$ is —(CH$_2$)$_q$-M-(CH$_2$)$_r$—R$_{51}$.

In some embodiments, R$_{34}$ is —(CH$_2$)$_q$-M-(CH$_2$)$_r$—Z—R$_{51}$.

In some embodiments, M is selected from the group consisting of —CH$_2$—CH$_2$—, —CH=CH—, —C≡C—, —O—, —S—, —NH—, —C(O)—, —C(O)O—, —C(O)NH— and —NHC(O)—. In further embodiments, M is selected from the group consisting of —CH$_2$—CH$_2$— and —CH=CH—.

In some embodiments, each of M and V are independently selected from the group consisting of CH$_2$—CH$_2$—, —CH=CH—, —C≡C—, —O—, —S—, —NH—, —C(O)—, —C(O)O—, —C(O)NH— and —NHC(O)—. In further embodiments, each of M and V are independently selected from the group consisting of —CH$_2$—CH$_2$— and —CH=CH—.

In some embodiments, R$_{51}$ is selected from the group consisting of —H, —F, —Cl, —Br, —I, —OH, —SH, —NH$_2$, —CN, and —N$_3$. In further embodiments, R$_{51}$ is —H.

In some embodiments, q is selected from the group consisting of 0, 1, 2, 3, 4, 5, 6 and 7.

In some embodiments, r is selected from the group consisting of 1, 2, 3 and 4.

In some embodiments, the compound is selected from the group consisting of:

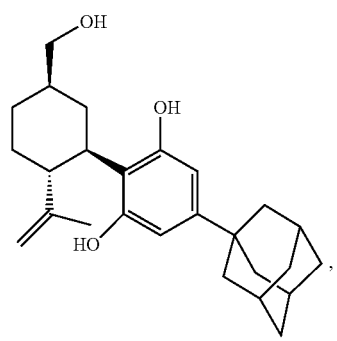

49

-continued

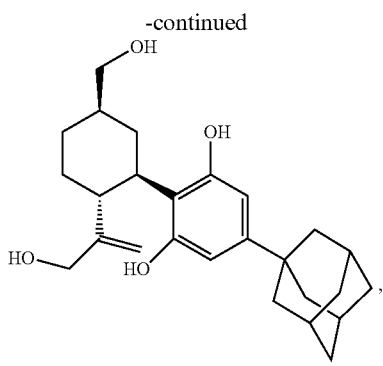

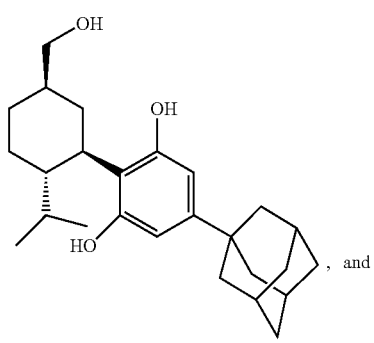
, and

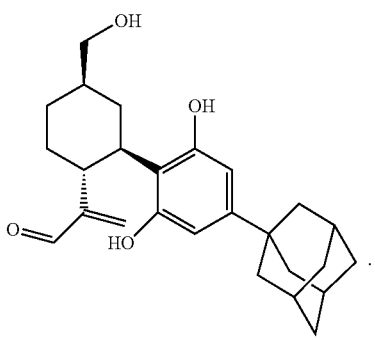
.

In another aspect, a compound or a pharmaceutically acceptable salt thereof, including all stereoisomers and enantiomers, is disclosed, wherein the compound is selected from the groups consisting of:

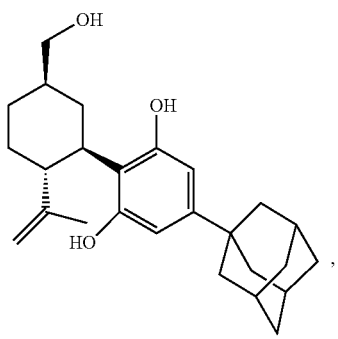
,

50

-continued

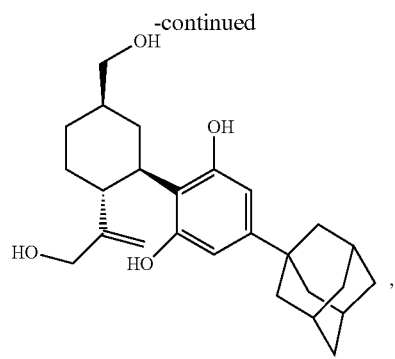
,

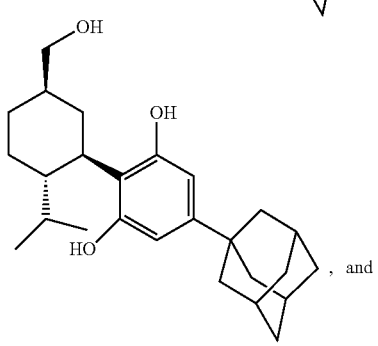
, and

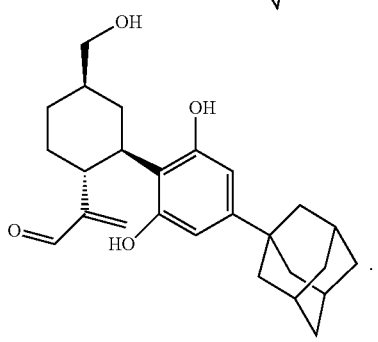
.

In another aspect, a compound of formula V or a pharmaceutically acceptable salt thereof, including all stereoisomers and enantiomers is disclosed:

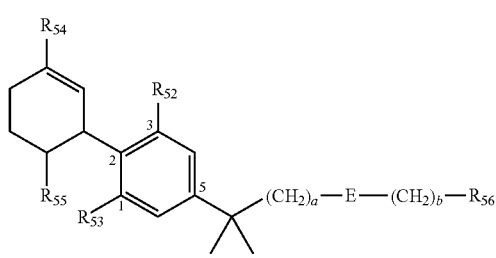

V wherein:
$R_{52}$ and $R_{53}$ are each independently selected from the group consisting of: —H, —F, —Cl, —Br, —I, —OH, —SH, —NH$_2$, —NO$_2$, —CN, —CF$_3$, —OC(O)CH$_3$, —C(O)CH$_3$, —C(O)CF$_3$, —OSi(alkyl)$_3$, —O—P(O)(OR)$_2$, —O—P(O)(OH)(OR) (wherein R is selected from the group consisting of H and alkyl), —P(O)(OR)$_2$, —P(O)(OH)(OR) (wherein R is selected from the group consisting of H and alkyl), —OC(O)—R (wherein R is selected from the group consisting of H and alkyl), —OC(O)—CH(OH)—CH$_2$OH, —OC(O)—C(CH$_2$OH)$_2$—CH$_3$, —OC(O)—CH$_2$OH, —OC (O)-alkyl-COOH, —OC(O)—CH═CHCOOH, —OC(O)-alkyl-NR$_{57}$R$_{58}$, —OC(O)-alkyl-C(O)NR$_{57}$R$_{58}$, —OC(O)—O— alkyl-NR$_{57}$R$_{58}$, and —OC(O)—CH(NH$_2$)—R$_8$ (wherein R$_8$ is selected from the group consisting of H, CH(OH)CH$_3$ and alkyl-X$_1$, and X$_1$ is selected from the group consisting of: H, —NH—C(═NH)NH$_2$, C(O)NH$_2$, COOH, SH, SCH$_3$, OH, NH$_2$, and an aromatic, heteroaromatic or heterocyclic ring);

R$_{57}$ and R$_{58}$ are each independently selected from the group consisting of: H and alkyl, or R$_{57}$ and R$_{58}$ together comprise part of a 3 to 7 membered saturated heterocyclic ring containing up to one additional heteroatom selected from the group consisting of N, O and S;

R$_{54}$ is selected from the group consisting of: —OC(O)-alkyl, C$_{1-3}$alkyl-C(O)O-alkyl, and —C$_{1-3}$alkyl-OC(O)-alkyl;

R$_{55}$ is selected from the group consisting of —H, -alkyl and -alkyl-R$_{59}$;

R$_{59}$ is selected from the group consisting of: —F, —Cl, —Br, —I, —OH, —SH, —NH$_2$, —NH-alkyl, —N(alkyl)$_2$, —CN, —N$_3$, —NCS, —OC(O)CH$_3$, —C(O)OCH$_3$, —SO$_2$NH$_2$, —C(O)NH$_2$, —COOH, —NO$_2$, —CHO, —CF$_3$, —Sn(alkyl)$_3$, —Si(alkyl)$_3$, —C≡CH, —CH═CH$_2$, —(CH$_2$)$_n$-Q (wherein Q is selected from the group consisting of —F, —Cl, —Br, —I, and —OH and n is an integer from 1 to 5), and an aromatic, heteroaromatic or heterocyclic ring;

E is selected from the group consisting of: —CH$_2$—CH$_2$—, —C≡C—, —CH═CH—, —O—, —S—, —NH—, —C(O)—, —C(O)O—, —OC(O)—, —C(O)NH—, —NHC(O)—, —S(O)—, —SO$_2$—, —SO$_2$NH—, —NHSO$_2$—, —SO$_2$O— and —OSO$_2$—;

R$_{56}$ is selected from the group consisting of —H, —F, —Cl, —Br, —I, —OH, —SH, —NH$_2$, —CN, —N$_3$, —NCS, —NCO, —SO$_2$Cl, —SO$_2$F, —SO$_2$NH$_2$, —C(O)NH$_2$, —COOH, —NO$_2$, —CHO, —CF$_3$, —SO$_3$H, —O—P(O)(OH)$_2$, —Sn(alkyl)$_3$, —Si(alkyl)$_3$, —C≡CH, —CH═CH$_2$, and an aromatic, heteroaromatic or heterocyclic ring;

a is an integer from 0 to 8; and b is an integer from 0 to 8.

In some embodiments, R$_{52}$ and R$_{53}$ are each independently selected from the group consisting of —H, —SH, —NH$_2$, —OH, —OSi(alkyl)$_3$, and —OC(O)CH$_3$. In further embodiments, R$_{52}$ and R$_{53}$ are —OH.

In some embodiments, R$_{54}$ is —OC(O)-alkyl.

In some embodiments, R$_{55}$ is -alkyl-R$_{59}$.

In some embodiments, R$_{59}$ is selected from the group consisting of —C≡CH and —CH═CH$_2$.

In some embodiments, E is selected from the group consisting of —CH$_2$—CH$_2$—, —C≡C—, and —CH═CH—. In further embodiments, E is —CH$_2$—CH$_2$—.

In some embodiments, R$_{56}$ is selected from the group consisting of —H, —F, —Cl, —Br, —I, —OH, —SH, —NH$_2$, —CN, —N$_3$, —NCS, —NCO, —NO$_2$ and —CF$_3$. In further embodiments, R$_{56}$ is —H. In still further embodiments, R$_{56}$ is —Br.

In some embodiments, a is selected from the group consisting of 0, 1, 2, 3 and 4.

In some embodiments, b is selected from the group consisting of 0, 1, 2, 3 and 4.

In some embodiments, the compound is selected from the group consisting of:

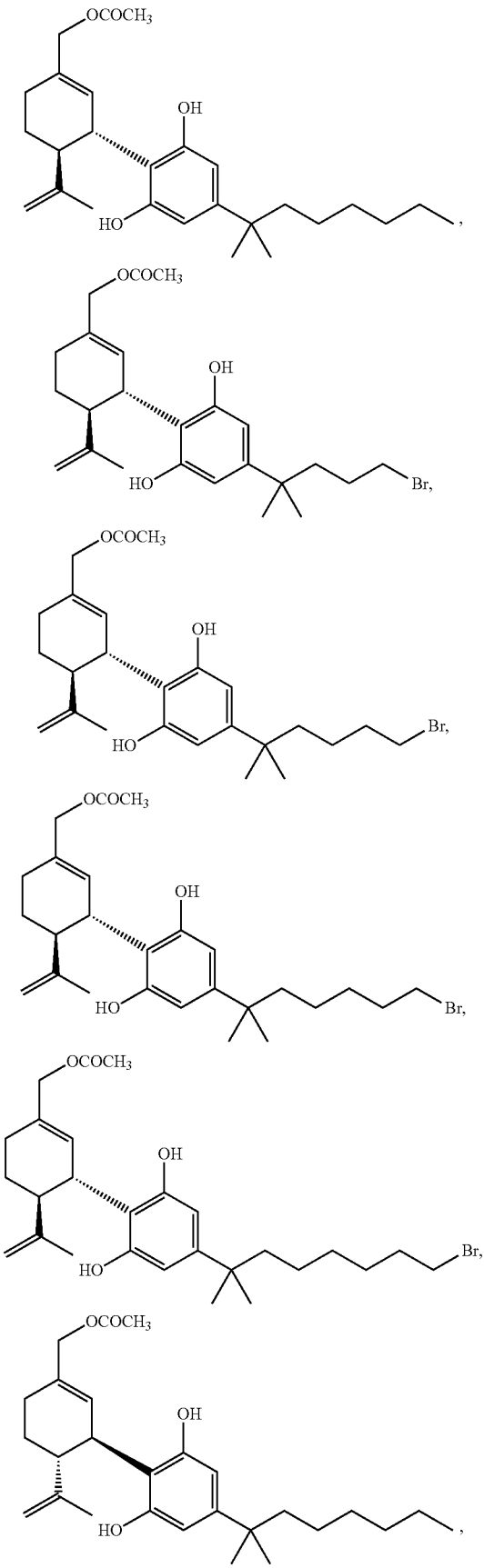

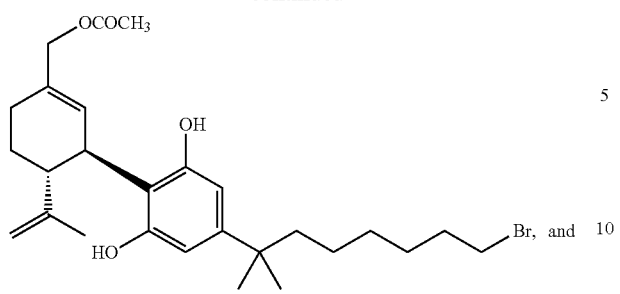
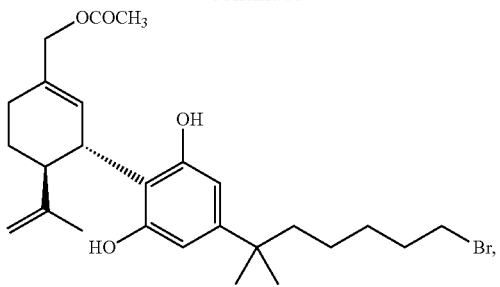
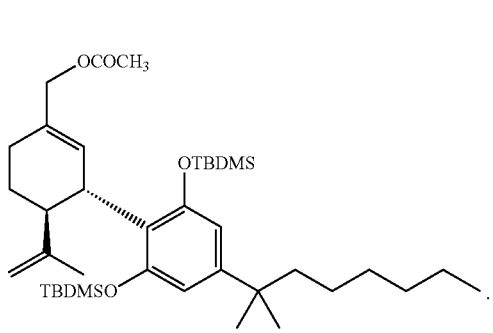
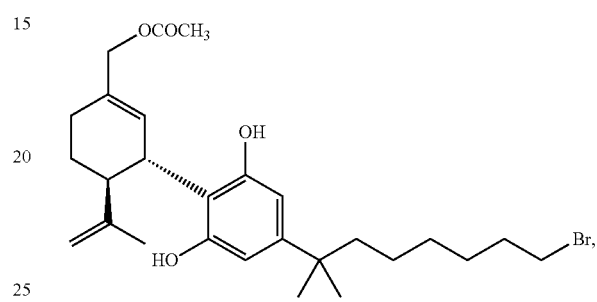
In another aspect, a compound or a pharmaceutically acceptable salt thereof, including all stereoisomers and enantiomers, is disclosed, wherein the compound is selected from the groups consisting of:
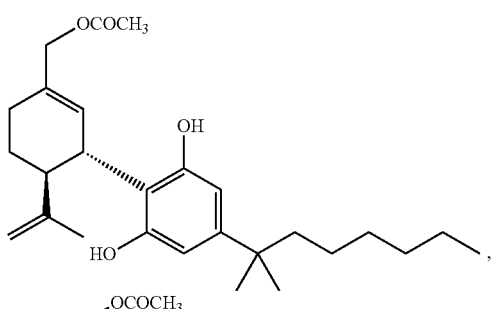
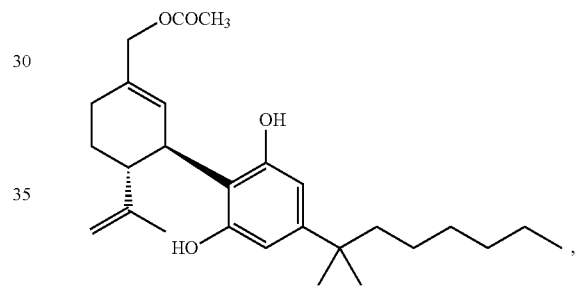
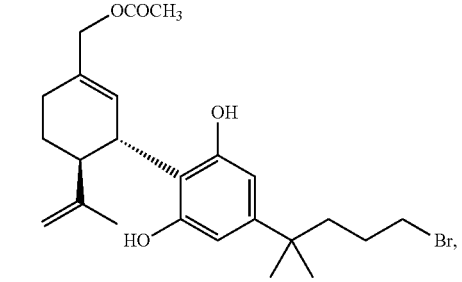
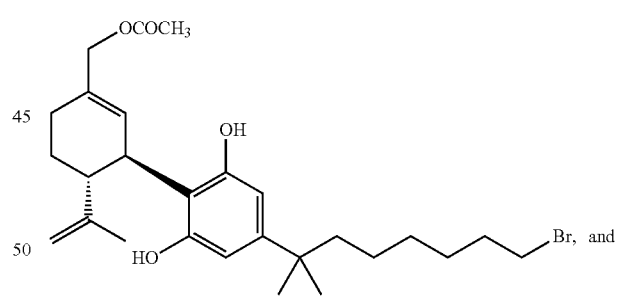
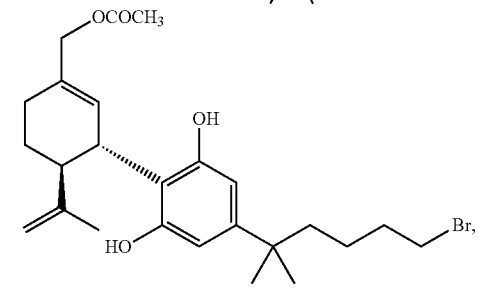
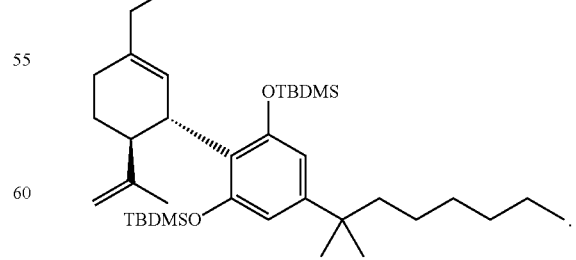
In another aspect, a compound of formula VI or a pharmaceutically acceptable salt thereof, including all stereoisomers and enantiomers is disclosed:

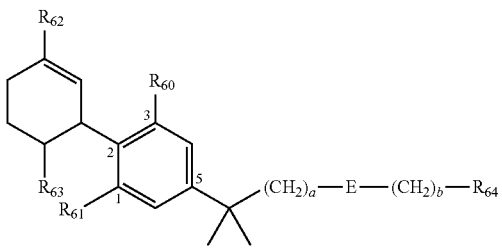

VI wherein:
$R_{60}$ and $R_{61}$ are each independently selected from the group consisting of: —OH and —O-alkyl;
$R_{62}$ is selected from the group consisting of —H, -alkyl, —$R_{65}$, and -alkyl-$R_{65}$;
$R_{65}$ is selected from the group consisting of: —F, —Cl, —Br, —I, —OH, —SH, —$NH_2$, —NH-alkyl, —$N(alkyl)_2$, —CN, —$N_3$, —NCS, —$OC(O)CH_3$, —$C(O)OCH_3$, —$SO_2NH_2$, —$C(O)NH_2$, —COOH, —$NO_2$, —CHO, —$CF_3$, —$Sn(alkyl)_3$, —$Si(alkyl)_3$, —C≡CH, —CH=$CH_2$, and an aromatic, heteroaromatic or heterocyclic ring;
$R_{63}$ is selected from the group consisting of —H, -alkyl, -alkenyl, and -alkynyl;
E is selected from the group consisting of: —$CH_2$—$CH_2$—, —C≡C—, and —CH=CH—;
$R_{64}$ is an aromatic, heteroaromatic or heterocyclic ring;
a is an integer from 0 to 8; and
b is an integer from 0 to 8.

In some embodiments, $R_{62}$ is -alkyl-$R_{65}$.
In some embodiments, $R_{65}$ is —OH.
In some embodiments, $R_{63}$ is -alkenyl.
In some embodiments, E is —$CH_2$—$CH_2$—.
In some embodiments, $R_{64}$ is an unsubstituted heterocyclic ring.
In some embodiments, a is selected from the group consisting of 0, 1 and 2.
In some embodiments, b is selected from the group consisting of 0, 1 and 2.
In some embodiments, the compound is selected from the group consisting of:

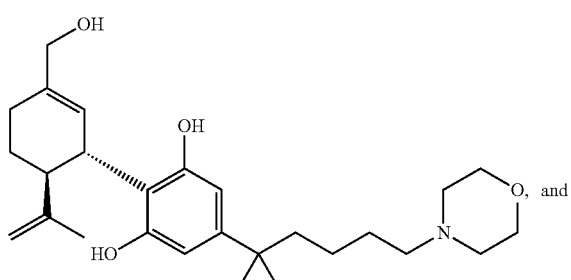

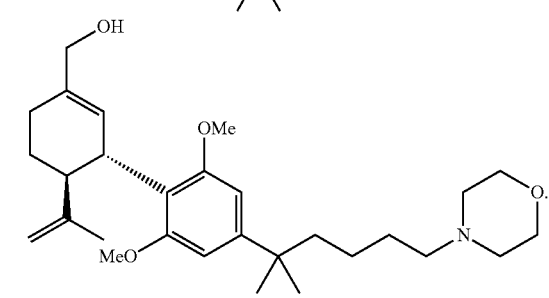

In another aspect, a compound or a pharmaceutically acceptable salt thereof, including all stereoisomers and enantiomers, is disclosed, wherein the compound is selected from the groups consisting of:

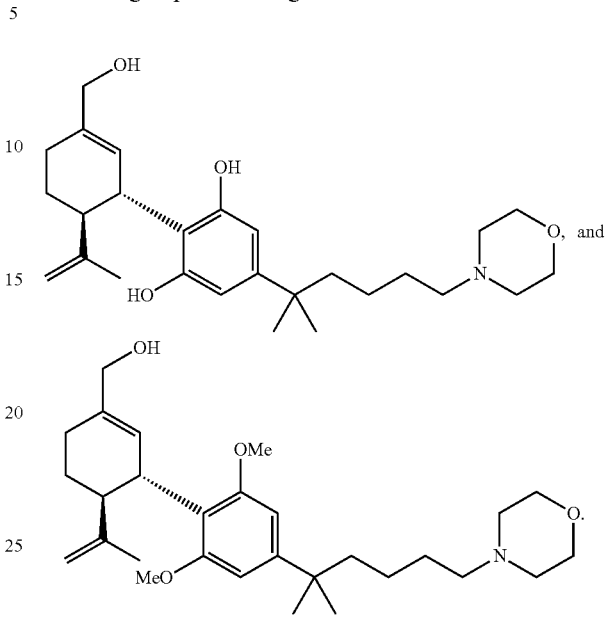

In another aspect, a pharmaceutical composition comprising a therapeutically effective amount of a compound of any preceding claim or a pharmaceutically acceptable salt thereof and a pharmaceutically acceptable carrier is disclosed.

In another aspect, method of treating a condition in a subject in need thereof is disclosed, the method comprising administering to the subject a therapeutically effective amount of a compound or pharmaceutically acceptable salt or a pharmaceutical composition disclosed herein; wherein the condition is selected from the group consisting of pain; central pain; peripheral pain; neuropathic pain; neuropathy; inflammatory pain; neurodegenerative diseases including multiple sclerosis, Parkinson's disease, Huntington's chorea, Alzheimer's disease and amyotrophic lateral sclerosis; mental disorders such as schizophrenia and depression; mood disorders; addiction disorders; memory disorders; gastrointestinal motility disorders such as irritable bowel syndrome and diarrhea; dyskinesia; migraine; osteoporosis, osteoarthritis; high blood pressure disease or hypertension; peripheral vascular disease; coronary artery disease; abnormal heart rate; cardiac insufficiency; pulmonary hypertension; ocular hypertension or glaucoma; endotoxic shock; hypotensive shock; appetite disorders; immune system disorders; fertility disorders; diseases associated with motor dysfunction such as Tourette's syndrome; inflammation; neurological disorders; epilepsy; nausea; AIDS wasting syndrome; cancer.

In some embodiments, the condition is selected from the group consisting of pain; central pain; and peripheral pain.

In another aspect, a method of stimulating a cannabinoid receptor in a subject is disclosed, the method comprising: administering to the subject an effective amount of a compound or pharmaceutically acceptable salt or a pharmaceutical composition disclosed herein.

In some embodiments, the compound is a cannabinoid receptor agonist.

In some embodiments, the compound is a cannabinoid receptor partial agonist.

In another aspect, a method of selectively stimulating a CB2 cannabinoid receptor in subject is disclosed, the method comprising: administering to the subject an effective amount of a compound or pharmaceutically acceptable salt or a pharmaceutical composition disclosed herein.

In another aspect, a method of selectively stimulating a cannabinoid receptor in the periphery of a subject is disclosed, the method comprising administering to the subject an effective amount of a compound or pharmaceutically acceptable salt or a pharmaceutical composition disclosed herein.

Some disclosed compounds were tested for CB1 and CB2 receptor binding affinity (Tables 1, 2, 3, 4, 5, 6). As used herein "binding affinity" is represented by the Ki value. The Ki value is the affinity constant and describes the affinity of the compound for the receptor. The lower the Ki value, the higher the affinity of the compound for the receptor. A detailed description of the methods used to test "binding affinity" of compounds is given in Makriyannis, et al., US 2007, 0135388 and in Papahatjis, et al. *J. Med. Chem.* (2007) 4048, the content of each of which is hereby incorporated by reference.

Functional characterization of some of the disclosed compounds was performed by using the cyclic adenosine monophosphate (cAMP) assay. The functional potency of the compound is represented by the $EC_{50}$ value. The lower the $EC_{50}$ value, the higher the functional potency. A detailed description of the cyclic adenosine monophosphate (cAMP) assay is given in Nikas et al. *J. Med. Chem.* (2010) 6996.

Some of the disclosed compounds were tested in vivo using two well defined rodent assays for cannabinergic activity, the analgesia and the hypothermia assays. The analgesia assay (tail immersion test) determines the ability of the test compound to activate cannabinergic signaling, through modulation of cannabinoid receptors, and thereby reduce nociceptive pain. The hypothermia test determines the ability of a test compound to act as a central CB1 agonist and decrease the body temperature. A peripherally acting cannabinergic compound does not show effects in the hypothermia test. The details of both assays are described below.

A. Analgesia Assay

C57BL6/J mice (Jackson Laboratories, Bar Harbor Me.) were single housed at least 1 h before start of experiment. Food and water are removed immediately before the first injection.

The test compounds were dissolved in a solution of ethanol:emulphor:saline (1:1:18) in several concentrations. $\Delta^9$-THC was dissolved in a solution of ethanol:emulphor:saline (1:1:18) in concentrations of 0.3 mg/ml (i.e. 3 mg/kg), 0.7 mg/ml, (i.e. 7 mg/kg), 2 mg/ml (i.e. 20 mg/kg), and 7 mg/ml (i.e. 70 mg/kg), which resulted in cumulative doses of 3, 10, 30, and 100 mg/kg. Route of administration=i.p. Volume=1 mL/100 g body weight.

Tail withdrawal test: 52° C. water bath (use bags).
  a. Bag is made of stapled surgery sheets to form a small pocket the size of a mouse.
  b. Mouse should be placed head first into bag gently and the bag should be pinched securely to ensure the mouse does not turn around, but not forcefully enough to be squeezing the mouse.
  c. The tip of the mouse's tail is dipped into the warm water, with 1 cm submerged.
  d. Time for the mouse to flick its tail or exhibit a gross tail movement such that it is no longer submerged is recorded; gross body movements are not considered a tail-flick.

B. Hypothermia Assay

C57BL/6 J mice (Charles River Breeding Laboratories, Wilmington, Mass., USA) weighing 30 to 35 g were group housed five to a cage, in a temperature-controlled (20° C.) animal facility. Mice were habituated to the animal facility for at least 1 week prior to experiments with a 12-h light/dark cycle (lights are on at 7:00 AM). Mice were given free access to food and water. Experimentally naïve mice were used for each dose condition, and the mice were tested during the light phase.

Rectal temperature was measured in mice using a rectal probe of a digital laboratory thermometer, RET-3-ISO, type T thermocouple (Physitemp Instruments Inc, Clifton, N.J.). The lubricated probe was inserted approximately 2.0 cm into the rectum for approximately 30 sec, prior to each recording. Rectal temperature recordings were taken from each mouse prior to dosing along with 20, 60, 180, 240, 360 and 1440-min post injection.

Testing of some compounds disclosed herein for their binding affinities for the CB1 and the CB2 cannabinoid receptors, showed very high affinity for the two cannabinoid receptors (see Tables 1-6). Therefore, another aspect of the present disclosure is use of at least one of the disclosed compounds, and physiologically acceptable salts thereof, to bind to cannabinoid receptors.

Some of the disclosed analogs showed high selectivity for the CB2 receptor (see Tables 1-6). These disclosed CB2 selective analogs are able to stimulate the CB2 receptor without affecting the CB1 receptor to the same degree. Therefore, another aspect of the present disclosure is use of at least one of the disclosed compounds, and physiologically acceptable salts thereof, to preferentially bind to and stimulate the CB2 receptor.

As used herein an analog is said to have "binding selectivity" if it has higher binding affinity for one receptor when compared to the other receptor. For example a cannabinergic analog which has a Ki of 0.1 nM for CB2 and 10 nM for CB1, is 100 times more selective for the CB2 receptor.

Testing of some compounds disclosed herein in the cyclic adenosine (cAMP) assay (Table 6) showed agonist or partial agonist activity at CB1 and/or CB2 cannabinoid receptors and the functional potency was determined. Therefore, another aspect of the present disclosure is to provide novel CB1 and CB2 receptor agonists and partial agonists.

Some compounds disclosed herein when tested in the analgesia assay, showed potent antinociceptive effects. For example, compound 41 (FIG. 1) induces analgesia in mice, and in a dose of 3 mg/Kg produces the maximum possible effect. In the same test (−)-$\Delta^9$-THC is approximately 10 times less potent than compound 41. Therefore, another aspect of the present disclosure is to provide novel cannabinergic compounds with potent analgesic activity.

Figure 2:
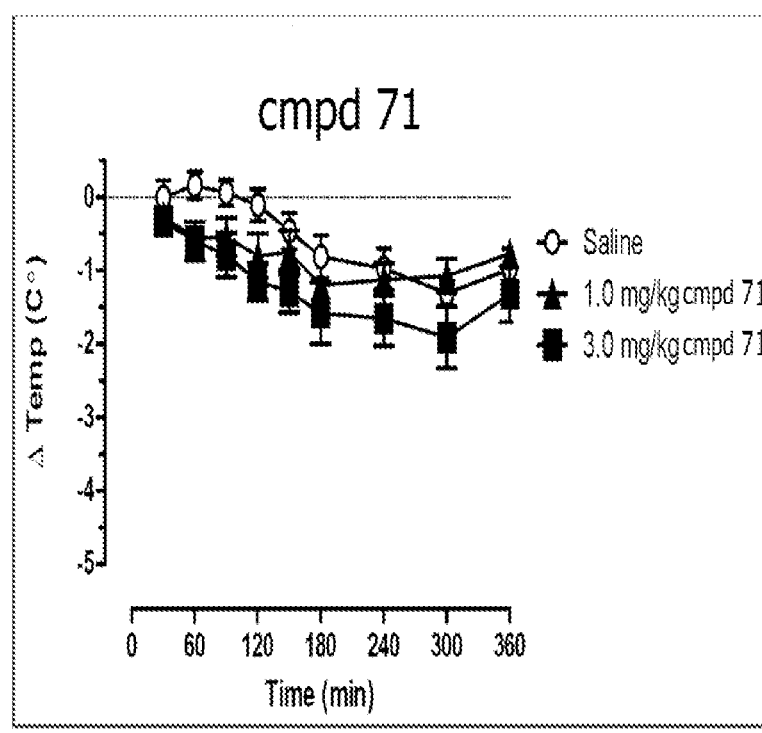
FIG. 2 is a chart showing the effects on centrally mediated hypothermia of a compound of the present invention in a hypothermia assay in mice.

Some of the disclosed compounds exhibit potent in vitro cannabinergic effects (e.g. affinity for CB receptors and functional potency and efficacy, Tables 1-7) but do not exhibit significant hypothermia in vivo. This indicates that the cannabinergic compound is partially peripherally restricted, meaning that is capable of modulating cannabinoid receptors mainly in the periphery and not in the central nervous system. For example, compound 71 (FIG. 2) does not show significant hypothermia at a dose of 3 mg/kg. However, this compound shows very high affinity for the cannabinoid receptors (see Table 5) and remarkable functional potency and efficacy (see Table 6, $EC_{50}$=1.4 and 0.4 nM). Therefore, another aspect of the present disclosure is to provide novel peripherally acting cannabinergic analogs that would not affect the central nervous system to the same degree.

The disclosed compounds and pharmaceutically acceptable salts thereof, have high potential to be used as research tools to probe cannabinoid receptors and to uncover the biological roles of such receptors. For example, the disclosed compounds can be used as in vivo imaging agents; as molecular probes to help obtaining information about the exact binding site; as labels to screen for cells which express cannabinoid receptors (CB1 or CB2). The cannabinoid receptor ligands disclosed in this application can also be used as an aid in drug design, for example as new druggable leads, or as controls in assays for testing other compounds for their ability to bind to cannabinoid receptors.

The disclosed compounds and physiologically acceptable salts thereof, when administered in therapeutically effective amounts, have high potential to bind to and modulate the CB1/CB2 cannabinoid receptors and thereby provide a physiological effect in an individual or animal that is useful to treat a condition in that individual or animal. Conditions that may be treated by modulation of the CB1/CB2 cannabinoid receptors include for example: pain; central pain; peripheral pain; neuropathic pain; neuropathy; inflammatory pain; neurodegenerative diseases including multiple sclerosis, Parkinson's disease, Huntington's chorea, Alzheimer's disease and amyotrophic lateral sclerosis; mental disorders such as schizophrenia and depression; mood disorders; addiction disorders; memory disorders; gastrointestinal motility disorders such as irritable bowel syndrome and diarrhea; dyskinesia; migraine; osteoporosis, osteoarthritis; high blood pressure disease or hypertension; peripheral vascular disease; coronary artery disease; abnormal heart rate; cardiac insufficiency; pulmonary hypertension; ocular hypertension or glaucoma; to prevent or reduce endotoxic shock and hypotensive shock; to modulate appetite; to modulate the immune system; to modulate fertility; to prevent or reduce diseases associated with motor dysfunction such as Tourette's syndrome; to prevent or reduce inflammation; to provide neuroprotection; to produce peripheral vasodilation; to treat epilepsy; to treat nausea such as associated with cancer chemotherapy; AIDS wasting syndrome; to treat several types of cancer as well as other ailments in which cannabinoid system is implicated.

Those skilled in the art will recognize, or be able to ascertain, using no more than routine experimentation, numerous equivalents to the specific substances and procedures described herein. Such equivalents are intended to be encompassed in the scope of the claims that follow the examples below.

Examples

Synthesis and Biological Testing of Compounds of General Formulas I, II, III, IV, V and VI Synthesized compounds represented by the general structures I, II, III, IV, V and VI are depicted in Tables 1, 2, 3, 4, 5 and 6 respectively, on the following pages. Biological testing results are provided in Tables 1, 2, 3, 4, 5, 6 and 7.

TABLE 1

Compounds of the general formula I

| Compound number | Structure | CB1 receptor Ki (nM) | CB2 receptor Ki (nM) |
|---|---|---|---|
| (−)-CBD[a] | 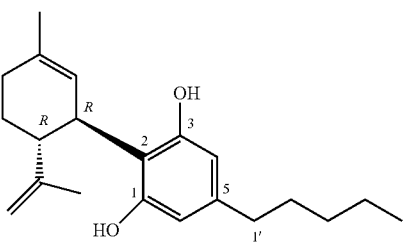 | >1200 | >200 |
| (+)-CBD[a] | 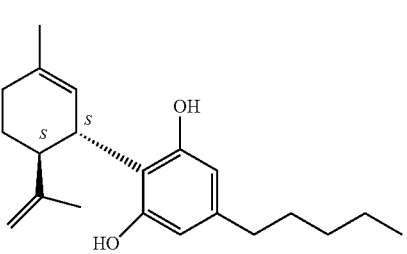 | >800 | >200 |

TABLE 1-continued

Compounds of the general formula I

| Compound number | Structure | CB1 receptor Ki (nM) | CB2 receptor Ki (nM) |
|---|---|---|---|
| 3.3 | 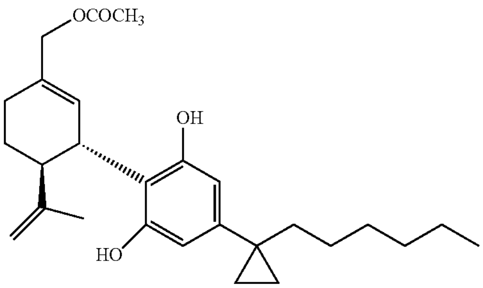 | 88 | 105 |
| 3.4 | 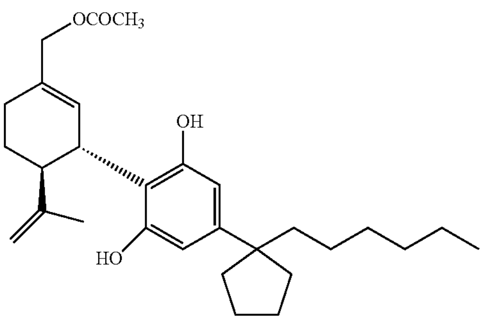 | 277 | 65 |
| 3.5 | 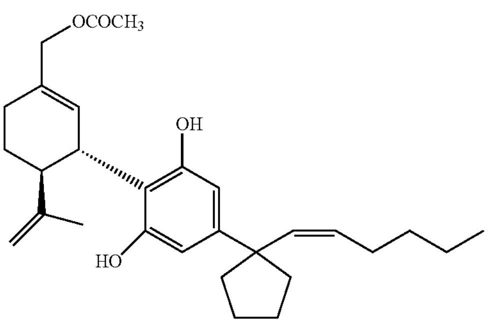 | 71 | 12 |
| 3.6 | 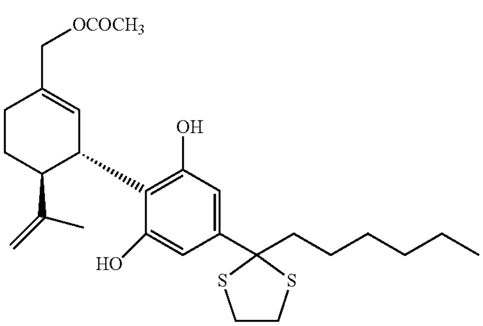 | 326 | 97 |

TABLE 1-continued

Compounds of the general formula I

| Compound number | Structure | CB1 receptor Ki (nM) | CB2 receptor Ki (nM) |
|---|---|---|---|
| 3.7 | 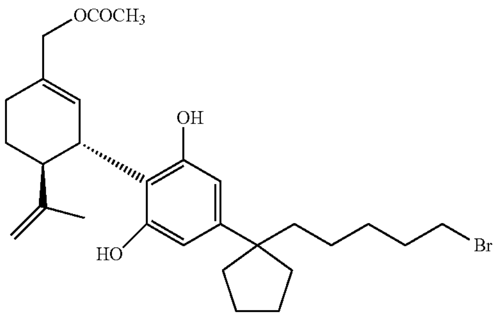 | 51 | 25 |
| 3.8 | 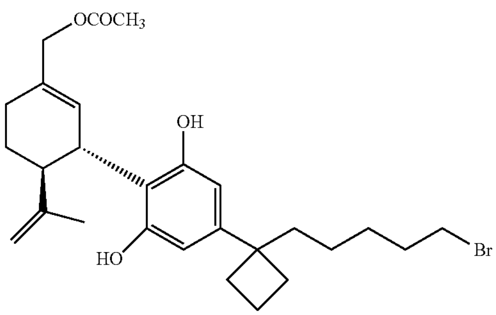 | 50 | 35 |
| 3.9 | 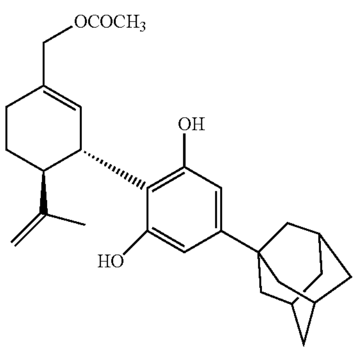 | 185 | 135 |
| 3.14 | 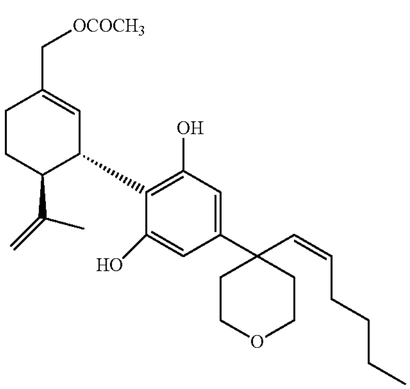 | 376 | 38 |

TABLE 1-continued
Compounds of the general formula I
| Compound number | Structure | CB1 receptor Ki (nM) | CB2 receptor Ki (nM) |
|---|---|---|---|
| 4.3 | 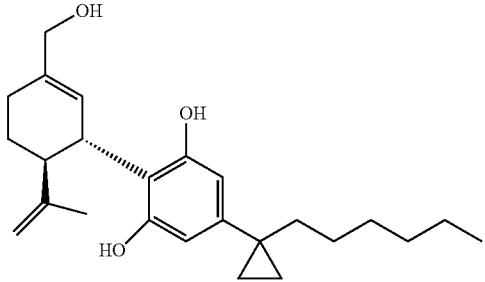 [SMILES: C=C(C)[C@H]1CCC(CO)=C[C@@H]1c1c(O)cc(C2(CCCCCC)CC2)cc1O] | 16 | 14 |
| 4.4 | 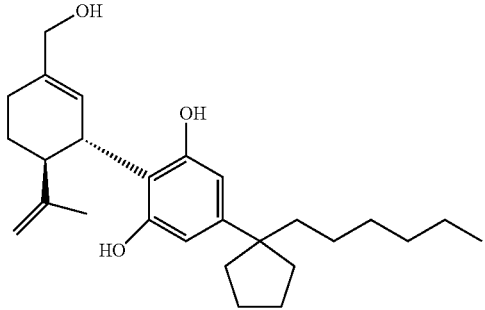 [SMILES: C=C(C)[C@H]1CCC(CO)=C[C@@H]1c1c(O)cc(C2(CCCCCC)CCCC2)cc1O] | 78 | 16 |
| 4.5 | 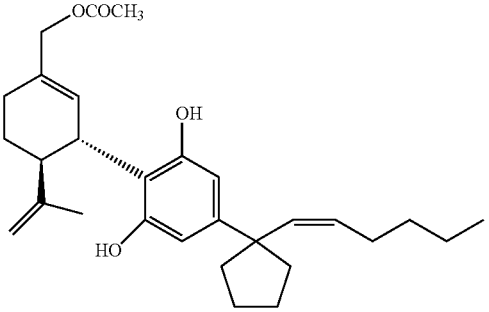 | 29 | 2.7 |
| 4.6 | 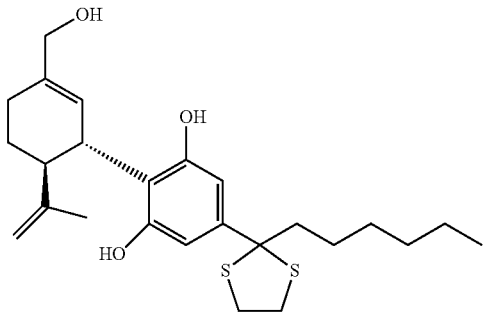 | 71 | 28 |

TABLE 1-continued

Compounds of the general formula I

| Compound number | Structure | CB1 receptor Ki (nM) | CB2 receptor Ki (nM) |
| --- | --- | --- | --- |
| 4.7 | 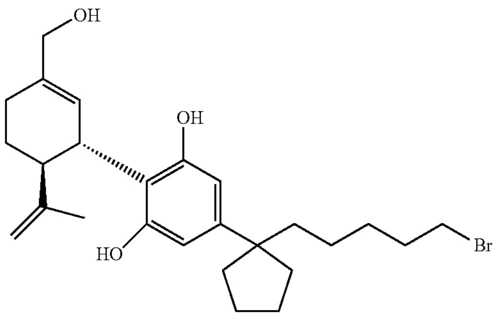 [SMILES: C=C(C)[C@H]1CCC(CO)=C[C@@H]1c1c(O)cc(C2(CCCCCBr)CCCC2)cc1O] | 16 | 5 |
| 4.8 | 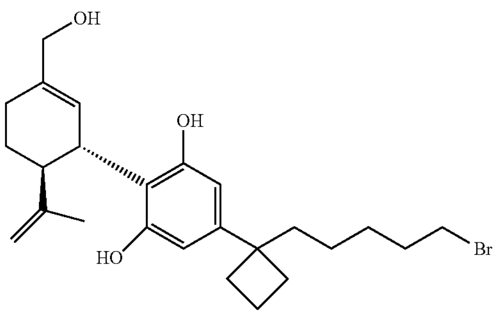 [SMILES: C=C(C)[C@H]1CCC(CO)=C[C@@H]1c1c(O)cc(C2(CCCCCBr)CCC2)cc1O] | 14 | 11 |
| 4.9 | 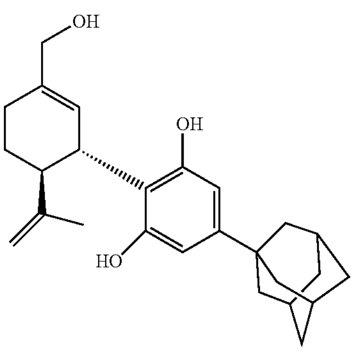 | 449 | 49 |
| 4.14 | 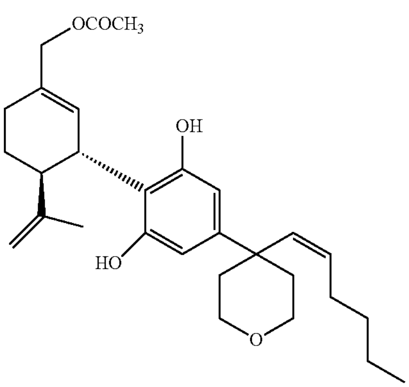 | 89 | 2 |

TABLE 1-continued

Compounds of the general formula I

| Compound number | Structure | CB1 receptor Ki (nM) | CB2 receptor Ki (nM) |
|---|---|---|---|
| 33 | 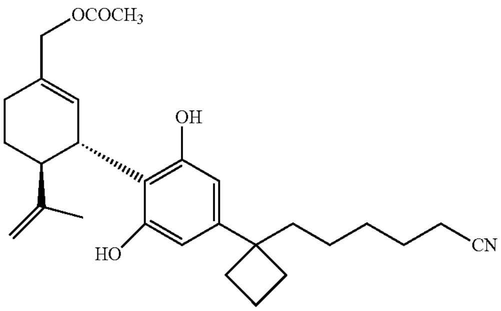 | 65 | 15 |
| 34 | 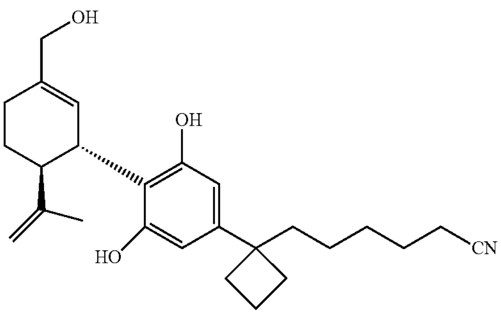 | 20 | 5.5 |
| 37 | 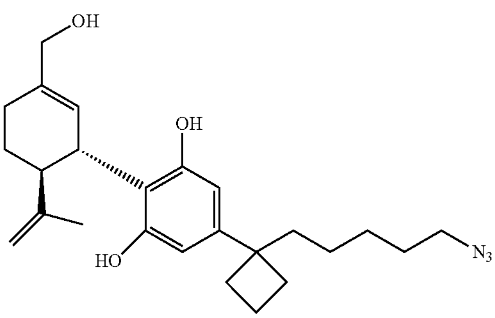 | 22 | 7.2 |

[a] Encompassed in the Table 1 for the purpose of comparison.

TABLE 2

Compounds of the general formula II

| Compound number | Structure | CB1 receptor Ki (nM) | CB2 receptor Ki (nM) |
|---|---|---|---|
| 40.1[a] | 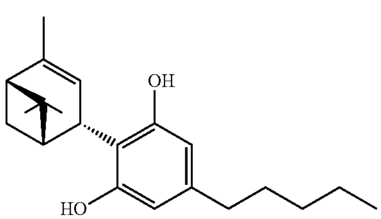 [SMILES: CCCCCc1cc(O)c([C@H]2C=C(C)[C@H]3C[C@@H]2C3(C)C)c(O)c1] | 671 | 47 |

TABLE 2-continued

| | Compounds of the general formula II | | |
|---|---|---|---|
| Compound number | Structure | CB1 receptor Ki (nM) | CB2 receptor Ki (nM) |
| 40.4 | | 23 | 17 |
| 40.5 | | 13.4 | 6.6 |
| 40.6 | | 19.2 | 7.9 |
| 40.7 | | 6.4 | 4.7 |
| 40.8 | | 1 | 2.1 |

TABLE 2-continued

Compounds of the general formula II

| Compound number | Structure | CB1 receptor Ki (nM) | CB2 receptor Ki (nM) |
|---|---|---|---|
| 40.15 | 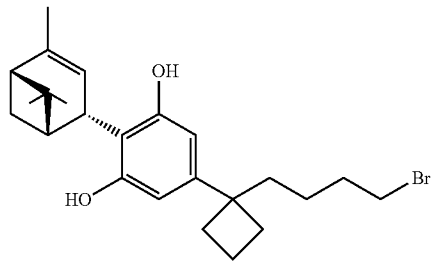 [SMILES: CC1=C[C@H](c2c(O)cc(C3(CCCCBr)CCC3)cc2O)[C@@H]2C[C@H]1C2(C)C] | 11 | 1.9 |
| 41 | 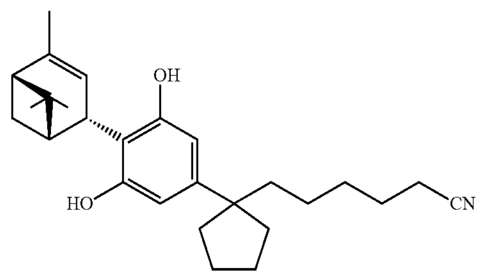 [SMILES: CC1=C[C@H](c2c(O)cc(C3(CCCCCC#N)CCCC3)cc2O)[C@@H]2C[C@H]1C2(C)C] | 2.6 | 0.8 |
| 43.1[a] | 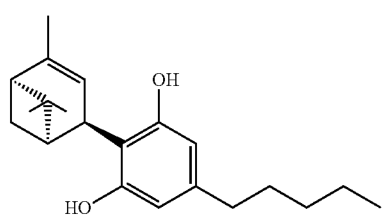 [SMILES: CCCCCc1cc(O)c([C@@H]2C=C(C)[C@@H]3C[C@H]2C3(C)C)c(O)c1] | 837 | 565 |
| 43.5 | 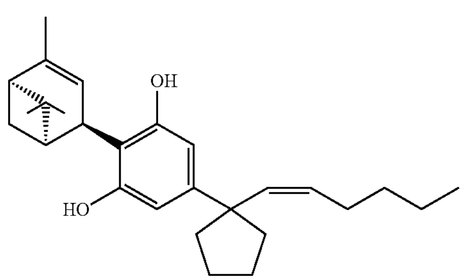 [SMILES: CCCC/C=C\C1(c2cc(O)c([C@@H]3C=C(C)[C@@H]4C[C@H]3C4(C)C)c(O)c2)CCCC1] | 45 | 29 |

[a]Encompassed in Makriyannis et al. WO 2011/006099 A1 and included here for the purpose of comparison.

TABLE 3

| Compounds of the general formula III | | | |
|---|---|---|---|
| Compound number | Structure | CB1 receptor Ki (nM) | CB2 receptor Ki (nM) |
| 48.2 | (structure) | 694 | >1000 |
| 49.2 | (structure) | 1760 | 375 |
| 50.2 | (structure) | NT | NT |
| 55 | (structure) | 2402 | 343 |

TABLE 3-continued

Compounds of the general formula III

| Compound number | Structure | CB1 receptor Ki (nM) | CB2 receptor Ki (nM) |
|---|---|---|---|
| 58.2 | 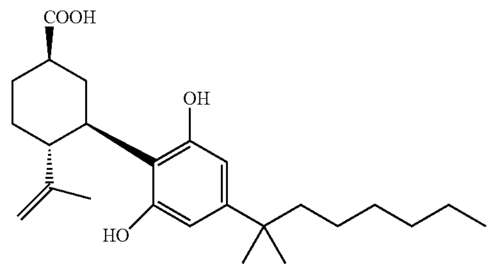 | >1000 | >1000 |
| 59.1 | 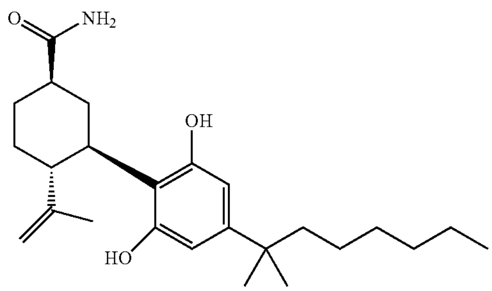 | >1000 | >1000 |
| 59.2 | 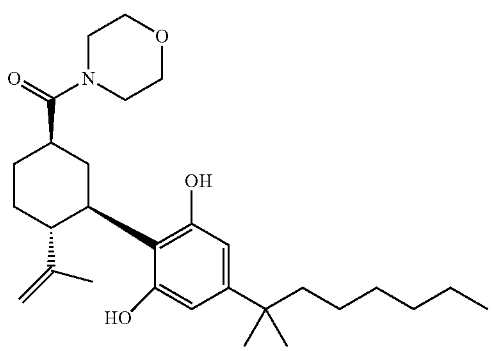 | NT | NT |
| 61.2 | 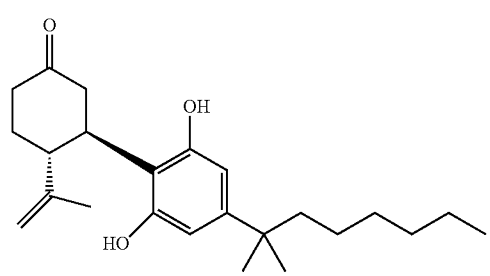 | >1000 | 37 |
| 62 | 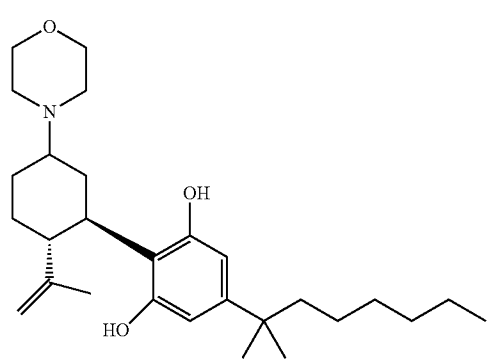 | 69 | 14 |

TABLE 3-continued

Compounds of the general formula III

| Compound number | Structure | CB1 receptor Ki (nM) | CB2 receptor Ki (nM) |
|---|---|---|---|
| 66.2 | 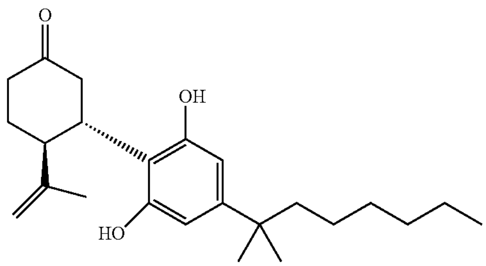 | 30-60 | 41 |
| 67.2 | 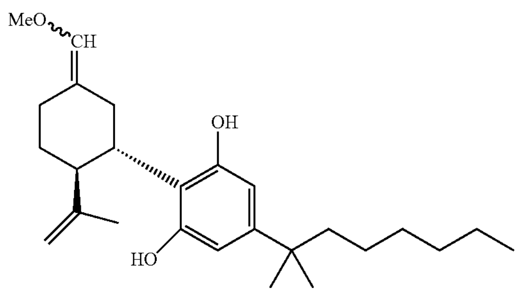 | NT | NT |
| 68 | 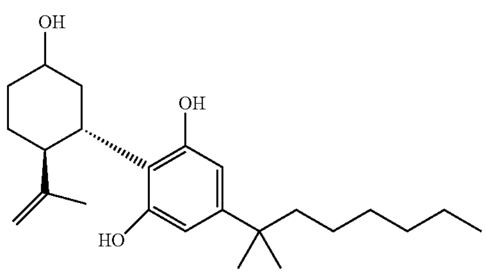 | >1000 | 33 |
| 69 | 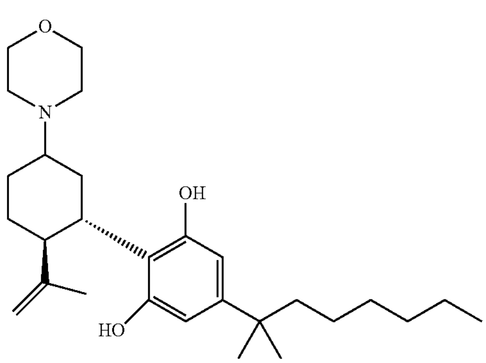 | NT | NT |

TABLE 4

| Compound number | Structure | CB1 receptor Ki (nM) | CB2 receptor Ki (nM) |
|---|---|---|---|
| 51.2 | 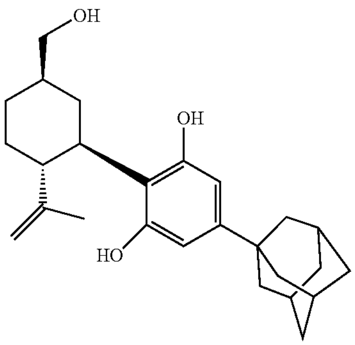 | 910 | 16 |
| 54.2 | 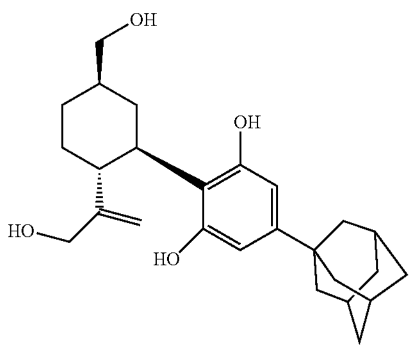 | 4140 | 185 |
| 56 | 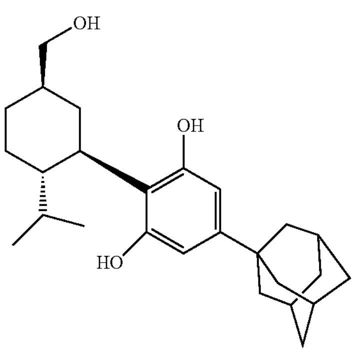 | 998 | 23 |
| 53.2 | 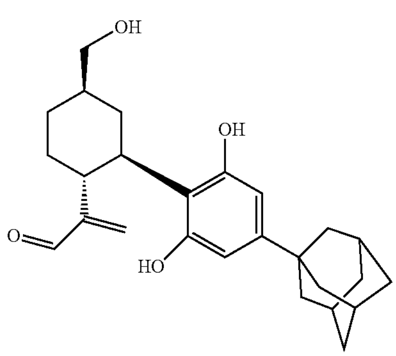 | 1400 | 20 |

TABLE 5

Compounds of the general formula V

| Compound number | Structure | CB1 receptor Ki (nM) | CB2 receptor Ki (nM) |
|---|---|---|---|
| 3.2 | 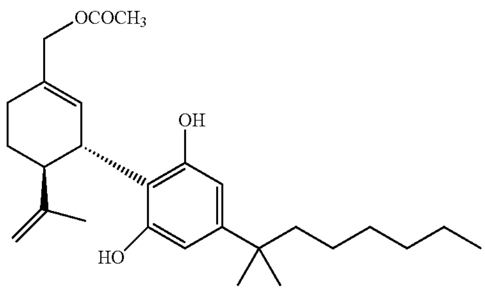 | 69 | 62 |
| 3.10 | 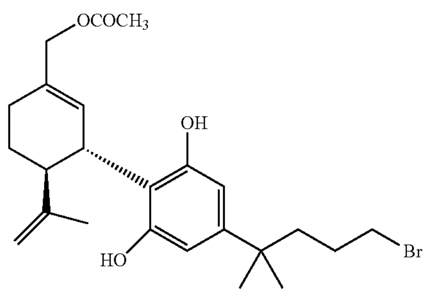 | 620 | 14 |
| 3.11 | 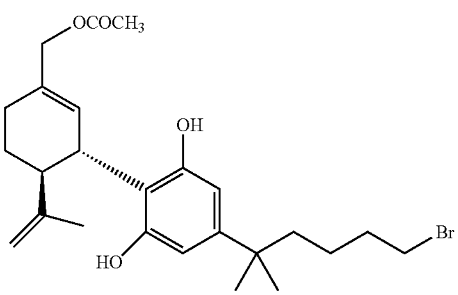 | 191 | 37 |
| 3.12 | 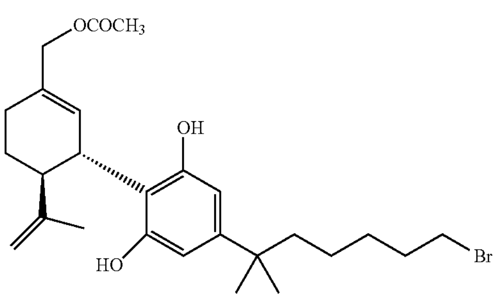 | 29 | 27 |
| 3.13 | 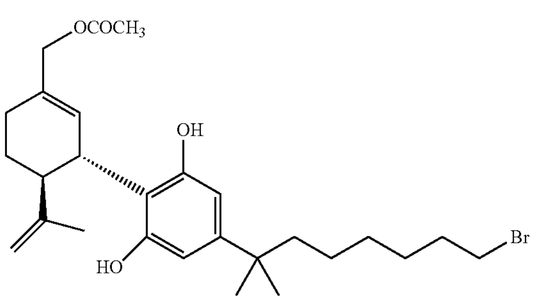 | NT | NT |

TABLE 5-continued

Compounds of the general formula V

| Compound number | Structure | CB1 receptor Ki (nM) | CB2 receptor Ki (nM) |
|---|---|---|---|
| 31.2 | 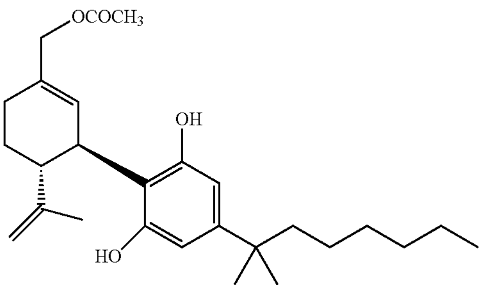 | 221 | 375 |
| 31.13 | 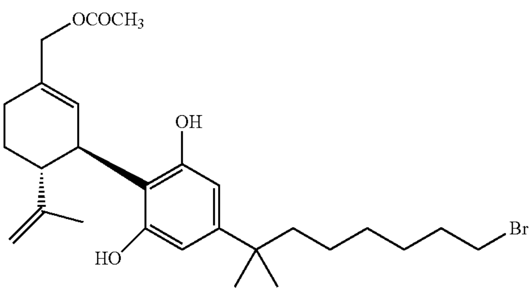 | 205 | 171 |
| 38 | 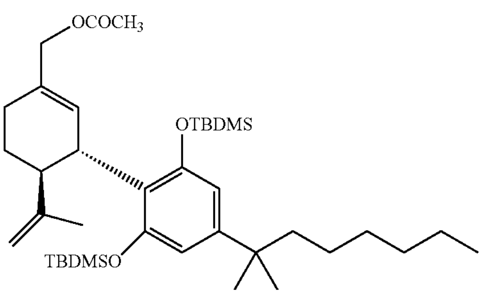 | NT | NT |

NT: Not tested.

TABLE 6

Compounds of the general formula VI

| Compound number | Structure | CB1 receptor Ki (nM) | CB2 receptor Ki (nM) |
|---|---|---|---|
| 71 | 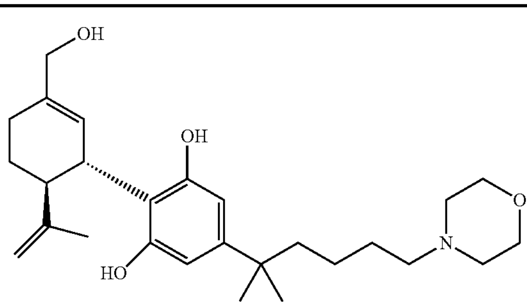 | 6 | 3 |

TABLE 6-continued

Compounds of the general formula VI

| Compound number | Structure | CB1 receptor Ki (nM) | CB2 receptor Ki (nM) |
|---|---|---|---|
| 74 | 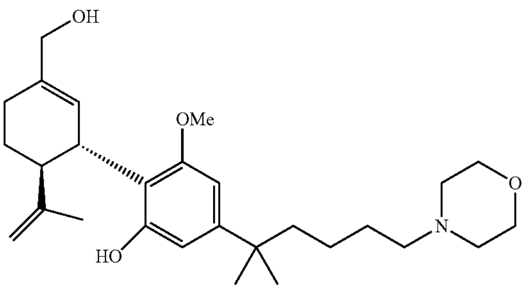 | 70 | 16 |

TABLE 7

Functional Data of Representative Compounds

| Compound number | Structure | Functional Potency (EC$_{50}$) and % Efficacy | Functional Activity |
|---|---|---|---|
| 4.6 | 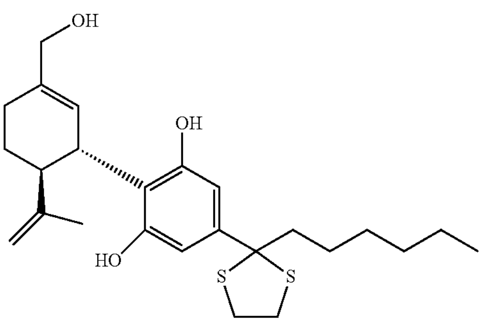 | 267 nM (84%) | Agonist at CB1 |
| 4.4 | 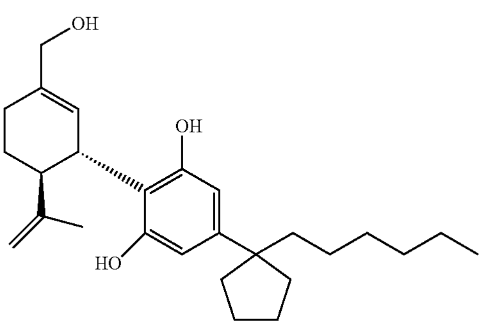 | 17 nM (81%) | Agonist at CB1 |
| 4.3 | 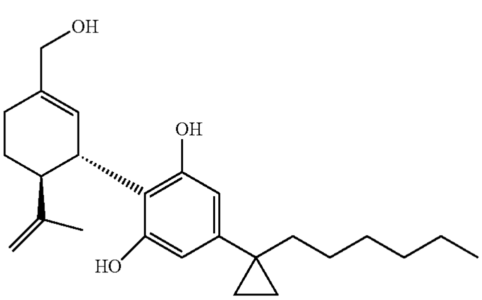 | 1.6 nM (58%)<br>12 nM (35%) | Agonist at CB1<br>Partial agonist at CB2 |

TABLE 7-continued

Functional Data of Representative Compounds

| Compound number | Structure | Functional Potency (EC$_{50}$) and % Efficacy | Functional Activity |
|---|---|---|---|
| 34 | 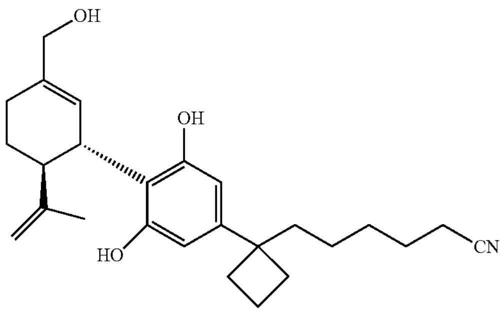 | 3.2 nM (83%) | Agonist at CB1 |
| 74 | 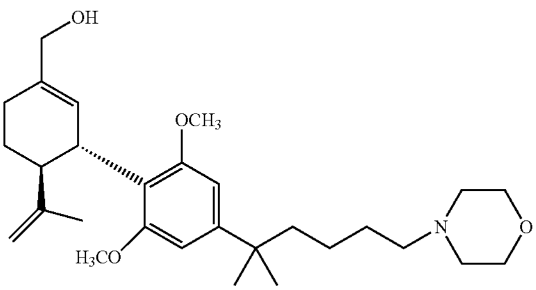 | 50.4 nM (51%)<br>6.7 nM (28%) | Agonist at CB1<br>Partial agonist at CB2 |
| 71 | 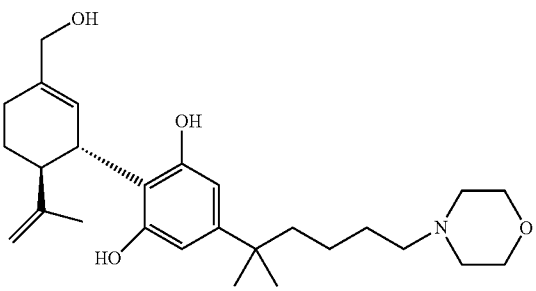 | 1.4 nM (88%)<br>0.4 nM (42%) | Agonist at CB1<br>Partial agonist at CB2 |
| 40.6 | 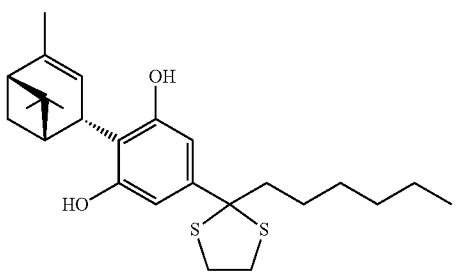 [SMILES: CCCCCCC1(c2cc(O)c([C@H]3C=C(C)[C@H]4C[C@@H]3C4(C)C)c(O)c2)SCCS1] | 21 nM (38%)<br>8.7 nM (38%) | Partial agonist at CB1<br>Partial agonist at CB2 |

A. Resorcinol Synthesis.

Resorcinol compounds 1.1 and 1.2 (shown in Scheme 5) were commercially available.

Resorcinol compound 1.3 (shown in Scheme 5) was synthesized in eight steps starting from commercially available 3,5-dimethoxybenzaldehyde, by a method disclosed in Papahatjis et al. *Bioorg. Med. Chem. Lett.* (2002) 12: 3583-3586, and in Papahatjis et al. *Chem. Lett.* (2001): 192-192, the contents of each of which are hereby incorporated by reference.

Resorcinol compound 1.4 (shown in Scheme 5) was synthesized in eight steps starting from commercially available 3,5-dimethoxybenzaldehyde, by a method disclosed in Papahatjis et al. *J. Med. Chem.* (2003) 46: 3221-3229, the content of which is hereby incorporated by reference.

Resorcinol compound 1.5 (shown in Scheme 5) was synthesized in seven steps starting from commercially available 3,5-dimethoxybenzaldehyde, by a method disclosed in Papahatjis et al. *J. Med. Chem.* (2007) 50: 4048-4060, and in Nikas et al. *J. Med. Chem.* (2010) 53: 6996-7010, the contents of each of which are hereby incorporated by reference.

Resorcinol compound 1.6 (shown in Scheme 5) was synthesized in four steps starting from commercially available 3,5-dimethoxybenzaldehyde, by the method disclosed in Papahatjis et al. *J. Med. Chem.* (1998) 41: 1195-1200, the content of which is hereby incorporated by reference.

Resorcinol compounds 1.7 and 1.8 (shown in Scheme 5) were synthesized in nine steps each, starting from commercially available 3,5-dimethoxybenzaldehyde, by a method disclosed in Nikas et al. *J. Med. Chem.* (2010) 53: 6996-7010, the content of which is hereby incorporated by reference.

Resorcinol compound 1.9 (shown in Scheme 5) was synthesized by the method disclosed in Lu et al. *J. Med. Chem.* (2005) 48: 4576, and in Dominianni et al. *J. Org. Chem.* (1977) 42: 344, the contents of each of which are hereby incorporated by reference.

Resorcinol compounds 1.11, 1.12, and 1.13 (shown in Scheme 1) were synthesized in five steps by the method depicted in Scheme 1 starting from commercially available 3,5-dimethoxyphenylacetonitrile (5). Similarly, resorcinol compound 1.10 was synthesized from compound 5.

Scheme 1

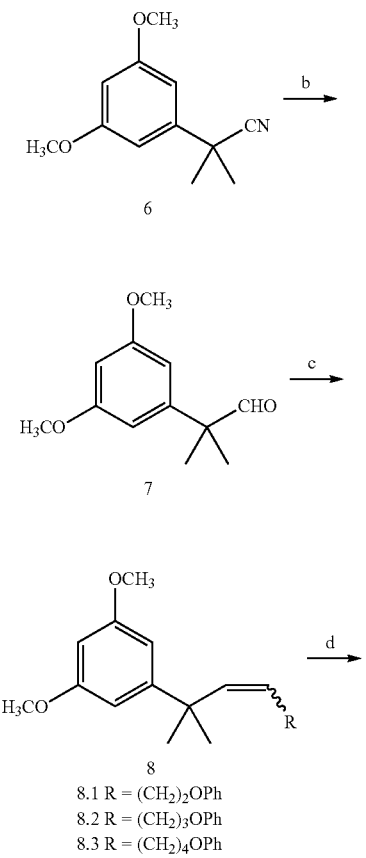

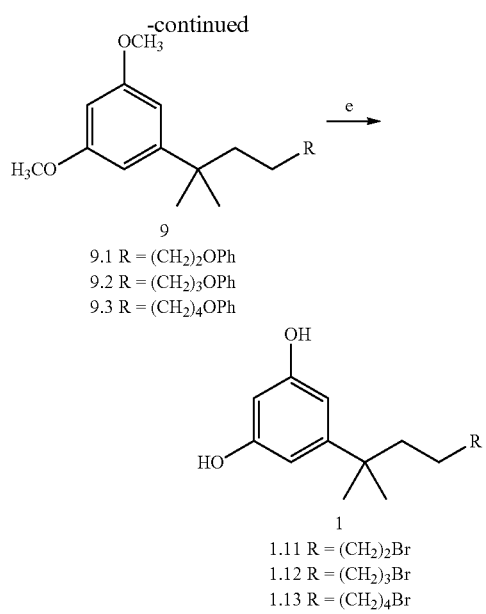

Reagents and conditions: (a) CH₃I, NaH, DMF, 0° C. to r t, 2 h, 97%;
(b) DIBAL—H, CH₂Cl₂, -78° C., 0.5 h, 75%; (c) Br⁻⁺PPh₃(CH₂)ₙOPh (n = 3, 4, 5), n-BuLi, THF, -78° C., 30 min, then addition of 7, -78° C. to r t, 2 h, 93% (8.1), 92% (8.2), 87% (8.3); (d) H₂, 10% Pd/C, EtOH, overnight, 89% (9.1), 89% (9.2), 96% (9.3); (e) BBr₃, CH₂Cl₂, -78° C. to r t, 1 day, 85% (1.11), 96% (1.12), 93% (1.13).

Experimental Procedures 2-(3,5-Dimethoxyphenyl)-2-methylpropanenitrile (compound 6)

A mixture of 3,5-dimethoxyphenyl acetonitrile (10 g, 56.43 mmol) and methyl iodide (10.5 mL) in anhydrous DMF (280 mL) under an argon atmosphere was added dropwise (via cannula) to a solution of sodium hydride (4.06 g, 169.20 mmol) in 30 mL DMF at 0° C. The mixture was warmed to room temperature and stirred for 1.5 hours. Upon completion, the reaction mixture was quenched by the addition of saturated aqueous NH₄Cl and diluted with diethyl ether. The organic layer was separated and the aqueous phase was extracted with diethyl ether. The combined organic layer was washed with brine and dried (MgSO₄) and the solvent was evaporated under reduced pressure. The residue was purified by flash column chromatography on silica gel (10-30% ethyl acetate in hexanes) to afford 11.3 g (98% yield) of compound 6 as a viscous oil. ¹H NMR (500 MHz, CDCl₃) δ 6.61 (d, J=2.0 Hz, 2H, 2-H, 6-H, ArH), 6.27 (t, J=2.0 Hz, 1H, 4-H, ArH), 3.81 (s, 6H, OMe), 1.70 (s, 6H, C(CH₃)₂C).

2-(3,5-Dimethoxyphenyl)-2-methylpropanal (compound 7)

To a solution of 6 (7.67 g, 37.36 mmol) in anhydrous CH₂Cl₂ (373 mL) at -78° C., under an argon atmosphere was added 1M solution of DIBAL-H in toluene (93.5 mL) dropwise. The reaction mixture was stirred for 20 min and then quenched by dropwise addition of potassium sodium tartrate (10% solution in water) at -78° C. Following the addition, the mixture was warmed to room temperature, stirred for an additional 50 minutes and then diluted with ethyl acetate. The organic phase was separated and the aqueous phase extracted with ethyl acetate. The combined organic layer was washed with brine, dried (MgSO$_4$), and the solvent was evaporated under reduced pressure. The crude product was purified by flash chromatography on silica gel (10-35% ethyl acetate in hexanes) to give 5.85 g (75% yield) of 7 as viscous oil. $^1$H NMR (500 MHz, CDCl$_3$) δ 9.46 (s, 1H, —CHO), 6.40 (d, J=2.0 Hz, 2H, 2-H, 6-H, ArH), 6.39 (t, J=2.0 Hz, 1H, 4-H, ArH), 3.78 (s, 6H, OMe), 1.43 (s, 6H, —C(CH$_3$)$_2$—).

(3-Phenoxypropyl)triphenylphosphonium bromide

A mixture of 3-phenoxypropyl bromide (11.3 g, 52.5 mmol) and triphenylphosphine (16.5 g, 63.0 mmol) in anhydrous toluene (65 mL) was refluxed for two days under argon. The reaction mixture was cooled to room temperature, and the precipitating product was isolated by filtration under reduced pressure as a white microcrystalline solid in 85% yield (21.37 g). m p=154-156° C. $^1$H NMR (500 MHz, CDCl$_3$) δ 7.87 (dd, J=12.5 Hz, J=7.5 Hz, 6H, —PPh$_3$), 7.79 (td, J=7.5 Hz, J=2.0 Hz, 3H, —PPh$_3$), 7.69 (td, J=7.5 Hz, J=3.5 Hz, 6H, —PPh$_3$), 7.24 (t, J=7.5 Hz, 2H, 3-H, 5-H, —OPh), 6.92 (t, J=7.5 Hz, 1H, 4-H, —OPh), 6.85 (d, J=9.0 Hz, 2H, 2-H, 6-H, —OPh), 4.33 (t, J=5.5 Hz, 2H, —CH$_2$OPh), 4.10 (dt, J=13.0 Hz, J=7.5 Hz, 2H, —CH$_2$PPh$_3$), 2.27-2.19 (m, 2H).

(4-Phenoxybutyl)triphenylphosphonium bromide

The synthesis was carried out analogous to the preparation of (3-phenoxypropyl)triphenylphosphonium bromide, using 4-phenoxybutyl bromide, (5.0 g, 21.82 mmol) and triphenylphosphine (6.86 g, 26.18 mmol) in anhydrous toluene (27 mL) and gave 6.6 g of white microcrystalline solid, (m p=185-186° C.) in 62% yield. $^1$H NMR (500 MHz, CDCl$_3$) δ 7.86 (dd, J=13.0 Hz, J=7.5 Hz, 6H, —PPh$_3$), 7.77 (td, J=7.5 Hz, J=2.0 Hz, 3H, —PPh$_3$), 7.67 (td, J=7.5 Hz, J=3.5 Hz, 6H, —PPh$_3$), 7.25 (t, J=8.0 Hz, 2H, 3-H, 5-H, —OPh), 6.92 (t, J=8.0 Hz, 1H, 4-H, —OPh), 6.82 (d, J=8.0 Hz, 2H, 2-H, 6-H, —OPh), 4.09 (t, J=5.3 Hz, 2H, —CH$_2$OPh), 4.01 (dt, J=12.6 Hz, J=8.1 Hz, 2H, —CH$_2$PPh$_3$), 2.25 (qt, J=6.5 Hz, 2H), 1.93-1.85 (m, 2H).

(5-Phenoxypentyl)triphenylphosphonium bromide

The synthesis was carried out analogous to the preparation of (3-phenoxypropyl)triphenylphosphonium bromide using 5-phenoxypentyl bromide (4.73 g, 19.33 mmol) and triphenylphosphine (6 g, 23.19 mmol) in anhydrous toluene (60 mL) and gave 6.6 g of white microcrystalline solid, (m p=174-176° C.) in 74% yield. $^1$H NMR (500 MHz, CDCl$_3$) δ 7.86 (dd, J=12.7 Hz, J=8.3 Hz, 6H, —PPh$_3$), 7.78 (td, J=8.3 Hz, J=1.0 Hz, 3H, —PPh$_3$), 7.68 (td, J=8.3 Hz, J=3.5 Hz, 6H, —PPh$_3$), 7.24 (t, J=8.0 Hz, 2H, 3-H, 5-H, —OPh), 6.91 (t, J=8.0 Hz, 1H, 4-H, —OPh), 6.78 (d, J=8.0 Hz, 2H, 2-H, 6-H, —OPh), 3.96-3.86 (t and dt overlapping, 4H, —CH$_2$OPh, —CH$_2$PPh$_3$), 1.90-1.79 (m, 4H), 1.77-1.69 (m, 2H).

(Z)-3,5-Dimethoxy-1-(2-methyl-6-phenoxyhex-3-en-2-yl)benzene (compound 8.1)

To a stirred suspension of (3-phenoxypropyl)triphenylphosphonium bromide (13.7 g, 28.8 mmol) in dry THF (90 mL) at −78° C., under an argon atmosphere was added n-butyl lithium (11.5 mL, 28.8 mmol, 2.5 M in hexanes). Stirring was continued for 30 minutes to ensure complete formation of the orange phosphorane. A solution of aldehyde 7 (4 g, 19.20 mmol) in 5 mL THF was added dropwise to the resulting slurry, at −78° C. The reaction was stirred for 2 hours at room temperature and upon completion (TLC) was quenched by the addition of saturated aqueous NH$_4$Cl. The organic layer was separated and the aqueous phase was extracted with diethyl ether. The combined organic layer was washed with brine and dried (MgSO$_4$) and the solvent was evaporated under reduced pressure. The residue was purified by flash column chromatography on a silica gel (5-15% ethyl acetate in hexanes) to give 5.82 g (93% yield) compound 8.1 as colorless oil. $^{13}$C NMR (125 MHz, CDCl$_3$) δ 161.22 (>C=C(-)—O—), 159.33 (>C=C(-)—O—), 153.33 (>C=C<), 142.01 (>C=C<), 129.58 (>C=C<), 126.34 (>C=C<), 121.02 (>C=C<), 114.23 (>C=C<), 105.03 (>C=C<), 97.44 (>C=C<), 67.32 (—CH$_2$—O—), 55.73 (—OCH$_3$), 40.07, 31.83, 28.72.

(Z)-3,5-Dimethoxy-1-(2-methyl-7-phenoxyhept-3-en-2-yl)benzene (compound 8.2)

The synthesis was carried out as described for 8.1 using (7 g, 14.4 mmol) (4-phenoxybutyl)triphenylphosphonium bromide, 7 (2 g, 9.60 mmol), (5.7 mL, 14.4 mmol, 2.5M in hexanes) n-butyllithium in anhydrous THF (45 mL). The crude product obtained after work up was purified by flash column chromatography on silica gel (5-15% ethyl acetate in hexanes) to give 3 g (92% yield) of compound 8.2 as a colorless oil. $^1$H NMR (500 MHz, CDCl$_3$) δ 7.25 (m as t J=7.0 Hz, 2H), 6.90 (m as t, J=7.0 Hz, 1H), 6.81 (m as d, J=7.0 Hz, 2H), 6.56 (d, J=2.5 Hz, 2H), 6.28 (t, J=2.5 Hz, 1H), 5.69 (dt, J=11.0 Hz, J=1.5 Hz, 1H), 5.31 (dt, J=11.0 Hz, J=7.8 Hz), 3.76 (s, 6H), 3.70 (t, J=6.5 Hz, 2H), 1.83 (dtd, J=6.7 Hz, J=6.7 Hz, J=2.0 Hz, 2H), 1.64 (m, 2H), 1.34 (s, 6H).

(Z)-3,5-Dimethoxy-1-(2-methyl-8-phenoxyoct-3-en-2-yl)benzene (compound 8.3)

The synthesis was carried out as described for 8.1 using (14.5 g, 28.8 mmol) (4-phenoxybutyl)triphenylphosphonium bromide, 7 (4 g, 19.2 mmol), (11.5 mL, 28.8 mmol, 2.5M in hexanes) n-butyllithium in anhydrous THF (95 mL). The crude product obtained after work up was purified by flash column chromatography on silica gel (5-15% ethyl acetate in hexanes) to give compound 8 (87% yield) of 8.3 as a colorless oil. $^1$H NMR (500 MHz, CDCl$_3$) δ 7.26 (m as t, J=7.5 Hz, 2H), 6.91 (m as t, J=7.5 Hz), 6.83 (m as d, J=7.5 Hz, 2H), 6.55 (d, J=2.5 Hz), 6.27 (t, J=2.5 Hz, 1H), 5.65 (dt, J=11.0 Hz, J=1.5 Hz), 5.29 (dt, J=11.0 Hz, J=7.8 Hz), 3.79-3.73 (t and s overlapping, 8H), 1.71 (dtd, 2H, 4'-H), 1.56 (qt, 2H), 1.39 (s, 6H), 1.31 (qt, 2H).

3,5-Dimethoxy-1-(2-methyl-6-phenoxyhexan-2-yl)benzene (compound 9.1)

To a solution of 8.1 (5.85 g, 17.92 mmol) in EtOH (20 mL) was added 10% Pd/C (3 g, 17% w/w) and the resulting suspension stirred vigorously under hydrogen atmosphere, overnight at room temperature. The catalyst was removed by filtration through Celite, and the filtrate was evaporated under reduced pressure to afford 5.2 g (89% yield) of the product 9.1 as colorless oil, which was used in the next step without further purification. $^{13}$C NMR (100 MHz, CDCl$_3$) δ 160.47 (C3 and C5 of Ph(OMe)$_2$), 159.09 (C1 of OPh), 152.34 (C1 of Ph(OMe)$_2$), 129.36 (C3 and C5 of OPh), 120.42 (C4 of OPh), 114.49 (C2 and C6 of OPh), 104.68 (C2 and C6 of Ph(OMe)$_2$), 96.60 (C2 of Ph(OMe)$_2$), 67.82 (C5'), 55.21 (—OMe), 44.40 (C2'), 37.97 (—C(CH₃)—), 29.17 (—C(CH₃)—), 28.96 (—C(CH₃)—), 26.72 (C4' or C3'), 24.48 (C3' or C4').

3,5-Dimethoxy-1-(2-methyl-7-phenoxyheptan-2-yl)benzene (compound 9.2)

The synthesis was carried out as described for 9.1 using 8.2 (1.36 g, 4.0 mmol) and 10% Pd/C (680 mg, 17% w/w) in EtOH (33 mL) and gave 1.21 g (89% yield) of product 9.2 as a colorless oil which was used in the next step without further purification. $^1$H NMR (500 MHz, CDCl₃) δ 7.25 (m as t, J=7.5 Hz, 2H), 6.91 (m as t, J=7.5 Hz), 6.86 (m as d, J=7.5 Hz, 2H), 6.49 (d, J=2.5 Hz, 2H) 6.30 (t, J=2.5 Hz, 1H), 3.88 (t, J=7.0 Hz), 3.78 (s, 6H), 1.74-1.68 (m, 2H), 1.62-1.57 (m, 2H), 1.4-1.33 (m, 2H), 1.26 (s, 6H), 1.17-1.11 (m, 2H).

3,5-Dimethoxy-1-(2-methyl-8-phenoxyoctan-2-yl)benzene (compound 9.3)

The synthesis was carried out as described for 9.1 using 8.3 (8 g, 22.5.0 mmol) and 10% Pd/C (3.83 mg, 17% w/w) in EtOH (188 mL) and gave 7.7 g (96% yield) of 9.3 as a colorless oil which was used in the next step without further purification.

5-(6-Bromo-2-methylhexan-2-yl)resorcinol (compound 1.11)

To a stirred solution of 9.1 (5.2 g, 15.83 mmol) in dry CH₂Cl₂ (500 mL), at −78° C., under an argon atmosphere, was added boron tribromide (6 mL, 63.3 mmol). Following the addition, the reaction mixture was gradually warmed to room temperature and the stirring was continued at that temperature until completion of the reaction (12 h). The reaction mixture was then poured into ice-water, the mixture was warmed to room temperature and volatiles were removed in vacuo. The residue was diluted with ethyl acetate and washed with saturated NaHCO₃ solution, water and brine. The organic layer was dried (MgSO₄), filtered and concentrated under reduced pressure. Purification by flash column chromatography on silica gel (40% ethyl acetate in hexanes) afforded 3.84 g (85% yield) of 1.11 as a white foam. $^1$H NMR (500 MHz, CDCl₃) δ 6.38 (d, J=2.0 Hz, 2H) 6.18 (t, J=2.0 Hz, 1H), 4.85 (s, 2H), 3.33 (t, J=7.0 Hz, 2H), 1.79-1.73 (m, 2H), 1.56-1.52 (m, 2H), 1.25-1.16 (s and m overlapping, 8H).

5-(7-Bromo-2-methylhept-2-yl)resorcinol (compound 1.12)

The synthesis was carried out as described for 1.11 using 9.2 (625 mg, 1.82 mmol) and boron tribromide (4.5 mL, 1M solution in CH₂Cl₂) in anhydrous CH₂Cl₂ (75 mL). The crude product obtained after work up was purified by flash column chromatography on silica gel (50% ethyl acetate in hexanes) to give 527 mg (96% yield) of pure 1.12 as a slightly brown viscous oil. $^1$H NMR (500 MHz, CDCl₃) δ 6.38 (d, J=2.0 Hz, 2H) 6.18 (t, J=2.0 Hz, 1H), 5.15 (br s, 2H), 3.34 (t, J=7.0 Hz, 2H), 1.80-1.75 (m, 2H), 1.55-1.50 (m, 2H), 1.35-1.28 (m, 2H), 1.23 (s, 6H), 1.10-1.02 (m, 2H).

5-(8-Bromo-2-methyloct-2-yl)resorcinol (compound 1.13)

The synthesis was carried out as described for 1.11 using 9.3 (8 g, 22.44 mmol) and boron tribromide (8.5 mL, 89.76 mmol) in anhydrous CH₂Cl₂ (350 mL). The crude product obtained after work up was purified by flash column chromatography on silica gel (50% ethyl acetate in hexanes) to give 6.57 g (93% yield) of pure 1.13 as a slightly brown viscous oil.

Those skilled in the art will understand that numerous variations to the synthetic process shown in Scheme 1 can be used to provide other compounds disclosed herein using no more than ordinary skill. For example, by eliminating the step reducing the double bond in compound 8, unsaturated analogs can readily be produced. Further, analogs comprising triple bonds can also be synthesized. See, e.g., Papahatjis, D. P. et al. *J. Med. Chem.* (1998), 41, 1195; Busch-Petersen, J. et al. *J. Med. Chem.* (1996), 39, 3790, the contents of which are hereby incorporated by reference in their entireties.

Resorcinol compound 1.14 (shown in Scheme 2) was synthesized in eight steps by the method depicted in Scheme 2 starting from commercially available 3,5-dimethoxyphenylacetonitrile.

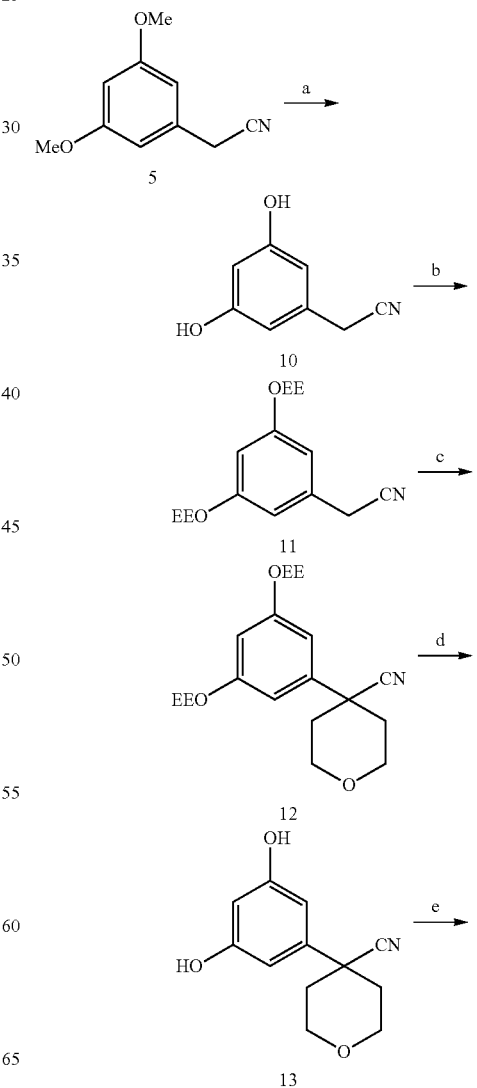

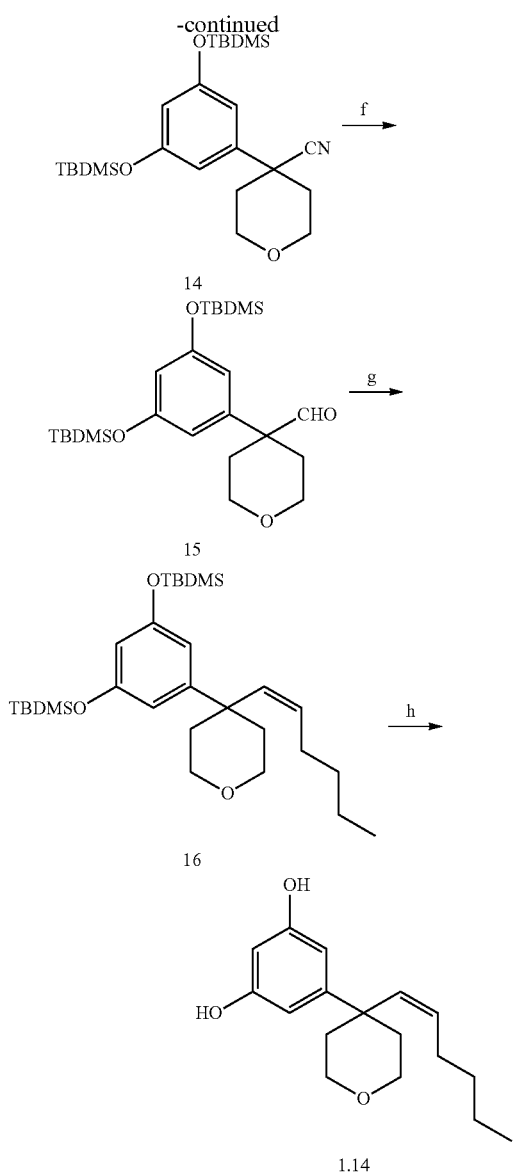

Reagents and conditions: (a) BBr$_3$, CH$_2$Cl$_2$, -78° C. to r t, 2 days, 85%; (b) H$_2$C=CHOCH$_2$CH$_3$, p-TSA, Et$_2$O, 0° C., 1 h, 95%; (c) (Me$_3$Si)$_2$N$^+$K$^-$, Br(CH$_2$)$_2$O(CH$_2$)$_2$Br, THF, 0° C., 1 h, 98%; (d) p-TSA, CH$_3$OH, 25° C., 0.5 h, 91%; (e) imidazole, TBDMSCl, DMF, 2 h, 91%; (f) DIBAL—H, CH$_2$Cl$_2$, -78° C., 2.5 h, 51%; (g) Br$^-$$^+$PPh$_3$(CH$_2$)$_4$CH$_3$, (Me$_3$Si)$_2$N$^+$K$^-$, THF, 0° C., 0.5 h, then addition of 15, 0° C., 10 min, 72%; (h) (n-Bu)$_4$N$^+$F$^-$ THF, 1 h, 98%.

Experimental Procedures 2-(3,5-Dihydroxyphenyl)acetonitrile (compound 10)

To a stirred solution of 5 (2.0 g, 11.28 mmol) in dry CH$_2$Cl$_2$ (125 mL), at -78° C., under an argon atmosphere, was added boron tribromide (3.75 mL, 39.48 mmol). Following the addition, the reaction mixture was gradually warmed to room temperature and the stirring was continued at that temperature until completion of the reaction (2 days). The reaction mixture was then poured into a mixture of aqueous saturated NaHCO$_3$/crushed ice. The mixture was warmed to room temperature and volatiles were removed in vacuo. The residue was diluted with ethyl acetate and washed with saturated NaHCO$_3$ solution, water and brine. The organic layer was dried (MgSO$_4$), filtered and concentrated under reduced pressure. Purification by flash column chromatography on silica gel (40% ethyl acetate in hexanes) afforded 1.42 g (85% yield) of 10 as a white solid, mp 144-146° C. $^1$H NMR (500 MHz, CDCl$_3$/DMSO-d$_6$) δ 8.69 (s, 2H, OH), 6.34 (m, 1H, 2-H), 6.33 (m, 2H, 4-H, 6-H), 3.59 (s, 2H, —CH$_2$CN).

2-[3,5-Bis(1-ethoxyethoxy)phenyl]acetonitrile (compound 11)

To a solution of pre-dried 10 (2.6 g, 17.43 mmol) and p-toluenesulfonic acid (120 mg, 4 mol %), in anhydrous diethyl ether (65 mL) at 0° C., under an argon atmosphere, was added a solution of ethyl vinyl ether (9.2 mL, 95.86 mmol) in anhydrous diethyl ether (10 mL). The reaction mixture was stirred at 0° C. for 1 h and then poured into a vigorously stirring saturated aqueous NaHCO$_3$ at 0° C. The organic phase was separated and the aqueous phase was extracted with diethyl ether. The combined organic layer was washed with brine and dried (MgSO$_4$). Solvent evaporation and purification by flash column chromatography on silica gel (15% ethyl acetate and 2% triethylamine in hexanes) gave 4.86 g (95% yield) of 11 as a viscous oil. $^1$H NMR (500 MHz, CDCl$_3$) δ 6.64 (m, 1H), 6.61 (m, 2H), 5.37 (q, 2H, J=5.5 Hz,), 3.76 (m as quintet, 2H, J=7.0 Hz), 3.67 (s, 2H), 3.55 (m as quintet, 2H, J=7.0 Hz), 1.49 (d, J=5.5 Hz, 6H), 1.22 (t, J=7.0 Hz, 6H).

4-[3,5-Bis(1-ethoxyethoxy)phenyl]tetrahydro-2H-pyran-4-carbonitrile (compound 12)

To a solution of 11 (4.9 g, 16.7 mmol) in dry THF (120 mL) at -16° C., under an argon atmosphere, was added potassium bis-(trimethylsilyl)amide (10 g, 50.1 mmol). The mixture was stirred at the same temperature for 5 min, and then a solution of 2-bromoethyl ether (2.5 mL, 20.0 mmol) in dry THF (10 mL) was added over a period of 5 min. Following the addition, the reaction was stirred for 1 h at -16° C. and then quenched by the addition of saturated aqueous NH$_4$Cl. The mixture was diluted with EtOAc, the organic layer separated, and the aqueous phase extracted with EtOAc. The combined organic layer was washed with brine and dried (MgSO$_4$) and the solvent evaporated under reduced pressure. Purification by flash column chromatography (30% ethyl acetate in hexanes) afforded 6 g (98% yield) of the compound 12 as a colorless oil. $^1$H NMR (500 MHz, CDCl$_3$) δ 6.77 (d, J=2.5 Hz, 2H), 6.68 (dd, J=2.5 Hz, J=2.5 Hz, 1H), 5.38 (q, J=5.5 Hz, 2H), 4.07 (dd, J=14.0 Hz, J=4.0 Hz, 2H), 3.89 (ddd, J=14.0 Hz, J=12.0 Hz, J=2.0 Hz, 2H), 3.81-3.72 (m, 2H), 3.61-3.52 (m, 2H,), 2.14-2.06 (m, 2H), 2.05-2.0 (m as d, J=11.5 Hz, 2H), 1.51 (d, J=5.0 Hz, 6H), 1.22 (t, J=7.0 Hz, 6H).

4-(3,5-Dihydroxyphenyl)tetrahydro-2H-pyran-4-carbonitrile (compound 13)

Compound 12 (3.26 g, 8.96 mmol) was dissolved in methanol (44 mL), and p-toluenesulfonic acid (61.6 mg, 4 mol %) was added. The reaction mixture was stirred at 25° C. for 0.5 h. The methanol was removed in vacuo, and the residue was dissolved in ethyl acetate and washed with NaHCO$_3$/brine (1:1). The aqueous phase was extracted twice with ethyl acetate. The combined organic phase was washed with brine and dried (MgSO$_4$). Solvent evaporation and purification by flash column chromatography (30% ethyl acetate in hexanes) gave 1.78 g of 13 (91% yield) as a white solid. m p=210-212° C.

4-[3,5-Bis(tert-butyldimethylsilyloxy)phenyl]tetrahydro-2H-pyran-4-carbonitrile (compound 14)

To a solution of 13 (1.32 g, 6.02 mmol) in DMF (30 mL) was added imidazole (3.1 g, 45.75 mmol). To this mixture was added TBDMSCl (5.45 g, 36.12 mmol) and the reaction was allowed to stir at 25° C. for 2 hours. The reaction was quenched with water and extracted with diethyl ether. The ethereal layer was washed with brine and dried (MgSO$_4$). Solvent evaporation and purification by flash column chromatography (10-25% diethyl ether in hexanes), afforded 2.45 g of compound 14 (91% yield) as a white solid. mp=122-123° C.

4-[3,5-Bis(tert-butyldimethylsilyloxy)phenyl]tetrahydro-2H-pyran-4-carboxaldehyde (compound 15)

To a solution of 14 (0.428 g, 0.955 mmol) in anhydrous CH$_2$Cl$_2$ (9.5 mL) at −78° C., under an argon atmosphere was added 1M solution of DIBAL-H in toluene (2.5 mL) dropwise. The reaction mixture was stirred for 2.5 h and then quenched by dropwise addition of potassium sodium tartrate (10% solution in water) at −78° C. Following the addition, the mixture was warmed to room temperature, stirred for an additional 50 minutes and then diluted with ethyl acetate. The organic phase was separated and the aqueous phase extracted with ethyl acetate. The combined organic layer was washed with brine, dried (MgSO$_4$), and the solvent was evaporated under reduced pressure. The crude product was purified by flash chromatography on silica gel (0-10% diethyl ether in hexanes) to give 217 mg of 15 (51% yield) as white foam. $^1$H NMR (500 MHz, CDCl$_3$) δ 9.35 (s, 1H), 6.37 (d, J=2.5 Hz), 6.27 (t, J=2.5 Hz), 3.89 (ddd, J=13.5 Hz, J=4.0 Hz, J=4.0 Hz, 2H), 3.57 (ddd, J=13.5 Hz, J=12.0 Hz, J=2.5 Hz, 2H), 2.32-2.26 (m as d, J=13.5 Hz, 2H), 2.02 (ddd, J=13.5 Hz, J=10.5 Hz, J=4.5 Hz, 2H), 0.96 (s, 18H), 0.18 (s).

3,5-[Bis(tert-butyldimethylsilyl)oxy]-1-[4-(1,2-cis-hexen-1-yl)tetrahydro-2H-pyran-4-yl]-benzene (compound 16)

To a stirred suspension of pentyltriphenylphosphonium bromide (1.58 g, 3.82 mmol, dried at 50° C./0.1 mmHg for 7 h) in dry THF (9.5 mL) at 0° C., under an argon atmosphere was added potassium bis(trimethylsilyl)amide (7.01 g, 35.6 mmol). The mixture was warmed to 10 OC and stirred for an additional 30 min to ensure complete formation of the orange (butylmethylene)triphenylphosphorane. To the resulting slurry, at the same temperature, was added dropwise a solution of 15 (0.245 g, 0.555 mmol) in dry THF (2 mL). The reaction was stirred for 10 min and upon completion was quenched by the addition of saturated aqueous NH$_4$Cl. The organic layer was separated, and the aqueous phase was extracted with diethyl ether. The combined organic layer was washed with brine and dried (MgSO$_4$), and the solvent was evaporated under reduced pressure. Purification by flash column chromatography on silica gel (5-25% diethyl ether in hexanes) gave 178 mg of compound 16 (72% yield) as colorless oil. $^1$H NMR (500 MHz, CDCl$_3$) δ 6.46 (d, J=2.0 Hz, 2H), 6.17 (t, J=2.0 Hz, 1H), 5.71 (dt, J=12.0 Hz, J=1.5 Hz, 1H), 5.42 (dt, J=12.0 Hz, J=7.5 Hz, 1H), 3.83 (ddd, J=13.5 Hz, J=4.0 Hz, J=4.0 Hz, 2H), 3.73 (ddd, J=13.5 Hz, J=11.0 Hz, J=2.0 Hz, 2H), 2.04-1.96 (m, 2H), 1.88-1.82 (m, 2H), 1.64 (dt, J=7.5 Hz, 2H), 1.12-1.06 (m, 4H), 0.96 (s, 18H), 0.75 (t, J=7.0 Hz, 3H), 0.17 (s).

5-[4-(1,2-cis-Hexen-1-yl)tetrahydro-2H-pyran-4-yl] resorcinol (compound 1.14)

To a solution of 16 (248 mg, 0.491 mmol) in THF (13 mL) at room temperature under an argon atmosphere was added tetra-n-butylammonium fluoride (0.568 mL, 1M solution in THF, 1.96 mmol). The reaction was stirred for 0.5 h and upon completion it was quenched with water and extracted with diethyl ether. The organic phase was washed with water and brine, dried (MgSO$_4$) and concentrated in vacuo. Purification by flash column chromatography on silica gel (30-45% ethyl acetate in hexanes) gave 134 mg (98% yield) as a white solid 1.14. m p=104-105° C.

Those skilled in the art will understand that numerous variations to the synthetic process shown in Scheme 2 can be used to provide other compounds disclosed herein using no more than ordinary skill. For example, the hydroxyl groups of 10 can be readily converted to halogens, either selectively or globally, by halogenation reactions. See, e.g., Prugh, J. D. et al. *J. Med. Chem.* (1990), 33, 758; Wiley, G. A. et al. *J. Am. Chem. Soc.* (1964), 86, 964; Bay, A. et al. *J. Org. Chem.* (1990) 55, 3415, the contents of which are incorporated herein by reference in their entireties. These aryl halides provide a convenient intermediate for a number of transformations which introduce structural diversity at these positions. By way of nonlimiting examples, halogens can be converted to nitriles, either selectively or globally. See, e.g., Zanon, J. et al. *J. Am. Chem. Soc.* (2003) 125, 2890; Ellis, G. P. et al. *Chem. Rev.* (1987), 87, 779, the contents of which are incorporated herein by reference in their entireties In turn, the resultant aryl nitriles can then be converted to the corresponding carboxylic acids, amides or carboxamides by nitrile hydrolysis, for example by treatment with alcohols under acidic conditions to provide the carboxylate, optionally followed by amidation to result in an amide or carboxamide. See, e.g., Larock, R. C. in Comprehensive Organic Transformations, 2$^{nd}$ Edition. John Wiley and Sons, Inc. 1999, pp. 1986-1990, the contents of which are incorporated herein by reference in their entirety. Aryl halides can also be converted to nucleophilic moieties by introduction of organolithium or magnesium to form a Grignard reagent, and these reagents can be used in a variety of reactions to introduce further structural diversity. Alternatively, these reagents can be treated with water to replace the metallic group with a proton. The phenolic groups can also be directly dehydroxylated, either selectively or globally, to result in the same proton substitution at the former site of the aryl halide. See, e.g., Musliner, W. J. et al. *Organic Syntheses Coll. Vol.* 6 (1988), p. 150; Rossi, R. A. et al. *J. Org. Chem.* (1973), 38, 2314; Kogan, V. et al. *Tetrahedron Lett.* (2006), 47, 7515, the contents of which are incorporated herein by reference in their entireties. Those skilled in the art will further understand that similar transformations can be performed on phenolic groups shown in any of the schemes disclosed herein.

In addition, the phenolic groups of 10 can be converted to amines, either selectively or globally via the corresponding sulfonate or halide intermediate using Ullman or Buchwald-Hartwig amination. See, e.g., Surry, D. S. et al. *Chem. Sci.* (2011), 2, 27; Hartwig, J. F. et al. *Acc. Chem. Res.* (2008), 41, 1534; Jiao, J. et al. *J. Org. Chem.* (2011), 76, 1180; Monnier, F. et al. *Angew. Chem. Int. Ed.* (2009), 48, 6954; Nakamura, Y. et al. *J. Org. Chem.* (2011), 76, 2168, the contents of which are incorporated herein by reference in their entireties. In addition, phenols can be converted to thiophenols, either selectively or globally. See, e.g., Newman, M. S. et al. *Org. Syntheses*, Coll. Vol. 6, (1988), p. 824, the contents of which are incorporated herein by reference in their entirety. Phenols can also be converted to esters by a Steglish esterification reaction. See, e.g., Neises, B. et al. *Angew. Chem. Int. Ed.* (1978), 17, 522; Vestberg, R. et al. *Chem. Mater.* (2004), 16, 2794, the contents of which are incorporated herein by reference in their entireties. Phenols are also readily converted to phosphates, either selectively or globally. See, e.g., Orloff, H. D. et al. *J. Am. Chem. Soc.* (1958), 80, 727; Rossi, R. A. *J. Org. Chem.* (1972), 38, 2314; Purnanand, B. S. et al. *Tetrahedron Lett.* (1989), 30, 1687, the contents of which are incorporated herein by reference in their entireties. Phenols can also be converted to phosphates, by reaction with POCl₃ followed by hydrolysis. Phosphonates, phosphites and phosphonates can also be prepared by reaction with the corresponding phosphorus halide reagent. Alternatively, phosphonates can be formed by reaction with perfluorosulfonates. See, e.g., Lu, X. et al. *Synthesis* (1987), 726; Gaspani, F. et al. *Bioorg. Med. Chem. Lett.* (2000), 10, 1241, the contents of which are incorporated herein by reference in their entireties. Still further, phenols can readily be converted to alkyl ethers by etherification reactions. See, e.g., Larock, R. C. in Comprehensive Organic Transformations, 2$^{nd}$ Edition. John Wiley and Sons, Inc. 1999, pp. 896-897, the contents of which are incorporated herein by reference in their entirety. Those skilled in the art will further understand that similar transformations can be performed on phenolic groups shown in any of the schemes disclosed herein.

B. Chiral Terpenoid Synthon Synthesis.

Optically pure (1R,4R,5R)-2-pinene-4-ol ((+)-cis-verbenol) compound 39 (shown in Scheme 10) was synthesized in eight steps starting from commercially available (1R)-(+)-α-pinene, by a method disclosed in Makriyannis et al. WO 2011/006099 A1, the content of which is hereby incorporated by reference.

Optically pure (1S,4S,5S)-2-pinene-4-ol ((−)-cis-verbenol) compound 42 (shown in Scheme 12) was commercially available.

Chiral terpene acetates compounds 45 (shown in Scheme 13) were synthesized in two steps starting from commercially available (1R)-(+)-nopinone, by a method disclosed in Nikas et al. *Tetrahedron* (2007) 63: 8112-8123, the content of which is hereby incorporated by reference.

Chiral terpene acetates compounds 63 (shown in Scheme 19) were synthesized in five steps starting from commercially available (+)-α-pinene, by a method disclosed in Makriyannis et al. U.S. Pat. No. 7,446,229 B2, the content of which is hereby incorporated by reference.

Chiral monoterpenoid alcohol compound 2 (shown in Scheme 3) was synthesized in six steps starting from commercially available (S)-(−)-perillyl alcohol (17) by the method depicted in Scheme 3.

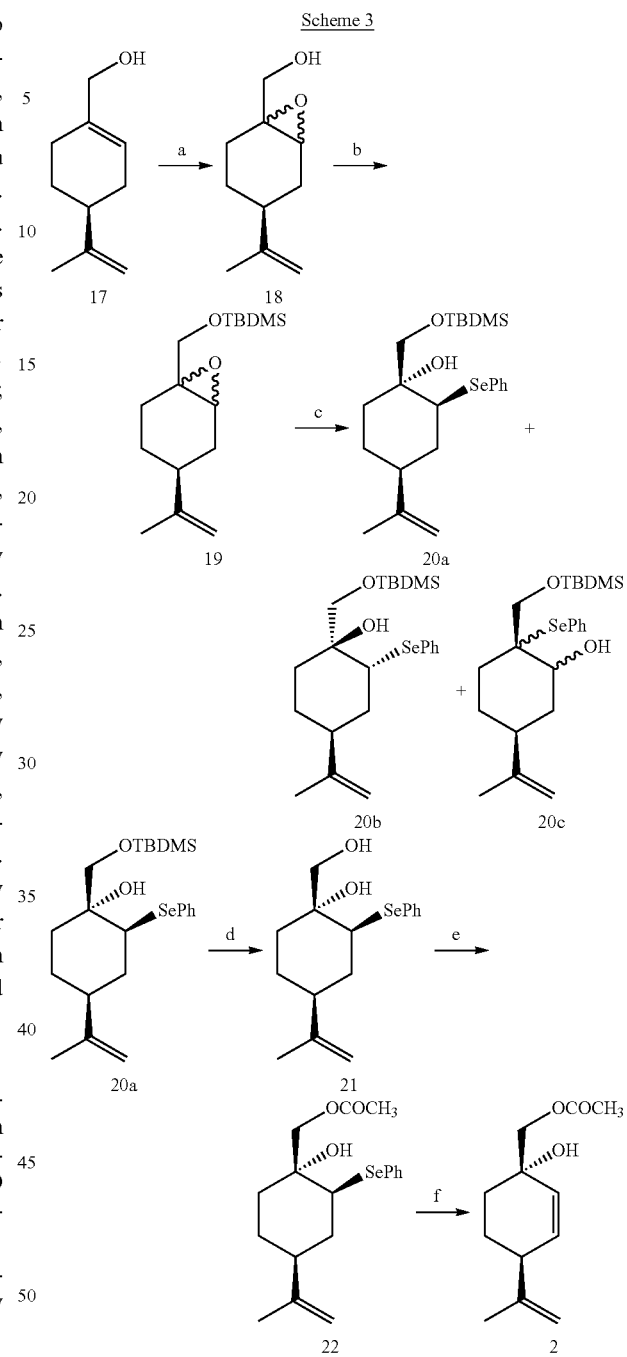

Reagents and conditions: (a) VO(acac)₂, t-BuOOH, toluene, r t, 3 h, 80%; (b) imidazole, TBDMSCl, DMF, r t, overnight, 96%; (c) Ph₂Se₂, NaBH₄, EtOH, 65° C., overnight, 46% (20a), 18% (20b), 16.7% (20c); (d) (n-Bu)₄N⁺F⁻, THF, r t, 4 h, 98%; (e) acetic anhydride, pyridine, CH₂Cl₂, 4 h, r t, 98%; (f) 30% H₂O₂, pyridine, THF, 3 h, r t, then 3 h reflux, 53%.

Experimental Procedures (S)-1,2-Epoxy-8-p-menthen-7-ol (compound 18)

To an ice cooled solution of 17 (10 g, 65.70 mmol) and VO(acac)₂ (300 mg, 1.13 mmol) in 100 mL anhydrous toluene was added tert-butyl hydroperoxide in tert-butyl alcohol (72.20 mmol) dropwise over 15 min. The reaction was allowed to stir at room temperature for 3 hours. On completion, the reaction was quenched with 20% aqueous Na$_2$SO$_3$ and extracted with diethyl ether. The ethereal extract was washed with brine, dried (MgSO$_4$) and concentrated under reduced pressure. The residue was purified by flash chromatography on silica gel (10-30% ethyl acetate in hexanes) to yield 8.87 g (80% yield) of diastereomeric mixture 18 as colorless oil. $^1$H NMR (500 MHz, CDCl$_3$) δ as a diastereomeric mixture 4.74 (m as t, J=1.4 Hz, 1H, =CH$_2$), 4.68 (s, 1H, =CH$_2$), 3.76-3.56 (m, 2H, —CH$_2$OH), 3.35 (m, 1H, —CH$_2$CHOC—), 2.2-2.0 (m, 1H, —CH$_2$CHCH$_2$—), 1.71 (s, 3H, =CCH$_3$), 2.0-1.6 (m, 6H).

(S)-tert-Butyldimethyl[(4-(prop-1-en-2-yl)-7-oxabicyclo[4.1.0]heptan-1-yl)methoxy]silane (compound 19)

To a stirred solution of 18 (7.5 g, 44.61 mmol) in 100 mL DMF was added imidazole (6 g, 89.22 mmol). After 10 minutes, TBDMSCl (7.39 g, 49.07 mmol) was added and stirring was continued for 14 hours. The reaction was quenched with water and extracted with diethyl ether. The ethereal layer was washed with brine, dried over MgSO$_4$ and concentrated. The crude residue was purified by flash column chromatography on silica gel (1-5% diethyl ether in hexanes) to give 7.2 g (96% yield) of 19 as colorless oil. $^1$H NMR (500 MHz, CDCl$_3$) δ as a diastereomeric mixture 4.73 (m as t, J=1.4 Hz, 1H, =CH$_2$), 4.68 (s, 1H, =CH$_2$), 3.62 (br s, 1H), 3.56 (d, J=5.0 Hz, 2H, —CH$_2$O—), 3.13 (br s, 1H), 1.90-2.12 (m, 4H), 1.70-1.20 (m, 6H), 0.88 (s, 9H, C(CH$_3$)$_3$), 0.83 (d, J=6.0 Hz, 3H, CHCH$_3$), 0.82 (d, J=6.0 Hz, 3H, CHCH$_3$), 0.04 (s, 3H, —OSiCH$_3$C(CH$_3$)$_3$), 0.03 (s, 3H —OSiCH$_3$C(CH$_3$)$_3$).

(1R,2S,4S)-1-[(tert-Butyldimethylsilyloxy)methyl]-2-(phenylselanyl)-4-(prop-1-en-2-yl)cyclohexanol (compound 20a)

Diphenyl diselenide (1 g, 3.54 mmol) was dissolved in 25 mL anhydrous ethanol and while stirring at room temperature, solid sodium borohydride (535 mg, 14.16 mmol) was added in portions. After stirring for about an hour, 19 (2.2 g, 7.08 mmol) was added and the reaction was heated overnight at 65° C. The reaction mixture was quenched with aqueous sodium bicarbonate, and extracted with diethyl ether. The organic phase was washed with brine, dried (MgSO$_4$) and concentrated to yield a yellow semisolid material. Flash column chromatography on silica gel (5% diethyl ether in hexanes) gave 20a, (0.71 g, 46%), 20b, (0.28 g, 18%) and 20c, (0.26 g, 17%) as oils. 20a: $^1$H NMR (500 MHz, CDCl$_3$) δ 7.61 (m, 2H, 3-H, 5-H, —SePh), 7.26 (m, 3H, 2-H, 4-H, 6-H, —SePh), 4.68 (m as qt, J=1.5 Hz, 1H, >C=CH$_2$), 4.66 (m, 1H, >C=CH$_2$), 3.90 (d, J=10.0 Hz, 1H, —CH$_2$—O—), 3.60 (d, J=10.0 Hz, 1H, —CH$_2$—O—), 3.34 (s, 1H, OH), 3.31 (dd, J=13.0 Hz, 1H, >CH—C(CH$_3$)=CH$_2$, axial), 2.19-2.13 (m, 1H), 2.08-2.04 (m, 1H), 2.0-1.92 (m, 1H), 1.80-1.72 (m, 2H), 1.67 (s, 3H, >CH—C(CH$_3$)=CH$_2$), 1.57-1.50 (m, 1H), 1.34-1.24 (m, 1H), 0.95 (s, 9H, —C(CH$_3$)$_3$), 0.14 (s, 3H, —OSiCH$_3$C(CH$_3$)$_3$), 0.13 (s, 3H —OSiCH$_3$C(CH$_3$)$_3$); 20b: $^1$H NMR (500 MHz, CDCl$_3$) δ 7.53 (m, 2H, 3-H, 5-H, —SePh), 7.23 (m, 3H, 2-H, 4-H, 6-H, —SePh), 4.69 (m as d, J=1.0 Hz, 1H, >C=CH$_2$), 4.69 (m as qt, J=1.5 Hz, 1H, >C=CH$_2$), 3.80 (d, J=9.5 Hz, 1H, —CH$_2$O—), 3.53-3.48 (m as d, J=8.5 Hz, 2H, —CH$_2$O—), 2.74 (s, 1H, OH), 2.42-2.34 (m, 1H), 2.26-2.19 (m, 1H), 1.85-1.80 (m, 1H), 1.74-1.58 (m and s overlapping, 6H, especially 1.70, s, >CH—C(CH$_3$)=CH$_2$), 1.57-1.50 (m, 1H), 1.34-1.24 (m, 1H), 0.86 (s, 9H, —C(CH$_3$)$_3$), 0.04 (s, 3H —OSiCH$_3$C(CH$_3$)$_3$), 0.03 (s, 3H —OSiCH$_3$C(CH$_3$)$_3$).

(1R,2S,4S)-1-(Hydroxymethyl)-2-(phenylselanyl)-4-(prop-1-en-2-yl)cyclohexanol (compound 21)

To a stirred solution of 20a (10.5 g, 23.88 mmol) in anhydrous THF (150 mL) at 25° C. under an argon atmosphere was added tetra-n-butylammonium fluoride in THF (17.0 mL, 1M solution in THF, 59.71 mmol). Stirring was continued for 4 hours and on completion, the reaction mixture was quenched with water, diluted with diethyl ether and the organic phase was separated. The aqueous layer was extracted with diethyl ether, the combined organic phase was washed with water and brine, dried (MgSO$_4$) and concentrated. The residue was purified by flash column chromatography on silica gel (20-45% ethyl acetate in hexanes) to give 8.5 g (98% yield) of 21 as a white solid. m p=66-68° C. $^1$H NMR (500 MHz, CDCl$_3$) δ 7.60 (m, 2H, 3-H, 5-H, —SePh), 7.29 (m, 3H, 2-H, 4-H, 6-H, —SePh), 4.70 (m as qt, J=1.5 Hz, 1H, >C=CH$_2$), 4.68 (m, 1H, >C=CH$_2$), 3.73 (s, 2H, —CH$_2$OH), 3.36 (dd, J=13.0 Hz, 1H, >CH—C(CH$_3$)=CH$_2$, axial), 2.97 (s, 1H, OH), 2.28-2.24 (m, 1H), 2.23-2.18 (m, 1H), 2.06-1.98 (m, 1H), 1.79-1.71 (m, 2H), 1.68 (s, 3H, >CH—C(CH$_3$)=CH$_2$), 1.48-1.33 (m, 2H).

[(1R,2S,4S)-1-Hydroxy-2-(phenylselanyl)-4-(prop-1-en-2-yl)cyclohexyl]methyl acetate (compound 22)

Acetic anhydride (26 mL) was added to a stirred and ice-cooled solution of 21 (8.43 g, 25.9 mmol) in anhydrous pyridine (12 mL) under argon. The reaction mixture was stirred for 3 hours at room temperature and then quenched with ice water. The mixture was diluted with ethyl acetate, the organic phase was separated, and the aqueous phase was extracted with ethyl acetate. The combined organic layer was washed successively with 0.5N HCl, water and brine and dried (MgSO$_4$). The crude residue was purified by flash column chromatography on silica gel (20-35% ethyl acetate in hexanes) to give 9.4 g (98% yield) of colorless oil 22. $^1$H NMR (500 MHz, CDCl$_3$) δ 7.61 (m, 2H), 7.29 (m, 3H, 2-H), 4.70 (m as qt, J=1.5 Hz, 1H), 4.69 (m as d, J=1.0 Hz), 4.40 (d, J=12.0 Hz), 4.20 (d, J=12.0 Hz, 1H), 3.33 (dd, J=13.5 Hz, J=4.0 Hz, ΣJ=17.5 Hz), 3.02 (s, 1H), 2.25-2.20 (m, 1H), 2.19-2.14 (m and s overlapping, 4H), 2.05-1.98 (m, 1H), 1.81-1.74 (m, 2H), 1.68 (s, 3H), 1.55-1.50 (m, 1H), 1.41-1.31 (m, 1H).

[(1S,4S)-1-Hydroxy-4-(prop-1-en-2-yl)cyclohex-2-enyl]methyl acetate (compound 2)

To a stirred and ice-cooled solution of 22 (1 g, 2.72 mmol) in a mixture of 20 mL THF and 1.5 mL pyridine was added 35% H$_2$O$_2$ (1.4 mL, 43.52 mmol). The reaction mixture was stirred for 3 hours at room temperature to ensure complete formation of the intermediate selenoxide and then the reaction temperature was raised to 65° C. and stirring was continued for 3 hours. The reaction mixture was cooled to 25° C. and diluted with water, ethyl acetate and hexane. The organic layer was separated and the aqueous layer was extracted with ethyl acetate. The combined organic phase was washed with aqueous CuSO$_4$, aqueous saturated NaHCO$_3$ and brine, dried (MgSO$_4$) and concentrated in vacuo. The crude residue was purified by flash chromatography on silica gel (20-45% ethyl acetate in hexanes) to give 300 mg (53% yield) of 2 as a pale orange oil. $^1$H NMR (500 MHz, CDCl$_3$) δ 5.82 (dd, J=10. Hz, J=3.0 Hz, 1H), 5.69 (dd, J=10. Hz, J=2.0 Hz, 1H), 4.80 (m as t, J=1.5 Hz, 1H), 4.66 (br s, 1H), 4.08 (d, J=11.0 Hz, 1H), 4.00 (d, J=11.0 Hz, 1H), 2.82-2.76 (m, 1H), 2.12 (s, 3H), 2.05 (s, 1H), 1.96-1.90 (m, 1H), 1.85 (dt, J=9.0 Hz, J=2.5 Hz, 1H), 1.74 (s, 3H), 1.64 (dt, J=8.5 Hz, J=2.5 Hz, 1H), 1.60-1.52 (m, 1H).

Chiral monoterpenoid alcohol compound 30 (shown in Scheme 4) was synthesized in seven steps starting from commercially available (R)-perillaldehyde (23) by the method depicted in Scheme 4.

Scheme 4

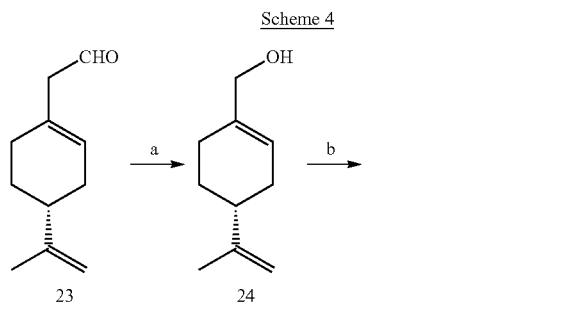

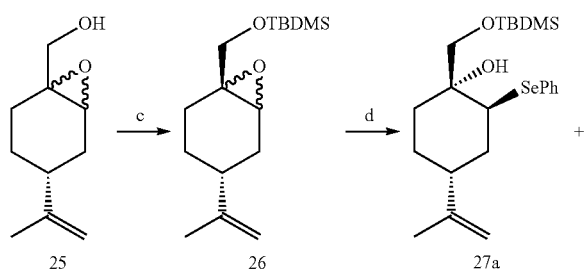

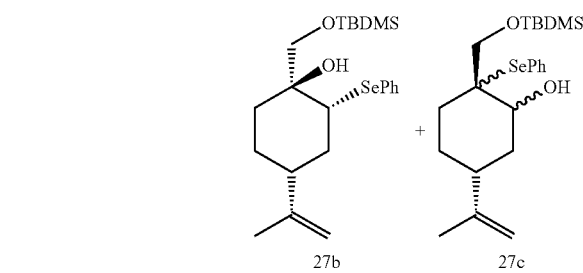

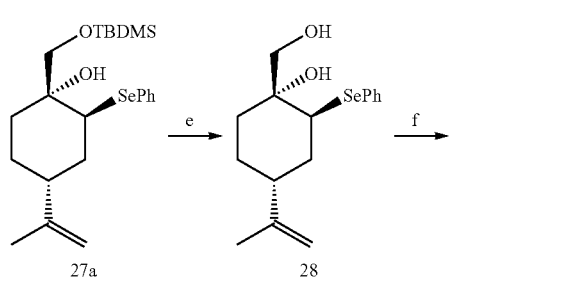

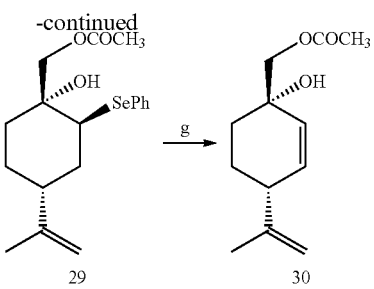

Reagents and conditions: (a) NaBH$_4$, CH$_3$OH, r t, 1 h, 93%; (b) VO(acac)$_2$, t-BuOOH, toluene, 3 h, 79%; (c) imidazole, TBDMSCl, DMF, r t, overnight, 97%;
(d) Ph$_2$Se$_2$, NaBH$_4$, EtOH, 65° C., overnight, 54% (27a), 20% (27b), 18% (27c);
(e) (n-Bu)$_4$N$^+$F$^-$, THF, 4 h, r t, 95%; (f) acetic anhydride, pyridine, CH$_2$Cl$_2$, 4 h, 98%;
(g) 30% H$_2$O$_2$, pyridine, THF, 3 h, r t, then 3 h reflux, 54%.

Experimental Procedures (R)-2-[4-(Prop-1-en-2-yl)cyclohex-1-enyl]acetaldehyde (compound 24)

To a solution of (R)-perillaldehyde 23 (4.75 g, 31.60 mmol) in 95 mL methanol was added NaBH$_4$ (46 mg, 1.22 mmol) in small portions and the reaction was stirred for 1 hour. On completion, the reaction was quenched with dilute 1 N HCl and diluted with ethyl acetate. The organic phase was separated and the aqueous phase was extracted with ethyl acetate. The combined organic layer was washed with brine, dried (MgSO$_4$), and concentrated under vacuo. The crude residue was purified by flash chromatography on silica gel (15-55% ethyl acetate in hexanes) to give 4.5 g (93% yield) of 24 as a colorless oil.

(R)-1,2-Epoxy-8-p-menthen-7-ol (compound 25)

The synthesis was carried out as described for 18 using (3.2 g, 21.02 mmol) 24, vanadyl acetylacetonate (37 mg, 0.15 mmol) and tert-butyl hydroperoxide in tert-butyl alcohol (4.5 ml, 5.0-6.0 M solution in decane) to give 2.78 g (79% yield) of 25 as a colorless oil. The $^1$H NMR (500 MHz, CDCl$_3$) was identical to that of 18.

(R)-tert-Butyldimethyl[(4-(prop-1-en-2-yl)-7-oxabicyclo[4.1.0]heptan-1-yl)methoxy]silane (compound 26)

The synthesis was carried out as described for 19 using 25 (1.5 g, 8.92 mmol), imidazole (1.21 g, 17.80 mmol) and TBDMSCl (1.47 g, 9.81 mmol) to give 2.44 g (97% yield) of 26 as a colorless oil. The $^1$H NMR (500 MHz, CDCl$_3$) was identical to that of 19.

(1S,2R,4R)-1-[(tert-Butyldimethylsilyloxy)methyl]-2-(phenylselanyl)-4-(prop-1-en-2-yl)cyclohexanol (compound 27a)

The synthesis was carried out as described for 20a using 26 (2.59 g, 9.16 mmol), diphenyl diselenide (5.72 g, 18.33 mmol) and NaBH$_4$ (1.38 g, 36.64 mmol) in 30 mL anhydrous ethanol to give 27a (1.78 g, 54%), 27b (800 mg, 20%) and 27c (725 mg, 18%) as oils. The $^1$H NMR (500 MHz, CDCl$_3$) spectra of 27a and 27b were identical to those of 20a and 20b respectively.

(1S,2R,4R)-1-(Hydroxymethyl)-2-(phenylselanyl)-4-(prop-1-en-2-yl)cyclohexanol (compound 28)

The synthesis was carried out as described for 21 using 27a (1.78 g, 4.04 mmol) and TBAF (2.93 mL, 10.12 mmol) in 40 mL THF to give 1.24 g (95% yield) of 28 as a white solid. (m p=66-68° C.). The $^1$H NMR (500 MHz, CDCl$_3$) was identical to that of 21.

[(1R,2S,4S)-1-Hydroxy-2-(phenylselanyl)-4-(prop-1-en-2-yl)cyclohexyl]methylacetate (compound 29)

The synthesis was carried out as described for 22 using 28 (1.1 g, 3.38 mmol), (3.1 mL) acetic anhydride and pyridine (2 mL) in 30 mL CH$_2$Cl$_2$ and gave 1.07 g (98% yield) of 29 as colorless oil. The $^1$H NMR (500 MHz, CDCl$_3$) was identical to that of 22.

[(1R,4R)-1-Hydroxy-4-(prop-1-en-2-yl)cyclohex-2-enyl]methyl acetate (compound 30)

The synthesis was carried out as described for 2 using 29 (1.3 g, 3.54 mmol), pyridine (1.95 mL, 24.7 mmol) and H$_2$O$_2$ (1.92 mL, 56.64 mmol) and gave 401 mg of 30 (54% yield). $^1$H NMR (500 MHz, CDCl$_3$) was identical to that of 2.

Compounds 3.1-3.14, 4.2-4.9, and 4.14 were synthesized by a method depicted in Scheme 5. The preparation of compounds 3.1 and 4.2 has been disclosed in Lander et al. *J. Chem. Soc. Perkin Trans* 1. (1976) 1: 8-16 and in Mechoulam et al. WO 2005/023741 respectively, using different synthetic approaches. Their preparation is reported here to demonstrate the expanded scope of our method for the synthesis of enantiomerically pure compounds 3 and 4. This method involves (a) condensation of resorcinol 1 with chiral terpenic synthon 2 in the presence of an appropriate acid catalyst and a solvent, and (b) conversion of the ester group in 3 to the alcohol.

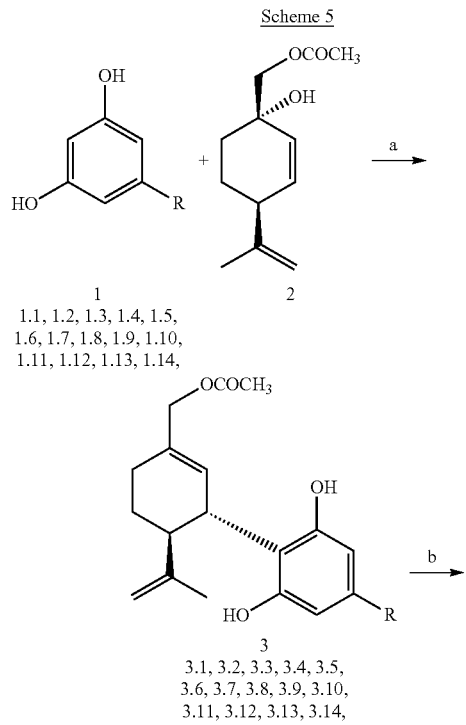

Scheme 5

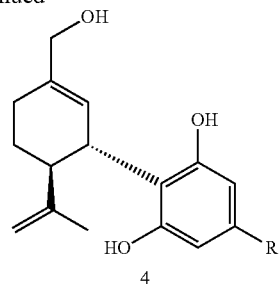

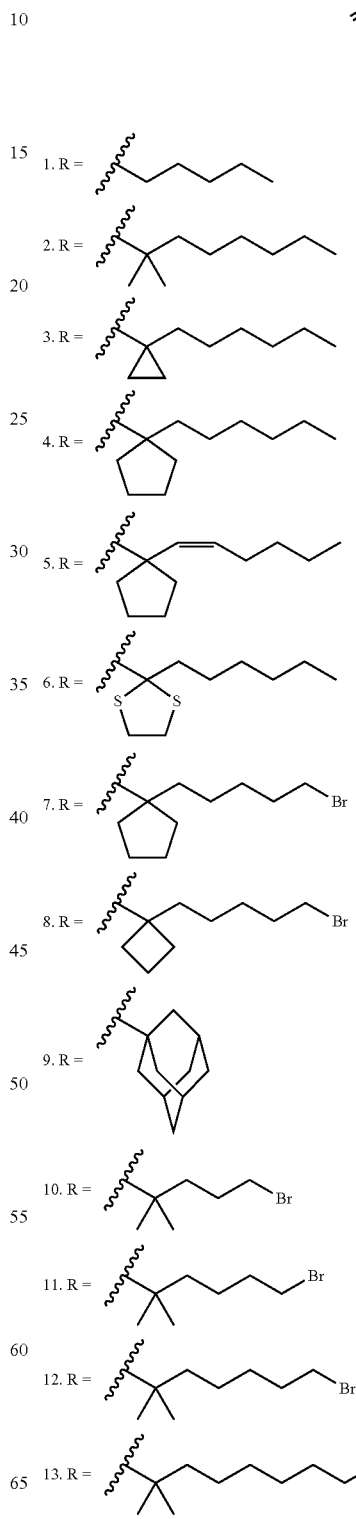

-continued

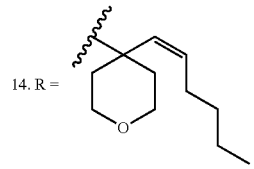

14. R =

Reagents and conditions: (a) p-TsOH, 0° C. to r t, CH$_2$Cl$_2$, 4 h, 12-63%;
(b) DIBAL—H, CH$_2$Cl$_2$, -78° C., 0.5 h, 63-75% or K$_2$CO$_3$, CH$_3$OH, r t, 3 h, 37-78%.

General Experimental Procedure

To a solution of resorcinol 1 (1 equiv.) in an organic solvent (e.g. benzene, CH$_2$Cl$_2$, CHCl$_3$, Et$_2$O, toluene) at 0° C. under an argon atmosphere was added an appropriate acid (e.g. p-toluenesulfonic acid, approximately 0.01-0.1 equiv.), and a solution of terpene 2 (approximately 1.1-2.0 equiv.) in an organic solvent (e.g. benzene, CH$_2$Cl$_2$, CHCl$_3$, Et$_2$O, toluene). The reaction mixture was stirred at 0° C. to room temperature for 4 hours, at which time TLC indicated the complete consumption of resorcinol. The reaction mixture was diluted with an organic solvent (e.g. benzene, CH$_2$Cl$_2$, CHCl$_3$, Et$_2$O, toluene), and washed sequentially with saturated NaHCO$_3$ solution, water and brine. The organic layer was dried (MgSO$_4$), filtered and concentrated under reduced pressure. Purification by flash column chromatography on silica gel (diethyl ether in hexanes) gave compound 3.

2-[(1S,6S)-3-(Acetoxymethyl)-6-(1-methylethenyl)-2-cyclohexen-1-yl]-5-pentylresorcinol (compound 3.1)

Viscous oil (12% yield). $^1$H NMR (500 MHz, CDCl$_3$) δ 6.24 (br s, 2H), 5.87 (s, 1H), 5.48 (br s, 1H), 4.65 (br s), 4.64 (m as t, J=1.5 Hz), 4.58-4.50 (d, d, br s, overlapping, 3H), 3.94 (m as br d, J=10.3 Hz, 1H), 2.49 (ddd, J=10.1 Hz, J=9.9 Hz, J=3.1 Hz, 1H), 2.44 (m as t, J=8.0 Hz, 2H), 2.30-2.13 (m, 2H), 2.09 (s, 3H), 1.92-1.86 (m, 1H), 1.84-1.75 (m, 1H), 1.66 (s, 3H), 1.59-1.52 (m, 2H), 1.35-1.24 (m, 4H), 0.84 (t, J=7.0 Hz, 3H).

2-[(1S,6S)-3-(Acetoxymethyl)-6-(1-methylethenyl)-2-cyclohexen-1-yl]-5-(1,1-dimethylheptyl)resorcinol (compound 3.2)

Colorless viscous oil (55% yield). MS (ESI): m/z (%): 451 (M+Na$^+$, 35), 429 (M+Hl$^+$, 73), 369 (100, M-OCOCH$_3$l$^+$); Exact mass (ESI) calculated for C$_{27}$H$_{41}$O$_4$ (M+Hl$^+$), 429.3005. found, 429.3017.

2-[(1S,6S)-3-(Acetoxymethyl)-6-(1-methylethenyl)-2-cyclohexen-1-yl]-5-(1-hexyl-cyclopropyl)resorcinol (compound 3.3)

Viscous oil (24% yield). MS (ESI): m/z (%): 449 (M+Na$^+$, 13), 427 (M+Hl$^+$, 74), 367 (100, M$^+$-OCOCH$_3$); Exact mass (ESI) calculated for C$_{27}$H$_{39}$O$_4$ (M+Hl$^+$), 427.2848. found, 427.2834.

2-[(1S,6S)-3-(Acetoxymethyl)-6-(1-methylethenyl)-2-cyclohexen-1-yl]-5-(1-hexyl-1-cyclopentyl)resorcinol (compound 3.4)

Viscous oil (36% yield). MS (ESI): m/z (%): 503 (M+2+Na$^+$, 17), 501 (M+Na$^+$, 17), 481 (M+2+Hl$^+$, 75), 479 (M+Hl$^+$, 75), 421 (100, M$^+$+2−OCOCH$_3$), 419 (100, M$^+$-OCOCH$_3$); Exact mass (ESI) calculated for C$_{25}$H$_{36}$BrO$_4$ (M$^+$), 479.1797. found, 479.1789.

2-[(1S,6S)-3-(Acetoxymethyl)-6-(1-methylethenyl)-2-cyclohexen-1-yl]-5-[1-(1,2-cis-hexen-1-yl)-cyclopent-1-yl]resorcinol (compound 3.5)

Viscous oil (33% yield).

2-[(1S,6S)-3-(Acetoxymethyl)-6-(1-methylethenyl)-2-cyclohexen-1-yl]-5-(2-hexyl-1,3-dithiolane-2-yl)resorcinol (compound 3.6)

Viscous oil (28% yield). MS (ESI): m/z (%): 491 (M+Hl$^+$, 62), 431 (100); Exact mass (ESI) calculated for C$_{27}$H$_{39}$O$_4$S$_2$ (M+Hl$^+$), 491.2290. found, 491.2308.

2-[(1S,6S)-3-(Acetoxymethyl)-6-(1-methylethenyl)-2-cyclohexen-1-yl]-5-[(5-bromopentyl)cyclopentyl)resorcinol (compound 3.7)

Viscous oil (26% yield). $^1$H NMR (500 MHz, CDCl$_3$) δ 6.34 (br s, 2H), 5.90 (s, 1H), 5.51 (br s, 1H), 4.69 (br s), 4.64 (m as t, J=1.5 Hz, 1H), 4.58 (d, J=13.0 Hz, 1H), 4.54 (d, J=13.0 Hz, 1H), 4.51 (br s, 1H), 3.91 (m as br d, J=10.3 Hz, 1H), 3.30 (t, J=7.0 Hz, 2H), 2.48 (ddd, J=10.1 Hz, J=9.9 Hz, J=3.1 Hz, 1H), 2.29-2.22 (m, 1H), 2.20-2.14 (m, 1H), 2.09 (s, 3H), 1.92-1.77 (m, 4H), 1.75-1.58 (m and s overlapping, 11H), 1.52-1.47 (m, 2H), 1.30-1.24 (m, 2H), 0.98-0.93 (m, 2H).

2-[(1S,6S)-3-(Acetoxymethyl)-6-(1-methylethenyl)-2-cyclohexen-1-yl]-5-[(5-bromopentyl)cyclobutyl)resorcinol (compound 3.8)

Viscous oil (35% yield). $^{13}$C (100 MHz, CDCl$_3$) 171.02 (—OC(O)—), 155.75 (brs), 155.62 (br s), 150.73, 148.67 137.36, 128.01, 112.89, 111.06, 107.65 (brs), 105.54 (brs), 67.75, 48.19, 42.20, 36.86, 33.94, 32.78, 32.67, 32.59, 28.50, 27.96, 26.29, 23.81, 20.91, 20.26, 15.80.

2-[(1S,6S)-3-(Acetoxymethyl)-6-(1-methylethenyl)-2-cyclohexen-1-yl]-5-(1-adamantyl)resorcinol (compound 3.9)

Viscous oil (45% yield). $^1$H NMR (500 MHz, CDCl$_3$) δ 6.40 (br s, 2H), 5.87 (s, 1H), 5.47 (br s), 4.70 (br s), 4.66 (m as t, J=1.5 Hz), 4.56 (d, J=13.0 Hz), 4.54 (d, J=13.0 Hz, 1H), 4.49 (br s), 3.93 (m as br d, J=10.2 Hz, 1H), 2.49 (ddd, J=10.1 Hz, J=9.9 Hz, J=3.1 Hz, 1H), 2.30-2.22 (m, 1H), 2.20-2.13 (m, 1H), 2.09 (s, 3H), 2.07-2.03 (m, 3H), 1.94-1.87 (m, 1H), 1.85-1.79 (m and s overlapping, 7H), 1.69-1.66 (m, 4H), 1.66 (s, 3H).

2-[(1S,6S)-3-(Acetoxymethyl)-6-(1-methylethenyl)-2-cyclohexen-1-yl]-5-(5-bromo-2-methypentan-2-yl)resorcinol (compound 3.10)

Viscous oil (61% yield).

2-[(1S,6S)-3-(Acetoxymethyl)-6-(1-methylethenyl)-2-cyclohexen-1-yl]-5-(6-bromo-2-methylhexan-2-yl)resorcinol (compound 3.11)

Viscous oil (34% yield). MS (ESI): m/z (%): 503 (M+2+Na$^+$, 17), 501 (M+Na$^+$, 17), 481 (M+2+Hl$^+$, 75), 479

(M+Hl⁺, 75), 421 (100, M⁺+2−OCOCH₃), 419 (100, M⁺-OCOCH₃); Exact mass (ESI) calculated for $C_{25}H_{36}BrO_4$ (M⁺), 479.1797. found, 479.1789.

2-[(1S,6S)-3-(Acetoxymethyl)-6-(1-methylethenyl)-2-cyclohexen-1-yl]-5-(7-bromo-2-methylheptan-2-yl)resorcinol (compound 3.12)

Viscous oil (56% yield). ¹H NMR (500 MHz, CDCl₃) δ 6.38 (br s, 2H), 5.87 (s, 1H), 5.52 (br s, 1H), 4.70 (br s, 1H), 4.64 (m as t, J=1.5 Hz, 1H), 4.56 (d, J=13.0 Hz, 1H), 4.53 (d, J=13.0 Hz, 1H), 4.52 (br s, 1H), 3.92 (m as br d, J=10.3 Hz, 1H), 3.33 (t, J=6.5 Hz, 2H), 2.47 (ddd, J=10.1 Hz, J=9.9 Hz, J=3.1 Hz, 1H), 2.31-2.22 (m, 1H), 2.21-2.13 (m, 1H), 2.09 (s, 3H), 1.91-1.86 (m, 1H), 1.85-1.73 (m, 3H, especially 1H), 1.65 (s, 3H), 1.50 (m, 2H), 1.36-1.28 (m, 2H), 1.16-1.23 (m, s and s overlapping, 8H), 1.05-0.98 (m, 2H).

2-[(1S,6S)-3-(Acetoxymethyl)-6-(1-methylethenyl)-2-cyclohexen-1-yl]-5-(8-bromo-2-methyloct-2-yl)resorcinol (compound 3.13)

Viscous oil (63% yield).

2-[(1S,6S)-3-(Acetoxymethyl)-6-(1-methylethenyl)-2-cyclohexen-1-yl]-5-[1-(1,2-cis-hexen-1-yl)-tetrahydro-2H-pyran-4-yl]resorcinol (compound 3.14)

Viscous oil (23% yield). ¹H NMR (500 MHz, CDCl₃) δ 6.41 (br s, 2H), 5.87 (s, 1H), 5.69 (dt, J=11.3 Hz, J=1.5 Hz, 1H), 5.41 (dt, J=11.3 Hz, J=7.5 Hz, 1H), 4.80 (br s, 1H), 4.62 (m as t, J=1.5 Hz, 1H), 4.55 (d, J=13.0 Hz, 1H), 4.52 (d, J=13.0 Hz, 1H), 4.50 (br s, 1H), 3.92 (m as br d, J=10.2 Hz, 1H), 3.87-3.79 (m as br d, J=12.0 Hz, 2H), 3.73 (ddd, J=12.0 Hz, J=12.0 Hz, J=1.5 Hz, 2H), 2.48 (ddd, J=10.1 Hz, J=9.9 Hz, J=3.1 Hz, 1H), 2.31-2.21 (m, 1H), 2.20-2.14 (m, 1H), 2.09 (s, 3H), 2.13-1.78 (m, 6H), 1.73-1.60 (m and s overlapping, 5H), 1.14-1.06 (m, 4H), 0.76 (t, J=7.0 Hz, 3H).

2-[(1S,6S)-3-(Hydroxymethyl)-6-(1-methylethenyl)-2-cyclohexen-1-yl]-5-(1,1-dimethylheptyl)resorcinol (compound 4.2)

To a solution of 3.2 (1 equiv.) in an organic solvent (e.g. CH₂Cl₂, toluene, hexane) at −78° C., under an argon atmosphere was added 1M solution of DIBAL-H in toluene (3 equiv.). The reaction mixture was stirred for approximately 1 hour and then quenched by dropwise addition of potassium sodium tartrate (10% solution in water) at −78° C. Following the addition, the mixture was warmed to room temperature, stirred for an additional 1 hour and then diluted with an organic solvent (e.g. CH₂Cl₂, toluene, hexane). The organic phase was separated and the aqueous phase extracted with an organic solvent (e.g. CH₂Cl₂, toluene, hexane). The combined organic layer was washed with brine, dried (MgSO₄), and the solvent was evaporated under reduced pressure. The crude product was purified by flash chromatography on silica gel to give 4.2 as colorless viscous oil in 72% yield. ¹³C NMR (125 MHz, CDCl₃) δ 155.82 (brs), 154.02 (brs), 150.65, 149.27, 142.28, 125.61, 113.44, 111.27, 107.88 (brs), 106.36 (brs), 66.77, 46.68, 44.93, 37.71, 37.24, 32.15, 30.29, 29.04, 29.00, 28.54, 26.34, 24.96, 22.95, 20.70, 14.43; MS (ESI): m/z (%): 409 (M+NaI⁺, 13), 387 (M+Hl⁺, 90), 369 (100, M−OHl⁺); Exact mass (ESI) calculated for $C_{25}H_{39}O_3$ (M+Hl⁺), 387.2899. found, 387.2898.

2-[(1S,6S)-3-(Hydroxymethyl)-6-(1-methylethenyl)-2-cyclohexen-1-yl]-5-(1-hexyl-cyclopropyl)resorcinol (compound 4.3)

The synthesis was carried out as described for 4.2 and the title compound was isolated as viscous oil in 75% yield. ¹³C NMR (100 MHz, CDCl₃) δ 155.32 (brs), 148.89, 145.87, 142.17, 125.13, 113.59, 111.00, 109.87 (brs), 108.29 (brs), 66.43, 46.36, 39.97, 36.89, 31.84, 29.42, 28.20, 27.15, 25.98, 25.14, 22.62, 20.34, 140.8, 13.31, 13.25; MS (ESI): m/z (%): 407 (M+NaI⁺, 12), 385 (M+Hl⁺, 74), 367 (100, (M⁺-OH); Exact mass (ESI) calculated for $C_{25}H_{37}O_3$ (M+Hl⁺), 385.2743. found, 385.2737.

2-[(1S,6S)-3-(Hydroxymethyl)-6-(1-methylethenyl)-2-cyclohexen-1-yl]-5-(1-hexyl-cyclopentyl)resorcinol (compound 4.4)

The synthesis was carried out as described for 4.2 and the title compound was isolated as viscous oil in 75% yield. MS (ESI): m/z (%): 435 (M+NaI⁺, 14), 413 (M+Hl⁺, 100), 395 (98, M⁺-OH); Exact mass (ESI) calculated for $C_{27}H_{41}O_3$ (M+Hl⁺), 413.3056. found, 413.3043.

2-[(1S,6S)-3-(Hydroxymethyl)-6-(1-methylethenyl)-2-cyclohexen-1-yl]-5-[1-(1,2-cis-hexen-1-yl)-cyclopent-1-yl]resorcinol (compound 4.5)

To a stirred solution of 3.5 (1 equiv.) in an organic solvent (e.g. methanol, ethanol, acetone) at room temperature, under an argon atmosphere was added K₂CO₃ (1.2 equiv.). The reaction mixture was stirred for 3 hours and then water was added. The mixture was extracted with an organic solvent (e.g. diethyl ether, ethyl acetate, methylene chloride) and the organic phase was washed with brine and dried (MgSO₄). Solvent evaporation and purification by flash column chromatography on silica gel gave 4.5 as viscous oil in 37% yield. ¹H NMR (500 MHz, CDCl₃) δ 6.36 (br s, 2H), 5.85 (s, 1H), 5.66 (dt, J=11.3 Hz, J=1.5 Hz), 5.55 (br s, 1H), 5.25 (dt, J=11.3 Hz, J=7.5 Hz, 1H), 4.63 (m as t, J=1.5 Hz, 1H), 4.53 (br s, 1H), 4.14 (d, J=14.0 Hz), 4.09 (d, J=14.0 Hz), 3.91 (m as br d, J=10.2 Hz, 1H), 2.47 (ddd, J=10.1 Hz, J=9.9 Hz, J=3.1 Hz, 1H), 2.28-2.22 (m, 2H), 1.98-1.75 (m, 6H), 1.73-1.60 (m and s overlapping, 9H), 1.13-1.08 (m, 4H), 0.78 (t, J=7.2 Hz, 3H).

2-[(1S,6S)-3-(Hydroxymethyl)-6-(1-methylethenyl)-2-cyclohexen-1-yl]-5-(2-hexyl-1,3-dithiolane-2-yl)resorcinol (compound 4.6)

The synthesis was carried out as described for 4.2 and the title compound was isolated as viscous oil in 63% yield. MS (ESI): m/z (%): 471 (M+NaI⁺, 100), 449 (M+Hl⁺, 17); Exact mass (ESI) calculated for $C_{25}H_{37}O_3S_2$ (M+Hl⁺), 449.2184. found, 449.2183.

2-[(1S,6S)-3-(Hydroxymethyl)-6-(1-methylethenyl)-2-cyclohexen-1-yl]-5-[(5-bromopentyl)cyclopentyl]resorcinol (compound 4.7)

The synthesis was carried out as described for 4.5 and the title compound was isolated as viscous oil in 74% yield. ¹³C NMR (CDCl₃ 125 MHz): δ 155.82 (brs), 154.03 (brs), 149.44, 149.28, 142.49, 125.33, 113.40, 111.19, 108.66 (brs), 107.10, 66.65, 50.95, 46.66, 41.89, 37.77, 37.73, 37.23, 34.26, 32.98, 28.94, 28.41, 26.28, 24.71, 23.45, 20.67.

2-[(1S,6S)-3-(Hydroxymethyl)-6-(1-methylethenyl)-2-cyclohexen-1-yl]-5-[(5-bromopentyl)cyclobutyl)resorcinol (compound 4.8)

The synthesis was carried out as described for 4.2 and the title compound was isolated as viscous oil in 75% yield. $^1$H NMR (500 MHz, CDCl$_3$) δ 6.12 (br s, 2H), 5.87 (s, 1H), 5.62 (br s, 1H), 4.70 (br s, 1H), 4.66 (m as t, J=1.5 Hz, 1H), 4.55 (br s, 1H), 4.14 (d, J=14.0 Hz, 1H), 4.09 (d, J=14.0 Hz, 1H), 3.91 (m as br d, J=10.2 Hz, 1H, 3.32 (t, J=6.5 Hz, 2H), 2.48 (ddd, J=10.1 Hz, J=9.9 Hz, J=3.1 Hz, 1H), 2.30-2.22 (m, 4H), 2.40-1.96 (m, 3H), 1.93-1.87 (m, 1H), 1.85-1.72 (m, 4H), 1.69 (m, 2H), 1.66 (s, 3H), 1.31 (quintet, J=7.0 Hz, 2H), 1.02-0.94 (m, 2H).

2-[(1S,6S)-3-(Hydroxymethyl)-6-(1-methylethenyl)-2-cyclohexen-1-yl]-5-(1-adamantyl)resorcinol (compound 4.9)

The synthesis was carried out as described for 4.5 and the title compound was isolated as viscous oil in 78% yield. $^1$H NMR (500 MHz, CDCl$_3$) δ 6.38 (br s, 2H), 5.86 (s, 1H), 5.54 (br s, 1H), 4.71 (br s, 1H), 4.67 (m as t, J=1.5 Hz, 1H), 4.58 (br s, 1H), 4.14 (d, J=14.0 Hz, 1H), 4.09 (d, J=14.0 Hz, 1H), 3.92 (m as br d, J=10.2 Hz, 1H), 2.49 (ddd, J=10.1 Hz, J=9.9 Hz, J=3.1 Hz, 1H), 2.28-2.22 (m, 2H), 2.10-2.03 (m, 3H), 1.94-1.87 (m, 1H), 1.84 (s, 6H), 1.84-1.79 (m, 1H), 1.78-1.68 (m, 4H), 1.65 (s, 3H).

2-[(1S,6S)-3-(Hydroxymethyl)-6-(1-methylethenyl)-2-cyclohexen-1-yl]-5-[1-(1,2-cis-hexen-1-yl)-tetrahydro-2H-pyran-4-yl]resorcinol (compound 4.14)

The synthesis was carried out as described for 4.5 and the title compound was isolated as viscous oil in 59% yield.

Those skilled in the art will understand that numerous variations to the synthetic process shown in Scheme 5 can be used to provide other compounds disclosed herein with diversity at position "R" of compound 4 using no more than ordinary skill. For example, ether and sulfide groups (including cyclic analogs) can be introduced using etherification or thioetherification reactions. See, e.g., Comprehensive Organic Transformations, 2$^{nd}$ Edition. John Wiley and Sons, Inc. 1999, pp. 893-898, the contents of which are hereby incorporated by reference in their entireties. As will further be apparent to those skilled in the art, sulfide groups can be readily oxidized to sulfoxide or sulfones. See, e.g., Kirihara, M. et al. *Synlett.* (2010), 1557; Bahrami, K. et al. *J. Org. Chem.* (2010), 75, 6208; Jana, N. K. et al. *Org. Lett.* (2003), 5, 3787; Kim, S. S. et al. *Synthesis* (2002), 2484, the contents of which are hereby incorporated by reference in their entireties. Amino groups can be introduced, for example, using halogen displacement reactions, as seen in Scheme 20. Aryl amino groups can be introduced using, for example, Ullman-type amination or Buchwald-Hartwig amination. Nitrile, carboxylate, carboxamide, amide and ester groups can also be introduced, as shown in Schemes 7, 11, 16 and 17. Keto groups can further be introduced via, for example, oxidation of secondary alcohols. See, e.g., Comprehensive Organic Transformations, 2$^{nd}$ Edition. John Wiley and Sons, Inc. 1999, pp. 1234-1250, the contents of which are hereby incorporated by reference in their entireties.

Compounds 31.2, 31.13, and 32.2 were synthesized by a method depicted in Scheme 6.

The preparation of compound 32.2 has been disclosed in Hanus et al. *Org. Biomol. Chem.* (2005) 3: 1116-1123 and in Mechoulam et al. WO 01/95899 A2 using different synthetic approaches. Its preparation is reported here to demonstrate the expanded scope of our method for the synthesis of enantiomerically pure compounds 31 and 32. This method involves (a) condensation of resorcinol 1 with chiral terpenic synthon 30 in the presence of an appropriate acid catalyst and a solvent, and (b) conversion of the ester group in 31 to the alcohol.

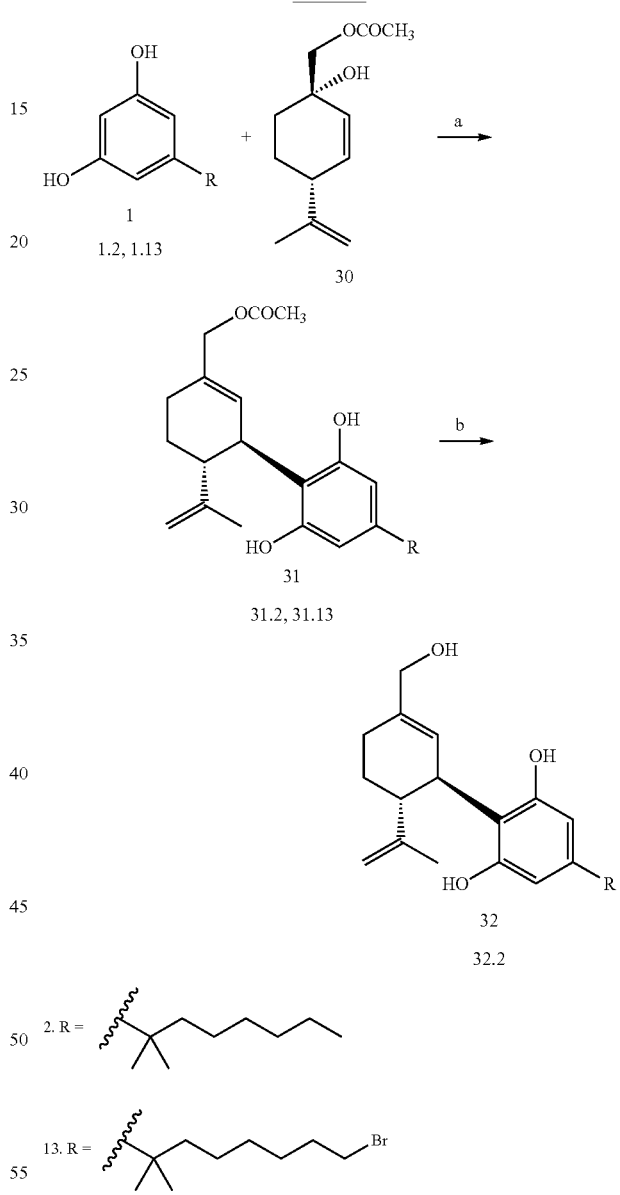

Scheme 6

Reagents and conditions:
(a) p-TsOH, CH$_2$Cl$_2$, 0° C. to r t, 4 h, 30-41%;
(b) K$_2$CO$_3$, CH$_3$OH, r t, 42%.

Experimental Procedures

The syntheses were carried out as described for enantiomers compounds 3.2 and 4.5.

2-[(1R,6R)-3-(Acetoxymethyl)-6-(1-methylethenyl)-2-cyclohexen-1-yl]-5-(1,1-dimethylheptyl)resorcinol (compound 31.2)

Colorless viscous oil; yield: 30%.

2-[(1R,6R)-3-(Acetoxymethyl)-6-(1-methylethenyl)-2-cyclohexen-1-yl]-5-(8-bromo-2-methyloct-2-yl) resorcinol (compound 31.13)

Light brown viscous oil; yield: 41%.

2-[(1R,6R)-3-(Hydroxymethyl)-6-(1-methylethenyl)-2-cyclohexen-1-yl]-5-(1,1-dimethylheptyl)resorcinol (compound 32.2)

Colorless viscous oil; yield: 42%. $^{13}$C NMR (125 MHz, CDCl$_3$) identical to that of 4.2.

Compounds 33 and 34 were synthesized by a method depicted in Scheme 7.

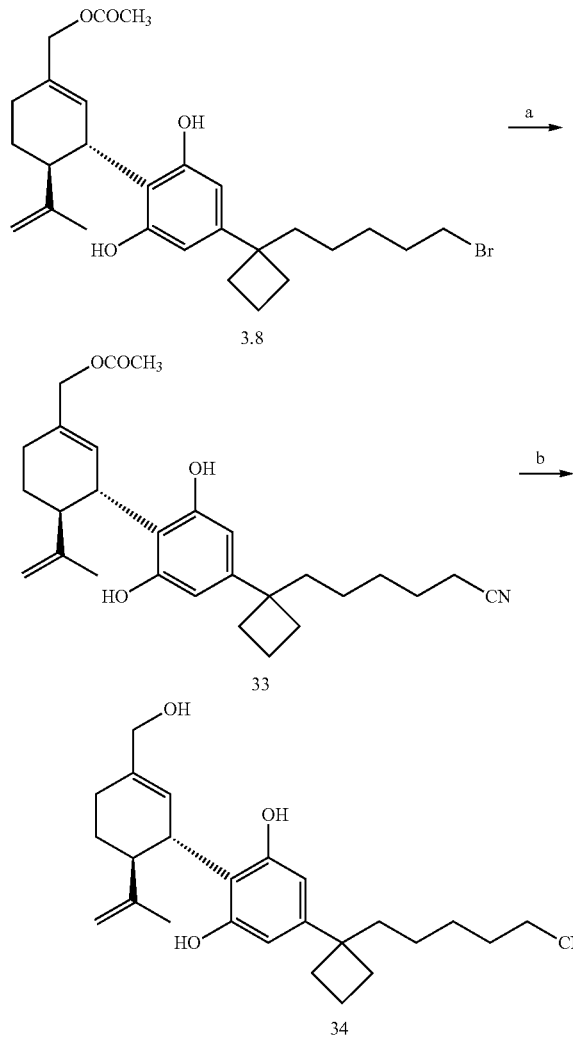

Reagents and conditions:
(a) NaCN, DMSO, r t, 84%;
(b) K$_2$CO$_3$, CH$_3$OH, r t, 42%.

Experimental Procedures

2-[(1S,6S)-3-(Acetoxymethyl)-6-(1-methylethenyl)-2-cyclohexen-1-yl]-5-[(5-cyanopentyl)cyclobutyl) resorcinol (compound 33)

To a stirred solution of 3.8 (200 mg, 0.395 mmol) in anhydrous DMSO (4 mL) was added NaCN (77 mg, 1.58 mmol) and stirring was continued overnight. On completion, the reaction mixture was quenched with brine and extracted with diethyl ether. The organic layer was washed with brine, dried (MgSO$_4$) and concentrated under reduced pressure. Purification by flash column chromatography on silica gel (40-55% ethyl acetate in hexanes) gave 150 mg (84% yield) of pure 33 as viscous oil.

2-[(1S,6S)-3-(Hydroxymethyl)-6-(1-methylethenyl)-2-cyclohexen-1-yl]-5-[(5-cyanopentyl)cyclobutyl] resorcinol (compound 34)

The synthesis was carried out as described for 4.5 and the title compound was isolated as viscous oil in 61% yield. $^1$H NMR (500 MHz, CDCl$_3$) δ 6.13 (br s, 2H), 5.87 (s, 1H), 5.62 (br s, 1H), 4.73 (br s, 1H), 4.64 (m as t, J=1.5 Hz, 1H), 4.53 (br s, 1H), 4.13 (d, J=14.0 Hz, 1H), 4.11 (d, J=14.0 Hz, 1H), 3.93 (m as br d, J=10.2 Hz, 1H), 2.48 (ddd, J=10.1 Hz, J=9.9 Hz, J=3.1 Hz, 1H), 2.32-2.22 (m and t overlapping, 6H), 2.02-1.95 (m, 3H), 1.93-1.87 (m, 1H), 1.86-1.75 (m, 2H), 1.72-1.68 (m, 2H), 1.67 (s, 3H), 1.59-1.52 (m, 2H), 1.34 (quintet, J=6.7 Hz, 2H), 1.15-0.95 (m, 2H).

Compounds 36 and 37 were synthesized by a method depicted in Scheme 8.

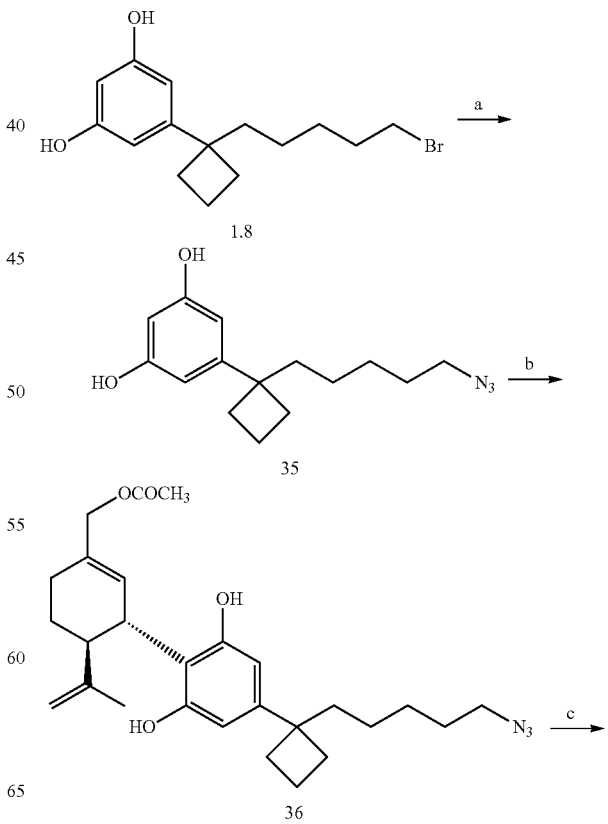

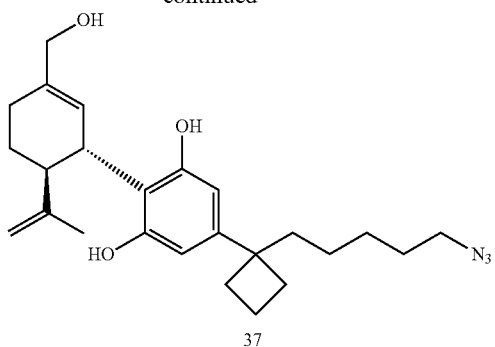

Reagents and conditions:
(a) n-Bu₄N⁺N₃⁻, CH₂Cl₂, 24 h, 66%;
(b) p-TSA, CH₂Cl₂, -10° C., 4 h, 30%;
(c) K₂CO₃, CH₃OH, r t, 72%.

Experimental Procedures 5-(1-(5-Azidopentyl)cyclobutyl)benzene-1,3-diol (compound 35)

A mixture of 1.8 (300 mg, 0.95 mmol) and tetra-n-butylammonium azide (1 g, 3.83 mmol) in anhydrous $CH_2Cl_2$ (6 mL) was stirred for 24 hours under argon. On completion, the reaction mixture was quenched with water and diluted with $CH_2Cl_2$. The aqueous layer was extracted with $CH_2Cl_2$, the combined organic phase was washed with brine, dried (MgSO₄) and concentrated. The residue was purified by flash column chromatography on silica gel (25-40% diethyl ether in hexanes) and gave 173 mg (66% yield) of 35 as a viscous oil. ¹H NMR (500 MHz, CDCl₃) δ 6.15 (s, 3H), 4.52 (br s, 2H), 3.19 (t, J=6.7 Hz, 2H), 2.31-2.24 (m, 2H), 2.07-1.97 (m, 3H), 1.84-1.77 (m, 1H), 1.74-1.68 (m, 2H), 1.52 (quintet, J=7.0 Hz), 1.26 (quintet, J=7.0 Hz), 1.07-0.98 (m, 2H).

2-[(1S,6S)-3-(Hydroxymethyl)-6-(1-methylethenyl)-2-cyclohexen-1-yl]-5-[(5-azidopentyl)cyclobutyl)resorcinol (compound 37)

Coupling of resorcinol derivative 35 with terpenic alcohol 2 was carried out as described for 3 and gave intermediate methyl ester 36. Hydrolysis of this material following the experimental procedure described for 4.5 gave azide 37 in 72% yield as a colorless viscous oil. ¹H NMR (500 MHz, CDCl₃) δ 6.14 (br s, 2H), 5.87 (s, 1H), 5.62 (br s, 1H), 4.73 (br s, 1H), 4.66 (m as t, J=1.5 Hz, 1H), 4.55 (br s, 1H), 4.13 (d, J=14.0 Hz, 1H), 4.11 (d, J=14.0 Hz, 1H), 3.93 (m as br d, J=10.2 Hz, 1H), 3.17 (t, J=7.5 Hz, 2H) 2.48 (ddd, J=10.1 Hz, J=9.9 Hz, J=3.1 Hz, 1H), 2.32-2.22 (m, 4H), 2.01-1.95 (m, 3H), 1.93-1.87 (m, 1H), 1.86-1.75 (m, 2H), 1.72-1.68 (m, 2H), 1.66 (s, 3H), 1.53-1.47 (m, 2H), 1.30-1.22 (m, 2H), 1.03-0.95 (m, 2H).

Compound 38 was synthesized by a method depicted in Scheme 9.

Scheme 9

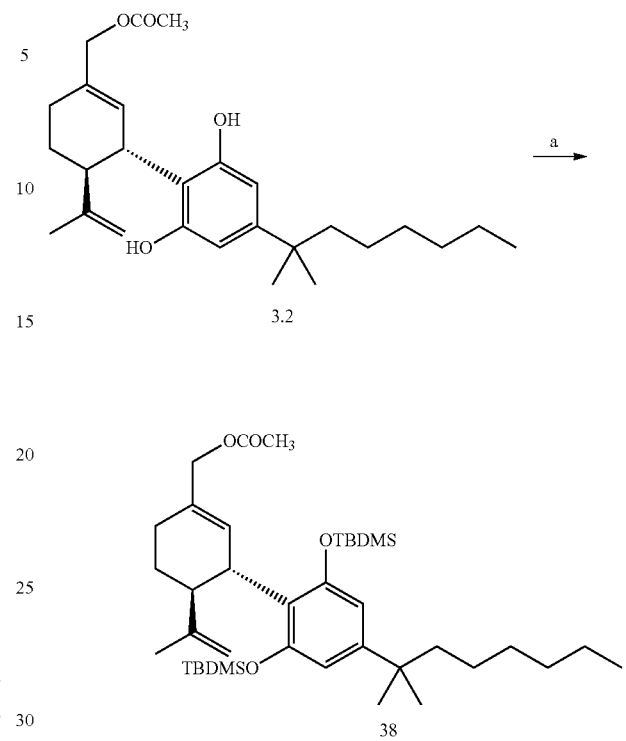

Reagents and conditions:
(a) Imidazole, TBDMSCl, DMF, overnight, r t, 98%

Experimental Procedures

2-[(1S,6S)-3-(Acetoxymethyl)-6-(1-methylethenyl)-2-cyclohexen-1-yl]-1,3-[bis(tert-butyldimethylsilyl)oxy]-5-(1,1-dimethylheptyl)-benzene (compound 38)

The synthesis was carried out as described for 19 (Scheme 3) and gave the title compound 38 in 98% yield as a viscous oil. ¹³CNMR (100 MHz, CDCl₃) δ 171.55 (—OC(O)—), 154.95 (brs), 148.99, 148.01, 132.29, 129.63, 120.75, 109.88, 109.63 (brs), 68.89, 444.79, 43.75, 37.52, 37.27, 31.81, 29.95, 29.38, 28.97, 28.63, 26.61, 26.16, 224.61, 22.56 21.02, 20.00, 14.07, −3.75.

Compounds 40.1, 40.2, 40.4-40.8, and 40.15 were synthesized by a method depicted in Scheme 10.

Scheme 10

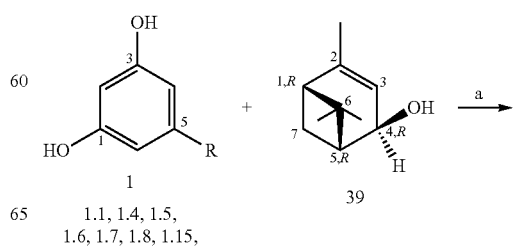

1.1, 1.4, 1.5,
1.6, 1.7, 1.8, 1.15,

-continued

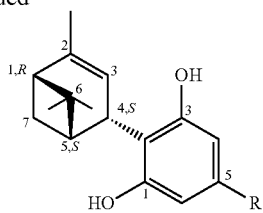

40

40.1, 40.4, 40.5,
40.6, 30.7, 40.8, 40.15,

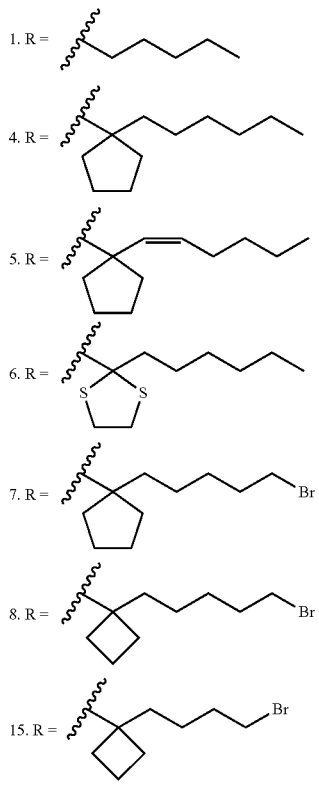

Reagents and conditions:
(a) CHCl₃, p-TSA, 0° C. to r t.

Experimental Procedures (+)-2-[(1R,4S,5S)-2,6,6-trimethylbicyclo[3.1.1]hept-2-en-4-yl]-5-pentyl-resorcinol (compound 40.1)

To a stirred solution of olivetol (1.1) (368 mg, 2.04 mmol) and p-TSA (39 mg, 0.225 mmol) in anhydrous CHCl₃ (70 mL) at 0° C. under an argon atmosphere, was added a solution of 39 (342 mg, 2.25 mmol) in anhydrous CHCl₃ (12 mL) over a period of 30 min. Following the addition, the reaction temperature was raised to room temperature and stirring was continued for 1.5 hours. The reaction was quenched by the addition of saturated sodium bicarbonate solution, the organic layer was separated and the aqueous phase was extracted with CHCl₃. The combined organic layer was washed with brine, dried (MgSO₄) and the solvent was evaporated under reduced pressure. Purification by flash column chromatography on silica gel (15-45% diethyl ether in hexanes) gave compound 40.1 (398 mg, 62% yield). Yellow gum; IR (neat) 3409, 2926, 2859, 1627, 1579, 1516, 1443, 1284, 1229, 1071, 1021, 872, 829 cm⁻¹; ¹H NMR (500 MHz, CDCl₃) δ: 6.20 (br s, 2H), 5.70 (m, 1H), 3.91 (m, 1H), 2.44 (dd as t, J=7.7 Hz, 1H), 2.33-2.29 (m, 1H), 2.27-2.24 (m, 1H), 2.18 (td, J=5.2 Hz, J=1.3 Hz, 1H), 1.85 (dd, J=2.3 Hz, J=1.6 Hz, 3H), 1.60-1.53 (m, 2H), 1.49 (d, J=9.7 Hz, 1H), 1.34-1.28 (m, 7H), 0.96 (s, 3H), 0.89 (t, J=7.0 Hz, 3H).

(+)-2-[(1R,4S,5S)-2,6,6-trimethylbicylco[3.1.1]hept-2-en-4-yl]-5-(1-hexyl-1-cyclopentyl)resorcinol (compound 40.4)

The synthesis was carried out as described for 40.1 and gave 40.4 as colorless viscous oil in 85% yield.

(+)-2-[(1R,4S,5S)-2,6,6-trimethylbicylco[3.1.1]hept-2-en-4-yl]-5-[1-(1,2-cis-hexen-1-yl)-cyclopent-1-yl]resorcinol (compound 40.5)

The synthesis was carried out as described for 40.1 and gave 40.5 as colorless viscous oil in 50% yield. ¹H NMR (500 MHz, CDCl₃) δ 6.35 (br s, 2H), 5.71 (m, 1H), 5.63 (dt, J=11.3 Hz, J=1.5 Hz, 1H), 5.27 (dt, J=11.3 Hz, J=7.5 Hz, 1H), 3.90 (m as q, J=2.5 Hz), 2.29 (ddd, J=10.0 Hz, J=5.5 Hz, J=5.5 Hz, 1H), 2.24 (tt, J=5.5 Hz, J=2.5 Hz, 1H), 2.17 (td, J=5.5 Hz, J=1.0 Hz, 1H), 1.98-1.92 (m, 2H), 1.91-1.82 (m and dd overlapping, 5H), 1.79-1.65 (m, 6H), 1.49 (d, J=10.0 Hz, 1H), 1.32 (s, 3H), 1.13-1.08 (m, 4H), 0.96 (s, 3H), 0.75 (t, J=7.0 Hz, 3H).

(+)-2-[(1R,4S,5S)-2,6,6-trimethylbicylco[3.1.1]hept-2-en-4-yl]-5-(2-hexyl-1,3-dithiolane-2-yl)resorcinol (compound 40.6)

The synthesis was carried out as described for 40.1 and gave 40.6 as white foam in 65% yield. ¹H NMR (500 MHz, CDCl₃) δ 6.69 (s, 2H), 5.69 (br s, 1H), 3.91 (m, 1H), 3.38-3.30 (m, 2H), 3.27-3.20 (m, 2H), 2.35-2.24 (m, 4H), 2.19 (m as td, J=5.5 Hz, J=1.0 Hz, 1H), 1.86 (dd, J=2.0 Hz, J=1.6 Hz), 1.48 (d, J=10.0 Hz, 1H), 1.32 (s, 3H), 1.30-1.18 (m, 8H), 0.96 (s, 3H), 0.85 (t, J=7.0 Hz, 3H).

(+)-2-[(1R,4S,5S)-2,6,6-trimethylbicylco[3.1.1]hept-2-en-4-yl]-5-[(5-bromopentyl)cyclopentyl]resorcinol (compound 40.7)

The synthesis was carried out as described for 40.1 and gave 40.7 as colorless viscous oil in 95% yield.

(+)-2-[(1R,4S,5S)-2,6,6-trimethylbicylco[3.1.1]hept-2-en-4-yl]-5-[(5-bromopentyl)cyclobutyl]resorcinol (compound 40.8)

The synthesis was carried out as described for 40.1 and gave 40.8 as white foam in 48% yield. ¹H NMR (500 MHz, CDCl₃) δ 6.09 (s, 2H, 5.71 (br s, 1H), 3.91 (m as quintet, J=2.0 Hz), 3.34 (t, J=7.0 Hz, 2H), 2.36-2.24 (m, 4H), 2.18 (t, J=5.5 Hz, 1H), 2.05-1.95 (m, 3H), 1.86 (br s, 3H), 1.84-1.75 (m, 3H), 1.70 (m, 2H), 1.50 (d, J=10.0 Hz, 1H), 1.37-1.28 (m and s overlapping, 5H), 1.09-1.03 (m, 2H), 0.97 (s, 3H).

(+)-2-[(1R,4S,5S)-2,6,6-trimethylbicylco[3.1.1]hept-2-en-4-yl]-5-[(5-bromobutyl)cyclobutyl]resorcinol (compound 40.15)

The synthesis was carried out as described for 40.1 and gave 40.15 as white foam in 84% yield. ¹H NMR (500 MHz, CDCl$_3$) δ 6.10 (s, 2H), 5.71 (br s, 1H), 3.91 (m as quintet, J=2.0 Hz), 3.33 (t, J=7.0 Hz, 2H), 2.36-2.24 (m, 4H), 2.19 (t, J=5.5 Hz, 1H), 2.06-1.96 (m, 3H), 1.86 (br s, 3H), 1.84-1.75 (m, 3H), 1.71 (m, 2H), 1.50 (d, J=10.0 Hz, 1H), 1.33 (s, 3H), 1.22-1.16 (m, 2H), 0.97 (s, 3H).

Compound 41 was synthesized by a method depicted in Scheme 11.

Scheme 11

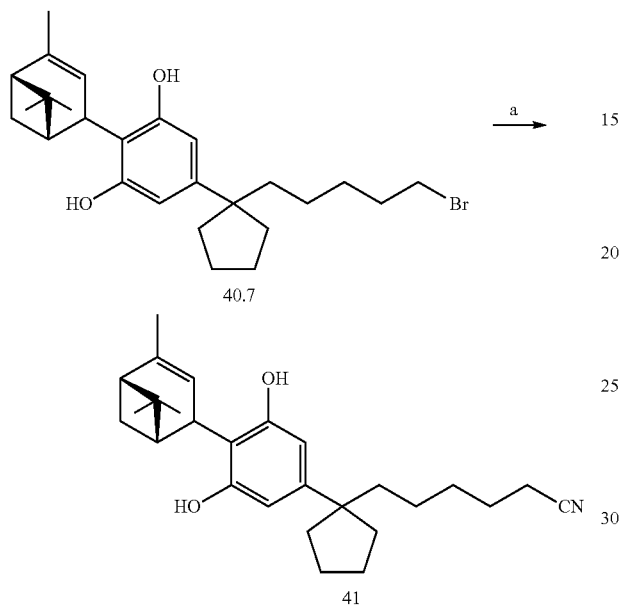

Reagents and conditions:
(a) NaCN, DMSO, r t, 75%.

Experimental Procedures (+)-2-[(1R,4S,5S)-2,6,6-trimethylbicylco[3.1.1]hept-2-en-4-yl]-5-[(5-cyanopentyl)cyclopentyl]resorcinol (compound 41)

To a stirred solution of 40.7 (1 equiv.) in DMSO, at room temperature, under an argon atmosphere, was added NaCN (3 equiv.). After stirring at the same temperature for 20 h, the reaction mixture was cooled to 0° C. and diluted with water. The mixture was extracted with diethyl ether and the organic layer was washed with brine, dried over MgSO$_4$ and the solvent was removed under reduced pressure. The residue was purified by flash column chromatography on silica gel (EtOAc in hexanes) to give 41 in 75% yield as a white foam.

Compounds 43.1, 43.2 and 43.5 were synthesized by a method depicted in Scheme 12.

Scheme 12

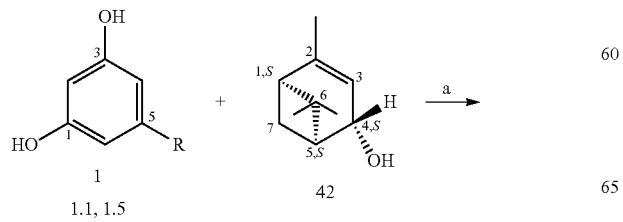

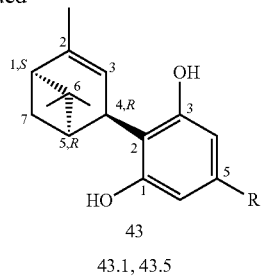

Reagents and conditions:
(a) CHCl$_3$, p-TSA, 0° C. to r t. yield 49-85%

Experimental Procedures (−)-2-[(1S,4R,5R)-2,6,6-trimethylbicyclo[3.1.1]hept-2-en-4-yl]-5-pentyl-resorcinol (compound 43.1)

The synthesis was carried out as described for 40.1. Yield: 61%; yellow gum. The $^1$H NMR (500 MHz, CDCl$_3$) spectrum was identical to that of the enantiomer 40.1.

(−)-2-[(1S,4R,5R)-2,6,6-trimethylbicyclo[3.1.1]hept-2-en-4-yl]-5-[1-(1,2-cis-hexen-1-yl)-cycolpentyl-1-yl]resorcinol (compound 43.5)

The synthesis was carried out as described for 40.1. Yield: 49%; colorless viscous oil. The $^1$H NMR (500 MHz, CDCl$_3$) spectrum was identical to that of the enantiomer 40.5.

Compounds 48.2, 49.2, 50.2, 51.2, 53.2 and 54.2 (shown in Scheme 13) were synthesized by the method depicted in Scheme 13.

Scheme 13

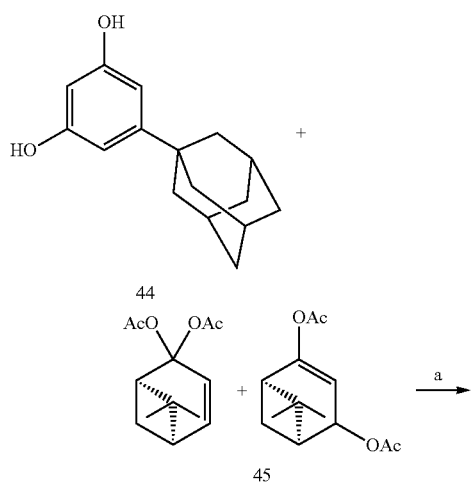

123
-continued
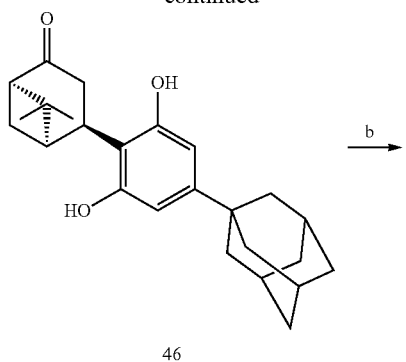
46
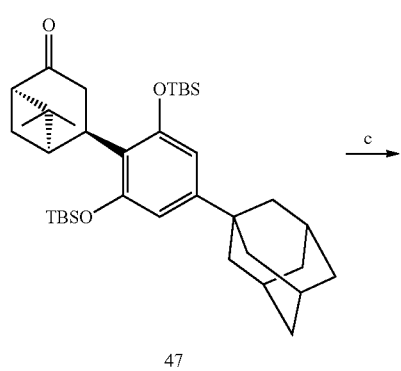
47
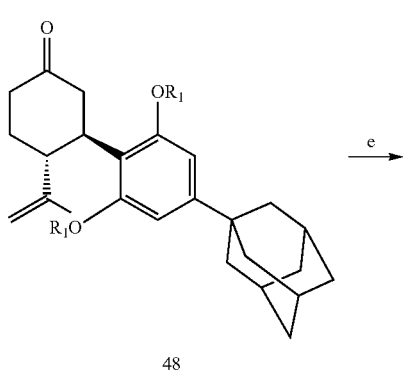
48
  48.1 R₁ = TBS
d ↓
  48.2 R₁ = H
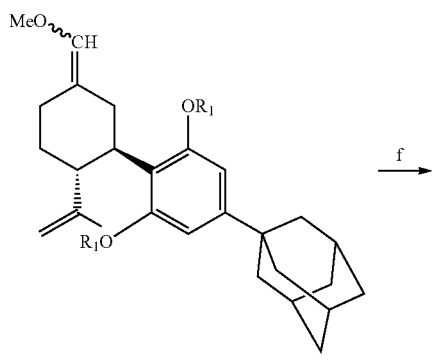
49
  49.1 R₁ = TBS
d ↓
  49.2 R₁ = H
124
-continued
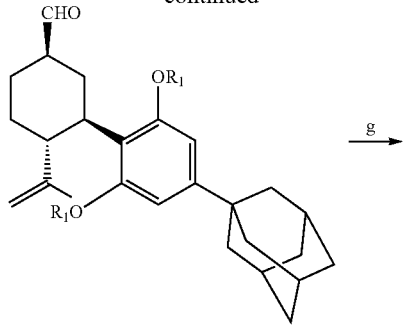
50
  50.1 R₁ = TBS
d ↓
  50.2 R₁ = H
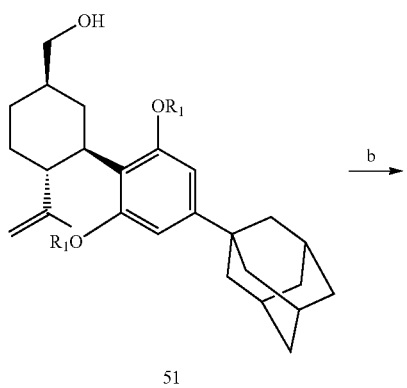
51
  51.1 R₁ = TBS
d ↓
  51.2 R₁ = H
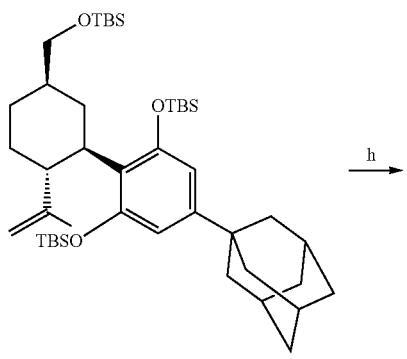
52

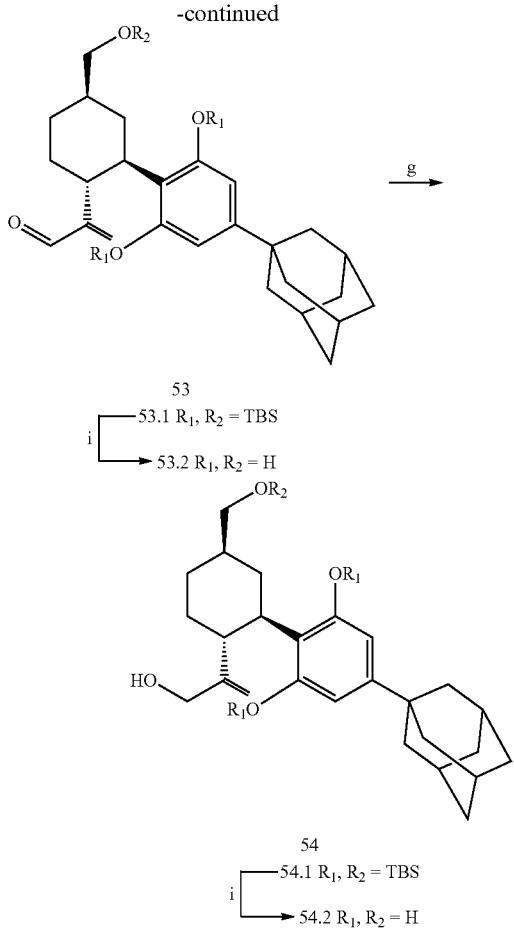

Reagents and conditions:
(a) TsOH·H₂O, CHCl₃, r t, 3 days, 85%;
(b) TBSCl, imidazole, DMAP, DMF, r t, 18 h, 87% for 47, 85% for 52;
(c) i. TMSI, CCl₄, cat. t-BuOH, 0° C., 12 h, ii. NaOAc, CH₃COOH, 90° C., 2 h, 74%;
(d) TBAF, THF, 0° C., 1 h 83% for 48.2, 86% for 49.2, 70% for 50.2 and 82% for 51.2;
(e) Ph₃PCH₂OMe⁺Cl⁻, n-BuLi, THF, -30° C., 1 h, 79%;
(f) i. CCl₃COOH, H₂O, DCM, r t, 3 h, ii. K₂CO₃, MeOH, r t, 12 h, 82%;
(g) NaBH₄, MeOH, 0° C., 1 h, 90%;
(h) SeO₂, salicyclic acid, t-BuOOH, CH₂Cl₂, r t, 12 h, 69%;
(i) TBAF, THF, r t, 6 h, 60% for 53.2 and 73% for 54.2.

Experimental Procedures (4R)-4-[4-(1-Adamantyl)-2,6-dihydroxyphenyl]-6,6-dimethyl-2-norpinanone (compound 46)

To a degassed solution of resorcinol 44.1 (11.0 g, 45.0 mmol) and diacetates 45 (14.48 g, ca. 75% pure by ¹H NMR, 60.8 mmol) in CHCl₃ (200 mL) at 0° C., under an argon atmosphere was added p-toluenesulfonic acid monohydrate (11.13 g, 58.5 mmol). The mixture was warmed to room temperature and stirred for 3 days to ensure complete formation of the product. The reaction mixture was diluted with diethyl ether and washed sequentially with water, saturated aqueous NaHCO₃, and brine. The organic phase was dried (MgSO₄) and the solvent removed under reduced pressure. The residue was chromatographed on silica gel (10-40% diethyl ether in hexane) and fractions containing almost pure product (TLC) were combined and evaporated. Further purification by recrystallization from CH₂Cl₂ and hexane (2:3) gave 46 (14.6 g, 38.4 mmol, 85% yield) as a white crystalline solid. ¹H NMR (500 MHz, CDCl₃+DMSO-d₆) δ: 6.50 (br s, 2H), 6.38 (s, 2H), 4.00 (t, J=8.0 Hz, 1H), 3.63 (dd, J=19.0 Hz, J=8.0 Hz, 1H), 2.60-2.52 (m, 3H), 2.50-2.44 (m, 1H), 2.28 (t, J=5.0 Hz, 1H), 2.06 (br s, 3H), 1.84-1.80 (m, 6H), 1.77 (d, J=12.5 Hz, 3H), 1.70 (d, J=12.5 Hz, 3H), 1.35 (s, 3H), 0.99 (s, 3H). HRMS (ESI) calculated for C₂₅H₃₂O₃: 381.2430. found 381.2433.

(4R)-4-[4-(1-Adamantyl)-2,6-bis(tert-butyldimethylsilyloxy)phenyl]-6,6-dimethyl-2-norpinanone (compound 47)

To a solution of 46 (3 g, 7.88 mmol), imidazole (4.29 g, 63.1 mmol, dried at 40° C./0.1 mmHg for 2 h) and DMAP (0.193 g, 1.577 mmol, resublimed) in anhydrous DMF (30 mL) was added tert-butyldimethylchlorosilane (7.13 g, 47.3 mmol in 25 mL of DMF, and the reaction mixture was stirred at room temperature for 18 h. The reaction mixture was quenched by the addition of saturated aqueous NaHCO₃ and extracted with diethyl ether (2×100 mL). The combined ethereal extracts were washed with water and brine and dried (MgSO₄). Solvent evaporation gave a pale yellow oil which was purified by flash chromatography (0-5% diethyl ether in hexane) to produce 47 (4.2 g, 6.90 mmol, 87% yield) as a white solid. HRMS (ESI) calculated for C₃₇H₆₀O₃Si₂: 608.4081. found 608.4082.

(3R,4R)-3-[4-(1-Adamantyl)-2,6-bis(tert-butyldimethylsilyloxy)phenyl]-4-isopropenylcyclohexan-1-one (compound 48.1)

To a solution of 47 (4.2 g, 6.90 mmol) in carbon tetrachloride (100 mL) at 0° C. was added iodotrimethylsilane (0.94 mL, 6.90 mmol) dropwise. To this yellow solution was added catalytic amount of tert-butanol (0.02 mL, 0.207 mmol) and the reaction mixture was gradually warmed to 5° C. and stirred for 8 h. The resultant orange colored solution was cooled to 0° C. and again iodotrimethylsilane (2.8 mL, 20.69 mmol) was added and reaction mixture was stirred at 5° C. for additional 8 h. The reaction mixture was quenched with saturated aqueous sodium thiosulfate (30 mL) and diluted with diethyl ether (300 mL). The organic layer was washed sequentially with saturated NaHCO₃, water, brine and dried (MgSO₄). Solvent evaporation gave crude iodo intermediate (4.6 g) which was used into the next step without further purification. The crude iodo intermediate (4.6 g, 6.24 mmol) and sodium acetate (2.05 g, 24.97 mmol) were dissolved in acetic acid (30 mL) and stirred for 1.5 h at 90° C. The reaction mixture was concentrated under reduced pressure. The crude was dissolved in 200 mL ether and was washed with water, saturated NaHCO₃ and brine. The combined organics were dried (MgSO₄) and concentrated under reduced pressure to give crude as brown oil. Purification by flash chromatography (0-8% ethyl acetate in hexane) yielded 48.1 (2.8 g, 4.60 mmol, 74% yield) as foam. HRMS (ESI) calculated for C₃₇H₆₀O₃Si₂: 608.4081. found 608.4081.

(3R,4R)-3-[4-(1-Adamantyl)-2,6-dihydroxyphenyl]-4-isopropenylcyclohexan-1-one (compound 48.2)

To a stirred solution of 48.1 (65 mg, 0.107 mmol) in dry THF (5 mL) at 0° C. was added a solution of tetra-n-butylammonium fluoride (0.28 mL, 0.28 mmol, 1M solution in THF) and stirring was continued for 30 min. The reaction was quenched with 5 mL saturated aqueous NaHCO₃ and the mixture was extracted with EtOAc (3×25 mL). The organic phase was washed with water and brine and dried (MgSO$_4$). Evaporation of volatiles gave crude as colorless oil which upon purification by flash chromatography (3-30% EtOAc in hexane) gave 48.2 (34 mg, 0.08 mmol, 83% yield) as a white foam. HRMS (ESI) calculated for C$_{25}$H$_{32}$O$_3$: 380.2352. found 380.2354. $^1$H NMR (500 MHz, CDCl$_3$) δ: 6.47 (d, J=1.5 Hz, 1H), 6.31 (d, J=1.5 Hz, 1H), 5.01 (s, 1H), 4.95 (s, 1H), 4.63 (s, 1H, OH), 3.61 (br s, 1H), 2.76 (s, 1H, OH), 2.36 (br s, 1H), 2.12 (dd, J=12.0 Hz, J=2.5 Hz, 1H), 2.07 (br s, 3H), 2.00 (dd, J=19.0 Hz, J=5.5 Hz, 1H), 1.95-1.90 (m, 2H), 1.89 (s, 3H), 1.85 (s, 3H), 1.84 (s, 3H), 1.77 (d, J=12.0 Hz, 3H), 1.72 (d, J=12.0 Hz, 3H), 1.68-1.60 (m, 1H), 1.30-1.24 (m, 1H).

(3R,4R)-3-[4-(1-Adamantyl)-2,6-bis(tert-butyldimethylsilyloxy)phenyl]-4-isopropenyl-1-(methoxymethylene)cyclohexane (compound 49.1)

To a suspension of (methoxymethyl)triphenylphosphonium chloride (9.46 g, 27.6 mmol) in anhydrous THF (30 mL) at −30° C. was added n-butyllithium (10.67 mL, 26.7 mmol, 2.5M solution in hexane) and stirring was continued for 30 min. To the resultant red color suspension was added 48.1 (2.8 g, 4.60 mmol) dissolved in THF (30 mL) through cannula and the reaction mixture was warmed to room temperature over a period of 15 min. The reaction mixture was quenched with water and diluted with diethyl ether (100 mL). The organic layer was separated and the aqueous phase was extracted with diethyl ether (3×70 mL). The combined organic layer was washed with brine, dried (MgSO$_4$) and evaporated under reduced pressure to give yellow crude. Purification by flash column chromatography (0-8% ether in hexanes) gave a mixture of enol ethers 49.1 (2.3 g, 3.61 mmol, 79% yield, 4:1 mixture of geometric isomers) as a white foam. HRMS (ESI) calculated for C$_{39}$H$_{64}$O$_3$Si$_2$: 636.4394. found 636.4391.

(3R,4R)-3-[4-(1-Adamantyl)-2,6-dihydroxyphenyl]-4-isopropenyl-1-(methoxymethylene)cyclohexane (compound 49.2)

To a stirred solution of 49.1 (70 mg, 0.11 mmol) in dry THF (5 mL) at 0° C. was added a solution of tetra-n-butylammonium fluoride (0.25 mL, 0.25 mmol, 1M solution in THF) and stirring was continued for 30 min. The reaction was quenched with saturated aqueous NaHCO$_3$ and diluted with EtOAc (50 mL). The organic phase was separated and aqueous layer extracted with EtOAc (2×25 mL). The combined organic layer was washed with water, brine and dried (MgSO$_4$). Evaporation of volatiles gave crude as colorless oil which on purification by flash chromatography (7-45% EtOAc in hexane) gave enol-ethers 49.2 (50 mg, 0.125 mmol, 86% yield). HRMS (ESI) calculated for C$_{27}$H$_{36}$O$_3$: 408.2665. found 408.2666. $^1$H NMR (500 MHz, CDCl$_3$) δ: 6.29 (s, 1H), 6.22 (s, 1H), 5.79 (s, 1H), 4.70-4.60 (m, 3H), 4.49 (d, J=1.5 Hz, 1H), 3.55 (s, 3H), 3.10-2.98 (m, 2H), 2.86 (td, J=13.0 Hz, J=2.0 Hz, 1H), 2.65 (t, J=12.5 Hz, 1H), 2.05 (br s, 3H), 2.01 (s, 1H), 1.82 (s, 3H), 1.81 (s, 3H), 1.76 (d, J=12.0 Hz, 3H), 1.72 (d, J=12.0 Hz, 3H), 1.56 (s, 3H), 1.48-1.36 (m, 2H) 1.25 (s, 1H).

(1R,3R,4R)-3-[4-(1-Adamantyl)-2,6-bis(tert-butyldimethylsilyloxy)phenyl]-4-isopropenyl-1-formylcyclohexane (compound 50.1)

To a solution of methyl enol ethers 49.1 (2.5 g, 3.92 mmol) in CH$_2$Cl$_2$ (60 mL) was added aqueous trichloroacetic acid solution (3.21 g, 19.62 mmol in 5 mL water) and the resultant mixture was stirred for 1 h at room temperature. The reaction was quenched by addition of saturated NaHCO$_3$ and diluted with CH$_2$Cl$_2$ (100 mL). The organic layer was separated and aqueous phase extracted with CH$_2$Cl$_2$ (2×50 mL). The combined organic layer was washed with water, brine and dried (MgSO$_4$). Solvent was evaporated to give crude. The crude product was dissolved in absolute ethanol (40 mL) and stirred with anhydrous K$_2$CO$_3$ (1.73 g, 12.52 mmol) for 9 h at room temperature. Examination of an aliquot by $^1$H NMR showed that epimerization was complete. Reaction mixture was filtered through a small pad of Celite and filtrate was concentrated under reduced pressure. Purification of the crude by flash chromatography (0-10% EtOAc in hexane) gave 50.1 (2.0 g, 3.21 mmol, 82% yield) as white foam.

(1R,3R,4R)-3-[4-(1-Adamantyl)-2,6-dihydroxyphenyl]-4-isopropenyl-1-formylcyclohexane (compound 50.2)

To a stirred solution of 50.1 (50 mg, 0.07 mmol) in dry THF (5 mL) at 0° C. was added a solution of tetra-n-butylammonium fluoride (0.25 mL, 0.250 mmol, 1M solution in THF) dropwise and the reaction mixture was stirred for 30 min. The reaction was quenched with saturated aqueous NaHCO$_3$ and the mixture was extracted with EtOAc (10 mL). The organic phase was washed with water and brine and dried (MgSO$_4$). Evaporation of volatiles gave colorless oil which upon purification by flash chromatography (15-65% EtOAc in hexane) gave 50.2 (24 mg, 0.05 mmol, 70% yield) as a white foam. $^1$H NMR (500 MHz, CDCl$_3$) δ: 9.63 (s, 1H), 6.30 (d, J=1.5 Hz, 1H), 6.23 (d, J=1.5 Hz, 1H), 5.03 (d, J=4.5 Hz, 1H), 4.97 (d, J=4.5 Hz, 1H), 4.69 (s, 1H), 4.52 (s, 1H), 3.22 (dt, J=12.0 Hz, J=3.5 Hz, 1H), 2.99 (dt, J=12.0 Hz, J=3.5 Hz, 1H), 2.50-2.40 (m, 1H), 2.10-2.02 (m, 4H, especially 2.06, s, 3H), 1.96 (dd, J=12.5 Hz, J=3.0 Hz, 1H), 1.92-1.87 (m, 1H), 1.82 (s, 3H), 1.81 (s, 3H), 1.80-1.74 (m, 4H, especially 1.77, d, J=12.0 Hz, 3H), 1.72 (d, J=12.0 Hz, 3H), 1.61 (s, 3H), 1.56-1.44 (m, 2H).

(1R,3R,4R)-3-[4-(1-Adamantyl)-2,6-bis(tert-butyldimethylsilyloxy)phenyl]-4-isopropenyl-1-(hydroxymethyl)cyclohexane (compound 51.1)

To a solution of 50.1 (2 g, 3.21 mmol) in MeOH (30 mL) at 0° C. was added sodium borohydride (0.850 g, 22.47 mmol) and the reaction mixture was stirred for 30 min. The reaction mixture was quenched by adding saturated aqueous NH$_4$Cl solution and the solvent was evaporated. The mixture was warmed to room temperature, diluted with water and extracted with ethyl acetate (2×100 mL). The combined organic layer was washed with brine and dried (MgSO$_4$). Solvent was evaporated to give crude which was purified by flash column chromatography (2-15% ethyl acetate in hexanes) to give 51.1 (1.8 g, 2.88 mmol, 90% yield) as a white solid. HRMS (ESI) calculated for C$_{38}$H$_{64}$O$_3$Si$_2$: calculated 624.4394. found 624.4396.

(1R,3R,4R)-3-[4-(1-Adamantyl)-2,6-dihydroxyphenyl]-4-isopropenyl-1-(hydroxymethyl)cyclohexane (compound 51.2)

To a stirred solution of 51.1 (100 mg, 0.160 mmol) in dry THF (7 mL) at 0° C. was added a solution of tetra-n-butylammonium fluoride (0.48 mL, 0.480 mmol, 1M solution in THF) dropwise and the reaction mixture was stirred for 30 min. The reaction was quenched with saturated aqueous NaHCO$_3$ and the mixture was extracted with EtOAc (10 mL). The organic phase was washed with water and brine and dried (MgSO$_4$). Evaporation of volatiles gave colorless oil which upon purification by flash chromatography (15-65% EtOAc in hexane) gave 51.2 (52 mg, 0.131 mmol, 82% yield) as white foam. HRMS (ESI) calculated for C$_{26}$H$_{36}$O$_3$: calculated 396.2665. found 396.2667. $^1$H NMR (500 MHz, CD$_3$OD) δ: 6.32 (d, J=2.0 Hz, 1H), 6.20 (d, J=2.0 Hz, 1H), 4.62 (d, J=2.5 Hz, 1H), 4.37 (d, J=2.5 Hz, 1H), 3.38 (d, J=4.0 Hz, 1H), 3.36 (d, J=4.0 Hz, 1H), 3.20 (dt, J=6.5 Hz, J=1.5 Hz, 1H), 3.10 (dt, J=11.5 Hz, J=3.0 Hz, 1H), 2.18 (s, 1H), 2.07 (s, 3H), 1.92-1.82 (m, 7H, especially 1.85, s, 3H and s, 1.84, 3H), 1.80 (d, J=12.5 Hz, 3H), 1.78 (d, J=12.5 Hz, 3H), 1.73-1.68 (m, 1H), 1.67-1.52 (m, 5H especially 1.57, s, 3H), 1.43 (dq, J=12.5 Hz, J=3.0 Hz, 1H), 1.08 (dq, J=12.5 Hz, J=3 Hz, 1H).

(1R,3R,4R)-3-[4-(1-Adamantyl)-2,6-bis(tert-butyldimethylsilyloxy)phenyl]-4-isopropenyl-1-[(tert-butyldimethylsilyloxy)methyl]cyclohexane (compound 52)

To a solution of 51.1 (2.1 g, 3.36 mmol), imidazole (1.83 g, 26.9 mmol) and DMAP (0.082 g, 0.672 mmol) in anhydrous DMF (30 mL) at room temperature was added tert-butyldimethylchlorosilane (3.04 g, 20.16 mmol) dissolved in DMF (40 mL) and the reaction mixture was stirred for 18 h. The reaction was quenched with saturated aqueous NaHCO$_3$ and reaction mixture was extracted with diethyl ether (3×100 mL). The combined organic extract was washed with water and brine and dried (MgSO$_4$). Solvent evaporation gave a pale yellow oil which was purified by flash chromatography (0-10% diethyl ether in hexane) to produce 52 (2.1 g, 2.84 mmol, 85% yield) as white foam. $^1$H NMR (500 MHz, CDCl$_3$) δ: 6.33 (d, J=2.0 Hz, 1H), 6.31 (d, J=2.0 Hz, 1H), 4.57 (d, J=2.5 Hz, 1H), 4.40 (dd, J=2.5 Hz, J=1.5 Hz, 1H), 3.40 (sept, 6.0 Hz, 2H), 3.22 (dt, J=12.0 Hz, J=3 Hz, 1H), 3.02 (dt, J=12.0 Hz, J=3.0 Hz, 1H), 2.07 (br s, 3H), 1.85 (br d, J=11.5 Hz, 1H), 1.80 (s, 3H), 1.79 (s, 3H), 1.78-1.65 (m, 8H, especially 1.77, d, J=12.0 Hz, 3H and 1.72, d, J=12.0 Hz, 3H), 1.65-1.58 (m, 1H), 1.58-1.52 (m, 5H, especially 1.54, s, 3H), 1.38 (dq, J=12.5 Hz, J=3.5 Hz, 1H), 1.06 (s, 9H), 1.02 (s, 9H), 0.88 (s, 9H), 0.31 (s, 6H), 0.25 (s, 3H), 0.16 (s, 3H), 0.02 (s, 3H), 0.01 (s, 3H).

(1R,3R,4R)-3-[4-(1-Adamantyl)-2,6-bis(tert-butyldimethylsilyloxy)phenyl]-4-[2'-(propenalyl)]-1-[(tert-butyldimethylsilyloxy)methyl]cyclohexane (compound 53.1)

To a suspension of 52 (500 mg, 0.676 mmol) and selenium dioxide (22.51 mg, 0.203 mmol) in CH$_2$Cl$_2$ (20 mL) at 0° C. was added tert-butyl hydroperoxide (0.983 mL, 10.14 mmol, 5.0-6.0 M solution in decane) dropwise and the reaction mixture was stirred at room temperature for 12 h. The reaction mixture was quenched by the addition of saturated sodium sulfite solution and diluted with diethyl ether (60 mL). The organic layer was separated and the aqueous layer extracted with diethyl ether (2×25 mL). The combined organic layer was washed with water and brine and dried (MgSO$_4$). Volatiles were evaporated under reduced pressure to give yellow crude which was purified by flash column chromatography (2-15% diethyl ether in hexane) to give 53.1 (350 mg, 0.465 mmol, 69% yield) as white foam. HRMS (ESI) calculated for C$_{44}$H$_{76}$O$_4$Si$_3$: 752.5051. found 752.5047.

(1R,3R,4R)-3-[4-(1-Adamantyl)-2,6-dihydroxyphenyl]-4-[2'-(propenalyl)]-1-(hydroxymethyl)cyclohexane (compound 53.2)

To a stirred solution of 53.1 (55 mg, 0.073 mmol) in dry THF (10 mL) at 0° C. was added a solution of tetra-n-butylammonium fluoride (19.09 mg, 0.073 mmol, 1M solution in THF) dropwise and stirring was continued for 5 h at room temperature. The reaction was quenched by the addition of saturated aqueous NaHCO$_3$ and the mixture was extracted with EtOAc (2×20 mL). The combined organic layer was washed with water, brine and dried (MgSO$_4$). Solvent was evaporated under reduced pressure to give colorless oil which upon purification by flash chromatography (15-75% EtOAc in hexane) gave 53.2 (18 mg, 0.044 mmol, 60% yield) as white foam. HRMS (ESI) calculated for C$_{26}$H$_{34}$O$_4$: 410.2457. found 410.2459. $^1$H NMR (500 MHz, CD$_3$OD) δ: 9.22 (s, 1H), 6.35 (s, 1H), 6.18 (d, J=1.5 Hz, 1H), 6.10 (d, J=1.5 Hz, 1H), 5.77 (s, 1H), 4.54 (s, 2H, phenolic OH), 3.55 (dt, J=11.5 Hz, J=3.0 Hz, 1H), 3.39-3.28 (m, 2H), 1.95 (br s, 3H), 1.88-1.48 (m, 16H, especially 1.75, s, 3H and 1.74, s, 3H), 1.33 (s, 2H), 1.22 (br s, 1H), 1.09 (q, J=8.5 Hz, 2H).

(1R,3R,4R)-3-[4-(1-Adamantyl)-2,6-bis(tert-butyldimethylsilyloxy)phenyl]-1-[(tert-butyldimethylsilyloxy)methyl]-4-[2'-(3'-hydroxyprop-1'-enyl)]cyclohexane (compound 54.1)

To a solution of 53.1 (220 mg, 0.292 mmol) in MeOH (15 mL) at 0° C. was added sodium borohydride (77 mg, 2.044 mmol) and the reaction mixture was continued to stir for 30 minutes. The reaction mixture was quenched by the addition of saturated aqueous NH$_4$Cl solution and partially concentrated under reduced pressure. The reaction mixture was diluted with ethyl acetate (60 mL) and the organic layer was separated. The aqueous layer was extracted with EtOAc (2×25 mL) and the combined organic layer was washed with water and brine and dried (MgSO$_4$). The solvent was evaporated under reduced pressure to give crude which was purified with flash column chromatography (2-20% ethyl acetate in hexanes) to give 54.1 (195 mg, 0.258 mmol, 88% yield) as a white solid.

(1R,3R,4R)-3-[4-(1-Adamantyl)-2,6-dihydroxyphenyl]-4-[2'-(3'-hydroxyprop-1'-enyl)]-1-(hydroxymethyl)cyclohexane (compound 54.2)

To a stirred solution of 54.1 (40 mg, 0.053 mmol) in dry THF (10 mL) at 0° C. was added a solution of tetra-n-butylammonium fluoride (0.265 mL, 0.265 mmol, 1M solution in THF) dropwise and reaction solution was stirred at room temperature for 5 h. The reaction mixture was quenched with saturated aqueous NaHCO$_3$ and diluted with EtOAc (40 mL). Organic layer was separated and washed with water, brine and dried (MgSO$_4$). Evaporation of volatiles under reduced pressure gave colorless oil which upon purification by flash chromatography (65% EtOAc in hexane) gave 54.2 (16 mg, 0.04 mmol, 73% yield) as white foam. HRMS (ESI) calculated for C$_{26}$H$_{36}$O$_4$: 412.2614. found 412.2616. $^1$H NMR (500 MHz, Acoene-d$_6$) δ: 7.76 (s, 1H, phenolic OH), 7.74 (s, 1H, phenolic OH), 6.35 (d, J=1.5 Hz, 1H), 6.31 (d, J=1.5 Hz, 1H), 4.85 (d, J=1.5 Hz, 1H), 4.80

(d, J=1.5 Hz, 1H), 4.03 (dd, J=14.5 Hz, J=4.0 Hz, 1H), 3.94 (dd, J=14.5 Hz, J=4.0 Hz, 1H), 3.52 (t, J=5.0 Hz, 1H), 3.42 (d, J=6.5 Hz, 1H), 3.37 (t, J=6.0 Hz, 2H), 3.34 (dd, J=14.5 Hz, J=4.0 Hz, 1H), 3.07 (dt, J=12.5 Hz, J=3.0 Hz, 1H), 2.90 (s, 1H), 2.02 (br s, 3H), 1.91-1.84 (m, 1H), 1.83 (t, J=4.0 Hz, 1H), 1.81 (s, 3H), 1.80 (s, 3H), 1.77 (d, J=12.0 Hz, 3H), 1.72 (d, J=12.0 Hz, 3H), 1.69-1.65 (m, 1H), 1.65-1.55 (m, 1H), 1.42 (dq, J=12.5 Hz, J=3.0 Hz, 1H), 1.06 (dq, J=12.5 Hz, J=3.0 Hz, 1H).

Those skilled in the art will understand that numerous variations to the adamantyl compound 44 shown in Scheme 13 can readily be made using no more than ordinary skill. For example, various adamantyl analogs (including, but not limited to, amino-adamantyl, amido-adamantyl, oxa-adamantyl and oxaza-adamantyl derivatives) can be made by Freidel-Crafts alkylation using commercially available 1-adamantanol, Grignard addition to commercially available adamantanone, Trapping of benzyne derivatives, generated in situ, with oxaza-adamantane, condensation of carboxylic acid derivatives with adamantyl amines and mesylate displacement. Using similar methods substituted adamantyl derivatives can be synthesized from commercially available substituted adamantanols, adamantyl amines and adamantanones. See generally Dixon, D. D. et al. *J. Med. Chem.* (2010), 53, 5656; Le Goanvic, D. et al. *J. Org. Chem.* (2006), 71, 7800; Lu, D. et al. *J. Med. Chem.* (2005), 48, 4576; Lu, D. et al. *Tetrahedron Lett.* (2012), 53, 4636.

Compound 55 (shown in Scheme 14) was synthesized by the method depicted in Scheme 14.

Scheme 14

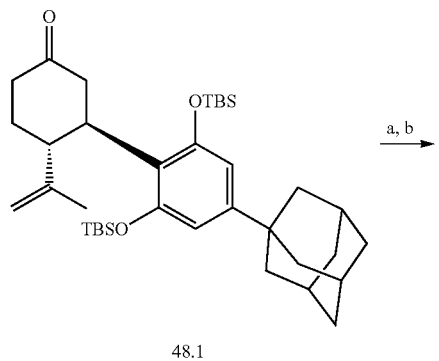

48.1

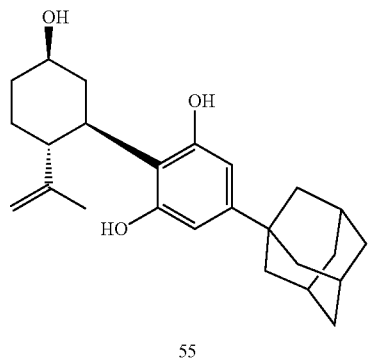

55

Reagents and conditions:
(a) NaBH$_4$, CH$_3$OH, 0° C., 1 h;
(b) TBAF, THF, 0° C., 1 h, 70% (2 steps).

Experimental Procedures (1R,3R,4R)-3-[4-(1-Adamantyl)-2,6-dihydroxyphenyl]-4-isopropenyl-1-hydroxycyclohexane (compound 55)

To a solution of 48.1 (75 mg, 0.123 mmol) in MeOH (15 mL) at 0° C. was added sodium borohydride (23.29 mg, 0.616 mmol) and the reaction mixture was stirred for 30 min. Reaction mixture was quenched by the addition of saturated aqueous NH$_4$Cl solution and partially concentrated. The mixture was extracted with ethyl acetate (2×60 mL) and the organic layer was washed with water and brine and dried (MgSO$_4$). Evaporation of volatiles under reduced pressure gave crude which was used into the next step without further purification. The crude was dissolved in dry THF (10 mL) at 0° C. and a solution of tetra-n-butylammonium fluoride (0.62 mL, 0.62 mmol, 1M solution in THF) was added dropwise and stirred for 30 min. The reaction was quenched with saturated aqueous NaHCO$_3$ and the mixture was extracted with EtOAc. The organic phase was washed with water, brine and dried (MgSO$_4$). Evaporation of volatiles under reduced pressure gave crude yellow oil which upon purification by flash chromatography (20-85% EtOAc in hexane) gave 55 (33 mg, 0.086 mmol, 70% yield over 2 steps) as white foam. $^1$H NMR (500 MHz, CD$_3$OD) δ: 6.25 (d, J=2.0 Hz, 1H), 6.22 (d, J=2.0 Hz, 1H), 4.62 (d, J=2.5 Hz, 1H), 4.39 (d, J=2.5 Hz, 1H), 3.62 (sept, J=4.5 Hz, 1H), 3.23 (dt, J=12.0 Hz, J=3.5 Hz, 1H), 3.08 (dt, J=12.0 Hz, J=3.5 Hz, 1H), 2.10 (q, J=12.0 Hz, 1H), 2.03 (br s, 3H), 1.99 (br d, J=10.0 Hz, 1H), 1.85 (s, 3H), 1.84 (s, 3H), 1.83-1.78 (m, 4H, especially, 1.80, d, J=12.5 Hz, 3H), 1.72 (d, J=12.5 Hz, 3H), 1.68 (dt, J=6.5 Hz, J=3.0 Hz, 1H), 1.56 (s, 3H), 1.49-1.34 (m, 2H).

Compound 56 (shown in Scheme 15) was synthesized by the method depicted in Scheme 15.

Scheme 15

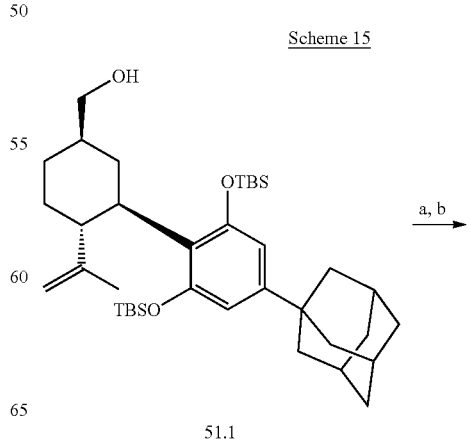

51.1

133

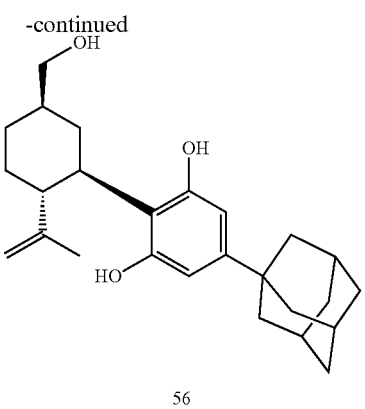

56

Reagents and conditions:
(a) Pd/C, H$_2$, CH$_3$OH, rt, 10 h;
(b) TBAF, THF, 0° C., 1 h, 67% (2 steps).

Experimental Procedures (1R,3R,4R)-3-[4-(1-Adamantyl)-2,6-dihydroxyphenyl]-4-isopropyl-1-(hydroxymethyl)cyclohexane (compound 56)

To a solution of 51.1 (30 mg, 0.048 mmol) in MeOH (55 mL) was added palladium on carbon (15.32 mg, 0.144 mmol) and the reaction mixture was stirred under hydrogen atmosphere for 10 h at room temperature. The reaction mixture was diluted with diethyl ether and filtered through a small Celite pad to remove the catalyst. Solvents were evaporated to give the crude material which was taken to the next step without further purification. The crude was dissolved in dry THF (10 mL), cooled to 0° C. and a solution of tetra-n-butylammonium fluoride solution (0.19 mL, 0.192 mmol, 1M solution in THF) dropwise and stirred for 30 min. Reaction was quenched with saturated aqueous NaHCO$_3$ and the mixture was extracted with EtOAc (2×20 mL). The organic phase was washed with water, brine and dried (MgSO$_4$). Evaporation of volatiles under reduced pressure gave crude yellow oil which upon purification by flash chromatography (20-85% EtOAc in hexane) gave 56 (16 mg, 0.032 mmol, 67.1% yield) as white foam. HRMS (ESI) calculated for C$_{26}$H$_{36}$O$_4$: 398.2821. found 398.2823.

Compounds 58.1, 58.2, 59.1 and 59.2 (shown in Scheme 16) were synthesized by the method depicted in Scheme 16. The starting material, compound 57 was in turn synthesized by a method disclosed in Drake et al. *J. Med. Chem.* (1998) 41: 3596-3608 the content of which is hereby incorporated by reference.

Scheme 16

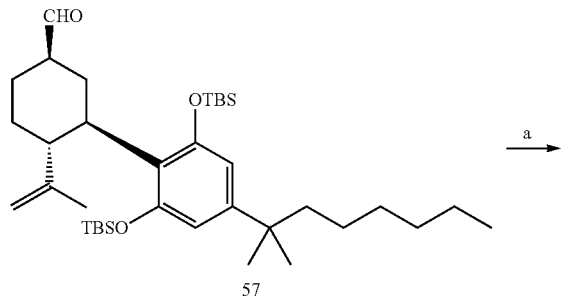

57

134

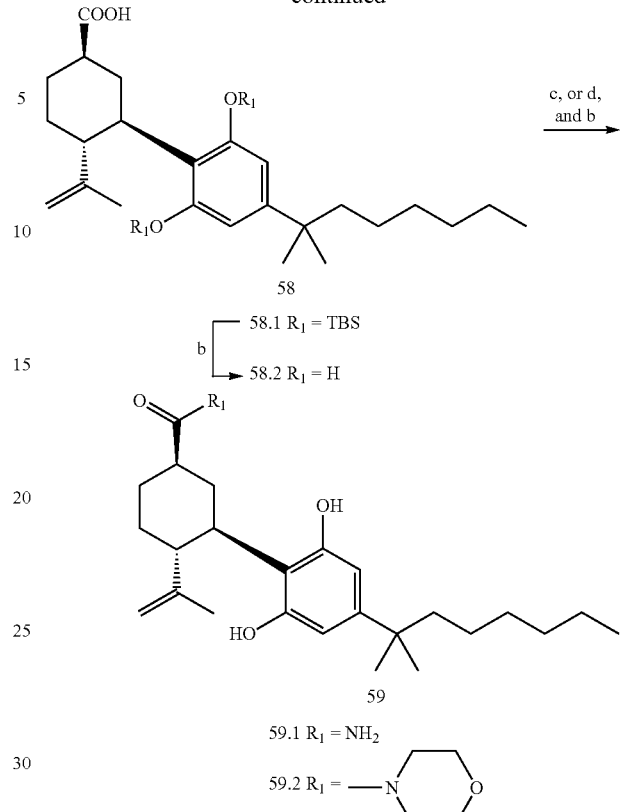

Reagents and conditions:
(a) NaH$_2$PO$_4$, 2-methyl-2-butene, NaClO$_2$, H$_2$O, t-BuOH, r t, 4 h, 63%;
(b) TBAF, THF, 0° C., 1 h, 69%;
(c) i. SOCl$_2$, toluene, 70° C., 2 h, ii. NH$_4$OH, CH$_2$Cl$_2$, 0° C., 12 h, 51% (2 steps);
(d) i. SOCl$_2$, toluene, 70° C., 2 h, ii. morpholine, CH$_2$Cl$_2$, 0° C., 12 h 57% (2 steps).

Experimental Procedures (1R,3R,4R)-3-[4-(1',1'-Dimethylheptyl)-2,6-bis(tert-butyldimethylsilyloxy)phenyl]-4-isopropenyl-1-carboxylylcyclohexane (compound 58.1)

To aldehyde 57 (900 mg, 1.463 mmol) and sodium dihydrogen phosphate (1.93 g, 16.10 mmol) was added water (15 mL), t-BuOH (10.50 mL, 110 mmol) and 2-methyl-2-butene (3.26 mL, 30.7 mmol) at room temperature and the reaction was stirred vigorously for 10 minutes. Sodium chlorite solution (397 mg, 4.39 mmol) in water was added and the reaction mixture was stirred for 4 h. Reaction mixture was diluted with diethyl ether (100 mL). Organic layer was separated, washed with water (2×50 mL), brine and dried (MgSO$_4$). Solvent was evaporated under reduced pressure to afford crude which upon purification by flash chromatography (5-45% EtOAc in hexane) afforded desired product 58.1 (580 mg, 0.919 mmol, 63% yield) as colorless oil.

(1R,3R,4R)-3-[4-(1',1'-Dimethylheptyl)-2,6-dihydroxyphenyl]-4-isopropenyl-1-carboxylylcyclohexane (compound 58.2)

To a stirred solution of 58.1 (25 mg, 0.040 mmol) in dry THF (3 mL) at 0° C. was added a solution of tetra-n-butylammonium fluoride (0.16 mL, 0.158 mmol, 1M solution in THF) dropwise and stirred for 30 min. Reaction was quenched with saturated aqueous NaHCO₃ (5 mL) and the mixture was extracted with EtOAc. The organic phase was washed with water and brine and dried (MgSO₄). Evaporation of volatiles under reduced pressure gave crude which upon purification by flash chromatography (0-7% methanol in dichloromethane) afforded 58.2 (11 mg, 0.027 mmol, 69% yield) as colorless oil. ¹H NMR (500 MHz, CDCl₃) δ: 6.23 (s, 1H), 6.15 (s, 1H), 4.66 (s, 1H), 4.49 (s, 1H), 3.15 (dt, J=12.0 Hz, J=3.0 Hz, 1H), 2.96 (dt, J=12.0 Hz, J=3.0 Hz, 1H), 2.51 (t, J=12.5 Hz, 1H), 2.27 (q, J=12.5 Hz, 1H), 2.08 (br d, J=11.5 Hz, 1H), 1.98 (br d, J=11.5 Hz, 1H), 1.83 (br d, J=13.0 Hz, 1H), 1.68-1.54 (m, 4H, especially 1.54, s, 3H), 1.53-1.40 (m, 3H), 1.36-1.11 (m, 12H), 0.99 (br s, 2H), 0.84 (t, J=7.0 Hz, 3H).

(1R,3R,4R)-3-[4-(1',1'-Dimethylheptyl)-2,6-dihydroxyphenyl]-4-isopropenyl-1-carboxamidocyclohexane (compound 59.1)

To a solution of 58.1 (40 mg, 0.063 mmol) in toluene (3 mL) was added thionyl chloride (0.014 mL, 0.190 mmol) in DMF (1 mL) and the reaction mixture was stirred for 2 h at 70° C. Volatiles were evaporated under reduced pressure to obtain yellow oil. To this yellow oil in DCM (3 mL) at -5 OC was added ammonium hydroxide (0.63 mL, 0.634 mmol, 1M solution in water). Following the addition the reaction mixture was gradually warmed to the room temperature and stirring was continued until the completion of the reaction (12 h). The reaction mixture was diluted with diethyl ether (20 mL) and the organic layer was washed with water and brine and dried (MgSO₄) to give crude which was used as such for the next step. The crude was dissolved in dry THF (3 mL) cooled to 0° C. and a solution of tetra-n-butylammonium fluoride (0.19 mL, 0.190 mmol) was added. The reaction mixture was stirred for 30 min. Reaction was quenched by the addition of saturated aqueous NaHCO₃ and the mixture was extracted with ethyl acetate (25 mL). The organic phase was washed with water, brine and dried (MgSO₄). Solvents were evaporated to give crude which upon purification by flash chromatography (65% EtOAc in hexane) afforded desired product 59.1 (13 mg, 0.032 mmol, 51% yield, over 2 steps) as colorless oil. ¹H NMR (500 MHz, CDCl₃) δ: 6.23 (d, J=2.0 Hz, 1H), 6.20 (d, J=2.0 Hz, 1H), 5.51 (br s, 1H), 5.39 (br s, 1H), 4.66 (s, 1H), 4.49 (s, 1H), 3.15 (dt, J=11.5 Hz, J=3.5 Hz, 1H), 3.01 (dt, J=11.5 Hz, J=3.5 Hz, 1H), 2.42-2.28 (m, 2H), 2.08-1.98 (m, 1H), 1.94-1.82 (m, 2H), 1.57 (s, 3H), 1.52-1.42 (m, 3H), 1.26-1.12 (m, 13H, especially 1.18, s, 6H), 1.03-0.94 (m, 2H), 0.84 (t, J=7.0 Hz, 3H).

(1R,3R,4R)-3-[4-(1',1'-Dimethylheptyl)-2,6-dihydroxyphenyl]-4-isopropenyl-1-morpholinocarboxamidocyclohexane (compound 59.2)

The synthesis was carried out analogous to the preparation of 59.1 using 58.1 (35 mg, 0.055 mmol), toluene (3 mL), thionyl chloride (0.01 mL, 0.166 mmol), DMF (1 mL), DCM (3 mL), morpholine (0.02 mL, 0.277 mmol), tetra-n-butylammonium fluoride (0.22 mL, 0.22 mmol, 1M solution in THF). Purification by flash chromatography (20-90% EtOAc in hexane) gave 59.2 (15 mg, 0.032 mmol, 57% yield, over 2 steps) as colorless oil. ¹H NMR (500 MHz, CDCl₃) δ: 6.23 (d, J=2.0 Hz, 1H), 6.21 (d, J=2.0 Hz, 1H), 4.64 (d, J=2.0 Hz, 1H), 4.44 (br s, 1H), 3.72-3.62 (m, 4H), 3.62-3.53 (m, 4H), 3.18 (dt, J=11.5 Hz, J=3.5 Hz, 1H), 3.11 (dt, J=11.5 Hz, J=3.5 Hz, 1H), 2.71-2.60 (m, 1H), 2.37 (q, J=12.5 Hz, 1H), 1.86-1.72 (m, 3H), 1.68 (br d, J=13.0 Hz, 1H), 1.59 (s, 3H), 1.52-1.40 (m, 3H), 1.32-1.12 (m, 12H, especially 1.18, s, 6H), 1.06-0.96 (m, 2H), 0.84 (t, J=7.5 Hz, 3H).

Methyl ester analogs 60.1 and 60.2 (shown in Scheme 17) were synthesized in a single step from acid 58.2 by a method depicted in Scheme 17.

Scheme 17

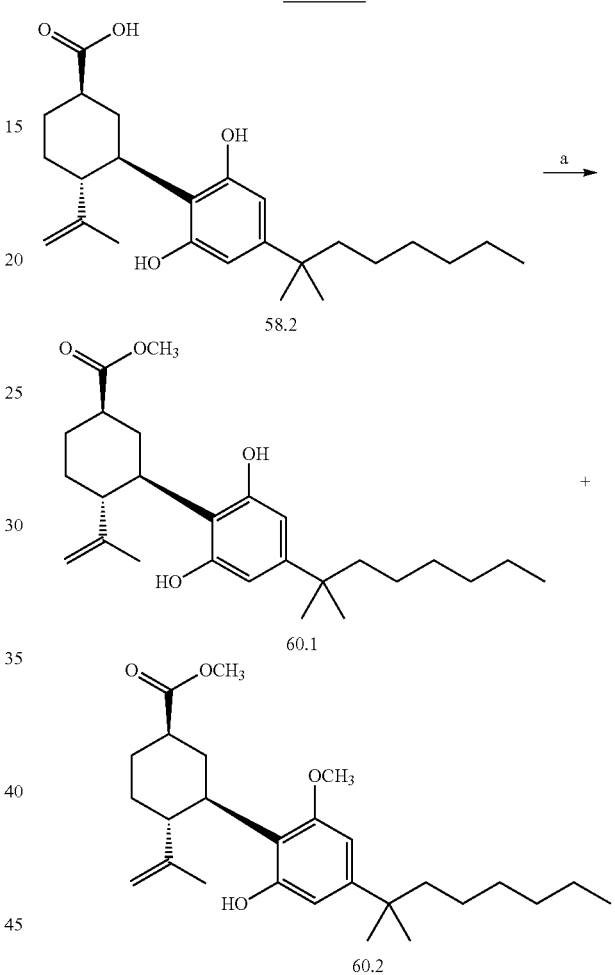

Reagents and conditions:
(a) (CH₃)₃SiCHN₂, CH₃OH, toluene, 0° C., 12 h, 71% for 60.1 and 27% for 60.2.

Experimental Procedures

(1R,3R,4R)-3-[4-(1',1'-Dimethylheptyl)-2,6-dihydroxyphenyl]-4-isopropenyl-1-methoxycarbonylcyclohexane (compound 60.1) and (1R,3R,4R)-methyl 3-(2-hydroxy-6-methoxy-4-(2-methyloctan-2-yl)phenyl)-4-(prop-1-en-2-yl)cyclohexanecarboxylate (compound 60.2)

To a solution of acid 58.2 (10 mg, 0.025 mmol) in methanol (3 mL) and toluene (3 mL) was added diazo(trimethylsilyl)methane (28.4 mg, 0.248 mmol) at 0° C. and the reaction mixture was warmed to room temperature and stirred overnight. The solvent was evaporated and the residue was purified by flash chromatography on silica gel (5-50% EtOAc in hexane) to afford products 60.1 (4 mg, 9.60 μmol, 71% yield) and 60.2 (2 mg, 4.64 μmol, 27% yield) as yellow oils. $^1$H NMR (500 MHz, CDCl$_3$) for 60.1 δ: 6.23 (d, J=1.5 Hz, 1H), 6.17 (d, J=1.5 Hz, 1H), 4.67 (s, 1H), 4.66 (d, J=2.0 Hz, 1H), 4.54 (s, 1H), 4.50 (d, J=2.0 Hz, 1H), 3.65 (s, 3H), 3.12 (dt, J=11.5 Hz, J=3.0 Hz, 1H), 2.96 (dt, J=11.5 Hz, J=3.0 Hz, 1H), 2.49 (tt, J=12.0 Hz, J=3.5 Hz, 1H), 2.25 (q, J=12.5 Hz, 1H), 2.05 (td, J=12.0 Hz, J=2.0 Hz, 1H), 1.96 (qd, J=12.0 Hz, J=2.0 Hz, 1H), 1.84 (qd, J=12.5 Hz, J=3.5 Hz, 1H), 1.63 (dq, J=12.5 Hz, J=3.5 Hz, 1H), 1.57 (s, 3H), 1.49-1.40 (m, 3H), 1.28-1.12 (m, 12H, especially 1.18, s, 6H), 1.04-0.94 (m, 2H), 0.84 (t, J=7.0 Hz, 3H).

The keto and the morpholino substituted analogs 61.2 and 62 respectively (shown in Scheme 18) were synthesized by the method depicted in Scheme 18. The keto analog compound 61.1, was in turn synthesized by a method disclosed in Drake et al. *J. Med. Chem.* (1998, 41: 3596-3608) the content of which is hereby incorporated by reference.

Scheme 18

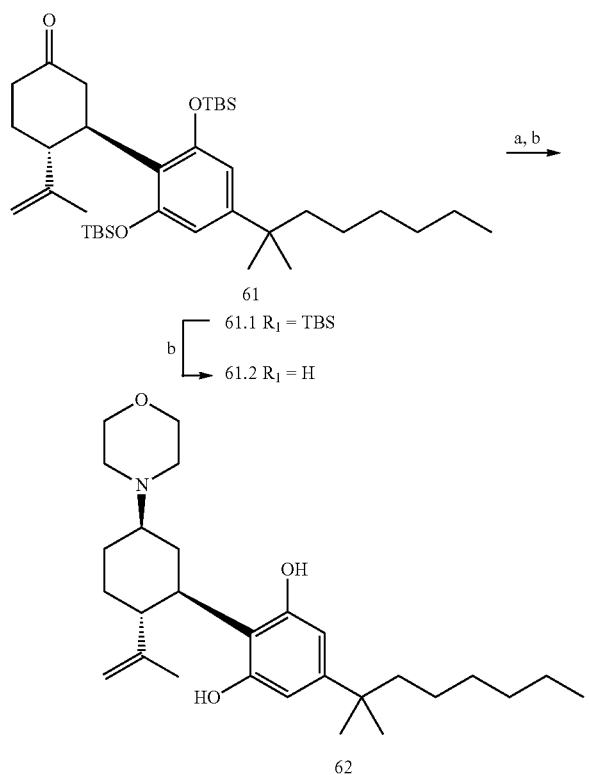

Reagents and conditions:
(a) Morpholine, (CH$_3$COO)$_3$BHNa, CH$_3$COOH, CH$_2$Cl$_2$, r t, 18 h;
(b) TBAF, THF, 0° C., 1 h, 60% (2 steps) for 62 and 78% for 61.2.

Experimental Procedures (1R,3R,4R)-3-[4-(1',1'-Dimethylheptyl)-2,6-dihydroxyphenyl]-4-isopropenyl-1-morpholinylcyclohexane (compound 62)

To a solution of 61.1 (200 mg, 0.33 mmol) and morpholine (0.07 mL, 0.832 mmol) in DCM (10 mL) was added sodium triacetoxyborohydride (176 mg, 0.832 mmol) at room temperature and reaction mixture was stirred for 1 h. Acetic acid (0.02 mL, 0.33 mmol) was added to the reaction mixture and stirring was continued for additional 18 h. The reaction mixture was quenched with saturated NaHCO$_3$ (10 mL) and diluted with diethyl ether (50 mL). the organic phase was separated and the aqueous layer was extracted with diethyl ether (2×25 mL). The combined organic layer was washed with water and brine and dried (MgSO$_4$). Solvent was evaporated under reduced pressure to afford the crude product which was used for the next step without further purification. To this crude in dry THF (3 mL) was added a solution of tetra-n-butylammonium fluoride (0.3 mL, 0.298 mmol, 1.0 M solution in THF) at 0° C. and stirred for 30 min. The reaction mixture was quenched with saturated aqueous NaHCO$_3$ and extracted with ethyl acetate (2×25 mL). The organic phase was washed with water and brine and dried (MgSO$_4$). Solvent was evaporated to give yellow oil which upon purification by flash chromatography (10-70% EtOAc in hexane) gave 62 (20 mg, 0.045 mmol, 60% yield) as colorless oil. $^1$H NMR (500 MHz, CDCl$_3$) δ: 6.22 (s, 2H), 5.30 (br s, 1H), 4.68 (d, J=2.0 Hz, 1H), 4.50 (d, J=2.0 Hz, 1H), 3.81 (t, J=4.5 Hz, 4H), 3.52 (dt, J=12.0 Hz, J=3.5 Hz, 1H), 3.0 (dt, J=12.0 Hz, J=3.5 Hz, 1H), 2.62 (br s, 2H), 2.56 (br s, 2H), 2.38 (t, J=2.5 Hz, 1H), 2.25-2.16 (m, 1H), 2.09 (td, J=14.0 Hz, J=3.0 Hz, 1H), 1.95 (qd, J=14.5 Hz, J=3.0 Hz, 1H), 1.88 (dq, J=12.5 Hz, J=3.0 Hz, 1H), 1.62-1.50 (m, 4H especially 1.57, s, 3H), 1.50-1.40 (m, 3H), 1.30-1.06 (m, 12H, especially 1.17, s, 6H), 1.06-0.94 (m, 2H), 0.84 (t, J=7.0 Hz, 3H).

(3R,4R)-3-[4-(1',1'-Dimethylheptyl)-2,6-dihydroxyphenyl]-4-isopropenylcyclohexan-1-one (61.2)

The deprotection reaction was carried out as described in the preparation of 62 and gave 61.2 as colorless oil in 78% yield. $^1$H NMR (500 MHz, CDCl$_3$) δ: 6.42 (d, J=1.5 Hz, 1H), 6.28 (d, J=1.5 Hz, 1H), 5.01 (d, J=1.5 Hz, 1H), 4.99 (s, 1H), 4.94 (s, 1H), 3.62 (d, J=2.0 Hz, 1H), 3.02 (s, 1H), 2.36 (br s, 1H), 2.12 (dd, J=12.0 Hz, J=2.0 Hz, 1H), 2.01 (dt, J=13.5 Hz, J=5.0 Hz, 1H), 1.93 (td, J=13.5 Hz, J=2.5 Hz, 1H), 1.88 (s, 3H), 1.85 (dd, J=14.5 Hz, J=3.5 Hz, 1H), 1.70-1.60 (m, 2H), 1.54-1.46 (m, 2H), 1.28-1.14 (m, 12H), 1.10-1.00 (m, 2H), 0.84 (t, J=6.5 Hz, 3H).

Compounds 66.1, 66.2, 67.1, 67.2, 68 and 69 (shown in scheme 19) were synthesized by a method depicted in Scheme 19. The starting point for the synthesis was the keto analog 64 which was in turn prepared from 1.2 and enol acetates 63 following a method disclosed in Makriyannis et al. U.S. Pat. No. 7,446,229B2, the content of which is hereby incorporated by reference.

Scheme 19

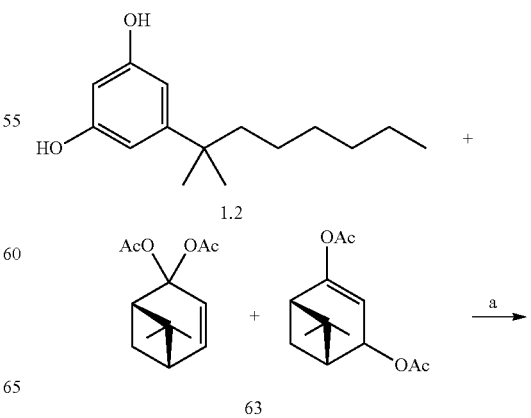

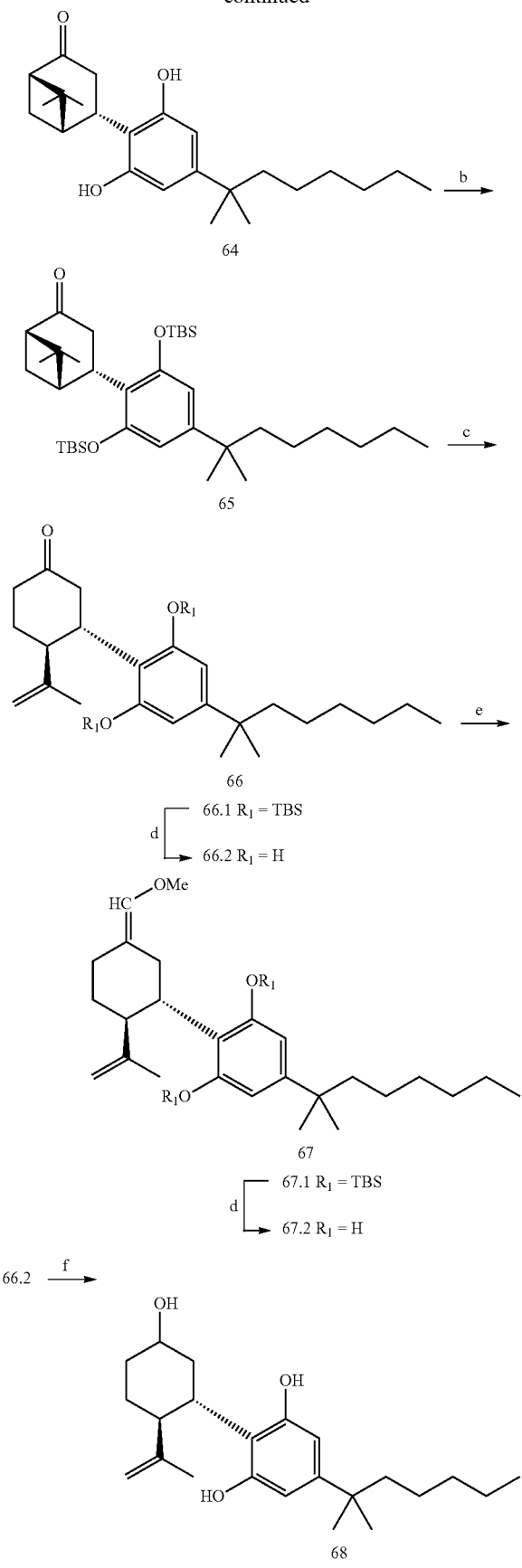

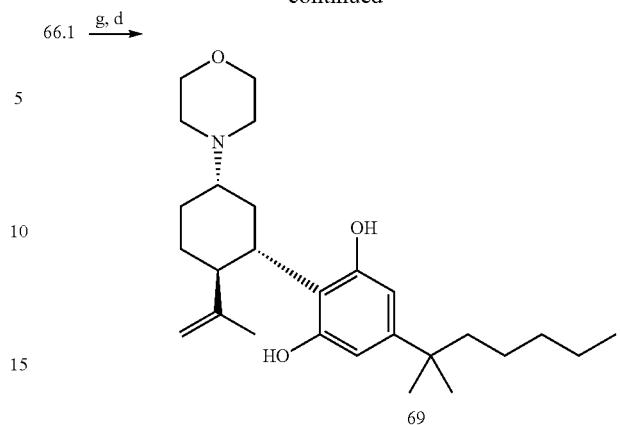

Reagents and conditions:
(a) TsOH·H₂O, CHCl₃, r t, 3 days, 60%;
(b) TBSCl, imidazole, DMAP, DMF, r t, 24 h, 80%;
(c) i. TMSI, CCl₄, cat. t-BuOH, 0° C., 12 h, ii. NaOAc, CH₃COOH, 90° C., 2 h, 60%;
(d) TBAF, THF, 0° C., 1 h 83% for 66.2, 77% for 67.2 and 62% for 69;
(e) Ph₃PCH₂OMe⁺Cl⁻, n-BuLi, THF, -30° C., 1 h, 72%;
(f) NaBH₄, MeOH, 0° C. 30 min, 82%
(g) morpholine, (CH₃COO)₃BHNa, CH₃COOH, CH₂Cl₂, rt, 18 h.

Experimental Procedures

The syntheses were carried out analogous to the preparation of 46, 47, 48.1, 48.2, 49.1 (shown in Scheme 13), 55 (shown in Scheme 14) and 62 (shown in Scheme 18).

(4S)-4-[4-(1',1'-Dimethylheptyl)-2,6-bis(tert-butyldimethylsilyloxy)phenyl]-6,6-dimethyl-2-norpinanone (compound 65)

Yield 80%, colorless oil. ¹H NMR (500 MHz, CDCl₃) δ: 6.40 (s, 2H), 3.99 (t, J=8.0 Hz, 1H), 3.70 (dd, J=17.0 Hz, J=7.5 Hz, 1H), 2.55 (t, J=5.5 Hz, 1H), 2.53 (q, J=9.0 Hz, 1H), 2.43 (sept, J=5.5 Hz, 1H), 2.39 (d, J=11.0 Hz, 1H), 2.24 (t, J=5.5 Hz, 1H), 1.52-1.46 (m, 2H), 1.32 (s, 3H), 1.28-1.14 (m, 12H), 1.10-1.02 (m, 2H), 1.02-0.94 (m, 21H, especially, 0.99, s, 18H), 0.85 (t, J=7.0 Hz, 3H), 0.27 (s, 12H).

(3S,4S)-3-[4-(1',1'-Dimethylheptyl)-2,6-bis(tert-butyldimethylsilyloxy)phenyl]-4-isopropenylcyclohexan-1-one (compound 66.1)

Yield 60%, colorless oil.

(3S,4S)-3-[4-(1',1'-Dimethylheptyl)-2,6-dihydroxyphenyl]-4-isopropenylcyclohexan-1-one (compound 66.2)

Yield 83%, colorless oil. ¹H NMR (500 MHz, CDCl₃) δ: 6.45 (d, J=2.0 Hz, 1H), 6.31 (d, J=2.0 Hz, 1H), 5.06 (s, 1H), 5.03 (s, 1H), 4.97 (s, 1H), 3.65 (s, 1H), 3.08 (s, 1H), 2.39 (br s, 1H), 2.15 (dd, J=12.0 Hz, J=2.0 Hz, 1H), 2.04 (dt, J=13.5 Hz, J=5.0 Hz, 1H), 1.95 (td, J=13.5 Hz, J=2.5 Hz, 1H), 1.90 (s, 3H), 1.87 (dd, J=14.5 Hz, J=3.5 Hz, 1H), 1.74-1.60 (m, 2H), 1.56-1.48 (m, 2H), 1.30-1.16 (m, 12H), 1.14-1.03 (m, 2H), 0.87 (t, J=6.5 Hz, 3H).

(3S,4S)-3-[4-(1',1'-Dimethylheptyl)-2,6-bis(tert-butyldimethylsilyloxy)phenyl]-4-isopropenyl-1-(methoxymethylene)cyclohexane (compound 67.1)

Yield 72%, colorless oil. ¹H NMR (500 MHz, CDCl₃) δ: 6.33 (s, 1H), 6.32 (s, 1H), 5.11 (t, J=7.5 Hz, 0.8H), 5.07 (t, J=7.5 Hz, 0.2H), 4.58 (d, J=2.0 Hz, 0.2H), 4.56 (d, J=2.0 Hz, 0.8H), 4.40 (br s, 1H), 3.30-3.10 (m, 2H), 2.81 (t, J=12.5 Hz, 0.2H), 2.67 (d, J=12.5 Hz, 0.2H), 2.60-2.46 (m, 1.6H), 2.28-2.16 (m, 1.6H), 2.10-2.01 (m, 0.4H), 1.95 (q, J=7.5 Hz, 2H), 1.89-1.74 (m, 1H), 1.52 (s, 3H), 1.50-1.44 (m, 2H), 1.33 (sept, J=7.0 Hz, 2H), 1.26-1.12 (m, 13H, especially 1.20, s, 3H and 1.19, s, 3H), 1.06 (s, 9H), 1.00 (s, 9H), 0.91 (t, J=7.5 Hz, 1H), 0.86 (t, J=7.0 Hz, 3H), 0.33 (s, 2.4H), 0.32 (s, 2.4H), 0.31 (s, 0.6H), 0.24 (s, 3H), 0.20 (s, 2.4H), 0.17 (s, 0.6H).

(3S,4S)-3-[4-(1',1'-Dimethylheptyl)-2,6-dihydroxyphenyl]-4-isopropenyl-1-(methoxymethylene)cyclohexane (compound 67.2)

Yield 77%, colorless oil.

(1R,3R,4R)-3-[4-(1',1'-Dimethylheptyl)-2,6-dihydroxyphenyl]-4-isopropenyl-1-hydroxycyclohexane (compound 68)

Yield 82%, colorless oil. $^1$H NMR (500 MHz, CDCl$_3$) δ: 6.23 (s, 1H), 6.17 (s, 1H), 5.32 (br s, 1H, phenolic OH), 5.05 (br s, 1H, phenolic OH), 4.64 (s, 1H), 4.48 (s, 1H), 3.79 (septet, J=4.5 Hz, 1H), 3.15 (dt, J=12.0 Hz, J=3.0 Hz, 1H), 2.92 (dt, J=12.0 Hz, J=3.0 Hz, 1H), 2.18 (q, J=12.0, 1H), 2.07 (br s, 1H), 1.97 (br d, J=12.5 Hz, 1H), 1.92-1.79 (m, 1H), 1.79-1.66 (m, 1H), 1.55 (s, 3H), 1.50-1.41 (m, 4H), 1.24-1.10 (m, 12H, especially, s, 1.17, 6H), 1.04-0.94 (m, 2H), 0.84 (t, J=6.5 Hz, 3H).

(1S,3S,4S)-3-[4-(1',1'-Dimethylheptyl)-2,6-dihydroxyphenyl]-4-isopropenyl-1-morpholinylcyclohexane (compound 69)

Yield 62%, yellow oil. $^1$H NMR (500 MHz, CDCl$_3$) δ: 6.22 (s, 2H), 5.30 (br s, 1H), 4.68 (d, J=2.0 Hz, 1H), 4.50 (d, J=2.0 Hz, 1H), 3.81 (t, J=4.5 Hz, 4H), 3.52 (dt, J=12.0 Hz, J=3.5 Hz, 1H), 3.0 (dt, J=12.0 Hz, J=3.5 Hz, 1H), 2.62 (br s, 2H), 2.56 (br s, 2H), 2.38 (t, J=2.5 Hz, 1H), 2.25-2.16 (m, 1H), 2.09 (td, J=14.0 Hz, J=3.0 Hz, 1H), 1.95 (qd, J=14.5 Hz, J=3.0 Hz, 1H), 1.88 (dq, J=12.5 Hz, J=3.0 Hz, 1H), 1.62-1.50 (m, 4H especially 1.57, s, 3H), 1.50-1.40 (m, 3H), 1.30-1.06 (m, 12H, especially 1.17, s, 6H), 1.06-0.94 (m, 2H), 0.84 (t, J=7.0 Hz, 3H).

The morpholino substituted analogs 71 and 74 respectively (shown in Scheme 20) were synthesized from 3.11 by the method depicted in Scheme 20.

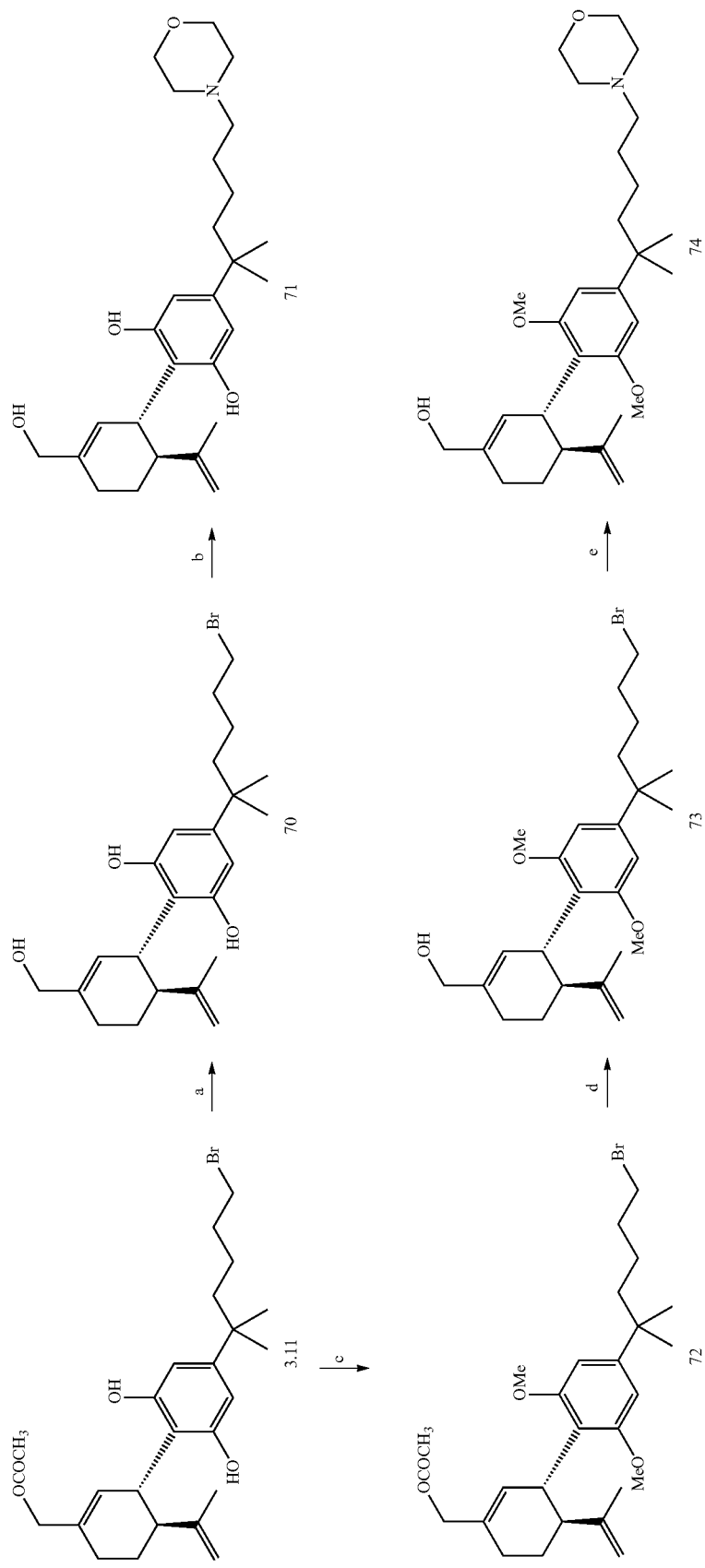
Scheme 20
Reagents and conditions:
(a) DIBAL-H, CH₂Cl₂, -78° C., 0.5 h, 52%;
(b) Et₃N, morpholine, CH₃CN, r t, 48 h, 23%;
(c) CH₃I, K₂CO₃, CH₃COCH₃, 50° C., 84%;
(d) K₂CO₃, CH₃OH, r t, 76%;
(e) Et₃N, morpholine, CH₃CN, r t, 48 h, 33%

Experimental Procedures

2-[(1S,6S)-3-(Hydroxymethyl)-6-(1-methylethenyl)-2-cyclohexen-1-yl]-5-(6-bromo-2-methylhexan-2-yl) resorcinol (compound 70)

The synthesis was carried out as described for 4.2 using 3.11 (190 mg, 0.398 mmol) and 1 M DIBAL-H in toluene (2.39 mL, 2.39 mmol) to give 90 mg of 4.2 as viscous oil in 52% yield. Mass spectrum (ESI) m/z (relative intensity) 461 ($M^+$+2+Na, 11), 459 ($M^+$+Na, 11), 439 ($M^+$+2+H, 89), 437 ($M^+$+H, 89), 421 ($M^+$+2−OH, 100), 419 ($M^+$-OH, 100).

2-[(1S,6S)-3-(Hydroxymethyl)-6-(1-methylethenyl)-2-cyclohexen-1-yl]-5-(6-morpholino-2-methyl-hexane-2-yl)resorcinol (compound 71)

To a stirred solution of 70 (200 mg, 0.457 mmol) in dry acetonitrile (12 mL) was added triethylamine (138 mg, 1.37 mmol) followed by morpholine (398 mg, 4.47 mmol). The reaction was stirred for 2 days at room temperature. On completion, it was quenched with water and diluted with ethyl acetate. The organic layer was separated and the aqueous phase was extracted with ethyl acetate. The combined organic layer was washed with brine and dried over $MgSO_4$. Solvent evaporation and purification under flash column chromatography on silica gel column gave 46 mg of 71 as viscous oil in 23% yield. Mass spectrum (ESI) m/z (relative intensity) 444 ($M^+$+H, 100). Exact mass (ESI) calculated for $C_{27}H_{42}NO_4$ ($M^+$+H), 444.3114. found, 444.3104.

2-[(1S,6S)-3-(Acetoxymethyl)-6-(1-methylethenyl)-2-cyclohexen-1-yl]-5-(6-bromo-2-methylhexane-2-yl)-1,3-dimethoxy-benzene (compound 72)

To a solution of 3.11 in anhydrous acetone was added $K_2CO_3$ (344 mg, 2.49 mmol), followed by iodomethane (0.24 mL, 4.16 mmol) and the reaction mixture was stirred overnight at 50 OC. The precipitate obtained was filtered and washed with acetone. The acetone filtrate was evaporated and the crude obtained was then partitioned between water and diethyl ether. The aqueous layer extracted twice with diethyl ether. The combined organic layer was then washed with brine and dried over $MgSO_4$. Solvent evaporation and purification by flash column chromatography (5-15% diethyl ether in hexanes) gave 176 mg of 72 as viscous oil in 84% yield. Mass spectrum (ESI) m/z (relative intensity) 507 ($M^+$+H, 10), 495 (100), 447 ($M^+$+H—$OCOCH_3$, 8).

2-[(1S,6S)-3-(Hydroxymethyl)-6-(1-methylethenyl)-2-cyclohexen-1-yl]-5-(6-bromo-2-methylhexane-2-yl)-1,3-dimethoxy-benzene (compound 73)

The synthesis was carried out as described for 4.5 using 72 (155 mg, 0.305 mmol) and $K_2CO_3$ (30 mg, 0.213 mmol) in methanol to give 111 mg of 73 as a viscous oil in 76% yield.

2-[(1S,6S)-3-(Hydroxymethyl)-6-(1-methylethenyl)-2-cyclohexen-1-yl]-5-(6-morpholino-2-methyl-hexane-2-yl)-1,3-dimethoxy-benzene (compound 74)

The synthesis was carried out as described for 71 using 73 (110 mg, 0.236 mmol), triethylamine (72 mg, 0.708 mmol) and morpholine (0.205 g, 2.36 mmol) in acetonitrile (6 mL) to give 37 mg of 74 in 33% yield; Mass spectrum (ESI) m/z (relative intensity) 472 ($M^+$+H, 100). Exact mass (ESI) calculated for $C_{29}H_{46}NO_4$ ($M^+$+H), 472.3427. found, 472.3429.

EQUIVALENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of formula I or a pharmaceutically acceptable salt thereof, including all stereoisomers and enantiomers:

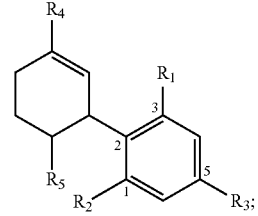

wherein:
$R_1$ and $R_2$ are each independently selected from the group consisting of: —H, —F, —Cl, —Br, —I, —OH, —SH, —$NH_2$, —$NO_2$, —CN, —$CF_3$, —OC(O)$CH_3$, —C(O)$CH_3$, —C(O)$CF_3$, —O-alkyl, OSi(alkyl)$_3$, —S—alkyl, —NH-alkyl, —N(alkyl)$_2$, —O—P(O)(OR)$_2$, —O—P(O)(OH)(OR) (wherein R is selected from the group consisting of H and alkyl), —P(O)(OR)$_2$, —P(O)(OH)(OR) (wherein R is selected from the group consisting of H and alkyl), —O-alkyl-COOR (wherein R is selected from the group consisting of H and alkyl), —O-alkyl-NR$_6$R$_7$, —O-alkyl-CONR$_6$R$_7$, —OC(O)—R (wherein R is selected from the group consisting of H and alkyl), —OC(O)—CH(OH)—$CH_2$OH, —OC(O)—C($CH_2$OH)$_2$—$CH_3$, —OC(O)—$CH_2$OH, —OC(O)-alkyl-COOH, —OC(O)—CH═CHCOOH, —OC(O)-alkyl-NR$_6$R$_7$, —OC(O)-alkyl-C(O)NR$_6$R$_7$, —OC(O)—O-alkyl-NR$_6$R$_7$, and —OC(O)—CH(NH$_2$)—R$_8$ (wherein R$_8$ is selected from the group consisting of H, CH(OH)$CH_3$ and alkyl-X$_1$, and X$_1$ is selected from the group consisting of: —H, —NHC(═NH)$NH_2$, —C(O)$NH_2$, —COOH, —SH, —$SCH_3$, —OH, —$NH_2$, and an aromatic, heteroaromatic or heterocyclic ring);
$R_6$ and $R_7$ are each independently selected from the group consisting of: H and alkyl, or $R_6$ and $R_7$ together comprise part of a 3 to 7 membered saturated heterocyclic ring containing up to one additional heteroatom selected from the group consisting of N, O and S;
$R_3$ is selected from the group consisting of: -cycloalkyl-$R_9$, -heterocyclic-$R_9$, -adamantyl, -adamantyl-$R_9$, and -heteroadamantyl-$R_9$;
$R_9$ is selected from the group consisting of: —(CH$_2$)$_j$—$R_{10}$, —(CH)$_j$-A-(CH$_2$)$_k$—$R_{10}$, and —(CH$_2$)$_j$-A-(CH$_2$)$_k$—B—$R_{10}$;

A and B are each independently selected from the group consisting of: —CH$_2$—CH$_2$—, —C≡C—, —CH=CH—, —O—, —S—, —NH—, —C(O)—, —C(O)O—, —OC(O)—, —C(O)NH—, —NHC(O)—, —S(O)—, —SO$_2$—, —SO$_2$NH—, —NHSO$_2$—, —SO$_2$O— and —OSO$_2$—;

R$_{10}$ is selected from the group consisting of: —H, —F, —Cl, —Br, —I, —OH, —SH, —NH$_2$, —CN, —N$_3$, —NCS, —NCO, —SO$_2$Cl, —SO$_2$F, —SO$_2$NH$_2$, —C(O)NH$_2$, —COOH, —NO$_2$, —CHO, —CF$_3$, —SO$_3$H, —O—P(O)(OH)$_2$, —Sn(alkyl)$_3$, —Si(alkyl)$_3$, —C≡CH, —CH=CH$_2$, and an aromatic, heteroaromatic or heterocyclic ring;

j is an integer from 0 to 8;

k is an integer from 0 to 8;

R$_4$ is selected from the group consisting of: -alkyl-R$_{11}$, and —C$_{1-3}$alkyl-OC(O)-alkyl;

R$_{11}$ is selected from the group consisting of: —F, —Cl, —Br, —I, —OH, —SH, —NH$_2$, —NH-alkyl, —N(alkyl)$_2$, —CN, —N$_3$, —NCS, —OC(O)CH$_3$, —C(O)OCH$_3$, —SO$_2$NH$_2$, —C(O)NH$_2$, —COOH, —NO$_2$, —CHO, —CF$_3$, —Sn(alkyl)$_3$, —Si(alkyl)$_3$, —C≡CH, —CH=CH$_2$, and an aromatic, heteroaromatic or heterocyclic ring;

R$_5$ is selected from the group consisting of: —H, -alkyl, -alkyl-R$_{12}$, -alkenyl, -alkenyl-R$_{12}$, -alkynyl and -alkynyl-R$_{12}$; and R$_{12}$ is selected from the group consisting of: —F, —Cl, —Br, —I, —OH, —SH, —NH$_2$, —NH-alkyl, —N(alkyl)$_2$, —CN, —N$_3$, —NCS, —OC(O)CH$_3$, —C(O)OCH$_3$, —SO$_2$NH$_2$, —C(O)NH$_2$, —COOH, —NO$_2$, —CHO, —CF$_3$, —Sn(alkyl)$_3$, —Si(alkyl)$_3$, —C≡CH, —CH=CH$_2$, —(CH$_2$)$_n$-Q (wherein Q is selected from the group consisting of —F, —Cl, —Br, —I, —OH, and n is an integer from 1 to 5), and an aromatic, heteroaromatic or heterocyclic ring.

2. The compound of claim 1, wherein each of R$_1$ and R$_2$ are independently selected from the group consisting of —H, —SH, —NH$_2$, —OH, —O-alkyl, —OSi(alkyl)$_3$, —OC(O)CH$_3$, and —O— alkyl-COOR (wherein R is selected from the group consisting of H and alkyl).

3. The compound of claim 2, wherein R$_1$ and R$_2$ are —OH.

4. The compound of claim 1, wherein R$_3$ is selected from the group consisting of -cycloalkyl-R$_9$, -heterocyclyl-R$_9$ and -adamantyl.

5. The compound of claim 4, wherein R$_3$ is selected from the group consisting of -cycloalkyl-R$_9$ and -heterocyclyl-R$_9$, and R$_9$ is selected from the group consisting of —(CH$_2$)$_j$-A-(CH$_2$)$_k$—R$_{10}$ and —(CH$_2$)$_j$-A-(CH$_2$)$_k$—B—R$_{10}$.

6. The compound of claim 5, wherein R$_9$ is —(CH$_2$)$_j$-A-(CH$_2$)$_k$—R$_{10}$.

7. The compound of claim 5, wherein R$_9$ is —(CH$_2$)$_j$-A-(CH$_2$)$_k$—B—R$_{10}$.

8. The compound of claim 6, wherein A is selected from the group consisting of —CH$_2$—CH$_2$—, —CH=CH—, —C≡C—, —O—, —S—, —NH—, —C(O)—, —C(O)O—, —C(O)NH— and —NHC(O)—.

9. The compound of claim 8, wherein A is selected from the group consisting of —CH$_2$—CH$_2$— and —CH=CH—.

10. The compound of claim 7, wherein each of A and B are independently selected from the group consisting of —CH$_2$—CH$_2$—, —CH=CH—, —C≡C—, —O—, —S—, —NH—, —C(O)—, —C(O)O—, —C(O)NH— and —NHC(O)—.

11. The compound of claim 10, wherein each of A and B are independently selected from the group consisting of —CH$_2$—CH$_2$— and —CH=CH—.

12. The compound of claim 1, wherein R$_{10}$ is selected from the group consisting of —H, —F, —Cl, —Br, —I, —OH, —SH, —NH$_2$, —CN, and —N$_3$.

13. The compound of claim 1, wherein j is selected from the group consisting of 0, 5 and 6.

14. The compound of claim 1, wherein k is selected from the group consisting of 1 and 3.

15. The compound of claim 1, wherein R$_{11}$ is —OH.

16. The compound of claim 1, wherein R$_5$ is -alkenyl.

17. The compound of claim 1, wherein the compound is selected from the group consisting of:

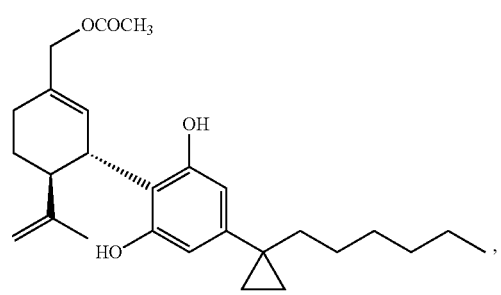

,

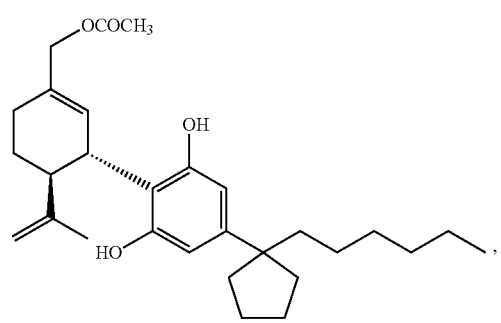

,

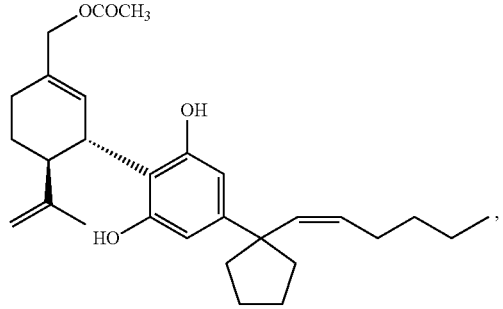

,

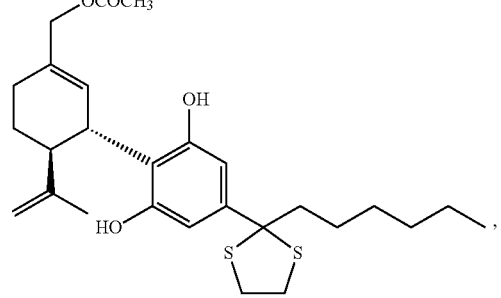

,

149
-continued
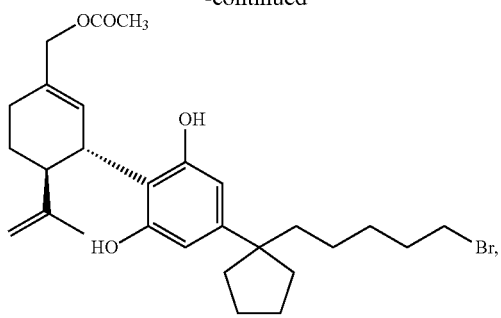
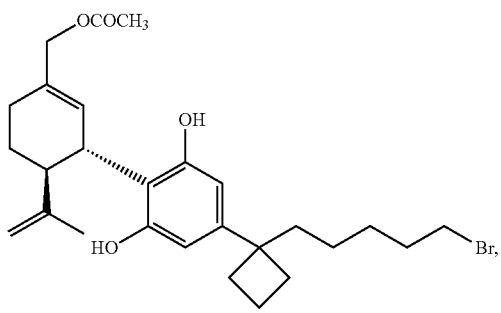
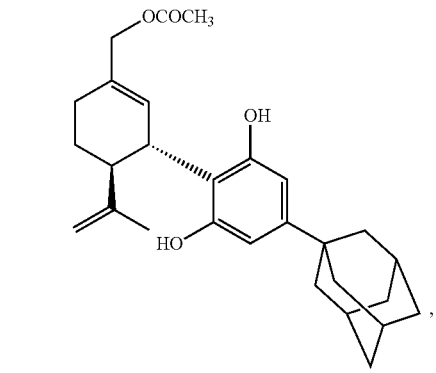
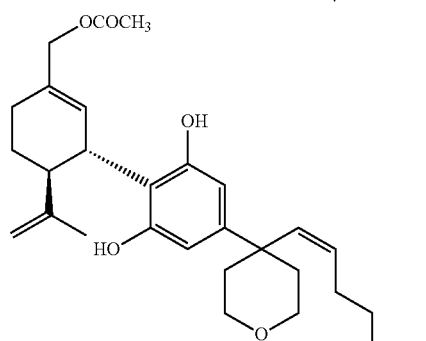
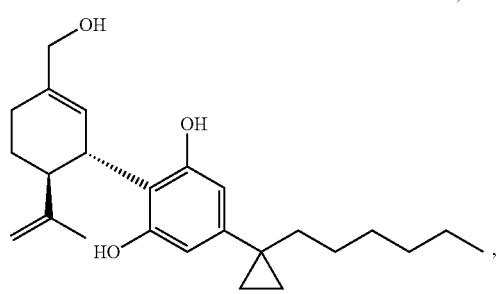
150
-continued
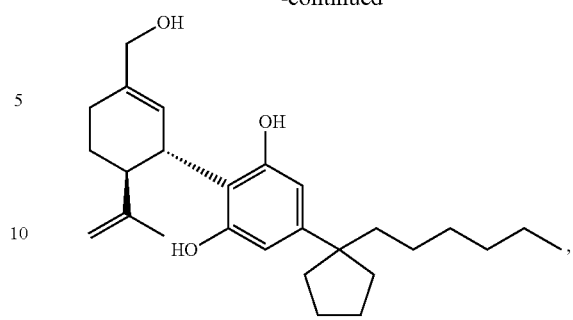
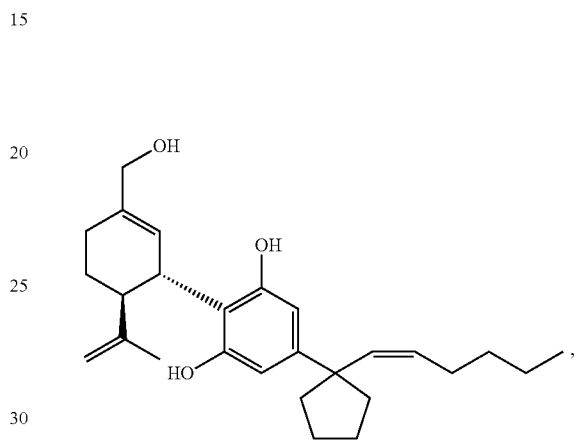
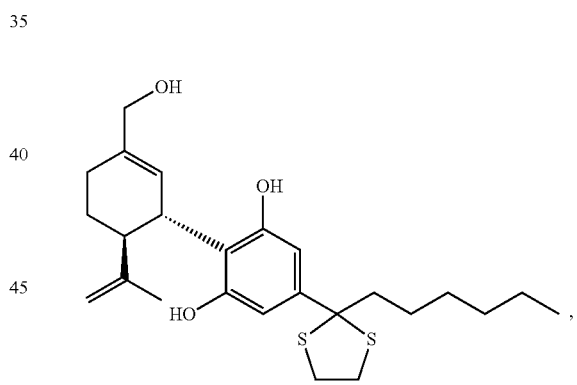
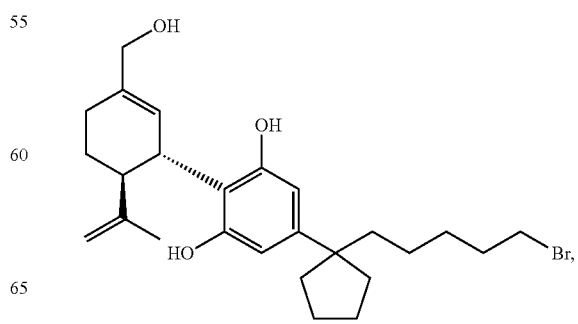

-continued
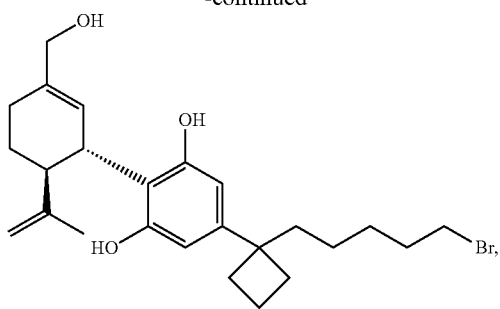
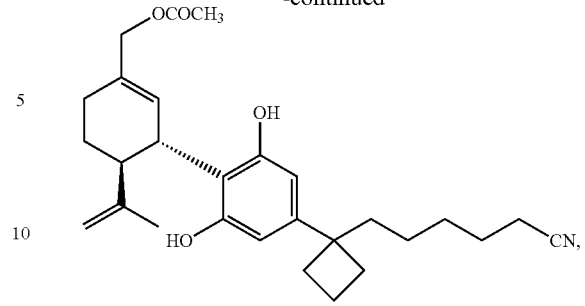
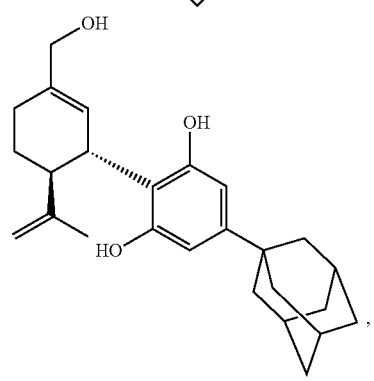
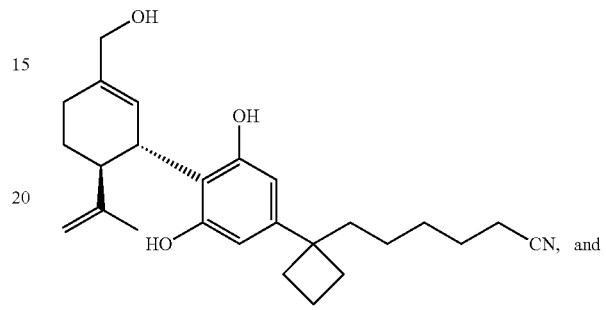
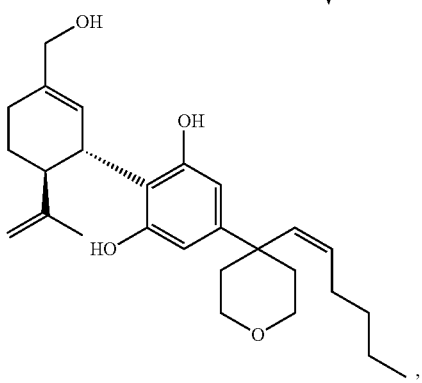
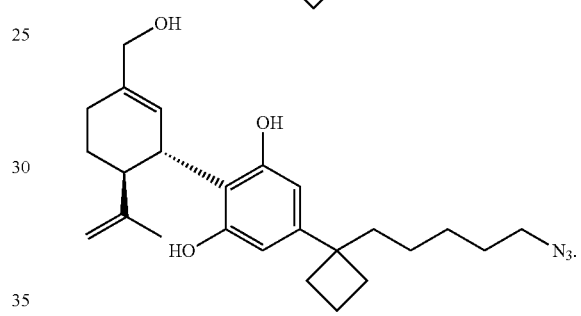
18. A pharmaceutical composition comprising a therapeutically effective amount of a compound of claim 1 or a pharmaceutically acceptable salt thereof and a pharmaceutically acceptable carrier.
* * * * *